US 10,351,558 B2

United States Patent
Meng et al.

(10) Patent No.: US 10,351,558 B2
(45) Date of Patent: Jul. 16, 2019

(54) FACTOR IXA INHIBITORS

(71) Applicants: Merck Sharp & Dohme Corp., Rahway, NJ (US); Dongfang Meng, Morganville, NJ (US); Hong Li, Edison, NJ (US); Meng Yang, Westfield, NJ (US); Manuel de Lera Ruiz, Perkasie, PA (US); Sunita V. Dewnani, Secaucus, NJ (US); Tianying Jian, Westfield, NJ (US); Dann L. Parker, Jr., Cranford, NJ (US); Ting Zhang, Princeton Junction, NJ (US); Louis-Charles Campeau, Morris Plains, NJ (US); Harold B. Wood, Westfield, NJ (US); Jiayi Xu, Marlboro, NJ (US); Richard Berger, Harleysville, PA (US); Jane Yang Wu, Marlboro, NJ (US); Robert K. Orr, Cranford, NJ (US); Shawn P. Walsh, Bridgewater, NJ (US); Bart Harper, New York, NY (US)

(72) Inventors: Dongfang Meng, Morganville, NJ (US); Hong Li, Edison, NJ (US); Meng Yang, Westfield, NJ (US); Manuel de Lera Ruiz, Perkasie, PA (US); Sunita V. Dewnani, Secaucus, NJ (US); Tianying Jian, Westfield, NJ (US); Dann L. Parker, Jr., Cranford, NJ (US); Ting Zhang, Princeton Junction, NJ (US); Louis-Charles Campeau, Morris Plains, NJ (US); Harold B. Wood, Westfield, NJ (US); Jiayi Xu, Marlboro, NJ (US); Richard Berger, Harleysville, PA (US); Jane Yang Wu, Marlboro, NJ (US); Robert K. Orr, Cranford, NJ (US); Shawn P. Walsh, Bridgewater, NJ (US); Bart Harper, New York, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/550,862

(22) PCT Filed: Feb. 12, 2016

(86) PCT No.: PCT/US2016/017652
§ 371 (c)(1),
(2) Date: Aug. 14, 2017

(87) PCT Pub. No.: WO2016/133793
PCT Pub. Date: Aug. 25, 2016

(65) Prior Publication Data
US 2018/0022747 A1    Jan. 25, 2018

Related U.S. Application Data

(60) Provisional application No. 62/116,698, filed on Feb. 16, 2015.

(51) Int. Cl.
C07D 471/04 (2006.01)
C07D 403/12 (2006.01)
(Continued)

(52) U.S. Cl.
CPC .............. *C07D 471/04* (2013.01); *A61P 9/00* (2018.01); *C07D 403/12* (2013.01);
(Continued)

(58) Field of Classification Search
CPC .. C07D 471/04; C07D 403/12; C07D 413/14; A61P 9/00
(Continued)

(56) References Cited

U.S. PATENT DOCUMENTS 8,637,671 B2 *  1/2014  Colucci .............. C07D 471/04
                                                           546/94
2011/0065682 A1  3/2011  Clasby et al.
2013/0157281 A1  6/2013  Beyer et al.

FOREIGN PATENT DOCUMENTS

| EP | 1975159 A1 | 10/2008 |
| WO | WO2008017989 A1 | 2/2008 |
| WO | 2016094260 A1 | 6/2016 |

OTHER PUBLICATIONS

Stefan Lober et al . Fused Azaindole derivatives (Year: 2002).*
(Continued)

*Primary Examiner* — Rita J Desai
(74) *Attorney, Agent, or Firm* — Nicole M. Beeler; John C. Todaro

(57) ABSTRACT

The present invention provides a compound of Formula I and pharmaceutical compositions comprising one or more said compounds, and methods for using said compounds for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The compounds are selective Factor IXa inhibitors.

11 Claims, No Drawings

(51) Int. Cl.
    *C07D 417/14* (2006.01)
    *A61P 9/00* (2006.01)
    *C07D 413/14* (2006.01)
    *C07D 471/14* (2006.01)
    *C07D 498/04* (2006.01)
    *C07D 513/04* (2006.01)

(52) U.S. Cl.
    CPC ......... *C07D 413/14* (2013.01); *C07D 417/14* (2013.01); *C07D 471/14* (2013.01); *C07D 498/04* (2013.01); *C07D 513/04* (2013.01)

(58) Field of Classification Search
    USPC .................................. 514/210.18, 210, 294
    See application file for complete search history.

(56) References Cited

OTHER PUBLICATIONS

Helmi Zaghdane, New indole amide derivative as potent CRTH2 receptor antagonists (Year: 2011).*
Nigel Mackman, Triggers, targets and treatments for thrombosis. (Year: 2008).*
International Search Report and Written Opinion for PCT/US2016/017652, dated Jun. 10, 2016, 10 pages.
PUBCHEM, Substance Recrod for SID-56362626, Nov. 3, 2008. https://pubchem.ncbi.nlm.nih.gov/substance/56362626/version/1#section=Top.
Extended European Search Report for 16752841.3, dated Oct. 2, 2018, 6 pages.

* cited by examiner

FACTOR IXA INHIBITORS

CROSS REFERENCE TO RELATED APPLICATIONS

This application is a U.S. National Phase application under 35 U.S.C. § 371 of PCT Application No. PCT/US2016/017652 filed Feb. 12, 2016, which claims priority from U.S. Provisional Application Ser. No. 62/116,698 filed Feb. 16, 2015.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijayku-mar et al., Bioorganic & Medicinal Chemistry Letters (2006), 16 (10), 2796-2799, discloses hydroxy pyrazole based factor IXa inhibitors.

SUMMARY OF THE INVENTION

The present invention relates to compounds of Formula I:

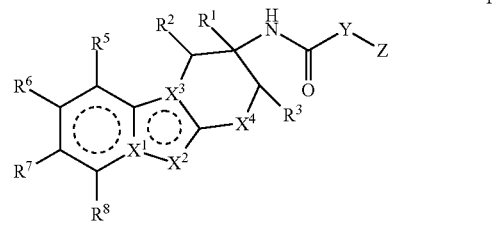

I or pharmaceutically acceptable salts thereof. The compounds of Formula I are selective Factor IXa inhibitors, and as such may be useful in the treatment, inhibition or amelioration of one or more disease states that could benefit from inhibition of Factor IXa, including unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The compounds of this invention could further be used in combination with other therapeutically effective agents, including but not limited to, other drugs useful for the treatment of including unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

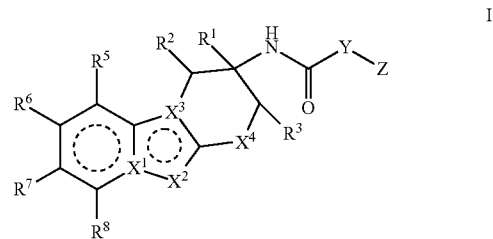

I wherein the dotted lines represent aromatic rings;
$X^1$ is N or C;
$X^2$ is N, $NR^{11}$, or $CR^{12}$;
$X^3$ is C or N;
$X^4$ is $CR^{4a}R^{4b}$, O or S;
Y is heteroaryl or aryl, which is optionally substituted with one or two substituents independently selected from the group consisting of halo, $R^9$, $OR^9$, (C=O)$NH_2$ and (C=O)OH;

Z is heteroaryl, which is optionally substituted with one or two substituents independently selected from the group consisting of halo, oxo, $R^9$, $OR^9$, $(C=O)NR^9R^{10}$, $(C=O)R^9$, $(C=O)OR^9$, $(C=O)$heterocyclyl-OH and $C_{3-6}$ cycloalkyl; or heterocyclyl, which is optionally substituted with one or two substituents independently selected from the halo, cyano, oxo or $C_{1-6}$ alkyl;

$R^1$ is
 a) H,
 b) $C_{1-6}$ alkyl, wherein said alkyl is optionally substituted with one to three substituents independently selected from the group consisting of halo and hydroxy,
 c) aryl, wherein said aryl is optionally substituted with one or two substituents independently selected from the group consisting of halo, $R^9$, $OR^9$ and $(C=O)OR^9$, or
 d) heteroaryl, wherein said heteroaryl group is optionally substituted with one or two substituents independently selected from the group consisting of halo, $R^9$, $OR^9$, $(C=O)NR^9$, $(C=O)OR^9$ and $C_{3-6}$ cycloalkyl (which is optionally substituted with $R^9$);

$R^2$ is H, halo, hydroxy, cyano or $C_{1-6}$ alkyl;
$R^3$ is H, halo, hydroxy, cyano or $C_{1-6}$ alkyl;
or $R^2$ and $R^3$ can be taken together with the carbon atoms to which they are attached to form a 5 or 6 membered cycloalkyl ring;
$R^{4a}$ is H, halo, hydroxy, cyano or $C_{1-6}$ alkyl;
$R^{4b}$ is H, halo, hydroxy, cyano or $C_{1-6}$ alkyl;
$R^5$ is H, halo, hydroxy, cyano or $C_{1-6}$ alkyl;
$R^6$ is H, halo, hydroxy, cyano or $C_{1-6}$ alkyl;
$R^7$ is H, halo, hydroxy, cyano or $C_{1-6}$ alkyl;
$R^8$ is H, halo, hydroxy, cyano or $C_{1-6}$ alkyl;
$R^9$ is H or $C_{1-6}$ alkyl, which is optionally substituted with one to three substituents independently selected from the group consisting of halo and hydroxy;
$R^{10}$ is H or $C_{1-6}$ alkyl, which is optionally substituted with one to three substituents independently selected from the group consisting of halo and hydroxy;
$R^{11}$ is hydrogen, $C_{1-6}$ alkyl or $C_{1-6}$ alkyl-$(C=O)OR^9$;
$R^{12}$ is
a) hydrogen,
b) halo,
c) cyano,
d) $(C=O)R^9$,
e) $(C=O)OR^9$,
e) $(C=O)NR^9R^{10}$,
f) $SO_2R^9$,
g) $C_{1-6}$ alkyl, which is optionally substituted with one to four substituents independently selected from the group consisting of halo, cyano, $C_{3-6}$ cycloalkyl, $OR^9$, $NR^9R^{10}$, $(C=O)OR^9$, $(C=O)NR^9R^{10}$, $CH=CH(C=O)OR^9$, $CH=CH(C=O)NR^9R^{10}$ and $CF_3$,
h) $C_{2-6}$ alkenyl, which is optionally substituted with one to four substituents independently selected from the group consisting of halo, $OR^9$, $NR^9R^{10}$, $(C=O)OR^9$ and $(C=O)NR^9R^{10}$,
i) heteroaryl, which is optionally substituted with one or two substitutents independently selected from the group consisting of halo, cyano, oxo, $C_{3-6}$ cycloalkyl, $R^9$, $OR^9$, $NR^9R^{10}$, $(C=O)R^9$ and $(C=O)OR^9$,
j) heterocyclyl, which is optionally substituted with one or two substituents independently selected from the halo, cyano, oxo or $C_{1-6}$ alkyl,
k) $C_{3-6}$ cycloalkyl, or
l) $C(R^9)=NOH$;
or a pharmaceutically acceptable salt thereof.

An embodiment of the present invention relates to compounds of Formula Ia:

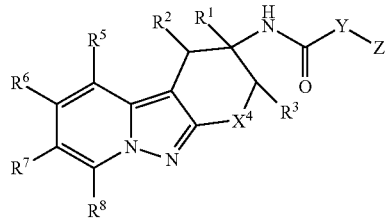

wherein $X^4$ is $CR^{4a}R^{4b}$, O or S;
Y is heteroaryl or aryl, which is optionally substituted with one or two substituents independently selected from the group consisting of halo, $R^9$, $OR^9$, $(C=O)NH_2$ and $(C=O)OH$;

Z is heteroaryl, which is optionally substituted with one or two substituents independently selected from the group consisting of halo, oxo, $R^9$, $OR^9$, $(C=O)NR^9R^{10}$, $(C=O)R^9$, $(C=O)OR^9$, $(C=O)$heterocyclyl-OH and $C_{3-6}$ cycloalkyl; or heterocyclyl, which is optionally substituted with one or two substituents independently selected from the halo, cyano, oxo or $C_{1-6}$ alkyl;

$R^1$ is
 a) H,
 b) $C_{1-6}$ alkyl, wherein said alkyl is optionally substituted with one to three substituents independently selected from the group consisting of halo and hydroxy,
 c) aryl, and wherein said aryl is optionally substituted with one or two substituents independently selected from the group consisting of halo, $R^9$, $OR^9$ and $(C=O)OR^9$, or
 d) heteroaryl, and wherein said heteroaryl group is optionally substituted with one or two substituents independently selected from the group consisting of halo, $R^9$, $OR^9$, $(C=O)NR^9$, $(C=O)OR^9$ and $C_{3-6}$ cycloalkyl (which is optionally substituted with $R^9$);

$R^2$ is H, halo, hydroxy, cyano or $C_{1-6}$ alkyl;
$R^3$ is H, halo, hydroxy, cyano or $C_{1-6}$ alkyl;
or $R^2$ and $R^3$ can be taken together with the carbon atoms to which they are attached to form a 5 or 6 membered cycloalkyl ring;
$R^{4a}$ is H, halo, hydroxy, cyano or $C_{1-6}$ alkyl;
$R^{4b}$ is H, halo, hydroxy, cyano or $C_{1-6}$ alkyl;
$R^5$ is H, halo, hydroxy, cyano or $C_{1-6}$ alkyl;
$R^6$ is H, halo, hydroxy, cyano or $C_{1-6}$ alkyl;
$R^7$ is H, halo, hydroxy, cyano or $C_{1-6}$ alkyl;
$R^8$ is H, halo, hydroxy, cyano or $C_{1-6}$ alkyl;
$R^9$ is H or $C_{1-6}$ alkyl, which is optionally substituted with one to three substituents independently selected from the group consisting of halo and hydroxy;
$R^{10}$ is H or $C_{1-6}$ alkyl, which is optionally substituted with one to three substituents independently selected from the group consisting of halo and hydroxy;
$R^{11}$ is hydrogen, $C_{1-6}$ alkyl or $C_{1-6}$ alkyl-$(C=O)OR^9$;
$R^{12}$ is
a) hydrogen,
b) halo,
c) cyano,
d) $(C=O)R^9$,
e) $(C=O)OR^9$,
e) $(C=O)NR^9R^{10}$,
f) $SO_2R^9$,
g) $C_{1-6}$ alkyl, which is optionally substituted with one to four substituents independently selected from the group consisting of halo, cyano, $C_{3-6}$ cycloalkyl, $OR^9$, $NR^9R^{10}$, (C=O)$OR^9$, (C=O)$NR^9R^{10}$, CH=CH(C=O)$OR^9$, CH=CH(C=O)$NR^9R^{10}$ and $CF_3$, h) $C_{2-6}$ alkenyl, which is optionally substituted with one to four substituents independently selected from the group consisting of halo, $OR^9$, $NR^9R^{10}$, (C=O)$OR^9$ and (C=O)$NR^9R^{10}$, i) heteroaryl, which is optionally substituted with one or two substitutents independently selected from the group consisting of halo, cyano, oxo, $C_{3-6}$ cycloalkyl, $R^9$, $OR^9$, $NR^9R^{10}$, (C=O)$R^9$ and (C=O)$OR^9$, j) heterocyclyl, which is optionally substituted with one or two substituents independently selected from the halo, cyano, oxo or $C_{1-6}$ alkyl, k) $C_{3-6}$ cycloalkyl, or l) $C(R^9)$=NOH;

or a pharmaceutically acceptable salt thereof.

An embodiment of the present invention also includes compounds of the following formulas:

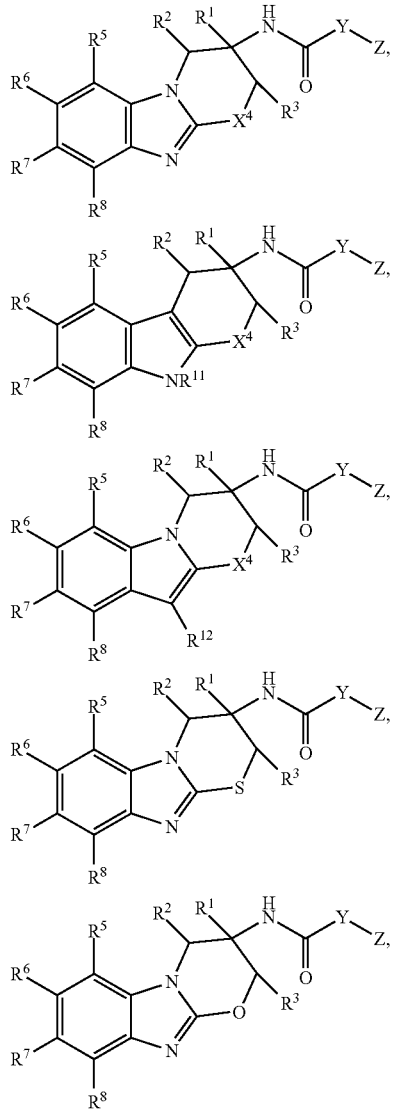

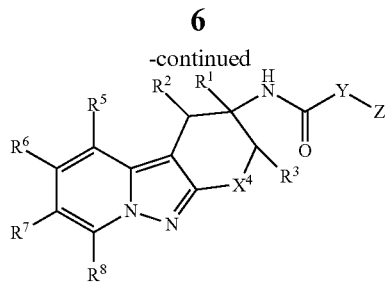

wherein $X^4$ is $CR^{4a}R^{4b}$, O or S;

Y is heteroaryl or aryl, which is optionally substituted with one or two substituents independently selected from the group consisting of halo, $R^9$, $OR^9$, (C=O)$NH_2$ and (C=O)OH;

Z is heteroaryl, which is optionally substituted with one or two substituents independently selected from the group consisting of halo, oxo, $R^9$, $OR^9$, (C=O)$NR^9R^{10}$, (C=O)$R^9$, (C=O)$OR^9$, (C=O)heterocyclyl-OH and $C_{3-6}$ cycloalkyl; or heterocyclyl, which is optionally substituted with one or two substituents independently selected from the halo, cyano, oxo or $C_{1-6}$ alkyl;

$R^1$ is
 a) H,
 b) $C_{1-6}$ alkyl, wherein said alkyl is optionally substituted with one to three substituents independently selected from the group consisting of halo and hydroxy,
 c) aryl, wherein said aryl is optionally substituted with one or two substituents independently selected from the group consisting of halo, $R^9$, $OR^9$ and (C=O)$OR^9$, or
 d) heteroaryl, wherein said heteroaryl group is optionally substituted with one or two substituents independently selected from the group consisting of halo, $R^9$, $OR^9$, (C=O)$NR^9$, (C=O)$OR^9$ and $C_{3-6}$ cycloalkyl (which is optionally substituted with $R^9$);

$R^2$ is H, halo, hydroxy, cyano or $C_{1-6}$ alkyl;
$R^3$ is H, halo, hydroxy, cyano or $C_{1-6}$ alkyl;
or $R^2$ and $R^3$ can be taken together with the carbon atoms to which they are attached to form a 5 or 6 membered cycloalkyl ring;
$R^{4a}$ is H, halo, hydroxy, cyano or $C_{1-6}$ alkyl;
$R^{4b}$ is H, halo, hydroxy, cyano or $C_{1-6}$ alkyl;
$R^5$ is H, halo, hydroxy, cyano or $C_{1-6}$ alkyl;
$R^6$ is H, halo, hydroxy, cyano or $C_{1-6}$ alkyl;
$R^7$ is H, halo, hydroxy, cyano or $C_{1-6}$ alkyl;
$R^8$ is H, halo, hydroxy, cyano or $C_{1-6}$ alkyl;
$R^9$ is H or $C_{1-6}$ alkyl, which is optionally substituted with one to three substituents independently selected from the group consisting of halo and hydroxy;
$R^{10}$ is H or $C_{1-6}$ alkyl, which is optionally substituted with one to three substituents independently selected from the group consisting of halo and hydroxy;
$R^{11}$ is hydrogen, $C_{1-6}$ alkyl or $C_{1-6}$ alkyl-(C=O)$OR^9$;
$R^{12}$ is
 a) hydrogen,
 b) halo,
 c) cyano,
 d) (C=O)$R^9$,
 e) (C=O)$OR^9$,
 e) (C=O)$NR^9R^{10}$,
 f) $SO_2R^9$,
 g) $C_{1-6}$ alkyl, which is optionally substituted with one to four substituents independently selected from the group consisting of halo, cyano, $C_{3-6}$ cycloalkyl, $OR^9$, $NR^9R^{10}$, (C=O)$OR^9$, (C=O)$NR^9R^{10}$, CH=CH(C=O)$OR^9$, CH=CH(C=O)$NR^9R^{10}$ and $CF_3$, h) $C_{2-6}$ alkenyl, which is optionally substituted with one to four substituents independently selected from the group consisting of halo, $OR^9$, $NR^9R^{10}$, $(C=O)OR^9$ and $(C=O)NR^9R^{10}$, i) heteroaryl, which is optionally substituted with one or two substituents independently selected from the group consisting of halo, cyano, oxo, $C_{3-6}$ cycloalkyl, $R^9$, $OR^9$, $NR^9R^{10}$, $(C=O)R^9$ and $(C=O)OR^9$, j) heterocyclyl, which is optionally substituted with one or two substituents independently selected from the halo, cyano, oxo or $C_{1-6}$ alkyl, k) $C_{3-6}$ cycloalkyl, or l) $C(R^9)=NOH$;

or a pharmaceutically acceptable salt thereof.

In an embodiment of the invention, $X^1$ is N. In another embodiment of the invention, $X^1$ is C.

In an embodiment of the invention, $X^2$ is N. In another embodiment of the invention, $X^2$ is $NR^{11}$. In another embodiment of the invention, $X^2$ is $CR^{12}$.

In an embodiment of the invention, $X^3$ is N. In another embodiment of the invention, $X^3$ is C.

In an embodiment of the invention, $X^4$ is $CR^{4a}R^{4b}$. In another embodiment of the invention, $X^4$ is O. In another embodiment of the invention, $X^4$ is S.

In an embodiment of the invention, Y is aryl, which is optionally substituted with one or two substituents independently selected from the group consisting of halo, $R^9$ and $OR^9$. In a class of the invention, Y is phenyl, which is optionally substituted with one or two substituents independently selected from the group consisting of halo, $R^9$ and $OR^9$. In a subclass of the invention, Y is phenyl, which is substituted with chloro. In another subclass of the invention, Y is phenyl, which is substituted with two chloro. In another subclass of the invention, Y is phenyl, which is substituted with chloro and methyl. In another subclass of the invention, Y is phenyl, which is substituted with methoxy. In another class of the invention, Y is piperidinyl.

In an embodiment of the invention, Z is triazolyl, benzimidazolyl, pyrimidinyl, imidazopyridinyl, imidazolyl or pyridinyl, wherein said groups are optionally substituted with one or two substituents independently selected from the group consisting of halo, oxo, $R^9$, $OR^9$, $(C=O)NR^9R^{10}$, $(C=O)R^9$, $(C=O)OR^9$, $(C=O)$heterocyclyl-OH and $C_{3-6}$ cycloalkyl. In a class of the embodiment, Z is triazolyl, which is optionally substituted with one or two substituents independently selected from the group consisting of halo, oxo, $R^9$, $OR^9$ and $C_{3-6}$ cycloalkyl. In a subclass of the invention, Z is triazolyl. In another subclass of the invention, Z is triazolyl which is substituted with methyl. In a class of the embodiment, Z is benzimidazolyl, which is optionally substituted with one or two substituents independently selected from the group consisting of halo, $R^9$, $OR^9$, $(C=O)NR^9R^{10}$, $(C=O)$heterocyclyl-OH, $(C=O)R^9$ and $(C=O)OR^9$.

In an embodiment of the invention, $R^1$ is $C_{1-2}$ alkyl, wherein said alkyl is optionally substituted with hydroxy. In another embodiment of the invention, $R^1$ is phenyl, which is optionally substituted with one or two substituents independently selected from the group consisting of halo, $R^9$, $OR^9$ and $(C=O)OR^9$. In a class of the invention, $R^1$ is phenyl, which is optionally substituted with halo. In another embodiment of the invention, $R^1$ is triazolyl, piperidinyl, quinolinyl, thiazolyl or oxadiazolyl, wherein said groups are optionally substituted with one or two substituents independently selected from the group consisting of halo, $R^9$ and $C_{3-6}$ cycloalkyl (which is optionally substituted with $R^9$). In another embodiment of the invention, $R^1$ is H.

In an embodiment of the invention, $R^2$ is H.

In an embodiment of the invention, $R^3$ is H.

In an embodiment of the invention, $R^2$ and $R^3$ can be taken together with the carbon atoms to which they are attached to form a 5 membered cycloalkyl ring.

In an embodiment of the invention, $R^{4a}$ is H. In another embodiment of the invention, $R^{4a}$ is deuterium. In another embodiment of the invention, $R^{4a}$ is halo. In a class of the invention, $R^{4a}$ is fluoro.

In an embodiment of the invention, $R^{4b}$ is H. In another embodiment of the invention, $R^{4b}$ is deuterium. In another embodiment of the invention, $R^{4b}$ is halo. In a class of the invention, $R^{4b}$ is fluoro.

In an embodiment of the invention, $R^5$ is H. In another embodiment of the invention, $R^5$ is halo. In another embodiment of the invention, $R^5$ is hydroxy. In another embodiment of the invention, $R^5$ is cyano. In another embodiment of the invention, $R^5$ is $C_{1-6}$ alkyl. In a class of the invention, $R^5$ is methyl.

In an embodiment of the invention, $R^6$ is H. In another embodiment of the invention, $R^6$ is halo. In another embodiment of the invention, $R^6$ is hydroxy. In another embodiment of the invention, $R^6$ is cyano. In another embodiment of the invention, $R^6$ is $C_{1-6}$ alkyl. In a class of the invention, $R^6$ is methyl.

In an embodiment of the invention, $R^7$ is H. In another embodiment of the invention, $R^7$ is halo. In another embodiment of the invention, $R^7$ is hydroxy. In another embodiment of the invention, $R^7$ is cyano. In another embodiment of the invention, $R^7$ is $C_{1-6}$ alkyl. In a class of the invention, $R^7$ is methyl.

In an embodiment of the invention, $R^8$ is H. In another embodiment of the invention, $R^8$ is halo. In another embodiment of the invention, $R^8$ is hydroxy. In another embodiment of the invention, $R^8$ is cyano. In another embodiment of the invention, $R^8$ is $C_{1-6}$ alkyl. In a class of the invention, $R^8$ is methyl.

Reference to the preferred classes and subclasses set forth above is meant to include all combinations of particular groups unless stated otherwise.

Specific embodiments of the present invention include, but are not limited to the compounds identified herein as EXAMPLE 2 to 215, or pharmaceutically acceptable salts thereof.

Also included within the scope of the present invention is a pharmaceutical composition which is comprised of a compound of Formula I or Formula Ia as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor IXa inhibitors and may have therapeutic value in, for example, preventing coronary artery disease.

It will be understood that, as used herein, compounds of the instant invention can include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I and Formula Ia. Unless a specific stereochemistry is indicated, the present invention is meant to comprehend all such isomeric forms of these compounds. Centers of asymmetry that are present in the compounds of Formula I and Formula Ia can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I and Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I or Formula Ia or any other generic structural formula or specific compound described or claimed herein, is intended to encompass the specific compound or compounds falling within the scope of the formula or embodiment.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I or Formula Ia simultaneously contain acidic and basic groups in the molecule the invention also includes, in addition to the salt forms mentioned, inner salts or betaines (zwitterions). Salts can be obtained from the compounds of Formula I and Formula Ia by customary methods which are known to the person skilled in the art, for example by combination with an organic or inorganic acid or base in a solvent or dispersant, or by anion exchange or cation exchange from other salts. The present invention also includes all salts of the compounds of Formula I and Formula Ia which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

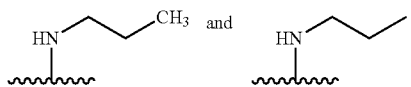

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic, and at least one ring contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzenyl, benzothiazolyl, benzothienyl, quinolinyl, isoquinolinyl, oxazoly, and tetra-hydroquinolinyl. Specific heteroaryl groups include 1,2,3-triazolyl, 1,2,4-triazolyl, imidazolyl, tetrazolyl, pyridyl, pyrimidinyl, pyrazolyl, pyridazinyl, quinolinyl, triazolopyridinyl, triazolonyl, pyridonyl and benzoimidazolyl. If the heteroaryl contains nitrogen atoms, it is understood that the corresponding N-oxides thereof are also encompassed by this definition.

Except where noted, the term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. As used herein, "heterocyclyl" includes 5- to 10-membered nonaromatic rings that contain one or more double bonds, and contain from 1 to 4 heteroatoms selected from the group consisting of O, N, S, SO, or $SO_2$. "Heterocyclyl" therefore includes, but is not limited to the following: azetidinyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

Except where noted herein, structures containing substituent variables such as variable "R" below:

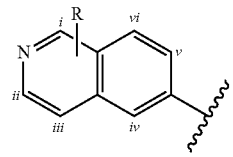

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I and Formula Ia, acting as prodrugs and solvates. Prodrugs, following administration to the patient, are converted in the body by normal metabolic or chemical processes, such as through hydrolysis in the blood, to the compound of Formula I or Formula Ia. Such prodrugs include those that demonstrate enhanced bioavailability, tissue specificity, and/or cellular delivery, to improve drug absorption of the compound of Formula I or Formula Ia. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I and Formula Ia capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I and Formula Ia form stable alkali metal, alkaline earth metal or optionally substituted ammonium salts. If the compounds of the Formula I and Formula Ia have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I or Formula Ia and/or of a pharmaceutically acceptable salt of the compound of the Formula I or Formula Ia and/or an optionally stereoisomeric form of the compound of the Formula I or Formula Ia or a pharmaceutically acceptable salt of the stereoisomeric form of the compound of Formula I or Formula Ia, together with a pharmaceutically suitable and pharmaceutically acceptable vehicle, additive and/or other active substances and auxiliaries.

The invention also relates to the use of a compound of the instant invention and/or of a pharmaceutically acceptable salt of the compound of the invention in the manufacture of a medicament for inhibiting thrombin, inhibiting thrombus formation, treating thrombus formation or preventing thrombus formation in a mammal.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor IXa inhibitors are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula I or Formula Ia into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably between 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I and Formula Ia can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor IXa inhibitors can also be co-administered with suitable anticoagulants, including, but not limited to, other Factor IXa inhibitors, thrombin inhibitors, thrombin receptor antagonists, factor VIIa inhibitors, factor Xa inhibitors, factor XIa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (coadministration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®, irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists;

peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; a stimulator of soluble guanylate cyclase (sGC), such as riociguat, vericiguat; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

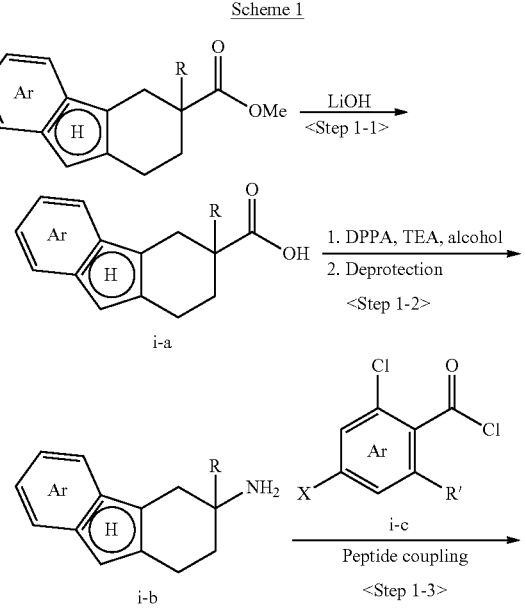

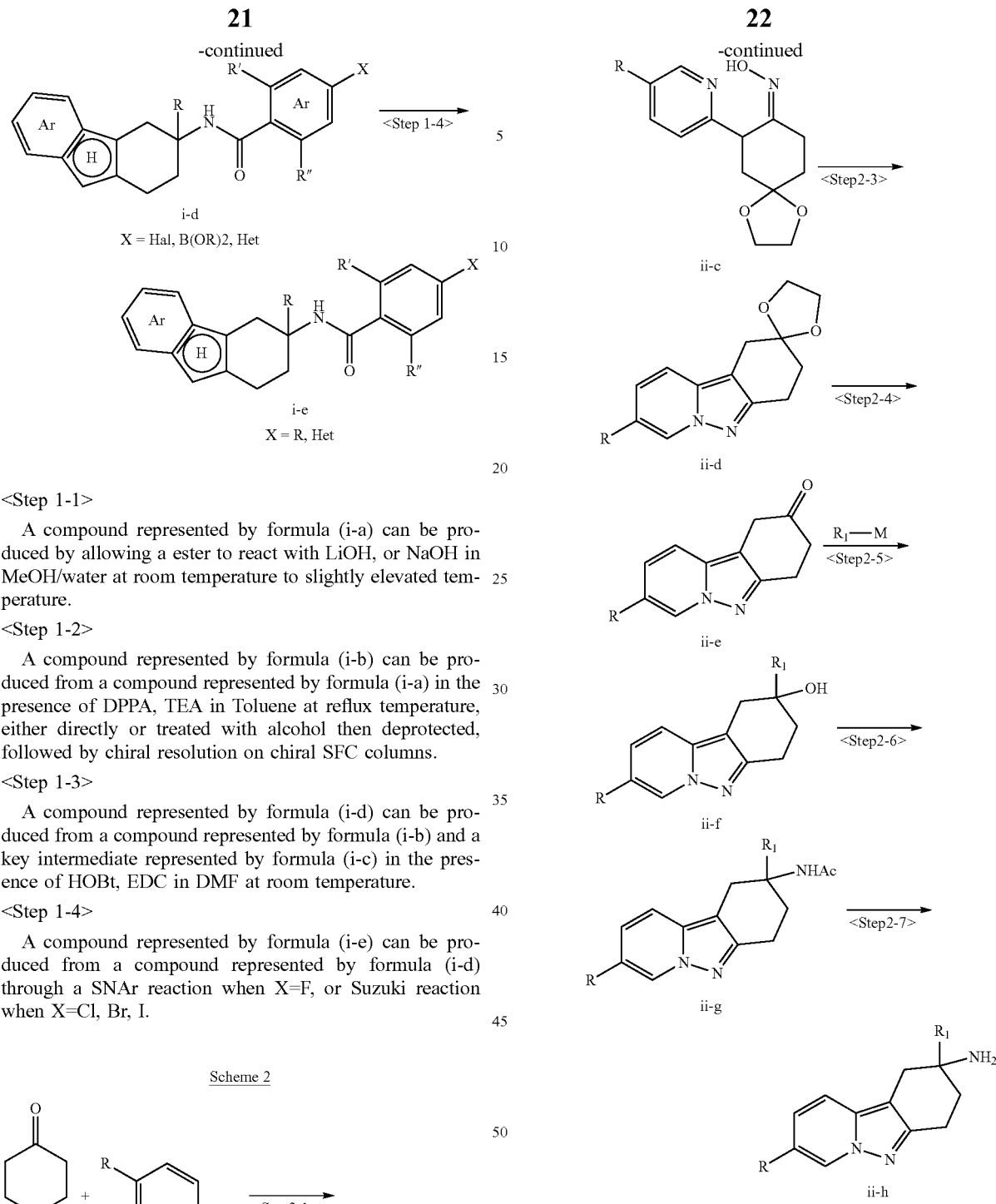

<Step 1-1>

A compound represented by formula (i-a) can be produced by allowing a ester to react with LiOH, or NaOH in MeOH/water at room temperature to slightly elevated temperature.

<Step 1-2>

A compound represented by formula (i-b) can be produced from a compound represented by formula (i-a) in the presence of DPPA, TEA in Toluene at reflux temperature, either directly or treated with alcohol then deprotected, followed by chiral resolution on chiral SFC columns.

<Step 1-3>

A compound represented by formula (i-d) can be produced from a compound represented by formula (i-b) and a key intermediate represented by formula (i-c) in the presence of HOBt, EDC in DMF at room temperature.

<Step 1-4>

A compound represented by formula (i-e) can be produced from a compound represented by formula (i-d) through a SNAr reaction when X=F, or Suzuki reaction when X=Cl, Br, I.

Scheme 2

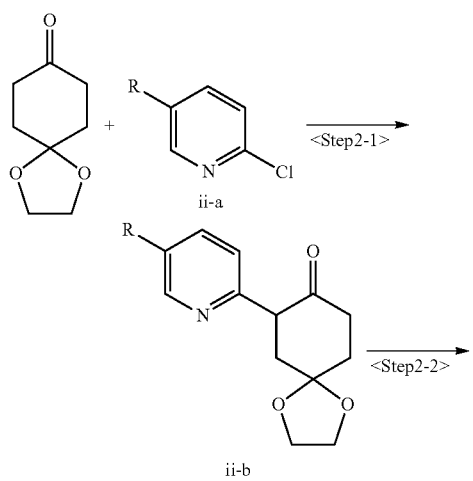

<Step 2-1>

A compound represented by formula (ii-b) can be produced by allowing a compound represented by formula i-a to react with 1,4-dioxaspiro[4.5]decan-8-one by a palladium mediated α-arylation of ketones which are similar to that described in published documents, for example, *J. Am. Chem. Soc,* 1997, 119, 11108, in the presence of a base such as sodium tert-butoxide, potassium tert-butoxide, lithium bis(trimethylsilyl)amide, sodium bis(trimethylsilyl)amide, potassium bis(trimethylsilyl)amide, sodium hydride, potassium hydride, sodium carbonate, potassium carbonate, cesium carbonate, or potassium phosphate tribasic, in the presence of a metal source, such as $Pd_2(dba)_3$, $Pd(OAc)_2$, Pd(Ph$_3$)$_4$, PdCl$_2$(PPh$_3$)$_2$, and/or in the presence of a ligand such as Xantphos (CAS number 161265-03-8), tert-Bu$_3$P, tBuMePhos (CAS number 255837-19-5), [1,1'-bis(di-tert-butylphosphino) ferrocene] dichloropalladium(II) using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 2-2>

A compound represented by formula (ii-c) can be produced from a compound represented by formula (ii-b) by a well-known or similar process that described in published documents, for example, *J. Org. Chem.*, 2011, 76, 4665, in the presence of inorganic or organic bases such as sodium acetate, potassium acetate, lithium hydroxide, sodium hydroxide, potassium hydroxide, sodium carbonate, potassium carbonate, cesium carbonate, calcium carbonate, sodium bicarbonate, potassium phosphate tribasic, triethyl amine with water or without water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

<Step 2-3>

A compound represented by formula (ii-d) can be produced from treating a compound represented by formula (ii-c) with p-toluenesulfonyl chloride in the presence of an organic or inorganic base, such as triethylamine, diisopropylethylamine, sodium hydride, potassium acetate, lithium hydroxide, sodium hydroxide, potassium hydroxide, sodium carbonate, potassium carbonate, cesium carbonate, calcium carbonate, sodium bicarbonate, and potassium phosphate tribasic in a solvent which is inactive to the reaction, such as dichloromethane, 1,2-dichloroethane, tetrahydrofuran, diethyl ether or a mixed solvent thereof at a temperature in the range of 0° C. to the solvent-reflux temperature.

<Step 2-4>

A compound represented by formula (ii-e) can be produced from a compound represented by formula (ii-d) by a well-known or similar process that described in published documents, for example, *J. Chem. Soc. Chem. Commun.* 1971, 858, in the presence of inorganic or organic acid such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid with water or without water and a solvent such as acetone, methanol, ethanol, 2-propanol, N,N-dimethylformamide, dioxane, or tetrahydrofuran, or a mixed solvent thereof at a temperature in the range of room temperature to the solvent-reflux temperature.

<Step 2-5>

A compound represented by formula (ii-f) can be produced allowing a compound represented by formula i-e to react with a compound represented by formula R$_1$-M (organometal reagent, wherein M represents lithium, sodium, or magnesium halide), which are similar to that described in published documents, for example, *Org. Syntheses.* 1944, 24, in a solvent which is inactive to the reaction, such as such as an ethereal solvent, e.g., diethyl ether, tetrahydrofuran, 1,2-dimethoxyethane, 1,4-dioxane, or a mixed solvent thereof at a temperature in the range of −78° C. to the room temperature.

<Step 2-6>

A compound represented by formula (ii-g) can be produced by allowing a compound represented by formula i-f to react with acetonitrile by a process known as a Ritter reaction which is similar to that described in published documents, for example, *Tetrahedron Lett.*, 2003, 44, 1453, in the presence of an acid such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, formic, acetic, oxalic, tartaric, succinic, glycerolphosphoric, lactic, malic, adipic, citric, fumaric, maleic, gluconic, glucuronic, palmitic or trifluoroacetic acid using a solvent which is inactive to the reaction, such as dichloromethane, 1,2-dichloroethane, acetonitrile, ethyl acetate or a mixed solvent thereof at a temperature in the range of room temperature to the solvent-reflux temperature.

<Step 2-7>

A compound represented by formula (ii-h) can be produced from treating a compound represented by formula ii-g with an acid such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, formic, acetic, oxalic, tartaric, succinic, glycerolphosphoric, lactic, malic, adipic, citric, fumaric, maleic, gluconic, glucuronic, palmitic or trifluoroacetic acid with water or without water and a solvent which is inactive to the reaction, such as dichloromethane, 1,2-dichloroethane, acetonitrile, ethyl acetate or a mixed solvent thereof at a temperature in the range of room temperature to the solvent-reflux temperature.

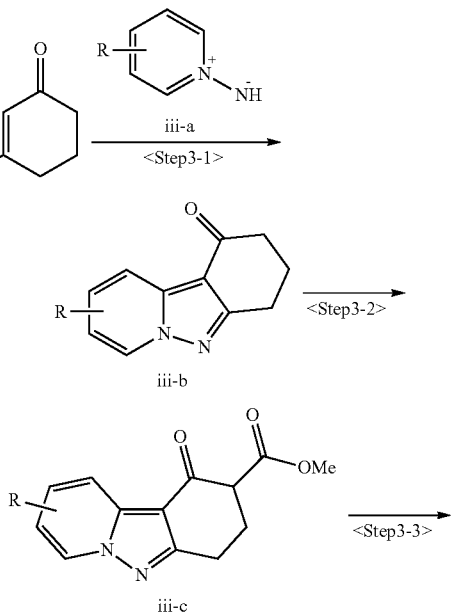

Scheme 3

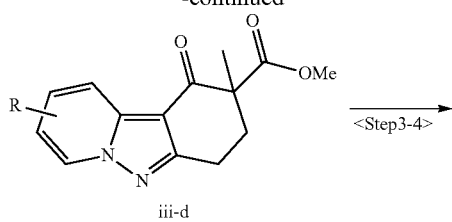

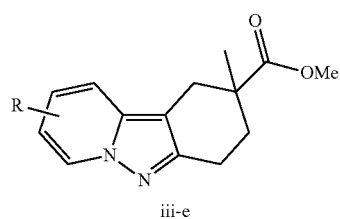

<Step 3-1>

A compound represented by formula (iii-b) can be produced by allowing 3-ethoxy-2-cyclohexen-1-one to react with (iii-a), $K_2CO_3$ in ethylene glycol at 130° C.

<Step 3-2>

A compound represented by formula (iii-c) can be produced from a compound represented by formula (iii-b) in the presence of LiHMDS, methyl chloroformate in THF at −78° C.

<Step 3-3>

A compound represented by formula (iii-d) can be produced from a compound represented by formula (iii-c) in the presence of NaH, iodomethane in DMF at room temperature.

<Step 3-4>

A compound represented by formula (iii-e) can be produced from a compound represented by formula (iii-d) through a sequential of reduction by sodium borohydride, then TFA and triethylsilane.

Scheme 4

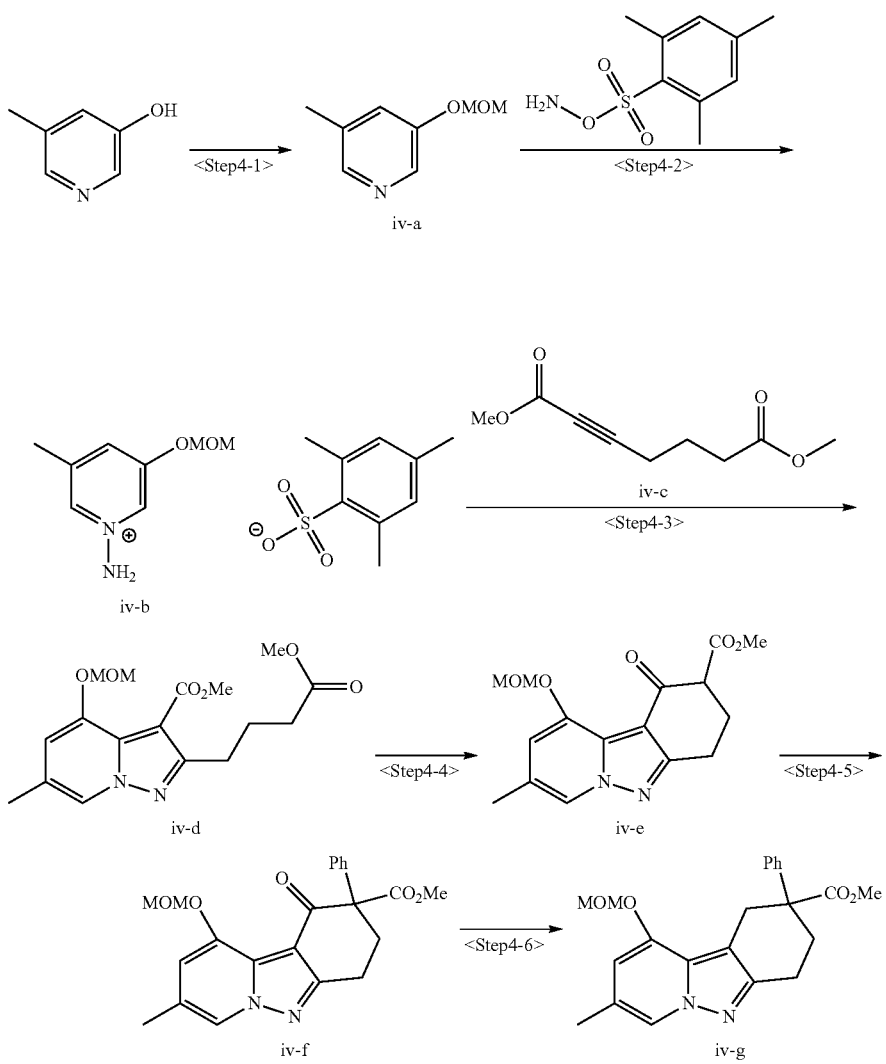

<Step 4-1>
A compound represented by formula (iv-a) can be produced by allowing 5-methylpyridin-3-ol to react with MOM-Cl in the presence of potassium tert-butoxide in DMF at 0° C.
<Step 4-2>
A compound represented by formula (iv-b) can be produced from a compound represented by formula (iv-a) to react with O-(mesitylsulfonyl)hydroxylamine in DCM at 0° C.
<Step 4-3>
A compound represented by formula (iv-d) can be produced from a compound represented by formula (iv-b) to react with (iv-c) in the presence of potassium carbonate in DMF at room temperature.
<Step 4-4>
A compound represented by formula (iv-e) can be produced from a compound represented by formula (iv-d) in the presence LiHMDS in THF at −78° C. to 0° C.
<Step 4-5>
A compound represented by formula (iv-f) can be produced from a compound represented by formula (iv-e) with diphenyliodonium chloride in the presence of of potassium tert-butoxide in THF at room temperature.
<Step 4-6>
A compound represented by formula (iv-g) can be produced from a compound represented by formula (iv-f) through a sequential of reduction by sodium borohydride, then TFA and triethylsilane.

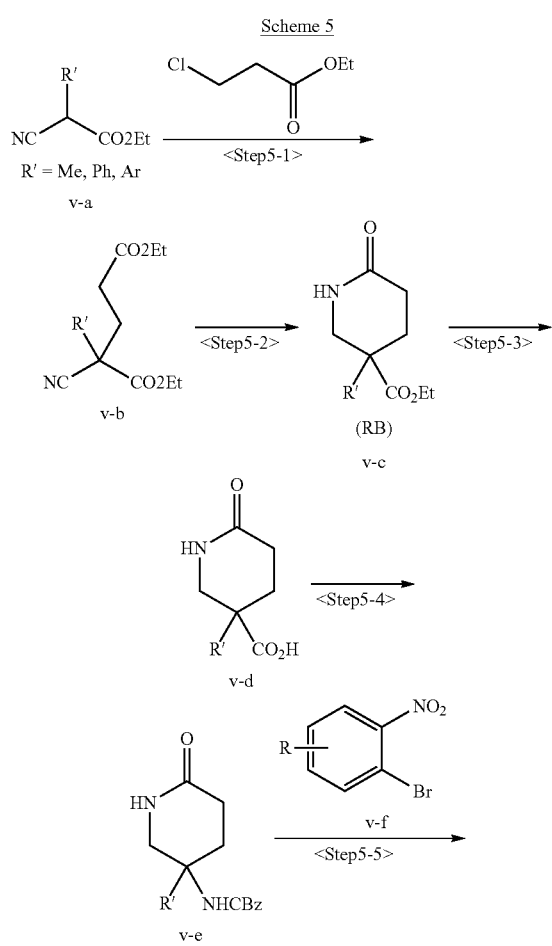

Scheme 5

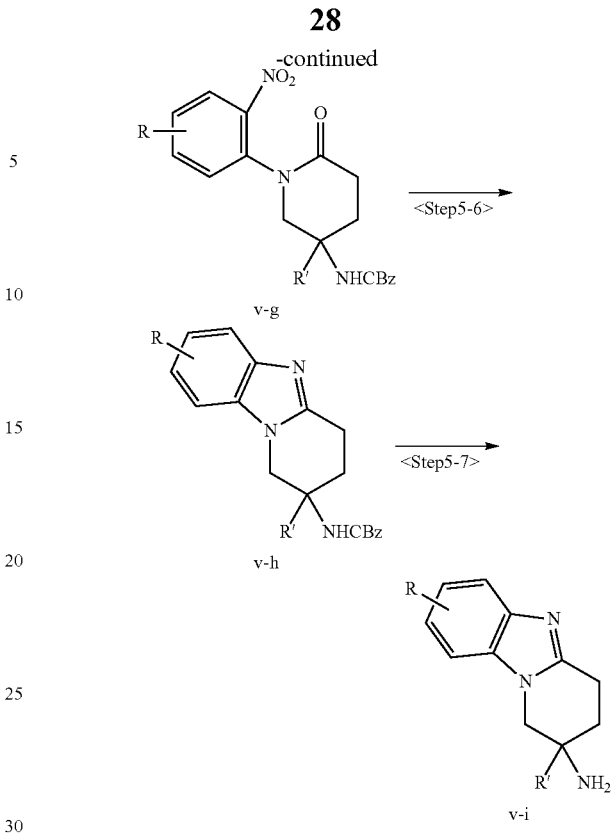

<Step 5-1>
A compound represented by formula (v-b) can be produced by allowing (v-a) to react with ethyl 3-chloropropanoate in the presence of sodium ethoxide in ethanol at 0° C.
<Step 5-2>
A compound represented by formula (v-c) can be produced from a compound represented by formula (v-b) to react with Raney® nickel and hydrogen in water at room temperature.
<Step 5-3>
A compound represented by formula (v-d) can be produced by allowing (v-c) to react with LiOH, or NaOH in MeOH/water at room temperature to slightly elevated temperature.
<Step 5-4>
A compound represented by formula (v-e) can be produced from a compound represented by formula (v-d) in the presence of DPPA, TEA in Toluene at reflux temperature, trapped with benzyl alcohol.
<Step 5-5>
A compound represented by formula (v-g) can be produced from a compound represented by formula (v-e) to react with (v-f) in the presence of XantPhos, tris(dibenzylideneacetone)dipalladium(0), cesium carbonate in toluene at 90° C.
<Step 5-6>
A compound represented by formula (v-h) can be produced from a compound represented by formula (v-g) with iron in acetic acid at 120° C.
<Step 5-7>
A compound represented by formula (v-i) can be produced from a compound represented by formula (v-h) to react with PdOH/C and hydrogen in MeOH at room temperature.

Scheme 6

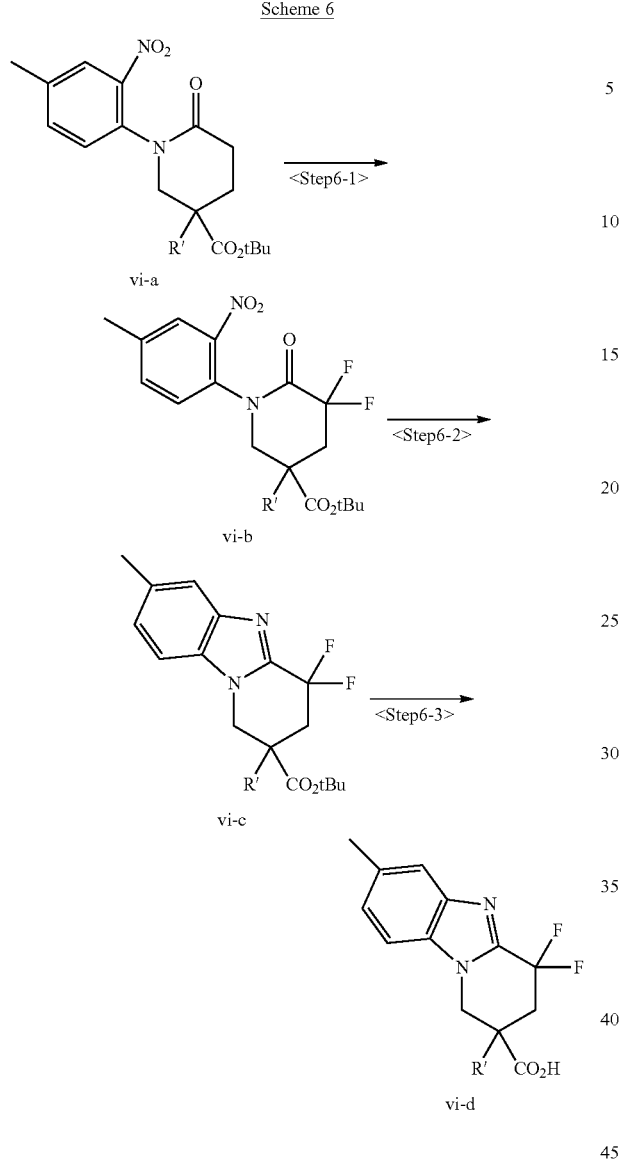

<Step 6-1>

A compound represented by formula (vi-b) can be produced by allowing (vi-a) to react with n-fluorobenzenesulfonimide in the presence of LiHMDS in THF at −20° C.

<Step 6-2>

A compound represented by formula (vi-c) can be produced from a compound represented by formula (vi-b) to react with iron in acetic acid at 120° C.

<Step 6-3>

A compound represented by formula (vi-d) can be produced by allowing (vi-c) to react with TFA at room temperature in DCM.

Scheme 7

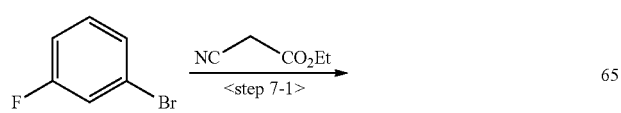

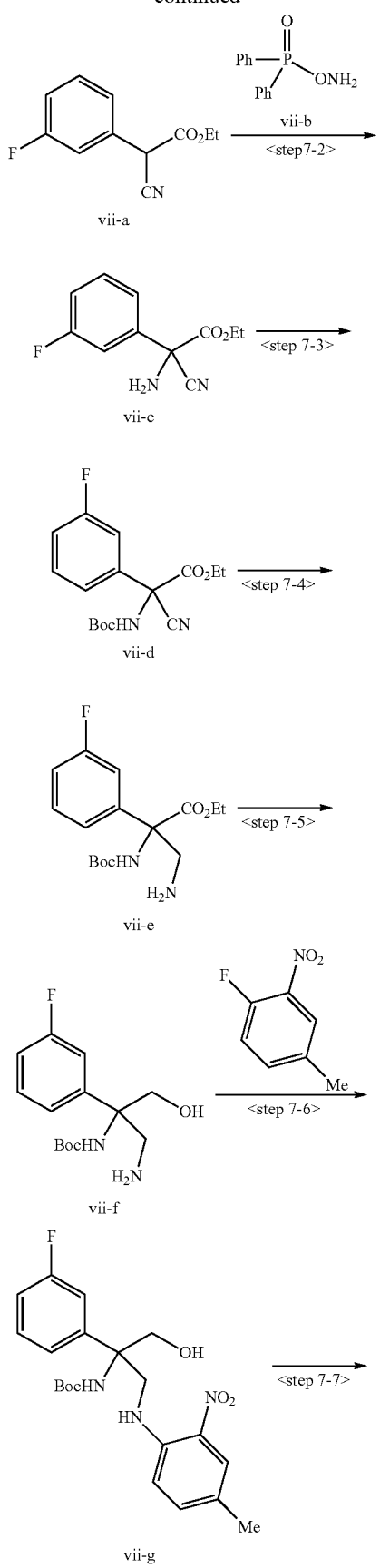

-continued

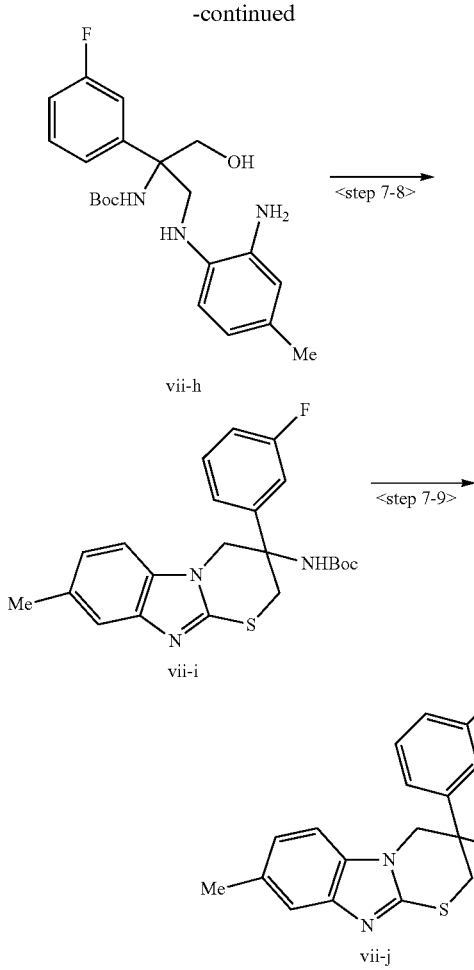

<Step 7-7>
A compound represented by formula (vii-h) can be produced from a compound represented by formula (vii-g) with Raney® Nickel, hydrogen in water at room temperature.

<Step 7-8>
A compound represented by formula (vii-i) can be produced from a compound represented by formula (vii-h) to react with thiocarbonyl diimidazole (3 eq) in THF at room temperature.

<Step 7-9>
A compound represented by formula (vii-j) can be produced from a compound represented by formula (vii-i) to react with TFA in DCM at room temperature.

Scheme 8

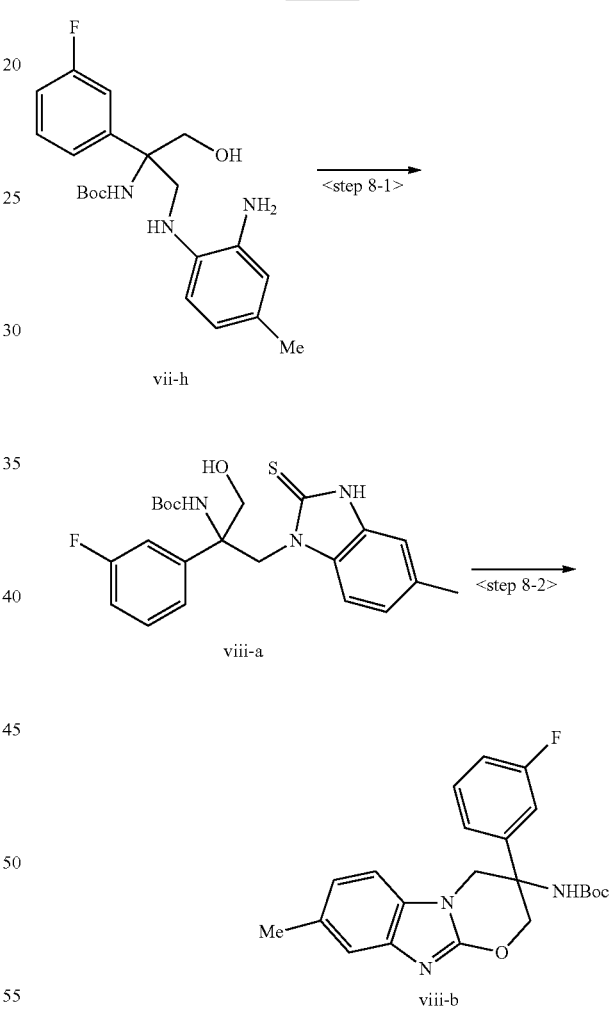

<Step 7-1>
A compound represented by formula (vii-a) can be produced by allowing 1-bromo-3-fluorobenzene to react with ethyl cyanoacetate in the presence of KOtBu, $Pd_2(dba)_3$, 2,8,9-triisobutyl-2,5,8,9-tetraaza-1-phosphabicyclo[3.3.3]undecane in toluene at 110° C.

<Step 7-2>
A compound represented by formula (vii-c) can be produced by allowing (vii-a) to react with (vii-b) in the presence of LDA in THF at −15° C.

<Step 7-3>
A compound represented by formula (vii-d) can be produced from a compound represented by formula (vii-c) to react with $Boc_2O$ at 100° C.

<Step 7-4>
A compound represented by formula (vii-e) can be produced by allowing (vii-d) to react with Cobalt (II) chloride, $NaBH_4$ in MeOH at −20° C.

<Step 7-5>
A compound represented by formula (vii-f) can be produced from a compound represented by formula (vii-e) to react with $LiAlH_4$ in THF at room temperature.

<Step 7-6>
A compound represented by formula (vii-g) can be produced from a compound represented by formula (vii-f) to react with 3-fluoro-4-nitrotoluene in the presence of potassium carbonate in dry DMF at room temperature.

<Step 8-1>
A compound represented by formula (viii-a) can be produced from a compound represented by formula (vii-h) to react with thiocarbonyl diimidazole (1 eq) in THF at room temperature.

<Step 8-2>
A compound represented by formula (viii-b) can be produced from a compound represented by formula (viii-a) to react with Mercuric acetate in DCM at 35° C.

Scheme 9

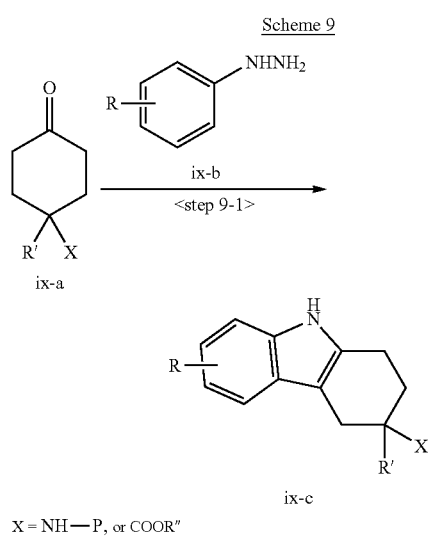

X = NH—P, or COOR"

<Step 9-1>

A compound represented by formula (ix-c) can be produced by reacting a compound represented by formula (ix-a) to react with (ix-b) in the presence of zinc trifluoromethanesulfonate in EtOH or THF at elevated temperature.

Scheme 10

<Step 10-1>

A compound represented by formula (x-c) can be produced from a compound represented by formula (x-a) to react with (x-b) in the presence of acetic acid at elevated temperature.

Scheme 11

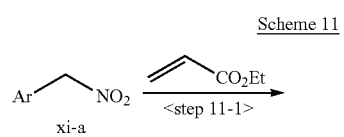

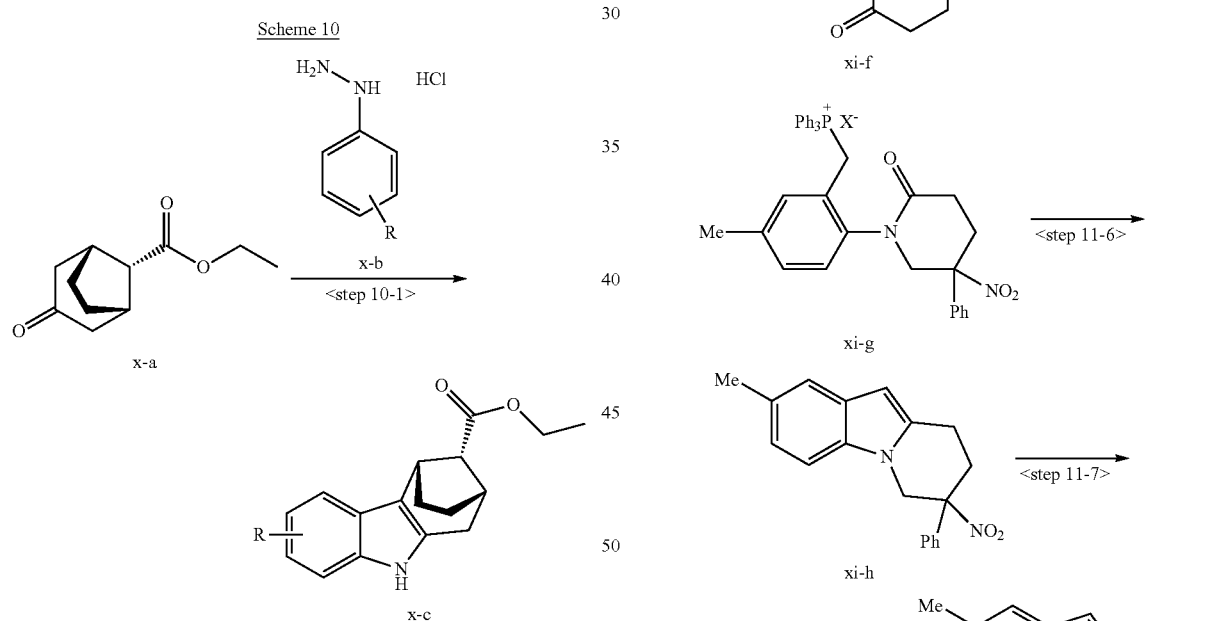

<Step 11-1>

A compound represented by formula (xi-b) can be produced by allowing (xi-a) to react with Ethyl acrylate in the presence of triethylamine in acetonitrile at room temperature.

<Step 11-2>
A compound represented by formula (xi-c) can be produced by allowing (xi-b) to react with ammonium acetate, formaldehyde in water, ethanol at 78° C.
<Step 11-3>
A compound represented by formula (xi-e) can be produced from a compound represented by formula (xi-c) to react with (xi-d) in the presence cesium carbonate, copper(I) iodide, Trans-(1R,2R)—N,N-dimethyl-cyclohexane-1,2-dimine in dioxane at 100° C.
<Step 11-4>
A compound represented by formula (xi-f) can be produced by allowing (xi-e) to react with thionyl chloride for X=Cl, or CBr$_4$, triphenylphosphine for X=Br in DCM at 0° C.
<Step 11-5>
A compound represented by formula (xi-g) can be produced from a compound represented by formula (xi-f) to react with triphenylphosphine in toluene at 100° C.
<Step 11-6>
A compound represented by formula (xi-h) can be produced from a compound represented by formula (xi-g) in the presence of LDA in dry toluene at 70° C.
<Step 11-7>
A compound represented by formula (xi-i) can be produced from a compound represented by formula (xi-h) with zinc dust in EtOH and acetic acid at room temperature.

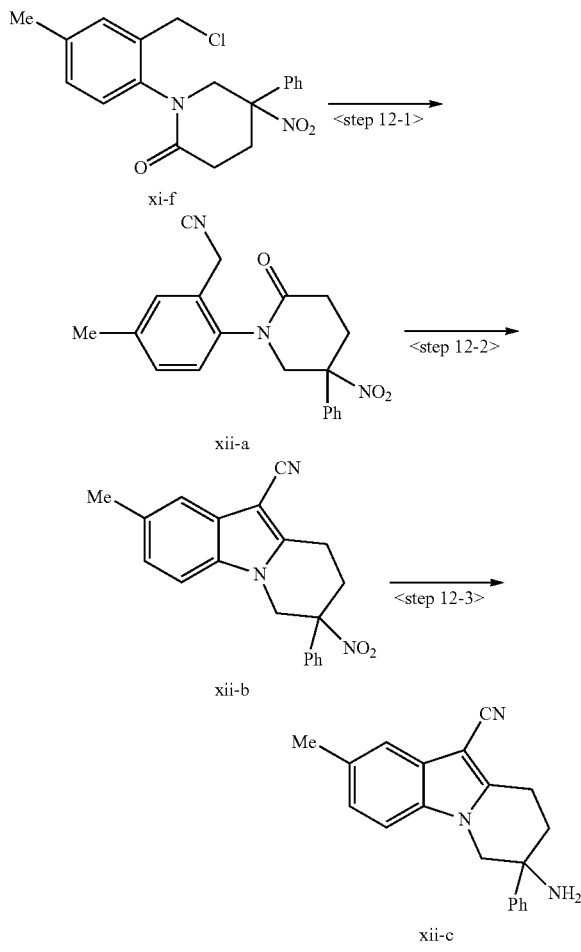

Scheme 12

<Step 12-1>
A compound represented by formula (xii-a) can be produced by allowing (xi-f) to react with KCN in the presence of 18-CROWN-6 in acetonitrile at 50° C.
<Step 12-2>
A compound represented by formula (xii-b) can be produced from a compound represented by formula (xiii-a) in the presence of LDA in dry THF at room temperature.
<Step 12-3>
A compound represented by formula (xii-c) can be produced from a compound represented by formula (xii-b) with zinc dust in EtOH and acetic acid at room temperature.

EXAMPLES

The present invention will now be described in more detail using examples, but the present invention is not limited to the examples.

Acronyms and abbreviations are as follows: aqueous solution (aq); tert-butyloxycarbonyl (Boc); acetic acid (AcOH); benzyloxycarbonyl (CBZ); 1,4,7,10,13,16-hexaoxacyclooctadecane (18-crown-6); Dibenzylideneacetone (dba); 1,2-dichloroethane (DCE); dichloromethane (DCM); N,N-Diisopropylethylamine (DIEA); dimethylacetamide (DMA); 4-dimethylaminopyridine (DMAP); 1,2-dimethoxyethane (DME); dimethylsulfoxide (DMSO); dimethylformamide (DMF); Diphenylphosphoryl azide (DPPA); 1-ethyl-3-(3-dimethylaminopropyl)carbodiimide (EDC); ethanol (EtOH); ethyl acetate (EtOAc); triethylamine (Et$_3$N); 1-[bis(dimethylamino)methylene]-1H-1,2,3-triazolo[4,5-b]pyridinium 3-oxid hexafluorophosphate (HATU); hexanes (Hex); 1-hydroxy-7-azabenzotriazole (HOAt); hydroxybenzotriazole (HOBt); High-performance liquid chromatography (HPLC); N,N-diisopropylethylamine (Hunig's base); lithium diisopropylamide (LDA); Lithium bis(trimethylsilyl)amide (LiHMDS); acetonitrile (MeCN); methanol (MeOH); Methoxymethyl ether (MOM); N-Iodosuccinimide (NIS); N-methylpyrrolidone (NMP); phenyl (Ph); polyphorsphoric acid (PPA); saturated (sat); 2-(trimethylsilyl)ethoxymethyl (SEM); tetrabutylammonium fluoride (TBAF); 2-Di-tert-butylphosphino-2'-methylbiphenyl (tBuMePhos); Triethanolamine (TEA); tetrahydrofuran (THF); trifluoromethanesulfonyl (Tf); trifluoroacetic acid (TFA); Trimethylsilyl iodide (TMSI); 4,5-Bis(diphenylphosphino)-9,9-dimethylxanthene (XantPhos); catalyst (cat.); anhydrous (anh.); aqueous solution (aq); concentrated (conc.); saturated (sat.); room temperature (RT).

The measurement of nuclear magnetic resonance (NMR) spectrum was performed using a JEOL JNM-ECX300 FT-NMR (manufactured by JEOL Ltd.), a JEOL JNM-ECX400 FT-NMR (manufactured by JEOL Ltd.), or a Varian Unity INOVAAS500 or AS600 FT-NMR (manufactured by Varian).

Liquid chromatography-mass spectrometry (LC-MS) was performed using a Waters FractionLynx MS system (manufactured by Waters Corporation) or a Waters Micromass ZQ Mass Spectromer/Agilent 1100 system. A Supelco Ascentis Express C18 Column™ (5 mm×30 cm, 5 micron) was used as an analytical column. 0.05% Ttrifluoroacetic acid MeCN solution or 0.05% aqueous trifluoroacetic acid solution were used as the mobile phase. The analysis was performed under the following gradient conditions: 0.05% ttrifluoroacetic acid MeCN solution: 0.05% aqueous trifluoroacetic acid solution=1:9 (0 min), 99:1 (2 min or 5 min). Liquid chromatography-mass spectrometry (UPLC-MS) was also performed using an ACQUITY UPLC+MS system (manufactured by Waters Corporation). A BEH column (1.0 mm 5 cm, 1.7 micron) (manufactured Waters Corporation) was used as an analytical column. Aqueous trifluoroacetic acid solution (0.05%) and MeCN was used as the mobile phase, and the analysis was performed under a gradient of 10%-95% MeCN in 2 minutes. Purification was performed using a Waters mass-directed preparative system. For compounds purified under acidic conditions, a Sunfire column (19 mm×50 m, 5 micron, manufactured by Waters Corporation) or a Sunfire column (19 mm×100 mm, 5 micron, manufactured by Waters Corporation) was used. The gradient mobile phase varied but is generally described as 10-98% MeCN over 6 minutes with one of the following aqueous mixtures—0.1% trifluoroacetic acid or 0.1% formic acid. For compounds purified under basic conditions a BEH column (19 mm×50 mm, 5 micron, manufactured by Waters corporation) or a BEH column (19 mm×100 mm, 5 micron, manufactured by Waters corporation) was used. The gradient mobile phase varied but is generally described as 10-98% MeCN and 0.1% aqueous $NH_3$—$H_2O$ over 6 minutes.

Intermediate 1

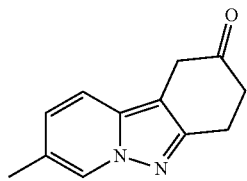

8-Methyl-3,4-dihydropyrido[1,2-b]indazol-2(1H)-one

Step A: 7-(5-Methylpyridin-2-yl)-1,4-dioxaspiro[4.5]decan-8-one

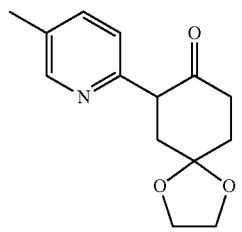 [SMILES: Cc1ccc(C2CC3(CCC2=O)OCCO3)nc1]

A solution of 1,4-dioxaspiro[4.5]decan-8-one (8 g, 51.2 mmol) and 2-chloro-5-methylpyridine (8.38 ml, 77 mmol) in anhydrous THF (200 ml) was degassed by sparging nitrogen through for 15 min. Chloro(2-dicyclohexylphosphino-2',4',6'-triisopropyl-1,1'-biphenyl)[2-(2'-amino-1,1'-biphenyl)]palladium(II) (Xphos-Pd-G2) (4.03 g, 5.12 mmol) was added to the reaction mixture at room temperature, followed by solid sodium tert-butoxide (9.85 g, 102 mmol). The reaction was stirred at rt and monitored by HPLC and LCMS. After overnight, it is quenched with pH 7 phosphate buffer and product is extracted with EtOAc (2×50 mL). The organic layer was separated and dried over sodium sulfate, filtered and concentrated in vacuo. The crude oil was chromatographed on a 330 g $SiO_2$ column with 100% hexanes to 100% EtOAc to afford the title compound. LCMS calc.=248.12; found=248.00 $(M+H)^+$.

Step B: (Z)-7-(5-Methylpyridin-2-yl)-1,4-dioxaspiro[4.5]decan-8-one oxime

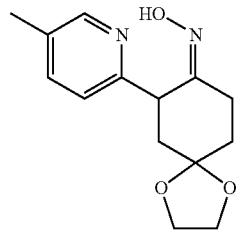 [SMILES: Cc1ccc(C2CC3(CC/C2=N/O)OCCO3)nc1]

To a stirred solution of 7-(5-methylpyridin-2-yl)-1,4-dioxaspiro[4.5]decan-8-one (2.5 g, 10.11 mmol) in MeOH (125 mL) was added hydroxylamine hydrochloride (1.12 g, 16.18 mmol) and potassium acetate (1.98 g, 20.22 mmol). The mixture was heated at 70° C. under a reflux condenser for 0.5 h. The reaction was cooled to room temperature and partitioned between EtOAc and saturated aq. $NaHCO_3$. The aqueous layer was extracted with EtOAc (2×). The combined organic extracts were dried with $Na_2SO_4$ and concentrated in vacuo to give the title compound. LCMS calc.=263.13; found=263.00 $(M+H)^+$.

Step C: 8'-Methyl-3',4'-dihydro-1'H-spiro[1,3]dioxolane-2,2'-pyrido[1,2-b]indazole

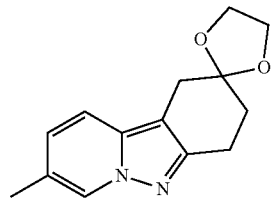 [SMILES: Cc1ccc2c3c(nn2c1)CCC1(C3)OCCO1]

To a stirred solution of 7-(5-methylpyridin-2-yl)-1,4-dioxaspiro[4.5]decan-8-one oxime (6.0 g, 65 wt % purity, 14.87 mmol) in dry $CH_2Cl_2$ (11.75 mL) at 0° C. under $N_2$, was added p-toluenesulfonyl chloride (2.98 g, 15.61 mmol) followed by triethylamine (3.11 mL, 22.30 mmol). The mixture was warmed to room temperature and stirred overnight. The mixture was diluted with water, the aqueous layer was separated and extracted with EtOAc (×2), the combined extracts were dried over $Na_2SO_4$ and concentrated in vacuo to give the crude product. This was purified by flash chromatography (ISCO Combiflash Rf, RediSep Silica, loaded using solid loading cartridge after dissolving in $CH_2Cl_2$, starting with 100% hexanes, gradient to 100% EtOAc over 12 column volume) to afford the title compound. LCMS calc.=245.12; found=245.05 $(M+H)^+$.

Step D: 8-Methyl-3,4-dihydropyrido[1,2-b]indazol-2 (1H)-one

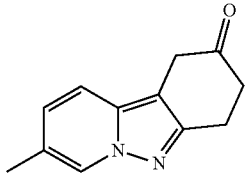

To a solution of 8'-methyl-3',4'-dihydro-1'H-spiro[[1,3]dioxolane-2,2'-pyrido[1,2-b]indazole](700 mg, 2.87 mmol) in THF (7 mL) was added HCl (7.16 mL, 14.33 mmol). The reaction mixture was stirred at room temperature for 19 h. It was diluted with EtOAc (20 mL) and neutralized with saturated aqueous sodium bicarbonate. It was transferred to a separatory funnel and extracted with EtOAc (2×20 mL). The combined organic layers were washed with brine, dried over sodium sulfate, filtered and concentrated in vacuo. The residue was purified by silica gel flash chromatography (eluent: Hexane:EtOAc=100:0-0:100) to give 8-methyl-3,4-dihydropyrido[1,2-b]indazol-2(1H)-one. LCMS calc.=201.09; found=201.01 (M+H)$^+$. $^1$H NMR (500 MHz, CDCl$_3$): δ 8.23 (s, 1H); 7.25 (d, 1H); 6.90 (d, 1H); 3.53 (s, 2H); 3.25 (t, 2H); 2.82 (t, 2H); 2.35 (s, 3H).

Intermediate 2

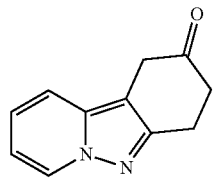 [SMILES: O=C1CCc2nn3ccccc3c2C1]

3,4-Dihydropyrido[1,2-b]indazol-2(1H)-one

The general procedure described in the synthesis of Intermediate 1 was followed. LCMS calc.=187.08; found=187.07 (M+H)$^+$.

Intermediate 3

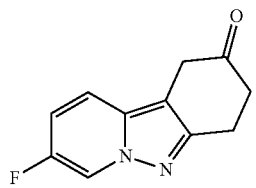 [SMILES: O=C1CCc2nn3cc(F)ccc3c2C1]

8-Fluoro-3,4-dihydropyrido[1,2-b]indazol-2(1H)-one

The general procedure described in the synthesis of Intermediate 1 was followed. LCMS calc.=205.07; found=205.11 (M+H)$^+$.

Intermediate 4

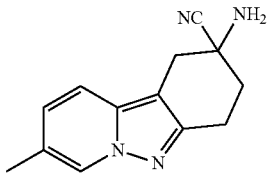 [SMILES: Cc1ccc2c3c(nn2c1)CCC(N)(C#N)C3]

2-Amino-8-methyl-1,2,3,4-tetrahydropyrido[1,2-b]indazole-2-carbonitrile

8-Methyl-3,4-dihydropyrido[1,2-b]indazol-2(1H)-one (250 mg, 1.25 mmol) was added to a stirred mixture of NaCN (76 mg, 1.551 mmol), ammonium chloride (99 mg, 1.848 mmol) and magnesium sulfate (150 mg; 1.25 mmol) in 25% ammonia (10 ml) at room temperature. The mixture was stirred at room temperature overnight. The mixture was cooled in an ice-water bath, water was added and the mixture was extracted with dichloromethane. The combined organic fractions were washed with water, dried over sodium sulfate, filtered and the solvent was evaporated under reduced pressure. It is used without further purification. LCMS calc.=227.13; found=227.20 (M+H)$^+$.

Intermediate 5

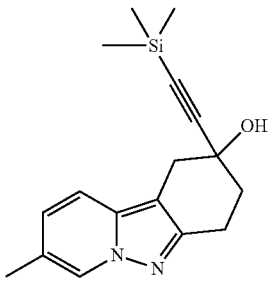 [SMILES: Cc1ccc2c3c(nn2c1)CCC(O)(C#C[Si](C)(C)C)C3]

8-Methyl-2-((trimethylsilyl)ethynyl)-1,2,3,4-tetrahydropyrido[1,2-b]indazol-2-ol In an oven-dried flask was charged with a magnetic stirring bar, trimethylsilylacetylene (1.226 ml, 8.74 mmol) and 5.5 ml of anhydrous THF were combined. The solution was cooled to −78° C. under nitrogen. n-Butyllithium (2.5 M in hexane, 3.5 ml, 8.74 mmol) was added dropwise and the reaction mixture was stirred for 30 minutes. 8-Methyl-3,4-dihydropyrido[1,2-b]indazol-2(1H)-one (1.00 g, 4.99 mmol) was added in one portion. The reaction mixture was stirred at −78° C. for 1 hour and then warmed to room temperature and stirred for 1 hour. The reaction was quenched with saturated aqueous potassium phosphate mono-basic and extracted with ethyl acetate. The organic layer was dried over sodium sulfate, filtered and concentrated under reduced pressure. The crude product was subjected to silica gel chromatography 40 g Redisep column (0-70% EtOAc/Hexanes. LCMS calc.=299.16; found=299.07 (M+H)$^+$.

Intermediate 6

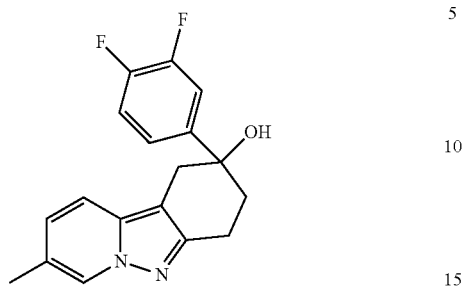

2-(3,4-Difluorophenyl)-8-methyl-1,2,3,4-tetrahydro-pyrido[1,2-b]indazol-2-ol

To a solution of 8-methyl-3,4-dihydropyrido[1,2-b]indazol-2(1H)-one (0.66 g, 3.30 mmol) in anhydrous THF (4 ml) at −78° C. was added a solution of (3,4-difluorophenyl) magnesium bromide in THF (0.5 M, 26.4 ml, 13.18 mmol) slowly. The resulting mixture was stirred at −78° C. for 1 h. It was quenched with saturated aqueous ammonium chloride solution and extracted with ethyl acetate. The organic layer was separated and dried over magnesium sulfate, filtered and concentrated. The residue was purified by ISCO (80 g silica gel column, 60% EtOAc/Hexane) to give the title compound. LCMS calc.=315.13; found=315.12 (M+H)$^+$.

Intermediate 7

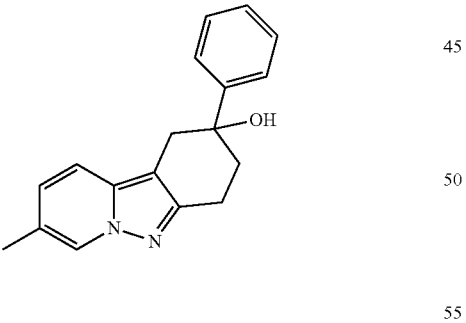

8-Methyl-2-phenyl-1,2,3,4-tetrahydropyrido[1,2-b]indazol-2-ol

The general procedure described in the synthesis of Intermediate 6 was followed employing 8-methyl-3,4-dihydropyrido[1,2-b]indazol-2(1H)-one (700 mg, 3.50 mmol) and 1 M solution of phenylmagnesium bromide in THF (14.0 ml, 14.0 mmol) to afford the title compound. LCMS calc.=279.14; found=279.20 (M+H)$^+$.

Intermediate 8

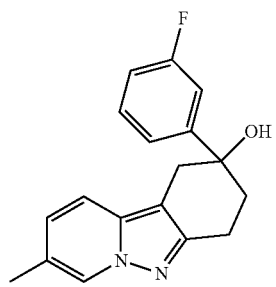 [SMILES: Cc1ccc2c3c(nn2c1)CCC(O)(c1cccc(F)c1)C3]

2-(3-Fluorophenyl)-8-methyl-1,2,3,4-tetrahydro-pyrido[1,2-b]indazol-2-ol

The general procedure described in the synthesis of Intermediate 6 was followed employing 8-methyl-3,4-dihydropyrido[1,2-b]indazol-2(1H)-one (170 mg, 0.854 mmol) and 1 M solution of (3-fluorophenyl)magnesium bromide in THF (1.50 ml, 1.50 mmol) to afford the title compound.

Intermediate 9

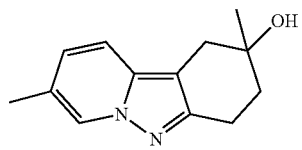 [SMILES: Cc1ccc2c3c(nn2c1)CCC(C)(O)C3]

2,8-Dimethyl-1,2,3,4-tetrahydropyrido[1,2-b]indazol-2-ol

The general procedure described in the synthesis of Intermediate 6 was followed employing 8-methyl-3,4-dihydropyrido[1,2-b]indazol-2(1H)-one (250 mg, 1.25 mmol) and 3 M solution of methylmagnesium bromide in diethyl ether (1.7 ml, 5.12 mmol) to afford the title compound. LCMS calc.=217.14; found=217.12 (M+H)$^+$.

Intermediate 10

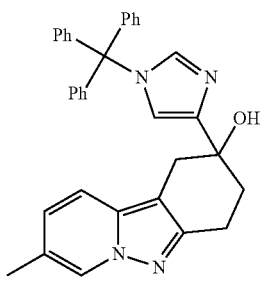 [SMILES: Cc1ccc2c3c(nn2c1)CCC(O)(c1cn(C(c2ccccc2)(c2ccccc2)c2ccccc2)cn1)C3]

8-Methyl-2-(1-trityl-1H-imidazol-4-yl)-1,2,3,4-tetra-hydropyrido[1,2-b]indazol-2-ol To a solution of 4-iodo-1-tritylimidazole (100 mg, 11.46 mmol) in CH$_2$Cl$_2$ (2 ml), was added ethylmagnesium bromide (0.23 ml, 0.23 mmol) dropwise at room temperature. After stirring for 30 min, a solution of 8-methyl-3,4-dihydropyrido[1,2-b]indazol-2(1H)-one (55.1 mg; 0.275 mmol) in CH$_2$Cl$_2$ (1 ml) was added dropwise. The reaction mixture was stirred at room temperature overnight. It was then quenched with saturated aqueous ammonium chloride and extracted with dichloromethane twice. The combined organic layers were washed with brine, dried over sodium sulfate, filtered and concentrated under reduced pressure. The residue was purified by preparative TLC (1000 μM, 10% MeOH in DCM) to afford the title compound. LCMS calc.=511.25; found=511.11 (M+H)$^+$.

Intermediate 11

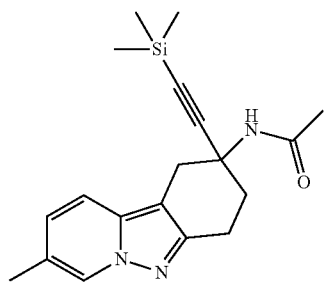 [SMILES: CC(=O)NC1(C#C[Si](C)(C)C)CCc2nn3cc(C)ccc3c2C1]

N-(8-Methyl-2-((trimethylsilyl)ethynyl)-1,2,3,4-tetrahydropyrido[1,2-b]indazol-2-yl)acetamide 8-Methyl-2-((trimethylsilyl)ethynyl)-1,2,3,4-tetrahydropyrido[1,2-b]indazol-2-ol (550 mg, 1.843 mmol) in acetonitrile (65 mL) was added concentrated sulfuric acid (3 mL) slowly at 0° C. After the addition, the reaction mixture was allowed to warm to room temperature and stirred for 3 days. It was diluted with 25 mL of EtOAc and the solution was cooled in an ice-water bath. A aqueous solution of NaOH (5 M) was added slowly to adjust pH of the solution to about 10. The organic layer was separated and the aqueous layer extracted twice with ethyl acetate (2×25 mL). The combined organic layers were washed with brine, dried over sodium sulfate, filtered and concentrated in vacuo. The residue was chromatographed on 40 g Redisep cartridge gradually eluted with 0 to 100% ethyl acetate in hexane to the title compound. LCMS calc.=340.18; found=339.99 (M+H)$^+$.

Intermediate 12

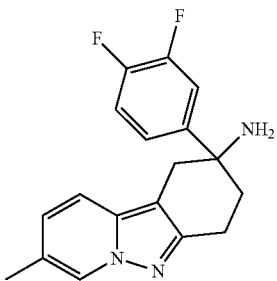 [SMILES: Cc1ccc2c3c(nn2c1)CCC(N)(c1ccc(F)c(F)c1)C3]

2-(3,4-Difluorophenyl)-8-methyl-1,2,3,4-tetrahydropyrido[1,2-b]indazol-2-amine

Step A:
The general procedure described in the synthesis of Intermediate 9 was followed employing 2-(3,4-difluorophenyl)-8-methyl-1,2,3,4-tetrahydropyrido[1,2-b]indazol-2-ol (490 mg, 1.65 mmol) to afford N-(2-(3,4-difluorophenyl)-8-methyl-1,2,3,4-tetrahydropyrido[1,2-b]indazol-2-yl)acetamide. LCMS calc.=356.16; found=356.20 (M+H)$^+$.

Step B:
A mixture of N-(2-(3,4-difluorophenyl)-8-methyl-1,2,3,4-tetrahydropyrido[1,2-b]indazol-2-yl)acetamide (190 mg, 0.535 mmol) and 2 M aqueous hydrogen chloride (5 ml, 10.00 mmol) in a sealed tube was heated at 95° C. for 2 days. It was concentrated under reduced pressure, the residue was purified by HPLC to afford the title compound. LCMS calc.=314.15 found=314.21 (M+H)$^+$.

Intermediate 13

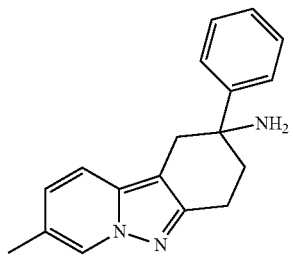 [SMILES: Cc1ccc2c3c(nn2c1)CCC(N)(c1ccccc1)C3]

8-Methyl-2-phenyl-1,2,3,4-tetrahydropyrido[1,2-b]indazol-2-amine

The general procedure described in the synthesis of Intermediate 12 was followed employing 8-methyl-2-phenyl-1,2,3,4-tetrahydropyrido[1,2-b]indazol-2-ol (610 mg, 2.19 mmol) to afford the title compound in two steps. LCMS calc.=278.16; found=278.14 (M+H)$^+$.

Intermediate 14

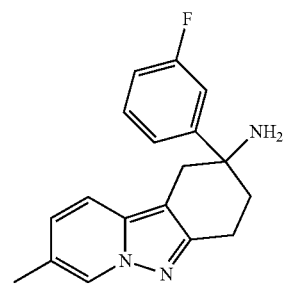 [SMILES: Cc1ccc2c3c(nn2c1)CCC(N)(c1cccc(F)c1)C3]

2-(3-Fluorophenyl)-8-methyl-1,2,3,4-tetrahydropyrido[1,2-b]indazol-2-amine

The general procedure described in the synthesis of Intermediate 12 was followed employing 2-(3-fluorophenyl)-8-methyl-1,2,3,4-tetrahydropyrido[1,2-b]indazol-2-ol (130 mg, 0.351 mmol) to afford the title compound in two steps.

Intermediate 15

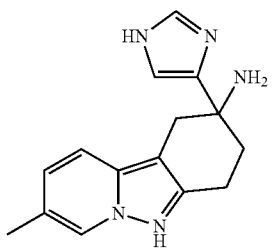 [SMILES: Cc1ccc2c3c(nn2c1)CCC(N)(c1c[nH]cn1)C3]

2-(1H-Imidazol-4-yl)-8-methyl-1,2,3,4-tetrahydropyrido[1,2-b]indazol-2-ol

The general procedure described in the synthesis of Intermediate 12 was followed employing 8-Methyl-2-(1-trityl-1H-imidazol-4-yl)-1,2,3,4-tetrahydropyrido[1,2-b]indazol-2-ol (50 mg, 0.098 mmol) to afford the title compound in two steps.

Intermediate 16

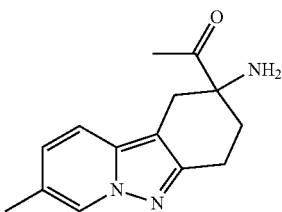 [SMILES: CC(=O)C1(N)CCc2nn3cc(C)ccc3c2C1]

1-(2-Amino-8-methyl-1,2,3,4-tetrahydropyrido[1,2-b]indazol-2-yl)ethanone

A mixture of N-(8-Methyl-2-((trimethylsilyl)ethynyl)-1,2,3,4-tetrahydropyrido[1,2-b]indazol-2-yl)acetamide (50 mg, 0.147 mmol) and 2 M HCl (2 mL) was heated in a sealed microwave vial at 95° C. overnight. It was concentrated under reduce pressure to afford title compound. LCMS calc.=244.14 found=244.08 (M+H)$^+$.

Intermediate 17

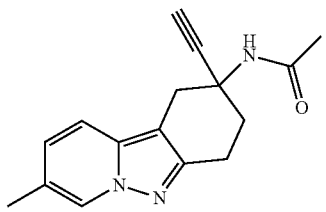 [SMILES: C#CC1(NC(C)=O)CCc2nn3cc(C)ccc3c2C1]

N-(2-Ethynyl-8-methyl-1,2,3,4-tetrahydropyrido[1,2-b]indazol-2-yl)acetamide

To the solution of N-(8-methyl-2-((trimethylsilyl)ethynyl)-1,2,3,4-tetrahydropyrido[1,2-b]indazol-2-yl)acetamide (340 mg; 1.001 mmol) in MeOH (9 ml) was added potassium carbonate (138 mg; 1.001 mmol). The reaction was stirred at room temperature for 4 h. It was diluted with dichloromethane and washed with water. The aqueous layer was extracted three times. The combined organic layers were washed with water, brine, dried over sodium sulfate and concentrated. The residue was purified by ISCO (Silica gel, 24 g column, 0-100% ethyl acetate in hexane) to afford the title compound. LCMS calc.=268.15 found=268.06 (M+H)$^+$.

Intermediate 18

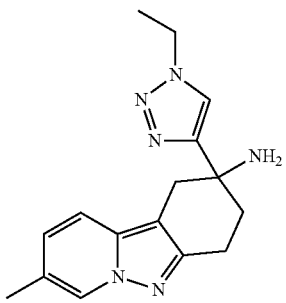 [SMILES: CCn1cc(C2(N)CCc3nn4cc(C)ccc4c3C2)nn1]

2-(1-Ethyl-1H-1,2,3-triazol-4-yl)-8-methyl-1,2,3,4-tetrahydropyrido[1,2-b]indazol-2-amine Step A: N-(2-(1-Ethyl-1H-1,2,3-triazol-4-yl)-8-methyl-1,2,3,4-tetrahydropyrido[1,2-b]indazol-2-yl)acetamide To a 1-dram vial wrapped in aluminum foil was added iodoethane (0.06 ml, 0.749 mmol), DMF (3.0 ml) and sodium azide (36.5 mg, 0.561 mmol). The solution was stirred at room temperature overnight. It was heated at 40° C. for 4-5 h. It was cooled to room temperature and added N-(2-ethynyl-8-methyl-1,2,3,4-tetrahydropyrido[1,2-b]indazol-2-yl)acetamide (25 mg, 0.094 mmol), copper(I) bromide (13.4 mg, 0.094 mmol), water (0.8 ml) and sodium ascorbate (46.3 mg, 0.234 mmol) in sequence. The solution was heated at 40° C. for 5 days. It was diluted with 10 ml ethyl acetate and wash with water. The aqueous layer was extracted three times. The combined organic layers were treated with 2-3 ml of ammonia. The mixture was stirred for 30 min. The organic layer was separated and washed with water, brine, dried over sodium sulfate, filtered and concentrated. The crude product was purified by TLC (1000 rpm, 10% MeOH in DCM) to afford the title compound. LCMS calc.=339.20 found=339.08 (M+H)$^+$.

Step B: 2-(1-Ethyl-1H-1,2,3-triazol-4-yl)-8-methyl-1,2,3,4-tetrahydropyrido[1,2-b]indazol-2-amine A mixture of N-(2-(1-ethyl-1H-1,2,3-triazol-4-yl)-8-methyl-1,2,3,4-tetrahydropyrido[1,2-b]indazol-2-yl)acetamide (12 mg, 0.036 mmol) and 2 M HCl (2 mL) was heated at 95° C. overnight. It was concentrated under reduced pressure. To the residue was added a few drops of methanol and concentrated under reduced pressure to afford the title compound. LCMS calc.=297.18; found=297.08 (M+H)⁺.

Intermediate 19

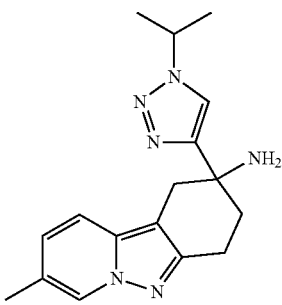 [SMILES: Cc1ccc2c3c(nn2c1)CCC(N)(c1cn(C(C)C)nn1)C3]

2-(1-Isopropyl-1H-1,2,3-triazol-4-yl)-8-methyl-1,2,3,4-tetrahydropyrido[1,2-b]indazol-2-amine Step A: N-(2-(1-Isopropyl-1H-1,2,3-triazol-4-yl)-8-methyl-1,2,3,4-tetrahydropyrido[1,2-b]indazol-2-yl)acetamide A mixture of N-(2-ethynyl-8-methyl-1,2,3,4-tetrahydropyrido[1,2-b]indazol-2-yl)acetamide (100 mg; 0.374 mmol), Cu (II) sulfate (59.7 mg; 0.374 mmol) and sodium L-ascorbate (89 mg; 0.449 mmol) was added 5 mL of a nitrogen sparged solvent of t-butanol and water (3:1 v/v). 2-Azidopropane (0.35 ml, 4.11 mmol) was added and the reaction mixture was capped and stirred at room temperature overnight. It was diluted with 10 ml of ethyl acetate and washed with water. The aqueous layer was extract three times and the combined organic layers were treated with 2 ml of ammonia. The reaction mixture was stirred for 30 min and then layers were separated. The organic layer was washed with water, brine and dried over sodium sulfate and concentrated. The crude product was purified by TLC (1000 µm, 10% MeOH in DCM) to afford the title compound. LCMS calc.=353.21; found=352.96 (M+H)⁺.

Step B: 2-(1-Isopropyl-1H-1,2,3-triazol-4-yl)-8-methyl-1,2,3,4-tetrahydropyrido[1,2-b]indazol-2-amine The general procedure described in Step B of the synthesis of Intermediate 10 was followed employing N-(2-(1-isopropyl-1H-1,2,3-triazol-4-yl)-8-methyl-1,2,3,4-tetrahydropyrido[1,2-b]indazol-2-yl)acetamide (70 mg, 0.199 mmol) to afford the title compound. LCMS calc.=311.20; found=311.01 (M+H)⁺.

Intermediate 20

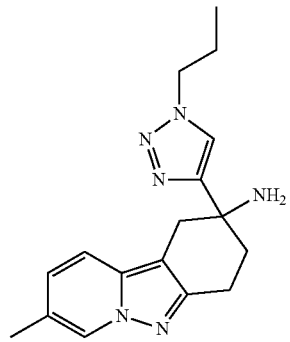 [SMILES: CCCn1cc(C2(N)CCc3nn4cc(C)ccc4c3C2)nn1]

8-Methyl-2-(1-propyl-1H-1,2,3-triazol-4-yl)-1,2,3,4-tetrahydropyrido[1,2-b]indazol-2-amine The general procedure in the synthesis of Intermediate 19 was followed employing N-(2-ethynyl-8-methyl-1,2,3,4-tetrahydropyrido[1,2-b]indazol-2-yl)acetamide (50 mg, 0.187 mmol) and 1-iodopropane (0.164 mL, 1.683 mmol) to afford the title compound in two steps. LCMS calc.=311.20; found=311.24 (M+H)⁺.

Intermediate 21

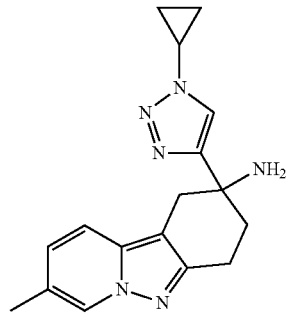 [SMILES: Cc1ccc2c3c(nn2c1)CCC(N)(c1cn(C2CC2)nn1)C3]

2-(1-Cyclopropyl-1H-1,2,3-triazol-4-yl)-8-methyl-1,2,3,4-tetrahydropyrido[1,2-b]indazol-2-amine Step A: N-(2-(1-cyclopropyl-1H-1,2,3-triazol-4-yl)-8-methyl-1,2,3,4-tetrahydropyrido[1,2-b]indazol-2-yl)acetamide To a microwave vial with a magnetic stirring bar was added water (0.75 ml), MeOH (1.5 ml), potassium carbonate (233 mg, 1.683 mmol), 1H-imidazole-1-sulfonyl azide hydrochloride (250 mg, 1.191 mmol), copper(II) sulfate (17.91 mg, 0.112 mmol) and cyclopropanamine (70 µl, 0.993 mmol) in sequence. The solution was stirred at room temperature for 2 h under nitrogen. To the solution was added N-(2-ethynyl-8-methyl-1,2,3,4-tetrahydropyrido[1,2-b]indazol-2-yl)acetamide (50 mg; 0.187 mmol) followed by sodium ascorbate (59.3 mg, 0.299 mmol). The reaction mixture was heated at 40° C. overnight. It was cooled to room temperature, added water (20 mL), extracted three times with ethyl acetate (50 mL) and CHCl₃:IPA (3:1 v/v).

To the combined organic phase was added ammonina (20 mL) and stirred at rt for 2 h. It was washed with brine (50 mL×2), dried over sodium sulfate, filtered and concentrated. The residue was purified by TLC (1000 μm, 10% MeOH in DCM) to afford the title compound. LCMS calc.=351.20; found=351.19 (M+H)+.

Step B: 2-(1-Cyclopropyl-1H-1,2,3-triazol-4-yl)-8-methyl-1,2,3,4-tetrahydropyrido[1,2-b]indazol-2-amine The general procedure described in Step B of the synthesis of Intermediate 10 was followed employing N-(2-(1-cyclopropyl-1H-1,2,3-triazol-4-yl)-8-methyl-1,2,3,4-tetrahydropyrido[1,2-b]indazol-2-yl)acetamide (69 mg) to afford the title compound. LCMS calc.=309.18; found=309.18 (M+H)+.

Intermediate 22

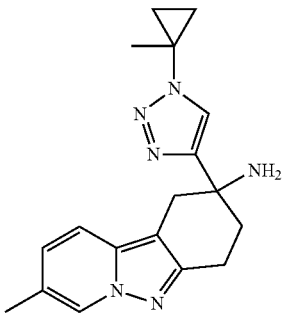 [SMILES: Cc1ccc2c3c(nn2c1)CCC(N)(c1cn(C2(C)CC2)nn1)C3]

8-Methyl-2-(1-(1-methylcyclopropyl)-1H-1,2,3-triazol-4-yl)-1,2,3,4-tetrahydropyrido[1,2-b]indazol-2-amine The general procedure in the synthesis of Intermediate 19 was followed employing N-(2-ethynyl-8-methyl-1,2,3,4-tetrahydropyrido[1,2-b]indazol-2-yl)acetamide (50 mg, 0.187 mmol) and 1-methylcyclopropanamine hydrochloride (101 mg, 0.935 mmol) to afford the title compound in two steps. LCMS calc.=323.20; found=323.21 (M+H)+.

Intermediate 23

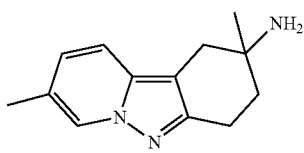

2,8-Dimethyl-1,2,3,4-tetrahydropyrido[1,2-b]indazol-2-amine

The general procedure described in the synthesis of Intermediate 10 was followed employing 2,8-dimethyl-1,2,3,4-tetrahydropyrido[1,2-b]indazol-2-ol (120 mg, 0.555 mmol) to afford the title compound in two steps. LCMS calc.=216.15; found=216.16 (M+H)+.

Intermediate 24

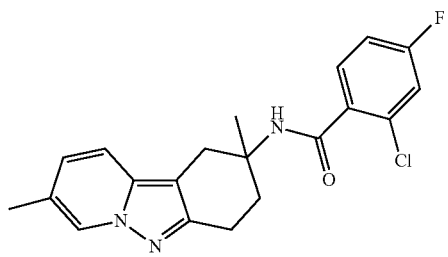 [SMILES: Cc1ccc2c3c(nn2c1)CCC(C)(NC(=O)c1ccc(F)cc1Cl)C3]

2-Chloro-N-(2,8-dimethyl-1,2,3,4-tetrahydropyrido[1,2-b]indazol-2-yl)-4-fluorobenzamide To a solution of 2,8-dimethyl-1,2,3,4-tetrahydropyrido[1,2-b]indazol-2-amine (240 mg, 0.557 mmol) and DIEA (0.3 ml, 1.718 mmol) in DCM (3 ml) cooled at 0° C. was added 2-chloro-4-fluorobenzoyl chloride (215 mg, 1.115 mmol) dropwise. It was stirred for 2 min and warmed to room temperature for 30 min. It was directly purified by ISCO (12 g, 0-100% ethyl acetate in hexane) to give the title compound. LCMS calc.=372.13; found=372.14 (M+H)+.

Intermediate 25

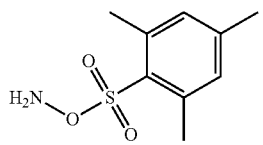

O-(Mesitylsulfonyl)hydroxylamine

Step A: (E)-Ethyl N-(mesitylsulfonyl)oxyacetimidate

A solution of ethyl N-hydroxyacetimidate (10.37 g, 101 mmol) and triethylamine (25.5 ml, 183 mmol) in DMF (40 ml) was cooled to 0° C. To the mixture was added solid 2-mesitylenesulfonyl chloride (20 g, 91 mmol) in portions over 2 min. It was stirred at 0° C. for 45 min and the reaction mixture was poured into ice water (300 g). The solid precipitation was filtered and washed with water (3×20 mL). It was dried under vacuum to give (E)-ethyl N(mesitylsulfonyl)oxyacetimidate.

Step B: O-(Mesitylsulfonyl)hydroxylamine

A solution of (E)-ethyl N-(mesitylsulfonyl)oxyacetimidate (10 g, 35.0 mmol) in dioxane (20 ml) was cooled to 0° C. To the solution was added dropwise perchloric acid (3.52 g, 35.0 mmol) and the reaction mixture was stirred for 45 min. It was poured into ice-water (100 mL) and the solid precipitated was filtered and washed with water, dried for 15 min in vacuum to give O-(mesitylsulfonyl)hydroxylamine. It was used immediately or stored in a plastic bottle at −20° C. (Caution! If too dry, it may be explosive at higher temperature).

Intermediates 26, 27 & 28

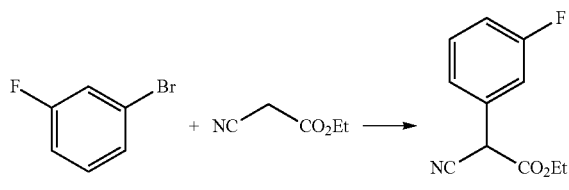

Intermediate 26

Preparation of Intermediate 26 is prepared via a palladium catalyzed cross-coupling reaction between ethyl 2-cyanoacetate and 1-bromo-3-fluorobenzene.

Intermediate 26—Ethyl 2-cyano-2-(3-fluorophenyl)acetate

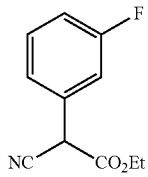 [SMILES: CCOC(=O)C(C#N)c1cccc(F)c1]

A 10 mL round bottom flask under and atmosphere of nitrogen was charged with palladium(II) acetate (0.12 g, 0.53 mmol) and 1,1'-bis(diphenylphosphino)ferrocene (0.59 g, 1.0 mmol). The resulting mixture was suspended in anhydrous 1,4-dioxane (5.0 ml) and nitrogen gas is then bubbled through the reaction mixture for 10 minutes. To a stirred suspension of potassium tert-butoxide (5.95 g, 53.0 mmol) in anhydrous 1,4-dioxane (10 ml), cooled to 0° C. under an atmosphere of nitrogen, in a 100 mL round bottom flask was added ethyl 2-cyanoacetate (2.80 ml, 26.5 mmol) slowly over 5 minutes so as to keep the internal temperature below 25° C. After complete addition, the resulting suspension was stirred for an additional 10 minutes. Neat 1-bromo-3-fluorobenzene (3.25 ml, 29.2 mmol) was added and then nitrogen gas was bubbled through the reaction mixture for 15 minutes. The catalyst solution, the preparation of which is described above, is then added vial syringe and the resulting solution was heated to 80° C. for 4 h. The reaction was allowed to cool to ambient temperature and then quenched with acetic acid (3.0 ml, 53 mmol) in water (10 mL). All volatiles were evaporated in vacuo and the remaining aqueous phase was extracted with ethyl acetate (3×25 mL). The combined organic layers were washed with brine, dried over magnesium sulfate, filtered and evaporated to dryness in vacuo. Purification by Silica Gel Chromatography (ISCO CombiFlash Rf Purification System®, 40 g column, gradient elution, 0-30% ethyl acetate in hexanes) afforded Intermediate 26. $^1$H NMR (500 MHz, CDCl$_3$) δ 7.42-7.38 (m, 1H), 7.27-7.25 (m, 1H), 7.21-7.19 (m, 1H), 7.11 (td, J=8.3, 2.4 Hz, 1H), 4.72 (s, 1H), 4.29-4.24 (m, 2H), 1.30-1.27 (m, 3H).

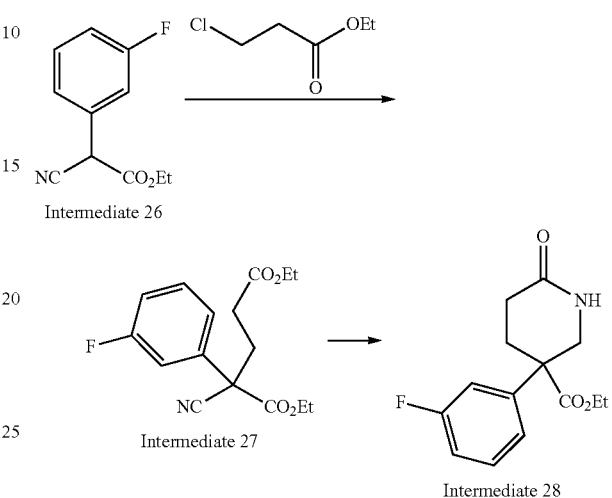

Intermediate 28 is prepared via initial alkylation of Intermediate 26 with ethyl 3-chloropropanoate under basic condition to afford Intermediate 27. Raney® Nickel catalyzed hydrogenation of the nitrile of Intermediate B2 followed by in situ cyclization affords Intermediate 28.

Step A. Intermediate 27—Diethyl 2-cyano-2-(3-fluorophenyl)pentanedioate

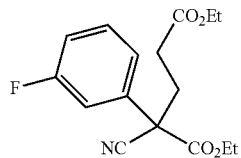 [SMILES: CCOC(=O)CCC(C#N)(C(=O)OCC)c1cccc(F)c1]

To a 21% sodium ethoxide in ethanol solution (6.7 mL, 18 mmol) cooled to 0° C. under an atmosphere of nitrogen was added a solution of Intermediate 26 ethyl 2-cyano-2-(3-fluorophenyl)acetate (3.38 g, 16.3 mmol) in ethanol (10 ml). After stirring for 10 minutes, neat ethyl 3-chloropropanoate (2.45 ml, 19.5 mmol) was added and the resulting mixture was slowly warmed to ambient temperature overnight. All volatiles were then removed in vacuo and the residue was diluted water (10 mL) and the resulting aqueous phase extracted with ethyl acetate (3×10 mL). The combined organic layers were washed with brine, dried over magnesium sulfate, filtered and evaporated to dryness in vacuo. Purification by Silica Gel Chromatography (ISCO CombiFlash Rf Purification System®, 40 g column, gradient elution, 0-40% ethyl acetate in hexanes) afforded Intermediate 27. $^1$H NMR (500 MHz, CDCl$_3$) δ 7.41 (td, J=8.0, 5.8 Hz, 1H), 7.36-7.34 (m, 1H), 7.29-7.25 (m, 1H), 7.10 (td, J=8.3, 2.4 Hz, 1H), 4.31-4.20 (m, 2H), 4.12 (q, J=7.2 Hz, 2H), 2.71-2.65 (m, 1H), 2.54-2.46 (m, 2H), 2.43-2.35 (m, 1H), 1.28-1.23 (m, 6H).

Step B. Intermediate 28—Ethyl 3-(3-fluorophenyl)-6-oxopiperidine-3-carboxylate

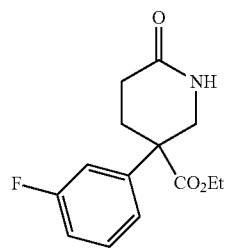 [SMILES: CCOC(=O)C1(c2cccc(F)c2)CCC(=O)NC1]

A 100 mL Parr® Bottle was charged with a 50% suspension of Raney® nickel in water (3.4 g, 58 mmol) and placed under an atmosphere of nitrogen. A solution of Intermediate 27 diethyl 2-cyano-2-(3-fluorophenyl)pentanedioate (3.4 g, 11.06 mmol) in ethanol (5 ml) and acetic acid (5 mL) was added and the mixture was placed under an atmosphere of hydrogen gas at 50 psi for 24 h. The reaction mixture was then filtered through a pad of Celite® and the pad was subsequently washed with ethanol (50 mL). The combined organic filtrates were combined and evaporated to dryness in vacuo. Purification by Silica Gel Chromatography (ISCO CombiFlash Rf Purification System®, 40 g column, gradient elution, 0-10% methanol in dichloromethane) afforded Intermediate 28. $^1$H NMR (500 MHz, CDCl$_3$) δ7.36-7.31 (m, 1H), 7.14 (d, J=7.8 Hz, 1H), 7.08 (dt, J=10.4, 2.2 Hz, 1H), 7.01 (td, J=8.2, 2.4 Hz, 1H), 6.74 (br s, 1H), 4.19-4.13 (m, 2H), 4.02 (ddd, J=12.5, 3.2, 2.0 Hz, 1H), 3.60-3.58 (m, 1H), 2.65-2.60 (m, 1H), 2.53-2.46 (m, 1H), 2.41-2.35 (m, 1H), 2.31-2.26 (m, 1H), 1.12 (t, J=7.1 Hz, 3H).

Intermediate 29

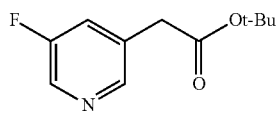 [SMILES: CC(C)(C)OC(=O)Cc1cncc(F)c1]

tert-butyl 2-(5-fluoropyridin-3-yl)acetate

A mixture of 3-bromo-5-fluoropyridine (1.00 g, 5.68 mmol), 2-tert-butoxy-2-oxoethylzinc chloride (0.5 M in Et$_2$O) (13.64 ml, 6.82 mmol), bis(dibenzylideneacetone) palladium (0.163 g, 0.284 mmol) and 1,2,3,4,5-pentaphenyl-1'-(di-tert-butylphosphino)ferrocene (0.404 g, 0.568 mmol) in dry THF (17.06 ml) in a sealed tube was degassed by bubbling N$_2$ for 1 min, then heated at 100° C. for 1 h. After this time LCMS showed presence of desired product but only around 50% conversion. The reaction was heated at 100° C. for a further 15 h. After this time LCMS showed no improvement so reaction was worked up. The reaction mixture was directly filtered through a plug of silica and eluted with EtOAc. The eluant was concentrated in vacuo to give the crude product. This was purified by flash chromatography (ISCO Combiflash Rf, RediSep Silica 80 g, 60 mL/min, 100% hexanes for 3 min, gradient to 20% EtOAc in hexanes over 27 min, isocratic at 20% EtOAc in hexanes for 15 min) to afford tert-butyl 2-(5-fluoropyridin-3-yl)acetate. LCMS calc.=212.10; found=212.21 (M+H)$^+$.

Intermediate 30

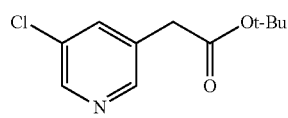 [SMILES: CC(C)(C)OC(=O)Cc1cncc(Cl)c1]

Tert-butyl 2-(5-chloropyridin-3-yl) acetate

Tris(dibenzylideneacetone)dipalladium(0) (0.487 g, 0.532 mmol) and 2-dicyclohexylphosphino-2'-(n,n-dimethylamino)biphenyl (0.419 g, 1.064 mmol) were added successively to a stirred solution of lithium bis(trimethylsilyl) amide (1M IN toluene) (19.33 ml, 19.33 mmol) in dry Toluene (20.59 ml) at 25° C. under N$_2$. The resulting mixture was stirred at 25° C. for 10 min, then cooled to −10° C. Tert-butyl acetate (2.390 ml, 17.73 mmol) was added over 10 min. This mixture was cannulated into a solution of 3,5-dichloropyridine (2.493 g, 16.85 mmol) in dry Toluene (19.99 ml) at −10° C. The resulting mixture was warmed to 25° C. and stirred for 2 h. Water was added and the resulting slurry was filtered and the filtrate was extracted with EtOAc. The combined organic layers were dried (Na$_2$SO$_4$) and concentrated in vacuo to give the crude product. This was purified by flash chromatography (ISCO Combiflash Rf, RediSep Silica 120 g, 85 mL/min, 100% hexanes for 4 min, gradient to 20% EtOAc in hexanes over 31 min, isocratic at 20% EtOAc in hexanes for 10 min) to afford tert-butyl 2-(5-chloropyridin-3-yl)acetate. LCMS calc.=228.07; found=228.15 (M+H)$^+$.

Intermediate 31

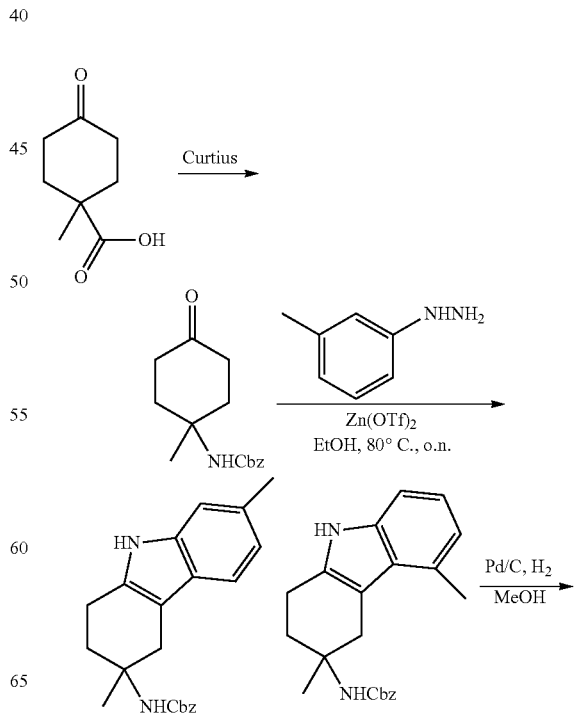

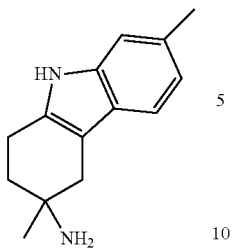

3,7-dimethyl-2,3,4,9-tetrahydro-1H-carbazol-3-amine

Step A: benzyl (1-methyl-4-oxocyclohexyl)carbamate

Triethylamine and diphenylphosphoryl azide were added successively to a stirred solution of 1-methyl-4-oxocyclohexanecarboxylic acid in dry Toluene at room temperature under $N_2$. After 30 min, benzyl alcohol was added and the resulting mixture was heated at 115° C. overnight. After this time the reaction was cooled to room temperature and concentrated in vacuo to give the crude product. This was purified by flash chromatography (ISCO Combiflash Rf, 120 g, 0-50% EtOAc in Hexane) to afford benzyl (1-methyl-4-oxocyclohexyl)carbamate. LCMS calc.=262.14; found=262.11 $(M+H)^+$.

Step B: benzyl (3,7-dimethyl-2,3,4,9-tetrahydro-1H-carbazol-3-yl)carbamate

A solution of benzyl (1-methyl-4-oxocyclohexyl)carbamate, m-tolylhydrazine and zinc trifluoromethanesulfonate in EtOH was heated at 50° C. overnight. LC/MS showed the reaction was completed. The reaction was concentrated in vacuo to afford the crude product. The residue was purified by preparative HPLC Reverse phase (C-18), eluting with Acetonitrile/Water, to give the mixture of two enantiomers, which was resolved by chiral SFC (AS-H, 2×25 cm, 70 mL/min, 25% MeOH (0.1% DEA) gradient/CO2) to afford two regioisomers benzyl (3,7-dimethyl-2,3,4,9-tetrahydro-1H-carbazol-3-yl)carbamate and benzyl (3,5-dimethyl-2,3,4,9-tetrahydro-1H-carbazol-3-yl)carbamate, which were separated by Achiral SFC (DEAP, 3×25 cm, 70 mL/min, 30% MeOH/CO2) to afford benzyl (3,7-dimethyl-2,3,4,9-tetrahydro-1H-carbazol-3-yl)carbamate as the first peak to elute from the column. LCMS calc.=349.18; found=349.15 $(M+H)^+$.

Step C: 3,7-dimethyl-2,3,4,9-tetrahydro-1H-carbazol-3-amine

A solution of benzyl (3,7-dimethyl-2,3,4,9-tetrahydro-1H-carbazol-3-yl)carbamate (250 mg, 0.717 mmol) in EtOH (7175 µl) was flushed with $N_2$ 2 times then Pd—C (7.64 mg, 0.072 mmol) was added to it. The $H_2$ (balloon) (1.446 mg, 0.717 mmol) was attached to the flask. The mixture was stirred under $H_2$ atmosphere overnight. The reaction was filtered and the filtrate was concentrated in vacuo to afford the crude product. The residue was purified by ISCO, silica gel HP Gold (24 g), eluting with DCM/MeOH (2N $NH_3$) (0% to 10% MeOH (2N $NH_3$) in DCM). Related fractions were pooled and evaporated under reduced pressure to give 3,7-dimethyl-2,3,4,9-tetrahydro-1H-carbazol-3-amine. LCMS calc.=215.15; found=215.20 $(M+H)^+$.

Intermediate 32

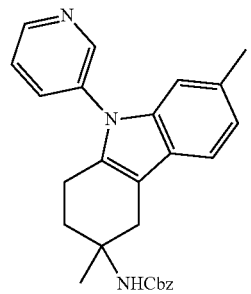 [SMILES: Cc1ccc2c3c(n(-c4cccnc4)c2c1)CCC(C)(NC(=O)OCc1ccccc1)C3]

Benzyl (3,7-dimethyl-9-(pyridin-3-yl)-2,3,4,9-tetrahydro-1H-carbazol-3-yl)carbamate To a sealed tube was added benzyl (3,7-dimethyl-2,3,4,9-tetrahydro-1H-carbazol-3-yl)carbamate (50 mg, 0.143 mmol), $Cs_2CO_3$ (94 mg, 0.287 mmol) and XPhos Biphenyl Precatalyst (11.29 mg, 0.014 mmol). The vessel was evacuated and back filled with $N_2$ 2 times. Then 3-bromopyridine (27.2 mg, 0.172 mmol) and Dioxane (1435 µl) were added successively at room temperature under $N_2$. The mixture was bubbled through $N_2$ for 5 min. The resulting mixture was heated at 100° C. overnight. LC/MS showed that the conversion is ~50%. The mixture was filtered through celite. The filtrate was concentrated in vacuo. The residue was purified by ISCO, HP Gold silica gel (12 g), eluting with Hex/EtOAc (0-50% EtOAc in Hex) to give benzyl (3,7-dimethyl-9-(pyridin-3-yl)-2,3,4,9-tetrahydro-1H-carbazol-3-yl)carbamate. LCMS calc.=426.21; found=426.12 $(M+H)^+$.

Intermediate 33

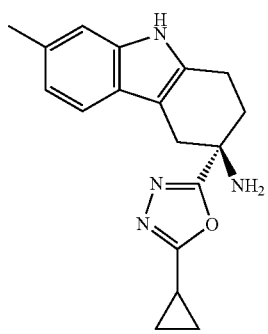 [SMILES: Cc1ccc2c3c([nH]c2c1)CC[C@](N)(c1nnc(C2CC2)o1)C3]

(R)-3-(5-cyclopropyl-1,3,4-oxadiazol-2-yl)-7-methyl-2,3,4,9-tetrahydro-1H-carbazol-3-amine Step A: (R)-3-((tert-butoxycarbonyl)amino)-7-methyl-2,3,4,9-tetrahydro-1H-carbazole-3-carboxylic acid LiOH (2.5N) (400 µl, 10.0 mmol) was added to (R)-methyl 3-((tert-butoxycarbonyl)amino)-7-methyl-2,3,4,9- tetrahydro-1H-carbazole-3-carboxylate (600 mg, 1.674 mmol) in 1,4-Dioxane (1.34E+04 μl). The resulting solution was stirred at room temperature overnight. The reaction was acidified with the equal amount of 2N HCl. The mixture was extracted with ethyl acetate (3×). The combined organic fractions were washed with brine, dried (Na₂SO₄), filtered and the solvent was evaporated under reduced pressure to give (R)-3-((tert-butoxycarbonyl)amino)-7-methyl-2,3,4,9-tetrahydro-1H-carbazole-3-carboxylic acid. The material was used in next step without further purification. LCMS calc.=367.17; found=367.09 (M+Na)⁺.

Step B: (R)-tert-butyl (3-(2-(cyclopropanecarbonyl) hydrazinecarbonyl)-7-methyl-2,3,4,9-tetrahydro-1H-carbazol-3-yl)carbamate N-ethyl-N-isopropylpropan-2-amine (101 μl, 0.581 mmol) was added to a stirred solution of cyclopropanecarbohydrazide (29.1 mg, 0.290 mmol) in DMF (303 μl). Separately N-ethyl-N-isopropylpropan-2-amine (101 μl, 0.581 mmol) was added to a solution of (R)-3-((tert-butoxycarbonyl)amino)-7-methyl-2,3,4,9-tetrahydro-1H-carbazole-3-carboxylic acid (100 mg, 0.290 mmol), EDC (92 mg, 0.479 mmol), 1-hydroxy-7-azabenzotriazole (65.2 mg, 0.479 mmol) in dry DMF (713 μl), the mixture was stirred at 25° C. for 30 min. The amine solution was added to the carboxylic acid solution via cannula and the resulting mixture was stirred at 25° C. overnight. The residue was purified by ISCO, reverse phase HP Gold C18 (50 g), eluting with acetonitrile/water (10-70% ACN in water). Related fractions were pooled and evaporated under reduced pressure to give (R)-tert-butyl (3-(2-(cyclopropanecarbonyl)hydrazinecarbonyl)-7-methyl-2,3,4,9-tetrahydro-1H-carbazol-3-yl)carbamate. LCMS calc.=427.23; found=427.08 (M+H)⁺.

Step C: (R)-3-(5-cyclopropyl-1,3,4-oxadiazol-2-yl)-7-methyl-2,3,4,9-tetrahydro-1H-carbazol-3-amine To a solution of (R)-tert-butyl (3-(2-(cyclopropanecarbonyl)hydrazinecarbonyl)-7-methyl-2,3,4,9-tetrahydro-1H-carbazol-3-yl)carbamate (28.6 mg, 0.067 mmol) in Acetonitrile (305 μl) under N₂, was added phosphorus oxychloride (25.7 mg, 0.168 mmol). The mixture was heated at 70° C. for 6 h. TLC showed that the reaction went to completion. The Boc fell off under this condition. The reaction was quenched carefully with saturated aqueous NaHCO₃ solution, and extracted with EtOAc (2×). The combined organic layers were dried (Na₂SO₄) and concentrated in vacuo to give the crude product. The residue was purified by ISCO, reverse phase HP Gold C18 (50 g), eluting with acetonitrile/water (10-50% ACN in water). Related fractions were pooled and evaporated under reduced pressure to give (R)-3-(5-cyclopropyl-1,3,4-oxadiazol-2-yl)-7-methyl-2,3,4,9-tetrahydro-1H-carbazol-3-amine. LCMS calc.=309.16; found=309.14 (M+H)⁺.

Intermediate 34

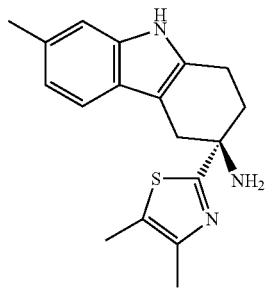 [SMILES: Cc1ccc2c3c([nH]c2c1)CC[C@](N)(c1nc(C)c(C)s1)C3]

(R)-3-(4,5-dimethylthiazol-2-yl)-7-methyl-2,3,4,9-tetrahydro-1H-carbazol-3-amine Step A: (R)-tert-butyl (3-carbamothioyl-7-methyl-2,3,4,9-tetrahydro-1H-carbazol-3-yl)carbamate To a pressure vessel, was added (R)-tert-butyl (3-carbamoyl-7-methyl-2,3,4,9-tetrahydro-1H-carbazol-3-yl)carbamate (147 mg, 0.428 mmol) followed by THF (8561 μl), then Lawesson's reagent (130 mg, 0.321 mmol) was added. The reaction was heated at 60° C. for 1 h. The mixture was diluted with EtOAc and washed with 1N NaOH followed by brine. The organic layer was dried over Na₂SO₄ and concentrated in vacuo. The residue was purified by ISCO, reverse phase HP Gold C18 (50 g), eluting with acetonitrile/water (10-80% ACN in water). Related fractions were pooled and evaporated under reduced pressure to give (R)-tert-butyl (3-carbamothioyl-7-methyl-2,3,4,9-tetrahydro-1H-carbazol-3-yl)carbamate. LCMS calc.=360.17; found=360.14 (M+H)⁺.

Step B: (R)-3-(4,5-dimethylthiazol-2-yl)-7-methyl-2,3,4,9-tetrahydro-1H-carbazol-3-amine To a solution of (R)-tert-butyl (3-carbamothioyl-7-methyl-2,3,4,9-tetrahydro-1H-carbazol-3-yl)carbamate (40 mg, 0.111 mmol) in Ethanol (2225 μl), was added 3-bromo-2-butanone (16.80 mg, 0.111 mmol). The reaction was heated at 60° C. overnight. The volatile was removed in vacuo. The residue was redissolved in DCM, then TFA (500 μl, 6.49 mmol) was added. The mixture was stirred at room temperature for 4 h. The mixture was diluted with EtOAc and washed with saturated aqueous NaHCO₃ followed by brine. The organic layer was dried over Na₂SO₄ and concentrated in vacuo to give the crude (R)-3-(4,5-dimethylthiazol-2-yl)-7-methyl-2,3,4,9-tetrahydro-1H-carbazol-3-amine, which was used in next step without further purification. LCMS calc.=312.15; found=312.06 (M+H)⁺.

Intermediate 35

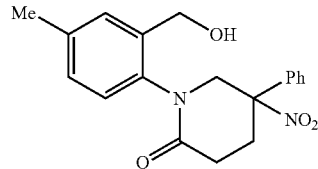 [SMILES: Cc1ccc(N2CC(c3ccccc3)([N+](=O)[O-])CCC2=O)c(CO)c1]

Step A: Ethyl 4-nitro-4-phenylbutanoate

To a solution of Ethyl acrylate (19.09 ml, 175 mmol) in acetonitrile (100 ml) and triethylamine (24.39 ml, 175 mmol) was added (nitromethyl)benzene (20 g, 146 mmol) portionwise wise while maintaining the temperature between 17-20° C. The reaction mixture was stirred at room temperature for 20 hours then diluted with aqueous NH$_4$Cl. The product was extracted with EtOAc. The combined organic solution was washed with H$_2$O/brine and concentrated. The product was purified on silica gel flash chromatography (eluent: 10-20% EtOAc/Hexanes) to give compound Ethyl 4-nitro-4-phenylbutanoate. $^1$H NMR (300 MHz, CHCl3-d): δ (ppm) 1.26 (3H, t, J=7.14 Hz), 2.35 (2H, t, J=7.03 Hz), 2.46-2.40 (1H, m), 2.77 (1H, m), 4.14 (2H, q, J=7.14 Hz), 5.58 (1H, dd, J=8.74, 6.38 Hz), 7.42-7.40 (3H, m), 7.47-7.45 (2H, m).

Step B: 5-nitro-5-phenylpiperidin-2-one

To a solution of ammonium acetate (16.00 g, 208 mmol) in water (430 ml) was added formaldehyde (7.79 ml, 105 mmol) at rt. Ethyl 4-nitro-4-phenylbutanoate (19.7 g, 83 mmol) in Ethanol (150 ml) was charged and the reaction mixture was heated to 78° C. After 18 hours; the mixture was slowly cool to room temperature and stirred for 4 hours. Water was added (440 ml) and the suspension was filtered and rinse with water. The product was dried in a vacuum oven at 35° C. to give 5-nitro-5-phenylpiperidin-2-one. LCMS 221 (M+H)$^+$

Step C: 1-(2-(hydroxymethyl)-4-methylphenyl)-5-nitro-5-phenylpiperidin-2-one In a dry 100 ml round bottom flask under nitrogen was charged (2-iodo-5-methylphenyl)methanol (1.2 g, 4.84 mmol); 5-nitro-5-phenylpiperidin-2-one (1.172 g, 5.32 mmol); cesium carbonate (2.364 g, 7.26 mmol); copper(I) iodide (0.046 g, 0.242 mmol) and Dioxane (20 ml). The mixture was sparged with nitrogen for 10 minutes. Trans-(1R,2R)—N,N-dimethyl-cyclohexane-1,2-dimine (0.153 ml, 0.968 mmol) was added and the mixture was heated to 95° C. for 30 hours. The reaction mixture was filtered; diluted with EtOAc; washed with 1N HCl/brine and concentrated. The product was purified on silica gel flash chromatography (eluent: 20-100% Ethyl acetate/Hexanes) to give compound 1-(2-(hydroxymethyl)-4-methylphenyl)-5-nitro-5-phenylpiperidin-2-one.
LCMS 341 (M+H)$^+$. $^1$H NMR (300 MHz, CHCl3-d): δ (ppm) 2.39 (3H, s), 2.89-2.65 (3H, m), 3.00 (1H, m), 3.36-3.31 (1H, m), 4.04 (0.5H, d, J=14.24 Hz), 4.15 (0.5H, d, J=14.04 Hz), 4.45-4.34 (1.5H, m), 4.55 (0.5H, d, J=12.13 Hz), 4.70 (0.5H, dd, J=14.05, 2.92 Hz), 4.86 (0.5H, dd, J=14.26, 2.99 Hz), 7.00 (0.5H, d, J=8.00 Hz), 7.18 (0.5H, dd, J=8.01, 1.96 Hz), 7.31-7.28 (2H, m), 7.45-7.42 (6H, m).

Intermediate 36

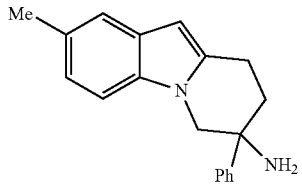 [SMILES: Cc1ccc2c(c1)cc1n2CC(N)(c2ccccc2)CC1]

2-methyl-7-phenyl-6,7,8,9-tetrahydropyrido[1,2-a]indol-7-amine

Step A: 1-(2-(chloromethyl)-4-methylphenyl)-5-nitro-5-phenylpiperidin-2-one To a solution of 1-(2-(hydroxymethyl)-4-methylphenyl)-5-nitro-5-phenylpiperidin-2-one (1.1 g, 3.23 mmole) in DCM (8 ml) at 0° C. was added thionyl chloride (0.354 ml, 4.85 mmol). After 4 hours; the reaction mixture was quenched into Aqueous NaHCO$_3$ and extracted with DCM. The product was purified on silica gel flash chromatography (eluent: 20% Ethyl acetate/Hexanes) to give compound 1-(2-(chloromethyl)-4-methylphenyl)-5-nitro-5-phenylpiperidin-2-one. LCMS 359 (M+H)$^+$. $^1$H NMR (300 MHz, CHCl3-d): δ (ppm) 2.38 (3H, s), 2.90-2.63 (3H, m), 3.35-3.28 (1H, m), 4.08 (0.3H, d, J=14.04 Hz), 4.28 (0.7H, d, J=14.30 Hz), 4.37 (0.7H, d, J=11.64 Hz), 4.53 (0.3H, d, J=12.28 Hz), 4.64 (1H, dd, J=11.69, 5.96 Hz), 4.89-4.82 (1H, m), 6.99 (0.3H, d, J=8.00 Hz), 7.18 (0.3H, d, J=7.96 Hz), 7.49-7.43 (7.1H, m), 7.68 (0.3H, m).

Step B: 1-(2-(bromomethyl)-4-methylphenyl)-5-nitro-5-phenylpiperidin-2-one

To a solution of 1-(2-(hydroxymethyl)-4-methylphenyl)-5-nitro-5-phenylpiperidin-2-one (10.1 g, 29.7 mmol) and triphenylphosphine (9.34 g, 35.6 mmol) in DCM (100 ml) at 0° C. was added CBr$_4$ (10.82 g, 32.6 mmol) (slightly exothermic). The reaction mixture was stirred at 0-20° C. for 2 hours. The reaction was quenched with Aqueous NaHCO$_3$ and extracted with DCM. The product was purified on silica gel flash chromatography (eluent: 90% Ethyl acetate/Hexanes) to give compound 1-(2-(bromomethyl)-4-methylphenyl)-5-nitro-5-phenylpiperidin-2-one. LCMS 403 (M+H)$^+$. $^1$H NMR (300 MHz, CHCl3-d): δ (ppm)

Step C: (5-methyl-2-(5-nitro-2-oxo-5-phenylpiperidin-1-yl)benzyl)triphenylphosphonium chloride To a suspension of 1-(2-(chloromethyl)-4-methylphenyl)-5-nitro-5-phenylpiperidin-2-one (2.0 g, 5.57 mmole) in toluene (15 ml) was added triphenylphosphine (1.6 g, 6.13 mmole).
The reaction mixture was heated to 100° C. over night. The suspension was filtered and the solid was washed with toluene and dried under vacuum.
The compound (5-methyl-2-(5-nitro-2-oxo-5-phenylpiperidin-1-yl)benzyl)triphenylphosphonium chloride was used as is in the next step.

Step D: 2-methyl-7-nitro-7-phenyl-6,7,8,9-tetrahydropyrido[1,2-a]indole

To a suspension of (5-methyl-2-(5-nitro-2-oxo-5-phenylpiperidin-1-yl)benzyl)triphenylphosphonium chloride (240 mg, 0.386 mmole) in dry Toluene (3 ml) was charged LDA (2.0M, 0.23 ml, 0.464 mmole) at 0° C. The reaction mixture was stirred 1 hour at room temperature and 2 hours at 70° C. The reaction mixture was cooled to room temperature and quenched with aqueous NH$_4$Cl. The product was extracted with EtOAc and the organic layer was concentrated to a crude oil. The product was purified on silica gel flash chromatography (eluent: 10% Ethyl acetate/Hexanes) to give compound 2-methyl-7-nitro-7-phenyl-6,7,8,9-tetrahydropyrido[1,2-a]indole. LCMS 307 (M+H)$^+$. $^1$H NMR (300 MHz, CHCl3-d): δ (ppm) 2.45 (3H, s), 2.77-2.71

(1H, m), 3.05 (2H, t, J=6.59 Hz), 3.13 (1H, d, J=5.75 Hz), 3.16 (1H, t, J=5.41 Hz), 4.47 (1H, d, J=13.21 Hz), 5.19 (1H, dd, J=13.21, 1.58 Hz), 6.17 (1H, s), 7.04 (1H, d, J=8.36 Hz), 7.28 (1H, d, J=8.64 Hz), 7.34 (1H, s), 7.44-7.43 (3H, m), 7.51-7.49 (2H, m).

Step E: 2-methyl-7-phenyl-6,7,8,9-tetrahydropyrido[1,2-a]indol-7-amine

To a solution of 2-methyl-7-nitro-7-phenyl-6,7,8,9-tetrahydropyrido[1,2-a]indole (67 mg, 0.219 mmole) in EtOH (1 ml) and acetic acid (1 ml) at room temperature was add zinc dust (143 mg, 2.19 mmole). The mixture was stirred at room temperature for 18 hours, filtered through celite and concentrated. The product was purified on silica gel flash chromatography (eluent: 5-methanol in DCM) to give compound 2-methyl-7-phenyl-6,7,8,9-tetrahydropyrido[1,2-a]indol-7-amine. LCMS 277 (M+H)+.

Intermediate 37

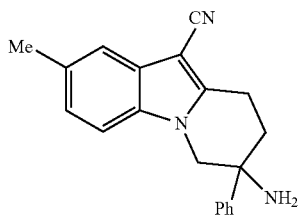

7-amino-2-methyl-7-phenyl-6,7,8,9-tetrahydropyrido[1,2-a]indole-10-carbonitrile

Step A: 2-(5-methyl-2-(5-nitro-2-oxo-5-phenylpiperidin-1-yl)phenyl)acetonitrile

To a solution of 1-(2-(chloromethyl)-4-methylphenyl)-5-nitro-5-phenylpiperidin-2-one (300 mg, 0.84 mmole) in dry acetonitrile (3 ml) was charged 18-crown-6 (221 mg, 0.84 mmol) and KCN (54.4 mg, 0.84 mmol). The reaction mixture was stirred at 50° C. for 5 hours. The reaction mixture was cooled to room temperature and quenched into aqueous NaHCO3 and the crude product was extracted with EtOAc. The product was purified on silica gel flash chromatography (eluent: 20-100% Ethyl acetate/Hexanes) to give compound 2-(5-methyl-2-(5-nitro-2-oxo-5-phenylpiperidin-1-yl)phenyl)acetonitrile.
LCMS 350 (M+H)+. Use as is in the next step.

Step B: 2-methyl-7-nitro-7-phenyl-6,7,8,9-tetrahydropyrido[1,2-a]indole-10-carbonitrile To a solution of 2-(5-methyl-2-(5-nitro-2-oxo-5-phenylpiperidin-1-yl)phenyl)acetonitrile (5.0 g, 14.31 mmol) dissolved in THF (50 ml) at −10° C. was charged LDA (0.160 ml, 0.240 mmol) (1.0M-THF/Hexane). The reaction mixture was stirred at −10° C. to room temperature for 2 hours. The reaction mixture was quenched with aqueous NH4Cl. The product was extracted with EtOAc and the organic layer was concentrated. The product was purified on silica gel flash chromatography (eluent: 40-100% DCM/Hexanes) to give compound 2-methyl-7-nitro-7-phenyl-6,7,8,9-tetrahydropyrido[1,2-a]indole-10-carbonitrile.

LCMS 332 (M+H)+. 1H NMR (300 MHz, CHCl3-d): δ (ppm) 2.48 (3H, s), 2.82-2.76 (1H, m), 3.18-3.11 (1H, m), 3.34-3.26 (2H, m), 4.44 (1H, d, J=13.71 Hz), 5.31 (1H, d, J=13.41 Hz), 7.16 (1H, d, J=8.44 Hz), 7.33 (1H, d, J=8.35 Hz), 7.49 (6H, m).

Step C: 7-amino-2-methyl-7-phenyl-6,7,8,9-tetrahydropyrido[1,2-a]indole-10-carbonitrile To a solution of 2-methyl-7-nitro-7-phenyl-6,7,8,9-tetrahydropyrido[1,2-a]indole-10-carbonitrile (60 mg, 0.18 mmole) in EtOH (1 ml) and acetic acid (1 ml) at room temperature was add zinc dust (118 mg, 1.81 mmole). The mixture was stirred at room temperature for 2 hours, filtered through celite and concentrated. The product was purified on silica gel flash chromatography (eluent: 5-methanol in DCM) to give compound 7-amino-2-methyl-7-phenyl-6,7,8,9-tetrahydropyrido[1,2-a]indole-10-carbonitrile. LCMS 302 (M+H)+.

Example 2

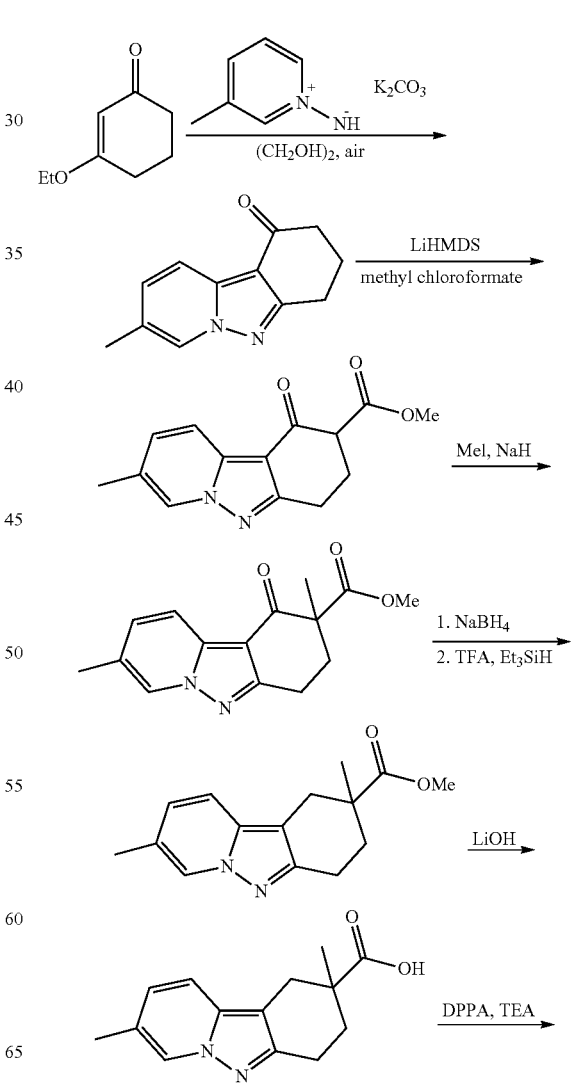

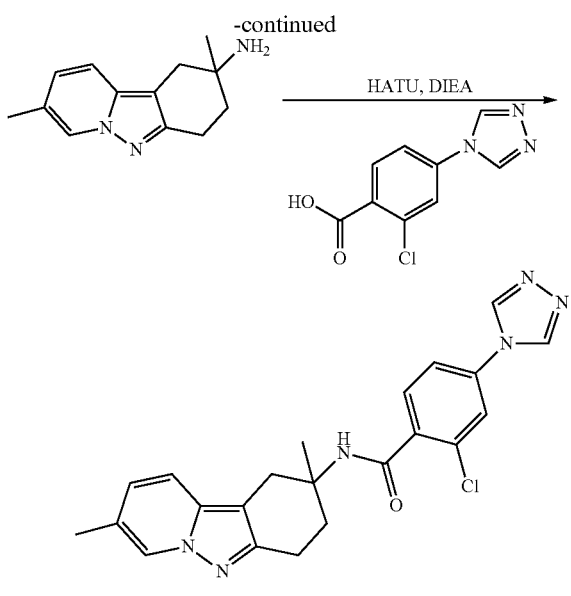

2-Chloro-N-(2,8-dimethyl-1,2,3,4-tetrahydropyrido[1,2-b]indazol-2-yl)-4-(4H-1,2,4-triazol-4-yl)benzamide Step A: (3-Methylpyridin-1-ium-1-yl)amide

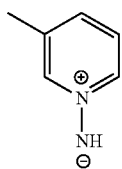

Hydroxylamine-o-sulfonic acid (11.5 g, 102 mmol) and 3-methylpyridine (12 g, 129 mmol) were heated in water (10 ml) at 90° C. for 30 min. It was cooled to room temperature, concentrated in vacuo at 45° C. to remove water. It was azeotropically distilled with 50 mL of toluene in vacuo to give a mixture of the title compound and inorganic salts.

Step B: 8-Methyl-3,4-dihydropyrido[1,2-b]indazol-1(2H)-one

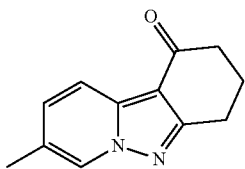

A mixture of 3-ethoxy-2-cyclohexen-1-one (1.426 g, 10.17 mmol), K$_2$CO$_3$ (2.81 g, 20.34 mmol) and (3-methylpyridin-1-ium-1-yl)amide (1.1 g, 10.17 mmol) in ethylene glycol (20 ml) was heated at 130° C. for 2 h under nitrogen. The flask was opened to air and stirred for 16 h at room temperature. It was diluted with water, extracted with ethyl acetate (3×50 mL). The combined organic layers were washed with brine, dried over sodium sulfate, filtered and purified by ISCO to afford the title compound. LCMS calc.=201.10; found=201.11 (M+H)$^+$. $^1$H NMR (499 MHz, CHCl$_3$-d): δ 8.30 (s, 1H), 8.08 (d, 1H), 7.34 (d, 1H), 3.01 (t, 3H), 2.59 (t, 2H), 2.42 (s, 3H), 2.20-2.25 (m, 2H).

The other isomer 10-methyl-3,4-dihydropyrido[1,2-b]indazol-1(2H)-one was also isolated. LCMS calc.=201.10; found=201.08 (M+H)$^+$. $^1$H NMR (499 MHz, CHCl$_3$-d): δ 8.33 (d, 1H), 7.19 (d, 1H), 6.90 (t, 1H), 3.03 (t, 2H), 2.94 (s, 3H), 2.62 (t, 2H), 2.17-2.22 (m, 2H).

Step C: Methyl 8-methyl-1-oxo-1,2,3,4-tetrahydropyrido[1,2-b]indazole-2-carboxylate

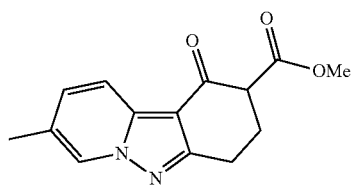 [SMILES: COC(=O)C1CCc2nn3cc(C)ccc3c2C1=O]

To a solution of LiHMDS (1 M in THF, 4.61 ml, 4.61 mmol) in toluene (5 ml) was added a solution of 8-methyl-3,4-dihydropyrido[1,2-b]indazol-1(2H)-one (420 mg, 2.098 mmol) in 2 mL of THF at −78° C. It was stirred for 30 min, then methyl chloroformate (0.195 ml, 2.52 mmol) was added in one portion. It was stirred for 10 min and quenched with saturated aqueous ammonium chloride, extracted with ethyl acetate. The combined organic layers were dried over sodium sulfate, filtered and concentrated. The residue was purified by ISCO (Gold 24 g, 0-100% ethyl acetate in hexane) to afford the title compound. LCMS calc.=259.11; found=259.05 (M+H)$^+$. $^1$H NMR (499 MHz, CHCl$_3$-d): δ 8.32 (s, 1H), 8.08 (d, 1H), 7.38 (d, 1H), 3.80 (s, 3H), 3.62 (dd, 1H), 3.20 (ddd, 1H), 3.01 (ddd, 1H), 2.57-2.64 (m, 1H), 2.40-2.50 (m, 1H), 2.43 (s, 3H).

Step D: Methyl 2,8-dimethyl-1-oxo-1,2,3,4-tetrahydropyrido[1,2-b]indazole-2-carboxylate

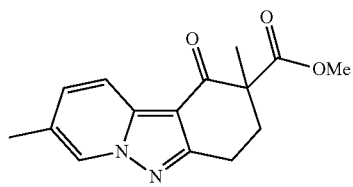 [SMILES: COC(=O)C1(C)CCc2nn3cc(C)ccc3c2C1=O]

To a suspension of methyl 8-methyl-1-oxo-1,2,3,4-tetrahydropyrido[1,2-b]indazole-2-carboxylate (450 mg, 1.74 mmol) in THF (1.5 ml) and DMF (1.5 ml) was added NaH (60 wt %, 72 mg, 1.80 mmol) at 0° C. The mixture was stirred for 10 min. To the solution was added iodomethane (113 μl, 1.8 mmol). It was stirred for 10 min, and warmed to room temperature, stirring for 2 h. It was added another portion of iodomethane (113 μl, 1.8 mmol) and the mixture was stirred for another 1.5 h. It was diluted with 20 mL of ethyl acetate and washed with brine (10 mL), dried over sodium sulfate, filtered and concentrated. The residue was purified by ISCO (50-100% ethyl acetate in hexane) to give methyl 2,8-dimethyl-1-oxo-1,2,3,4-tetrahydropyrido[1,2-b]indazole-2-carboxylate. LCMS calc.=273.13; found=273.06 (M+H)⁺.

Step E: Methyl 1-hydroxy-2,8-dimethyl-1,2,3,4-tetrahydropyrido[1,2-b]indazole-2-carboxylate

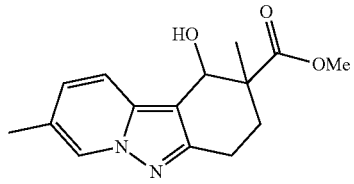 [SMILES: COC(=O)C1(C)CCc2nn3cc(C)ccc3c2C1O]

A solution of methyl 2,8-dimethyl-1-oxo-1,2,3,4-tetrahydropyrido[1,2-b]indazole-2-carboxylate (420 mg, 1.542 mmol) in MeOH (10 ml) was treated with sodium borohydride (200 mg, 5.29 mmol) at 0° C. for 30 min. It was warmed to room temperature and stirred for 3 h. It was diluted with saturated aqueous ammonium chloride and extracted with ethyl acetate (3×20 mL). The combined organic layers were dried over sodium sulfate, filtered and concentrated. The residue was purified by ISCO (40 g, 0-100% ethyl acetate in hexane) to give methyl 1-hydroxy-2,8-dimethyl-1,2,3,4-tetrahydropyrido[1,2-b]indazole-2-carboxylate. LCMS calc.=275.14; found=275.09 (M+H)⁺.

Step F: Methyl 2,8-dimethyl-1,2,3,4-tetrahydropyrido[1,2-b]indazole-2-carboxylate

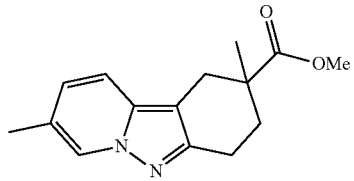 [SMILES: COC(=O)C1(C)CCc2nn3cc(C)ccc3c2C1]

Methyl 1-hydroxy-2,8-dimethyl-1,2,3,4-tetrahydropyrido[1,2-b]indazole-2-carboxylate (215 mg, 0.784 mmol) in TFA (5 mL, 64.9 mmol) was treated with triethylsilane (0.5 mL, 3.13 mmol) at room temperature for 15 min. It was concentrated and purified by ISCO (24 g, 0-100% ethyl acetate in hexane) to give the title compound.

Step G: 2,8-Dimethyl-1,2,3,4-tetrahydropyrido[1,2-b]indazole-2-carboxylic acid

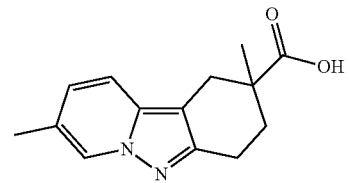 [SMILES: Cc1ccc2c3c(nn2c1)CCC(C)(C(=O)O)C3]

Methyl 2,8-dimethyl-1,2,3,4-tetrahydropyrido[1,2-b]indazole-2-carboxylate (170 mg, 0.658 mmol) in THF (2 ml) and MeOH (2) was treated with LiOH (2 M, 2 ml, 4.00 mmol) at room temperature and stirred for 2 h. It was acidified by 2 mL of 1 M HCl, dried on 3 g of silica gel, flashed with ISCO (4 g, 0-10% methanol in DCM) to give 2,8-dimethyl-1,2,3,4-tetrahydropyrido[1,2-b]indazole-2-carboxylic acid. LCMS calc.=242.12; found=242.18 (M+H)⁺.

Step H: 2,8-Dimethyl-1,2,3,4-tetrahydropyrido[1,2-b]indazol-2-amine

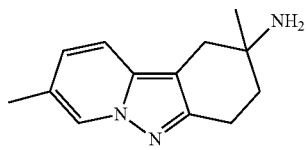 [SMILES: Cc1ccc2c3c(nn2c1)CCC(C)(N)C3]

The general procedure of Curtis Rearrangement was followed employing 2,8-Dimethyl-1,2,3,4-tetrahydropyrido[1,2-b]indazole-2-carboxylic acid (161 mg, 0.659 mmol) to afford the title compound.

Step I: 2-Chloro-N-(2,8-dimethyl-1,2,3,4-tetrahydropyrido[1,2-b]indazol-2-yl)-4-(4H-1,2,4-triazol-4-yl)benzamide

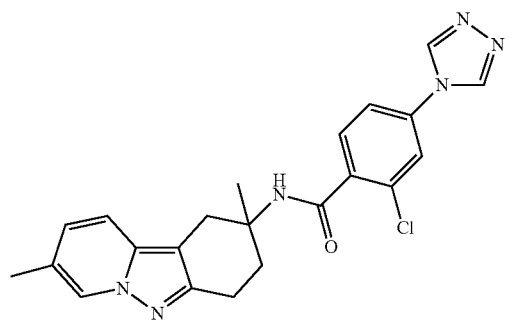 [SMILES: Cc1ccc2c3c(nn2c1)CCC(C)(NC(=O)c1ccc(-n2cnnc2)cc1Cl)C3]

The general procedure of amide coupling for EXAMPLE 7 was followed employing 2,8-Dimethyl-1,2,3,4-tetrahydropyrido[1,2-b]indazol-2-amine (48 mg, 50% purity, 0.111 mmol) and 2-chloro-4-(4H-1,2,4-triazol-4-yl)benzoic acid (50 mg, 0.224 mmol) to afford the title compound. LCMS calc.=421.16; found=420.89 (M+H)⁺. ¹H NMR (499 MHz, DMSO-d₆): δ 9.20 (s, 2H), 8.31 (s, 1H), 8.10 (s, 1H), 7.91 (d, 1H), 7.68 (dd, 1H), 7.44 (d, 1H), 7.35 (d, 1H), 6.95 (d, 1H), 3.15 (s, 3H), 3.12 (d, 1H), 2.87 (s, 1H), 2.70-2.77 (m, 4H), 2.23 (s, 3H), 1.77-1.83 (m, 1H), 1.54 (s, 3H).

Example 5

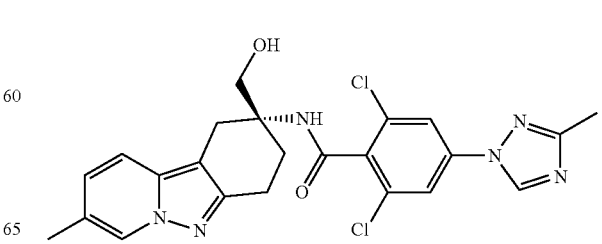

(R)-2,6-Dichloro-N-(2-(hydroxymethyl)-8-methyl-1,2,3,4-tetrahydropyrido[1,2-b]indazol-2-yl)-4-(3-methyl-1H-1,2,4-triazol-1-yl)benzamide Step A: 8-Methyl-2-vinyl-1,2,3,4-tetrahydropyrido[1,2-b]indazol-2-ol

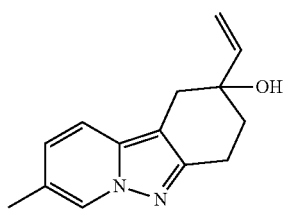 [SMILES: C=CC1(O)CCc2nn3cc(C)ccc3c2C1]

8-methyl-3,4-dihydropyrido[1,2-b]indazol-2(1H)-one (1 g, 4.99 mmol) in THF (2 ml) at −40° C. was added lanthanum trichloride (2.61 ml, 7.49 mmol). To the solution was added 0.5 M vinylmagnesium bromide (0.366 ml, 1.783 mmol) in THF dropwise. The reaction was stirred at −40° C. for 2 h, then warmed to room temperature and continued to stir for 1 h. The reaction was quenched with saturated aqueous ammonium chloride solution (30 ml). The mixture was extracted with ethyl acetate (2×100 ml). The combined organic layers were dried over magnesium sulfate, filtered and concentrated. The residue was purified by flash chromatography (ISO Combiflash Rf, RediStep Silica 40 g column, load as a solution in DCM, gradient 0-100% ethyl acetate in hexane) to afford the title compound. LCMS calc.=229.13; found=229.09 (M+H)+.

Step B: N-(8-Methyl-2-vinyl-1,2,3,4-tetrahydropyrido[1,2-b]indazol-2-yl)acetamide

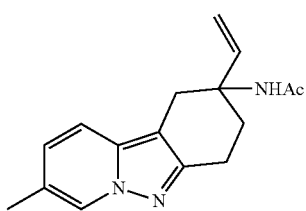 [SMILES: C=CC1(NC(C)=O)CCc2nn3cc(C)ccc3c2C1]

The general procedure described in the synthesis of Intermediate 12 Step A was followed employing 8-methyl-2-vinyl-1,2,3,4-tetrahydropyrido[1,2-b]indazol-2-ol (150 mg, 0.657 mmol) to afford the title compound. LCMS calc.=270.15; found=270.16 (M+H)+.

Step C: N-(2-(1,2-Dihydroxyethyl)-8-methyl-1,2,3,4-tetrahydropyrido[1,2-b]indazol-2-yl)acetamide

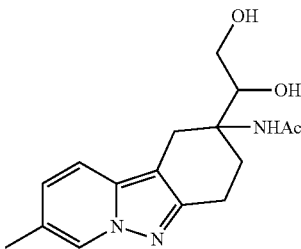 [SMILES: CC(=O)NC1(C(O)CO)CCc2nn3cc(C)ccc3c2C1]

To a solution of N-(8-methyl-2-vinyl-1,2,3,4-tetrahydropyrido[1,2-b]indazol-2-yl)acetamide (73 mg, 0.27 mmol) in BuOH (1 mL)/THF (0.10 mL)/Water (0.30 mL) was added trimethylamine oxide dehydrate (32.6 mg, 0.43 mmol) and osmium(VIII) oxide (86 mg, 0.014 mmol). The reaction mixture was stirred at room temperature for 4 h. The solution became a suspension. A lot of solid precipitated. The solid was filtered and washed with water, dried under vacuum to afford the title compound. LCMS calc.=304.16; found=304.21 (M+H)+.

Step D: N-(2-Formyl-8-methyl-1,2,3,4-tetrahydropyrido[1,2-b]indazol-2-yl)acetamide

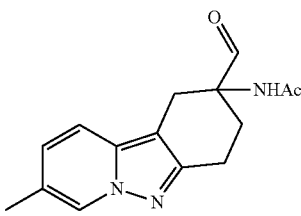 [SMILES: CC(=O)NC1(C=O)CCc2nn3cc(C)ccc3c2C1]

To a suspension solution of N-(2-(1,2-dihydroxyethyl)-8-methyl-1,2,3,4-tetrahydropyrido[1,2-b]indazol-2-yl)acetamide (56 mg, 0.18 mmol) in Et$_2$O (2 mL)/THF (2 mL) at 0° C. was added lead tetraacetate (98 mg, 0.22 mmol) and potassium carbonate (38.3 mg, 0.28 mmol). After stirring at 0° C. for 30 min, the reaction mixture was quenched with saturated aqueous NaHCO$_3$ solution and extracted with EtOAc (2×20 mL). The extracts were combined and washed with brine, dried over Na$_2$SO$_4$, filtered and concentrated in vacuo. The residue was purified by PTLC (eluent: EtOAc) to give the title compound. LCMS calc.=272.13; found=272.13 (M+H)+.

Step E: N-(2-(Hydroxymethyl)-8-methyl-1,2,3,4-tetrahydropyrido[1,2-b]indazol-2-yl)acetamide

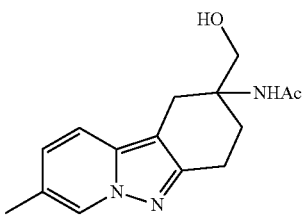 [SMILES: CC(=O)NC1(CO)CCc2nn3cc(C)ccc3c2C1]

To a solution of N-(2-formyl-8-methyl-1,2,3,4-tetrahydropyrido[1,2-b]indazol-2-yl)acetamide (40 mg, 0.15 mmol) in anhydrous MeOH (2 mL) at 0° C. was added sodium borohydride (27.9 mg, 0.74 mmol). The mixture was stirred at 0° C. for 2 h. The reaction was warmed to room temperature and partitioned between EtOAc and saturated aqueous. NaHCO₃. The aqueous layer was extracted with EtOAc twice. The combined organic extracts were dried with Na₂SO₄ and concentrated in vacuo to afford the title compound. LCMS calc.=274.15; found=274.22 (M+H)⁺.

Step F: (2-Amino-8-methyl-1,2,3,4-tetrahydropyrido[1,2-b]indazol-2-yl)methanol

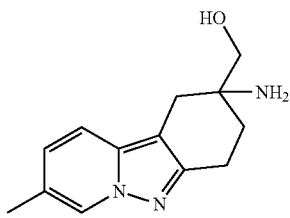 [SMILES: Cc1ccc2c3c(nn2c1)CCC(N)(CO)C3]

The general procedure described in the synthesis of Intermediate 12 Step B was followed employing N-(2-(hydroxymethyl)-8-methyl-1,2,3,4-tetrahydropyrido[1,2-b]indazol-2-yl)acetamide (31 mg) to afford the title compound. LCMS calc.=232.14; found=232.13 (M+H)⁺.

Step G: 2,6-Dichloro-N-(2-(hydroxymethyl)-8-methyl-1,2,3,4-tetrahydropyrido[1,2-b]indazol-2-yl)-4-(3-methyl-1H-1,2,4-triazol-1-yl)benzamide

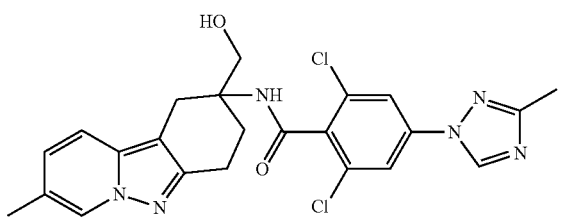

The general procedure described in the synthesis of EXAMPLE 7 was followed employing (2-amino-8-methyl-1,2,3,4-tetrahydropyrido[1,2-b]indazol-2-yl)methanol (60 mg, 0.26 mmol) and 2,6-dichloro-4-(3-methyl-1H-1,2,4-triazol-1-yl)benzoic acid (78 mg, 0.29 mmol) to afford the title compound. The enantiomers were separated by HPLC on a column with chiral stationary phase (OJ; 21×250 mm, ~50 mL/min, 100 bar, 230 nm, 35° C., eluted with 50% MeOH (0.2% NH₄OH)/CO₂). LCMS calc.=485.12; found=485.30 (M+H)⁺. ¹H NMR (500 MHz, CD₃OD): δ 9.01 (s, 1H); 8.18 (s, 1H); 7.82 (s, 2H); 7.37 (d, 1H); 7.01 (d, 1H); 3.31 s, 2H); 3.15 (m, 2H), 2.91 (m, 2H); 2.80 (m, 1H); 2.40 (s, 3H); 2.30 (s, 3H); 2.06 (m, 1H).

Example 7

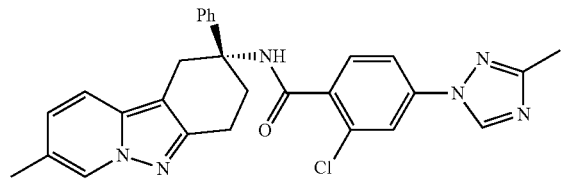

(R)-2-Chloro-4-(3-methyl-1H-1,2,4-triazol-1-yl)-N-(8-methyl-2-phenyl-1,2,3,4-tetrahydropyrido[1,2-b]indazol-2-yl)benzamide To a solution of 2-chloro-4-(3-methyl-1H-1,2,4-triazol-1-yl)benzoic acid (45.4 mg, 0.19 mmol) in DMF (1 mL) was added HATU (74 mg, 0.20 mmol). The resulting mixture was stirred at 40° C. for 30 min, and then 8-methyl-2-phenyl-1,2,3,4-tetrahydropyrido[1,2-b]indazol-2-amine (50 mg, 0.18 mmol) and N,N-diisopropylethylamine (0.09 ml, 0.54 mmol) was added to the mixture. The reaction was stirred at 40° C. for 16 h. The reaction mixture was diluted with DMSO and directly purified by reversed phase HPLC (Sunfire, C18, 10×100 mm, ~20 mL/min, gradient from 90% water in MeCN to 10% water in MeCN over 10 min, gradient to 100% MeCN over 2 min, both solvent containing 0.05% TFA, fractions containing desired product combined, lyophilized) to afford the title compound. The enantiomers were separated by HPLC on a column with chiral stationary phase (AD 30×250 mm, ~70 mL/min, 100 bar, 230 nm, 35° C., eluted with 55% MeOH/CO₂). LCMS calc.=497.18; found=497.24 (M+H)⁺. ¹H NMR (500 MHz, CD₃OD): δ 9.08 (s, 1H); 8.24 (s, 1H); 7.84 (s, 1H); 7.73 (d, 1H); 7.59 (d, 2H); 7.42 (d, 2H); 7.38 (d, 2H); 7.24 (m, 1H); 7.07 (d, 1H); 3.11 (m, 2H); 2.85 (m, 2H); 2.55 (m, 2H); 2.40 (s, 3H); 2.33 (s, 3H).

Example 8

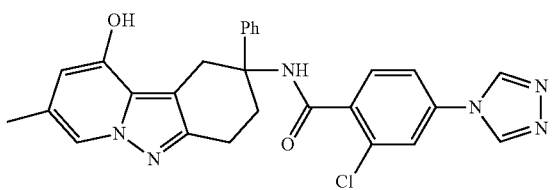 [SMILES: Cc1cc(O)c2c3c(nn2c1)CCC(NC(=O)c1ccc(-n2cnnc2)cc1Cl)(c1ccccc1)C3]

2-Chloro-N-(10-hydroxy-8-methyl-2-phenyl-1,2,3,4-tetrahydropyrido[1,2-b]indazol-2-yl)-4-(4H-1,2,4-triazol-4-yl)benzamide Step A: 3-(Methoxymethoxy)-5-methylpyridine

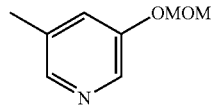

To a solution of 5-methylpyridin-3-ol (2 g, 18.33 mmol) in DMF (10 ml) was added potassium tert-butoxide (2.2 g, 19.61 mmol) at 0° C. It was stirred for 5 min and to the mixture was added a solution of MOM-Cl (1.46 ml, 19.22 mmol) in THF (10.00 ml) by a syringe pump over 1 h. It was stirred for another 1 h after the addition. The reaction was quenched with water (100 mL) and the mixture was extracted with ethyl acetate (3×50 mL). The combined organic layers were washed with water (50 mL), brine (50 mL), dried over sodium sulfate, filtered and concentrated. The residue was purified by ISCO (80 g, 0-50% ethyl acetate in hexane) to give 3-(methoxymethoxy)-5-methylpyridine. LCMS calc.=154.09; found=154.04 (M+H)⁺.

Step B:
1-Amino-3-(methoxymethoxy)-5-methylpyridin-1-ium 2,4,6-trimethylbenzenesulfonate

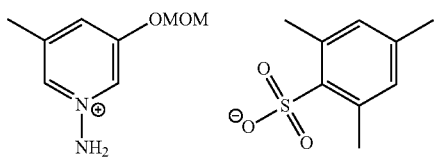

To a solution of 3-(methoxymethoxy)-5-methylpyridine (2.3 mg, 15.02 mmol) in DCM (20 ml) was added a solution (43% w/w) of O-(mesitylsulfonyl)hydroxylamine (7.52 g, 15.02 mmol) in DCM at 0° C. It was stirred for at room temperature overnight. It was purified by ISCO (125 g, 0-10% methanol in DCM) to give the title compound.

Step C: Dimethyl hept-2-ynedioate

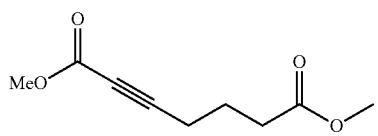

To a solution of 5-hexynoic acid (5 g, 44.6 mmol) in THF (100 ml) at −78° C. was added n-butyllithium (48 ml, 96 mmol) slowly. The solution was stirred for 20 min. Solids were formed. Methyl chloroformate (4.2 ml, 54.2 mmol) was added in one portion. The mixture was stirred for 15 min then the bath was removed to allow the reaction warm to room temperature. It was quenched with saturated aqueous ammonium chloride, extracted with ethyl acetate. The organic layer was dried over sodium sulfate, filtered and concentrated under reduced pressure. The residue was purified by ISCO (120 g, 0-20% ethyl acetate in hexane) to give methyl hex-5-ynoate and dimethyl hept-2-ynedioate. ¹H NMR (499 MHz, CHCl₃-d): δ 3.77 (s, 3H), 3.70 (s, 3H), 2.46 (dt, 4H), 1.92 (p, 2H).

Step C: Methyl 2-(4-methoxy-4-oxobutyl)-4-(methoxymethoxy)-6-methylpyrazolo[1,5-a]pyridine-3-carboxylate

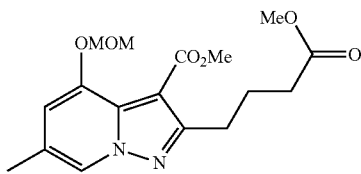

A mixture of 1-amino-3-(methoxymethoxy)-5-methyl-pyridin-1-ium 2,4,6-trimethylbenzenesulfonate (2.9 g, 7.87 mmol), dimethyl hept-2-ynedioate (1.450 g, 7.87 mmol) and potassium carbonate (2.176 g, 15.74 mmol) in DMF (40 ml) was stirred at rt for 2 h. It was diluted with 200 mL of ethyl acetate, washed with water (3×100 mL). The combined aqueous layers were extracted with ethyl acetate (2×50 mL). The combined organic layers were washed with brine, dried over sodium sulfate, filtered and concentrated. The residue was purified by ISCO (gold 120 g, 0-40% ethyl acetate in hexane) to give methyl 2-(4-methoxy-4-oxobutyl)-6-(methoxymethoxy)-4-methylpyrazolo[1,5-a]pyridine-3-carboxylate and methyl 2-(4-methoxy-4-oxobutyl)-6-(methoxymethoxy)-4-methylpyrazolo[1,5-a]pyridine-3-carboxylate. Methyl 2-(4-methoxy-4-oxobutyl)-6-(methoxymethoxy)-4-methylpyrazolo[1,5-a]pyridine-3-carboxylate LCMS calc.=351.17; found=350.94 (M+H)⁺. ¹H NMR (500 MHz, CHCl₃-d): δ 7.98 (s, 1H), 6.81 (s, 1H), 5.30 (s, 2H), 3.90 (s, 3H), 3.69 (s, 3H), 3.59 (s, 3H), 3.06 (t, 2H), 2.44 (t, 2H), 2.34 (s, 3H), 2.11 (p, 2H).

methyl 2-(4-methoxy-4-oxobutyl)-6-(methoxymethoxy)-4-methylpyrazolo[1,5-a]pyridine-3-carboxylate LCMS calc.=351.17; found=350.94 (M+H)⁺. ¹H NMR (500 MHz, CHCl₃-d): δ 8.23 (d, 1H), 6.98 (s, 1H), 5.16 (s, 2H), 3.89 (s, 3H), 3.69 (s, 3H), 3.52 (s, 3H), 3.06 (t, 2H), 2.69 (s, 3H), 2.44 (t, 2H), 2.11 (p, 2H).

Step D: Methyl 10-(methoxymethoxy)-8-methyl-1-oxo-1,2,3,4-tetrahydropyrido[1,2-b]indazole-2-carboxylate

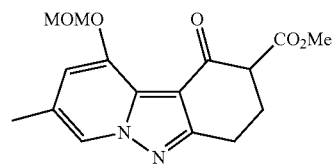

To a solution of methyl 2-(4-methoxy-4-oxobutyl)-4-(methoxymethoxy)-6-methylpyrazolo[1,5-a]pyridine-3-carboxylate (820 mg, 2.340 mmol) in THF (20 ml) was added LiHMDS (5.8 ml, 5.80 mmol) at −78° C. dropwise. It was stirred for 30 min and warmed to 0° C. for 20 min. The reaction was quenched by saturated aqueous ammonium chloride. The mixture was extracted with ethyl acetate. The organic layer was dried over sodium sulfate, filtered and concentrated. The residue was purified by ISCO (40 g, 0-100% ethyl acetate in hexane) to give methyl 10-

(methoxymethoxy)-8-methyl-1-oxo-1,2,3,4-tetrahydropyrido[1,2-b]indazole-2-carboxylate.

Step E: Methyl 10-(methoxymethoxy)-8-methyl-1-oxo-2-phenyl-1,2,3,4-tetrahydropyrido[1,2-b]indazole-2-carboxylate

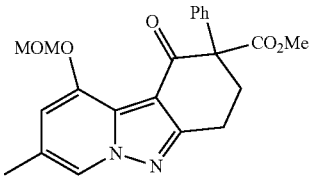

To a solution of methyl 10-(methoxymethoxy)-8-methyl-1-oxo-1,2,3,4-tetrahydropyrido[1,2-b]indazole-2-carboxylate (700 mg, 2.199 mmol) and diphenyliodonium chloride (835 mg, 2.64 mmol) in THF (17.5 ml) was added potassium tert-butoxide (2.5 ml, 2.500 mmol). It was stirred for 3 h at rt. LC-MS showed the formation of the desired product. It was quenched with ammonium chloride, extracted with ethyl acetate (2×50 mL), dried over sodium sulfate, filtered and concentrated. The residue was purified by ISCO (40 g, 0-100% ethyl acetate in hexane) to give the title compound. LCMS calc.=395.16; found=394.99 (M+H)$^+$. $^1$H NMR (499 MHz, CHCl$_3$-d): δ 8.01 (s, 1H), 7.27-7.34 (m, 5H), 6.98 (s, 1H), 5.37 (s, 2H), 3.77 (s, 3H), 3.60 (s, 3H), 3.02-3.07 (m, 2H), 2.74-2.82 (m, 2H), 2.37 (s, 3H).

Step F: Methyl 10-(methoxymethoxy)-8-methyl-2-phenyl-1,2,3,4-tetrahydropyrido[1,2-b]indazole-2-carboxylate

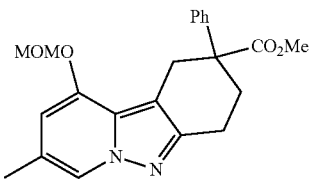

To a solution of methyl 10-(methoxymethoxy)-8-methyl-1-oxo-2-phenyl-1,2,3,4-tetrahydropyrido[1,2-b]indazole-2-carboxylate (770 mg, 1.952 mmol) in MeOH (7 ml) was added sodium borohydride (369 mg, 9.76 mmol) at room temperature in small portions over 2 h. It was concentrated and the residue was dispensed in water and ethyl acetate. The aqueous layer was extracted with ethyl acetate. The combined organic layers were washed with brine, dried over sodium sulfate, filtered and concentrated. The residue was dissolved in DCM (12 mL) and was added triethylsilane (1 mL, 6.26 mmol) and TFA (0.210 mL, 2.72 mmol) at rt. The reaction was stirred for 1 h, quenched with sat. aq. sodium bicarbonate and extracted with ethyl acetate (20 mL). The organic layer was separated and washed with brine, dried over sodium sulfate, filtered and concentrated. The residue was purified by ISCO (24 g, 0-40% ethyl acetate in hexane) to give methyl 10-(methoxymethoxy)-8-methyl-2-phenyl-1,2,3,4-tetrahydropyrido[1,2-b]indazole-2-carboxylate. LCMS calc.=381.18; found=381.01 (M+H)$^+$. $^1$H NMR (499 MHz, CHCl$_3$-d): δ 7.85 (s, 1H), 7.41 (d, 2H), 7.33 (t, 2H), 7.26 (t, 1H), 6.48 (s, 1H), 5.33 (s, 2H), 3.73 (d, 1H), 3.67 (s, 3H), 3.56 (s, 3H), 3.47 (d, 1H), 2.89-2.95 (m, 1H), 2.60-2.72 (m, 2H), 2.51 (ddd, 1H), 2.28 (s, 3H).

Step G: 10-(Methoxymethoxy)-8-methyl-2-phenyl-1,2,3,4-tetrahydropyrido[1,2-b]indazole-2-carboxylic acid

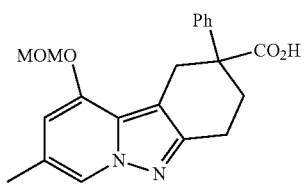

A suspension of methyl 10-(methoxymethoxy)-8-methyl-2-phenyl-1,2,3,4-tetrahydropyrido[1,2-b]indazole-2-carboxylate (500 mg, 1.314 mmol) in THF (4 ml) and MeOH (4 mL) was treated with 4 M LiOH (4 mL, 16.00 mmol) at 45° C. for 10 h. It was cooled to room temperature and was added 16 mL of 1 M HCl to adjust pH to about 5. It was extracted with ethyl acetate (3×40 mL). The combined organic layers was washed with brine (30 mL), dried over sodium sulfate, filtered and concentrated to give 10-(methoxymethoxy)-8-methyl-2-phenyl-1,2,3,4-tetrahydropyrido[1,2-b]indazole-2-carboxylic acid. LCMS calc.=367.17; found=366.87 (M+H)$^+$. $^1$H NMR (500 MHz, CHCl$_3$-d): ? 7.89 (s, 1H), 7.47 (d, 2H), 7.28-7.36 (m, 3H), 6.50 (s, 1H), 5.33 (s, 2H), 3.74 (d, 1H), 3.56 (s, 3H), 3.52 (d, 1H), 2.95-3.01 (m, 1H), 2.70 (t, 1H), 2.59-2.66 (m, 1H), 2.49-2.53 (m, 1H), 2.29 (s, 3H).

Step H: 10-(Methoxymethoxy)-8-methyl-2-phenyl-1,2,3,4-tetrahydropyrido[1,2-b]indazol-2-amine

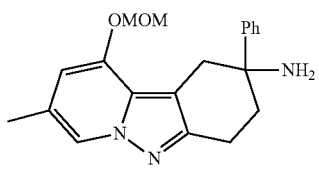

A solution of 10-(methoxymethoxy)-8-methyl-2-phenyl-1,2,3,4-tetrahydropyrido[1,2-b]indazole-2-carboxylic acid (482 mg, 1.315 mmol), diphenylphosphoryl azide (0.8 ml, 3.70 mmol) and DIEA (0.8 ml, 4.58 mmol) in toluene (12 ml) was heated to reflux for 10 h. It was cooled to rt and concentrated. The residue was dissolved in 3 mL of THF and treated with 3 mL of saturated LiOH for 1 h. LC-MS showed the formation of the desired product. It was diluted with brine (10 mL), extracted with 2-methylTHF (3×20 mL). The combined organic layer were washed with brine (10 mL), dried over sodium sulfate, filtered and concentrated. The residue suspension in DCM was loaded and purified by ISCO (40 g, 0-10% 2 M NH3/MeOH in DCM) to give the desired product, 10-(methoxymethoxy)-8-methyl-2-phenyl-1,2,3,4-tetrahydropyrido[1,2-b]indazol-2-amine. LCMS calc.=338.19; found=338.00 (M+H)$^+$.

Step I: 2-Chloro-N-(10-(methoxymethoxy)-8-methyl-2-phenyl-1,2,3,4-tetrahydropyrido[1,2-b]indazol-2-yl)-4-(4H-1,2,4-triazol-4-yl)benzamide

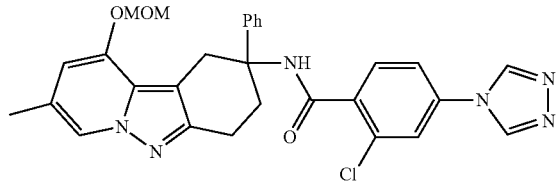

The general procedure of amide coupling described in the synthesis of EXAMPLE 7 was followed employing 10-(methoxymethoxy)-8-methyl-2-phenyl-1,2,3,4-tetrahydropyrido[1,2-b]indazol-2-amine (52 mg, 0.154 mmol) to afford the title compound. LCMS calc.=543.19; found=543.01 (M+H)$^+$. $^1$H NMR (499 MHz, CH$_3$OH-d$_4$): δ 9.24 (s, 2H), 8.89 (s, 1H), 7.90 (s, 1H), 7.84 (d, 1H), 7.60-7.66 (m, 3H), 7.52 (d, 1H), 7.39 (t, 2H), 7.29 (t, 1H), 6.62 (s, 1H), 5.29 (s, 2H), 3.66 (d, 1H), 3.47 (s, 3H), 3.41 (d, 1H), 3.10 (t, 2H), 2.90 (t, 1H), 2.49-2.55 (m, 1H), 2.29 (s, 3H).

Step J: 2-Chloro-N-(10-hydroxy-8-methyl-2-phenyl-1,2,3,4-tetrahydropyrido[1,2-b]indazol-2-yl)-4-(4H-1,2,4-triazol-4-yl)benzamide

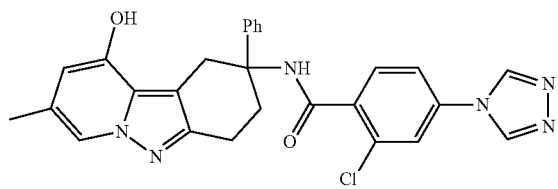 [SMILES: Cc1cc(O)c2c3c(nn2c1)CCC(NC(=O)c1ccc(-n2cnnc2)cc1Cl)(c1ccccc1)C3]

To a solution of 2-chloro-N-(10-(methoxymethoxy)-8-methyl-2-phenyl-1,2,3,4-tetrahydropyrido[1,2-b]indazol-2-yl)-4-(4H-1,2,4-triazol-4-yl)benzamide in THF (1.5 ml) was added concentrated HCl (300 μl, 3.65 mmol). It was sonicated for a few seconds to make a homogenous solution, which was stirred at room temperature for 3 h. It was concentrated to give 2-chloro-N-(10-hydroxy-8-methyl-2-phenyl-1,2,3,4-tetrahydropyrido[1,2-b]indazol-2-yl)-4-(4H-1,2,4-triazol-4-yl)benzamide hydrochloride. LCMS calc.=499.17; found=498.93 (M+H)$^+$. $^1$H NMR (499 MHz, CH$_3$OH-d$_4$): δ 9.78 (s, 2H), 9.05 (s, 1H), 8.06 (s, 1H), 7.93 (s, 1H), 7.76 (d, 1H), 7.62 (t, 3H), 7.42 (t, 2H), 7.32 (t, 1H), 6.72 (s, 1H), 3.73 (d, 1H), 3.48 (d, 1H), 3.11-3.20 (m, 2H), 2.96 (d, 1H), 2.60 (d, 1H), 2.36 (s, 3H).

Example 9 & 10

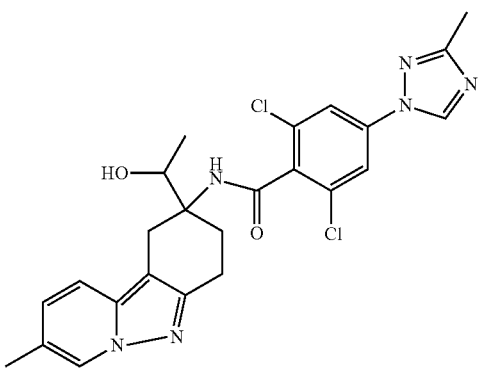 [SMILES: Cc1ccc2c3c(nn2c1)CCC(NC(=O)c1c(Cl)cc(-n2cnc(C)n2)cc1Cl)(C(C)O)C3]

2,6-Dichloro-N-(2-(1-hydroxyethyl)-8-methyl-1,2,3,4-tetrahydropyrido[1,2-b]indazol-2-yl)-4-(3-methyl-1H-1,2,4-triazol-1-yl)benzamide Step A: N-(2-Acetyl-8-methyl-1,2,3,4-tetrahydropyrido[1,2-b]indazol-2-yl)-2,6-dichloro-4-(3-methyl-1H-1,2,4-triazol-1-yl)benzamide The general procedure described in the synthesis of EXAMPLE 7 was followed employing 1-(2-amino-8-methyl-1,2,3,4-tetrahydropyrido[1,2-b]indazol-2-yl)ethanone (200 mg, 0.822 mmol) and 2,6-dichloro-4-(3-methyl-1H-1,2,4-triazol-1-yl)benzoic acid (317 mg, 1.028 mmol) to afford the title compound. LCMS calc.=497.13; found=497.04 (M+H)$^+$.

Step B: 2,6-Dichloro-N-(2-(1-hydroxyethyl)-8-methyl-1,2,3,4-tetrahydropyrido[1,2-b]indazol-2-yl)-4-(3-methyl-1H-1,2,4-triazol-1-yl)benzamide Sodium borohydride (35 mg, 0.925 mmol) was added to a stirred solution of N-(2-acetyl-8-methyl-1,2,3,4-tetrahydropyrido[1,2-b]indazol-2-yl)-2,6-dichloro-4-(3-methyl-1H-1,2,4-triazol-1-yl)benzamide (230 mg, 0.462 mmol) in THF (10 ml) and MeOH (5 ml) at 0° C. After a few minutes, the ice bath was removed and the reaction mixture was allowed to warm to room temperature stirring for 2.5 h. Another portion of sodium borohydride (35 mg) was added and the mixture was stirred for another 2 hours. It was quenched with water, and extracted with chloroform/isopropanol (3:1 v/v) three times. The combined organic fractions were washed with brine, dried over sodium sulfate, filtered and concentrated under reduced pressure. The residue was purified by MPLC (24 g silica gel column, 50% to 100% EA) to afford the title compound as a mixture of two diasteromers. It was separated by HPLC on chiral solid phase. LCMS calc.=499.14; found=499.13 (M+H)$^+$.

Example 26

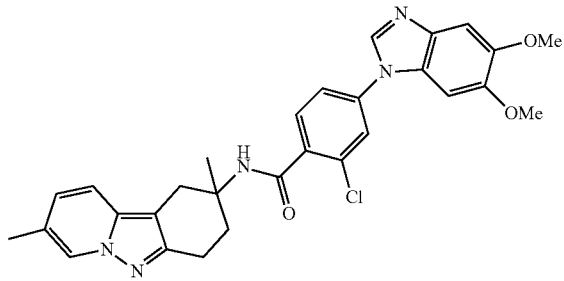 [SMILES: COc1cc2ncn(-c3ccc(C(=O)NC4(C)CCc5nn6cc(C)ccc6c5C4)c(Cl)c3)c2cc1OC]

2-Chloro-4-(5,6-dimethoxy-1H-benzo[d]imidazol-1-yl)-N-(2,8-dimethyl-1,2,3,4-tetrahydropyrido[1,2-b]indazol-2-yl)benzamide A clean dry microwave tube charged with a magnetic stirring bar and 5,6-dimethoxybenzimidazole (53.9 mg, 0.303 mmol) was sealed and purged with nitrogen. To the flask was added a solution of potassium tert-butoxide (37.7 mg, 0.336 mmol). The mixture was stirred at rt for 5 min, then it was added a solution of 2-chloro-N-(2,8-dimethyl-1,2,3,4-tetrahydropyrido[1,2-b]indazol-2-yl)-4-fluorobenzamide (25 mg, 0.067 mmol) in 1 mL of DMF. The mixture was heated by a microwave reactor at 150° C. for 20 min. It was purified by HPLC to afford the title compound. LCMS calc.=530.20; found=530.19 (M+H)+.

The following compounds were synthesized using methods analogous to those described above from commercially available materials or intermediates whose syntheses are described above.

| Ex. | Structure | hFIXa IC50 (nM) | Exact Mass [M + H]+ | LCMS [M + H]+ |
|---|---|---|---|---|
| 1 | 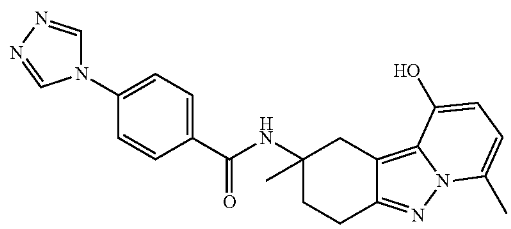 [SMILES: Cc1ccc(O)c2c3c(nn12)CCC(C)(NC(=O)c1ccc(-n2cnnc2)cc1)C3] | 506.8 | 403 | 402.98 |
| 2 | 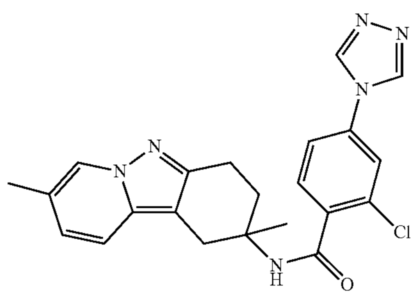 [SMILES: Cc1ccc2c3c(nn2c1)CCC(C)(NC(=O)c1ccc(-n2cnnc2)cc1Cl)C3] | 63.31 | 421.16 | 420.89 |
| 3 | 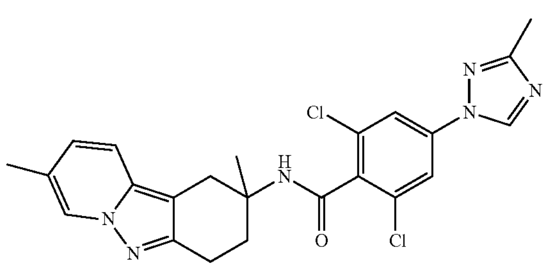 [SMILES: Cc1ccc2c3c(nn2c1)CCC(C)(NC(=O)c1c(Cl)cc(-n2cnc(C)n2)cc1Cl)C3] | 10.23 | 469.13 | 469.08 |

-continued

| Ex. | Structure | hFIXa IC50 (nM) | Exact Mass [M + H]+ | LCMS [M + H]+ |
|---|---|---|---|---|
| 4 | 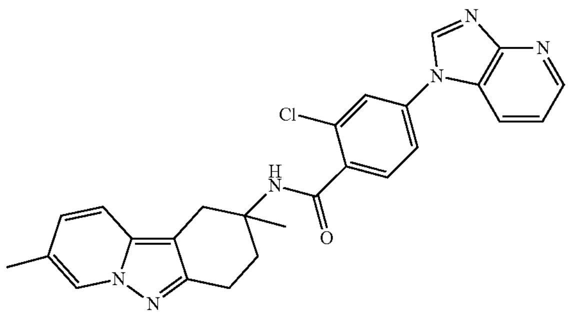 [SMILES: Cc1ccc2c3c(nn2c1)CCC(C)(NC(=O)c1ccc(-n2cnc4ncccc42)cc1Cl)C3] | 13.66 | 471.17 | 471.09 |
| 5 | 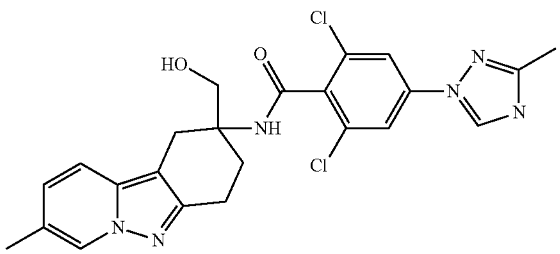 | 13.85 | 485.13 | 485.30 |
| 6 | 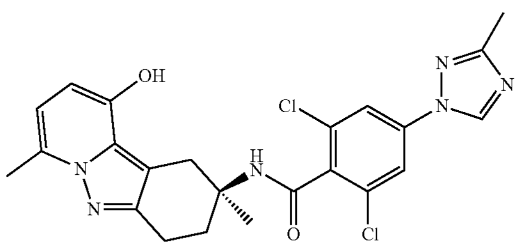 [SMILES: Cc1ncn(-c2cc(Cl)c(C(=O)N[C@@]3(C)CCc4nn5c(C)ccc(O)c5c4C3)c(Cl)c2)n1] | 12.12 | 485.13 | 485.09 |
| 7 | 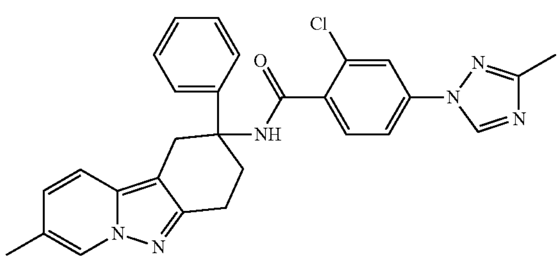 | 6.878 | 497.19 | 497.22 |
| 8 | 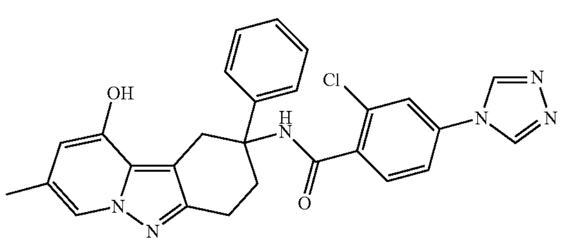 [SMILES: Cc1cc(O)c2c3c(nn2c1)CCC(NC(=O)c1ccc(-n2cnnc2)cc1Cl)(c1ccccc1)C3] | 9.793 | 499.16 | 499.26 |

-continued

| Ex. | Structure | hFIXa IC50 (nM) | Exact Mass [M + H]+ | LCMS [M + H]+ |
|---|---|---|---|---|
| 9 | 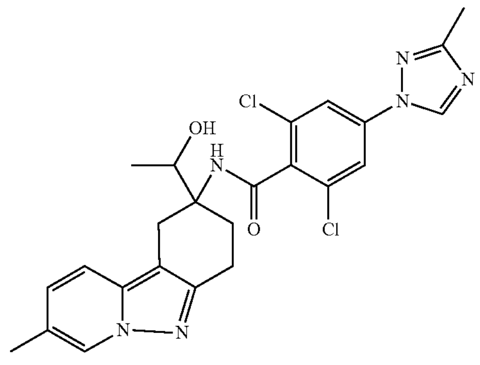 [SMILES: Cc1ccc2c3c(nn2c1)CCC(NC(=O)c1c(Cl)cc(-n2cnc(C)n2)cc1Cl)(C(C)O)C3] | 12.48 | 499.14 | 499.10 |
| 10 | 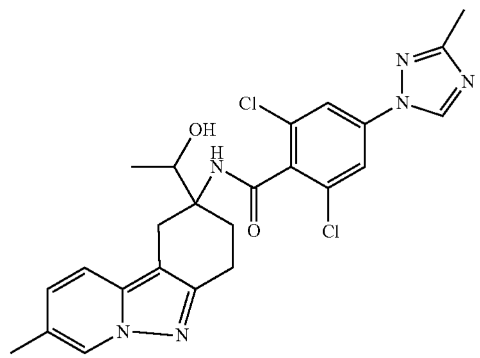 [SMILES: Cc1ccc2c3c(nn2c1)CCC(NC(=O)c1c(Cl)cc(-n2cnc(C)n2)cc1Cl)(C(C)O)C3] | 12.63 | 499.14 | 499.10 |
| 11 | 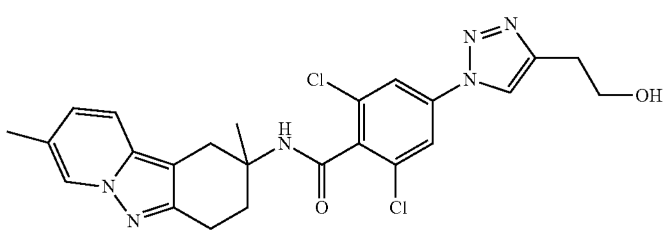 [SMILES: Cc1ccc2c3c(nn2c1)CCC(C)(NC(=O)c1c(Cl)cc(-n2cc(CCO)nn2)cc1Cl)C3] | 16.29 | 499.14 | |
| 12 | 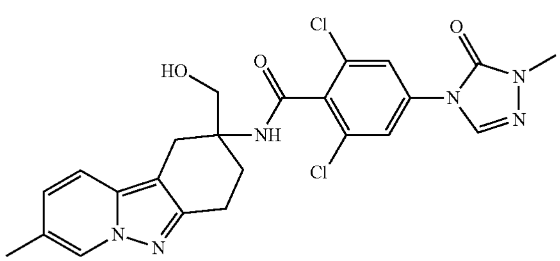 | 7.103 | 501.12 | 501.24 |
| 13 | 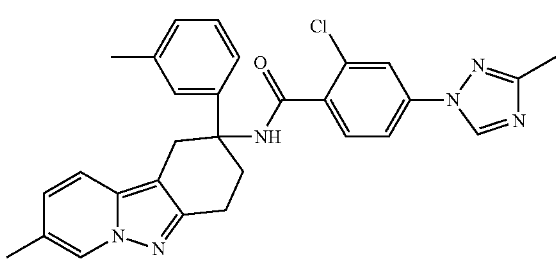 | 2.075 | 511.2 | 511.34 |

-continued

| Ex. | Structure | hFIXa IC50 (nM) | Exact Mass [M + H]+ | LCMS [M + H]+ |
|---|---|---|---|---|
| 14 | 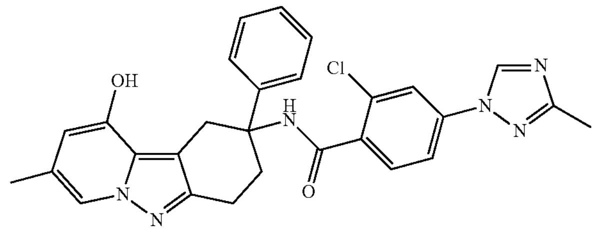 | 12.12 | 513.18 | 513.24 |
| 15 | 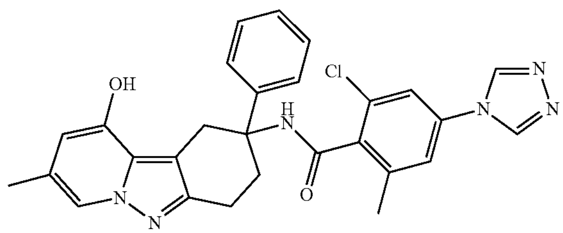 [SMILES: Cc1cc(O)c2c3c(nn2c1)CCC(NC(=O)c1c(C)cc(-n2cnnc2)cc1Cl)(c1ccccc1)C3] | 4.812 | 513.18 | 513.30 |
| 16 | 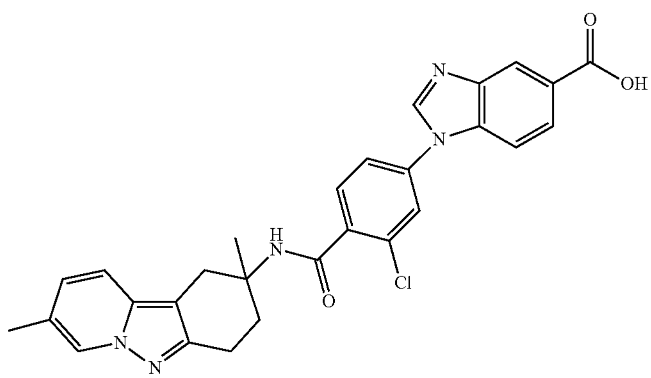 [SMILES: Cc1ccc2c3c(nn2c1)CCC(C)(NC(=O)c1ccc(-n2cnc4cc(C(=O)O)ccc42)cc1Cl)C3] | 10.54 | 514.16 | 514.06 |
| 17 | 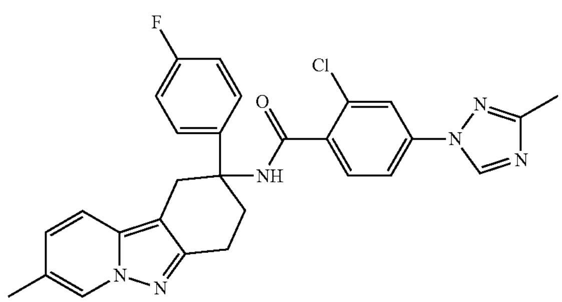 | 8.068 | 515.18 | 515.28 |
| 18 | 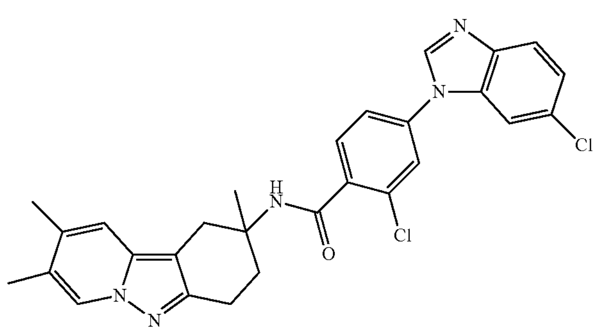 [SMILES: Cc1cc2c3c(nn2cc1C)CCC(C)(NC(=O)c1ccc(-n2cnc4ccc(Cl)cc42)cc1Cl)C3] | 16.29 | 518.15 | 517.89 |

-continued
| Ex. | Structure | hFIXa IC50 (nM) | Exact Mass [M + H]+ | LCMS [M + H]+ |
|---|---|---|---|---|
| 19 | 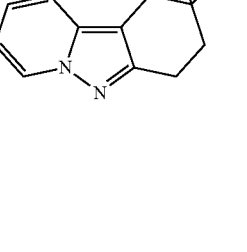 | 9.134 | 527.2 | NA |
| 20 | 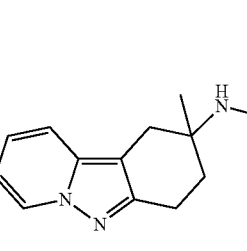 | 10.53 | 527.2 | 527.23 |
| 21 | 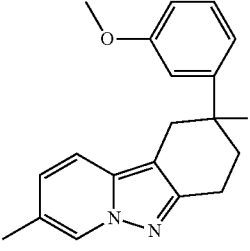 | 3.002 | 527.2 | 527.29 |
| 22 | 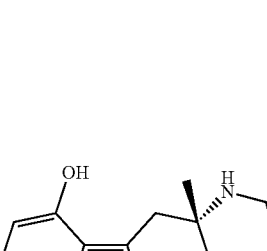 | 2.382 | 529.18 | 528.94 |

-continued
| Ex. | Structure | hFIXa IC50 (nM) | Exact Mass [M + H]+ | LCMS [M + H]+ |
|---|---|---|---|---|
| 23 | 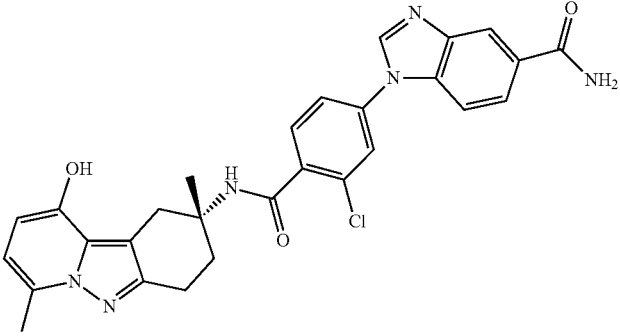 [SMILES: Cc1ccc(O)c2c3c(nn12)CC[C@@](C)(NC(=O)c1ccc(-n2cnc4cc(C(N)=O)ccc42)cc1Cl)C3] | 2.441 | 529.18 | 528.87 |
| 24 | 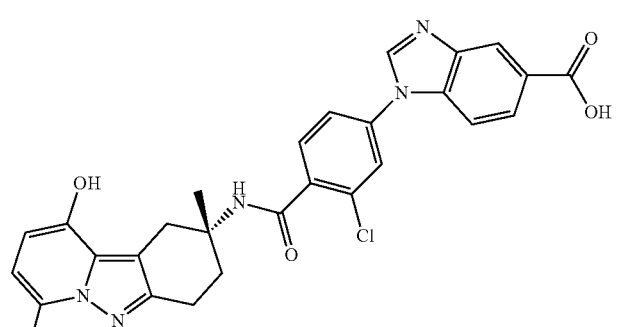 | 2.783 | 530.16 | 529.78 |
| 25 | 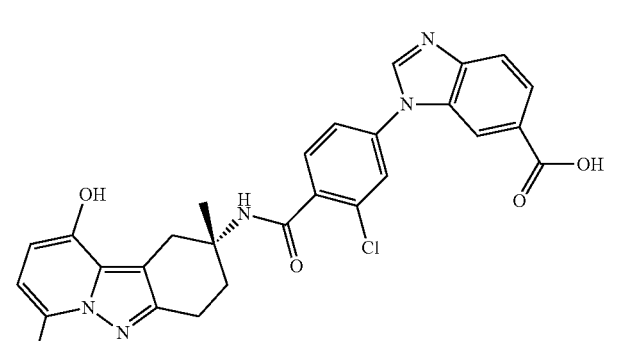 | 4.876 | 530.16 | 529.72 |
| 26 | 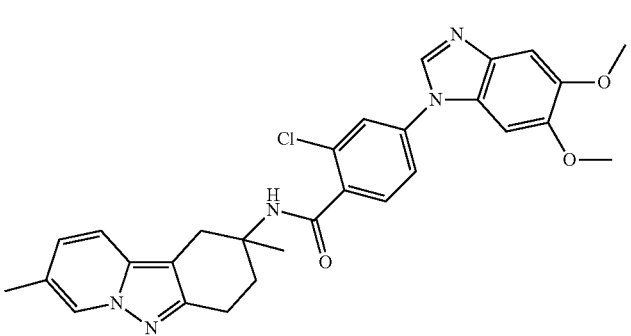 | 3.565 | 530.2 | 530.19 |

-continued

| Ex. | Structure | hFIXa IC50 (nM) | Exact Mass [M + H]+ | LCMS [M + H]+ |
|---|---|---|---|---|
| 27 | 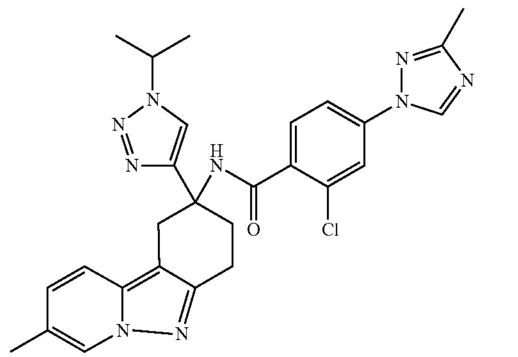 [SMILES: Cc1ccc2c3c(nn2c1)CCC(NC(=O)c1ccc(-n2cnc(C)n2)cc1Cl)(c1cn(C(C)C)nn1)C3] | 17.86 | 530.22 | 530.02 |
| 28 | 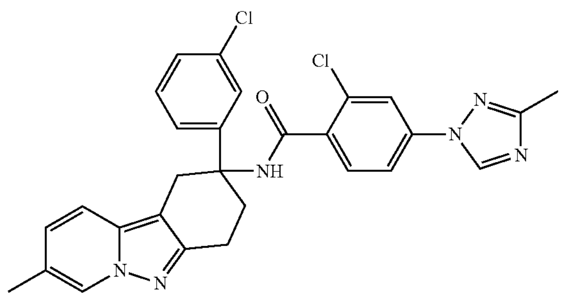 | 2.631 | 531.15 | 531.20 |
| 29 | 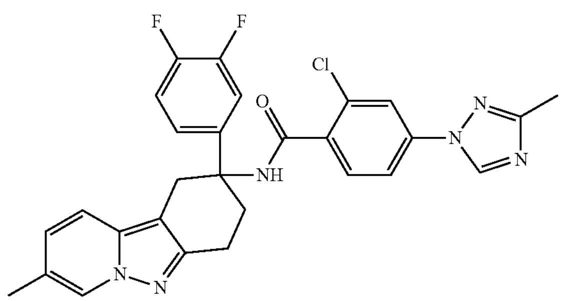 | 15.99 | 533.17 | 533.27 |
| 30 | 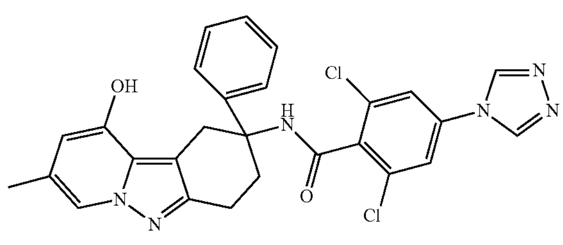 [SMILES: Cc1cc(O)c2c3c(nn2c1)CCC(NC(=O)c1c(Cl)cc(-n2cnnc2)cc1Cl)(c1ccccc1)C3] | 3.655 | 533.13 | 533.26 |
| 31 | 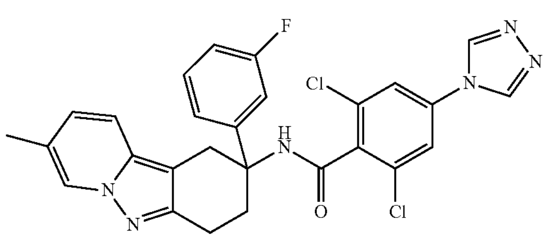 [SMILES: Cc1ccc2c3c(nn2c1)CCC(NC(=O)c1c(Cl)cc(-n2cnnc2)cc1Cl)(c1cccc(F)c1)C3] | 6.945 | 535.12 | 535.11 |

-continued

| Ex. | Structure | hFIXa IC50 (nM) | Exact Mass [M + H]+ | LCMS [M + H]+ |
|---|---|---|---|---|
| 32 | 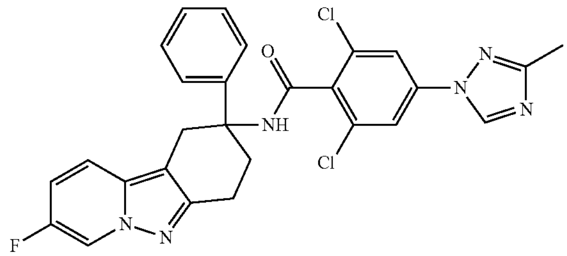 [SMILES: Cc1ncn(-c2cc(Cl)c(C(=O)NC3(c4ccccc4)CCc4nn5cc(F)ccc5c4C3)c(Cl)c2)n1] | 17.7 | 535.12 | 535.22 |
| 33 | 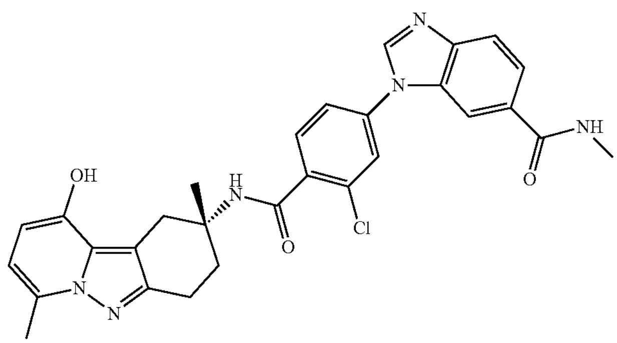 [SMILES: CNC(=O)c1ccc2ncn(-c3ccc(C(=O)N[C@]4(C)CCc5nn6c(C)ccc(O)c6c5C4)c(Cl)c3)c2c1] | 6.924 | 543.19 | 542.83 |
| 34 | 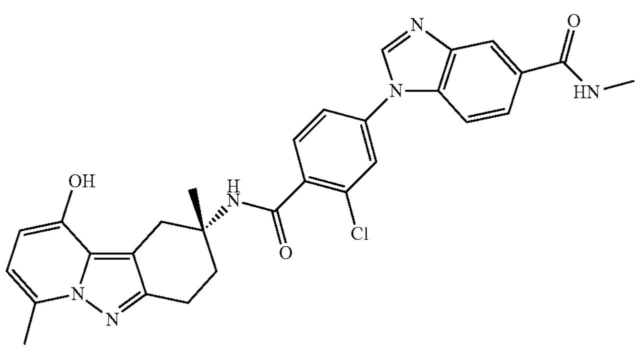 [SMILES: CNC(=O)c1ccc2c(c1)ncn2-c1ccc(C(=O)N[C@]2(C)CCc3nn4c(C)ccc(O)c4c3C2)c(Cl)c1] | 5.336 | 543.19 | 542.83 |
| 35 | 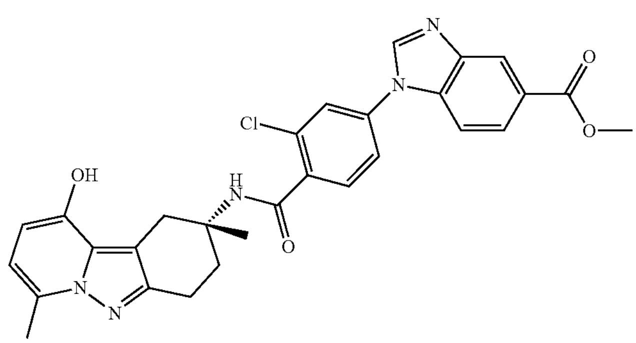 [SMILES: COC(=O)c1ccc2c(c1)ncn2-c1ccc(C(=O)N[C@]2(C)CCc3nn4c(C)ccc(O)c4c3C2)c(Cl)c1] | 5.963 | 544.17 | 543.89 |

-continued

| Ex. | Structure | hFIXa IC50 (nM) | Exact Mass [M + H]+ | LCMS [M + H]+ |
|---|---|---|---|---|
| 36 | 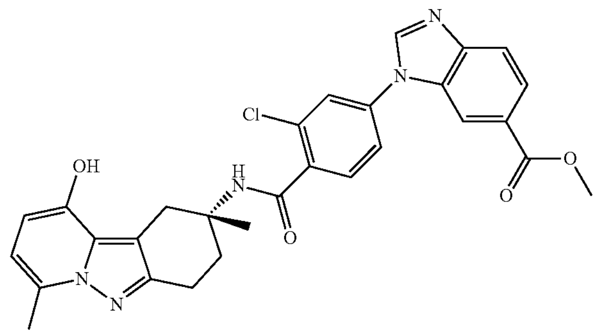 [SMILES: COC(=O)c1ccc2ncn(-c3ccc(C(=O)N[C@]4(C)CCc5nn6c(C)ccc(O)c6c5C4)c(Cl)c3)c2c1] | 11.1 | 544.17 | 543.94 |
| 37 | 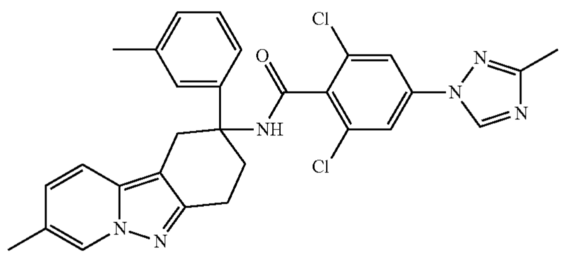 | 1.839 | 545.16 | 545.17 |
| 38 | 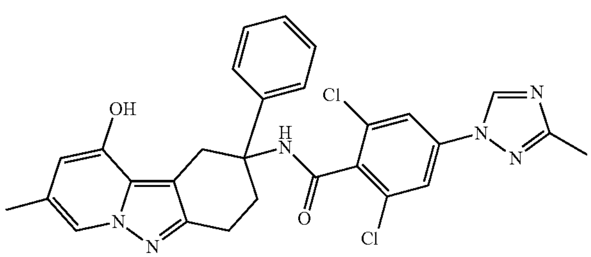 | 10.88 | 547.14 | 547.28 |
| 39 | 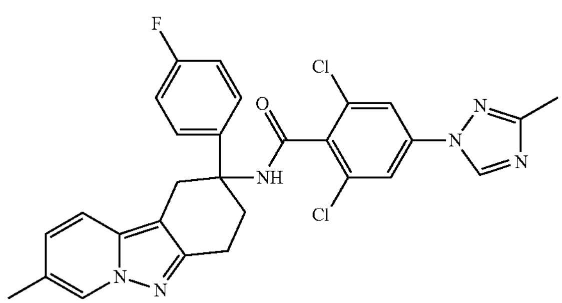 | 4.24 | 549.14 | 549.24 |
| 40 | 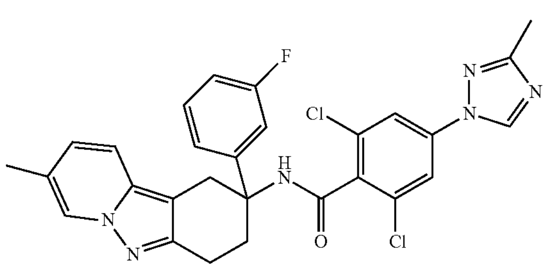 [SMILES: Cc1ccc2c3c(nn2c1)CCC(NC(=O)c1c(Cl)cc(-n2cnc(C)n2)cc1Cl)(c1cccc(F)c1)C3] | 6.622 | 549.14 | NA |

-continued

| Ex. | Structure | hFIXa IC50 (nM) | Exact Mass [M + H]+ | LCMS [M + H]+ |
|---|---|---|---|---|
| 41 | 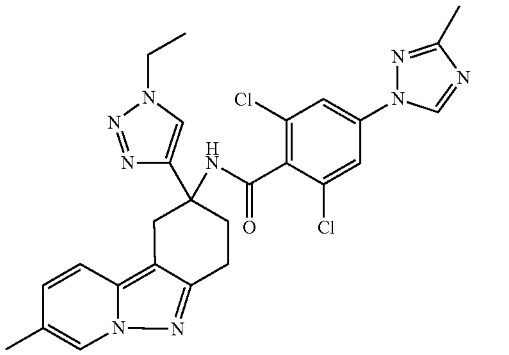 [SMILES: CCn1cc(C2(NC(=O)c3c(Cl)cc(-n4cnc(C)n4)cc3Cl)CCc3nn4cc(C)ccc4c3C2)nn1] | 7.844 | 550.16 | 550.16 |
| 42 | 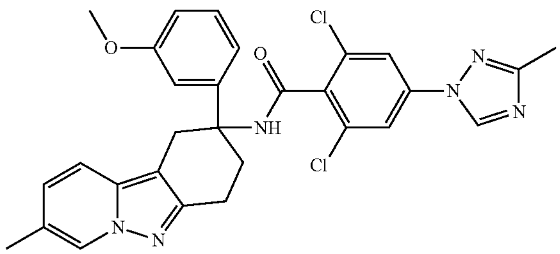 | 2.924 | 561.16 | 561.34 |
| 43 | 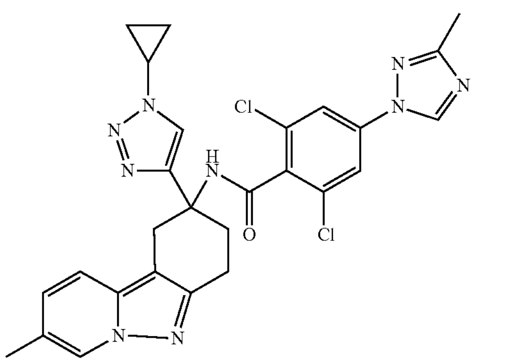 [SMILES: Cc1ccc2c3c(nn2c1)CCC(NC(=O)c1c(Cl)cc(-n2cnc(C)n2)cc1Cl)(c1cn(C2CC2)nn1)C3] | 10.26 | 562.16 | 562.10 |
| 44 | 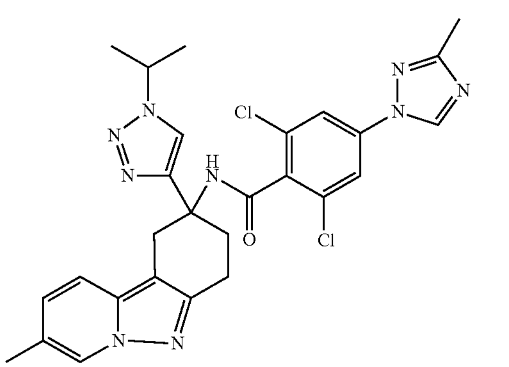 [SMILES: Cc1ccc2c3c(nn2c1)CCC(NC(=O)c1c(Cl)cc(-n2cnc(C)n2)cc1Cl)(c1cn(C(C)C)nn1)C3] | 5.047 | 564.18 | 564.12 |

-continued

| Ex. | Structure | hFIXa IC50 (nM) | Exact Mass [M + H]+ | LCMS [M + H]+ |
|---|---|---|---|---|
| 45 | 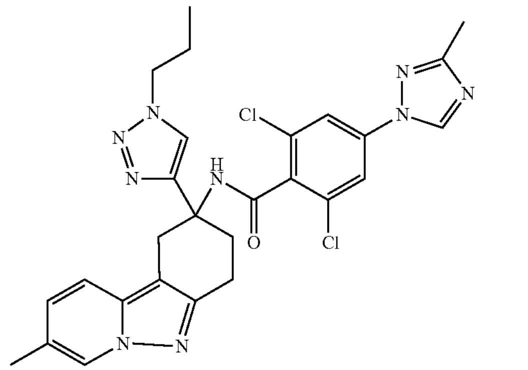 [SMILES: CCCn1cc(C2(NC(=O)c3c(Cl)cc(-n4cnc(C)n4)cc3Cl)CCc3nn4cc(C)ccc4c3C2)nn1] | 7.799 | 564.18 | 564.25 |
| 46 | 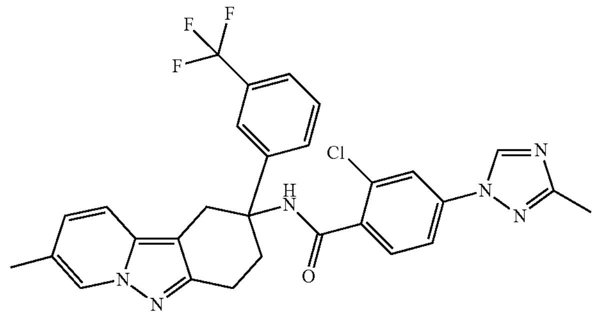 | 4.836 | 565.17 | 565.18 |
| 47 | 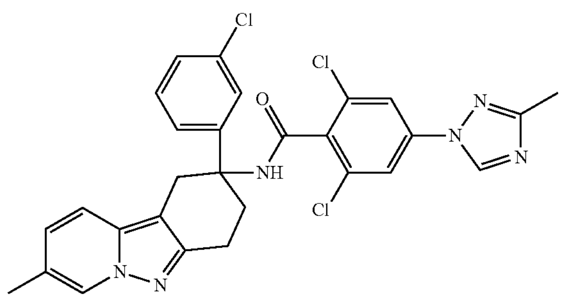 | 3.143 | 565.11 | 567.10 |
| 48 | 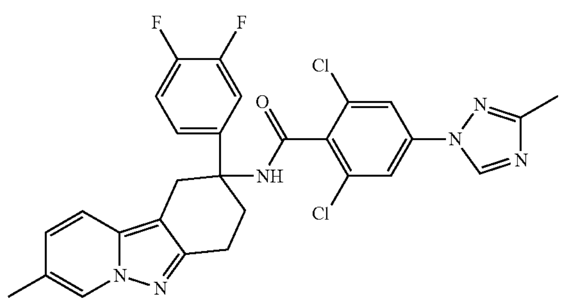 | 10.51 | 567.13 | 567.23 |
| 49 | 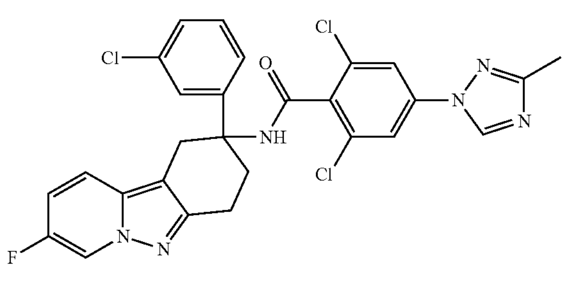 [SMILES: Cc1ncn(-c2cc(Cl)c(C(=O)NC3(c4cccc(Cl)c4)CCc4nn5cc(F)ccc5c4C3)c(Cl)c2)n1] | 17.26 | 569.08 | 571.23 |

-continued

| Ex. | Structure | hFIXa IC50 (nM) | Exact Mass [M + H]+ | LCMS [M + H]+ |
|---|---|---|---|---|
| 50 | 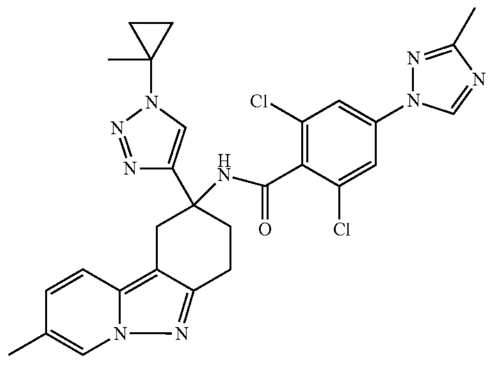 [SMILES: Cc1ccc2c3c(nn2c1)CCC(NC(=O)c1c(Cl)cc(-n2cnc(C)n2)cc1Cl)(c1cn(C2(C)CC2)nn1)C3] | 11.35 | 576.18 | 576.13 |
| 51 | 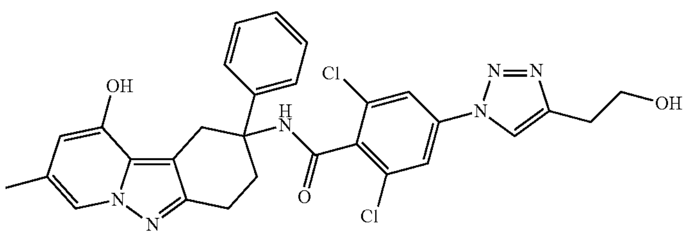 [SMILES: Cc1cc(O)c2c3c(nn2c1)CCC(NC(=O)c1c(Cl)cc(-n2cc(CCO)nn2)cc1Cl)(c1ccccc1)C3] | 5.306 | 577.15 | 577.28 |
| 52 | 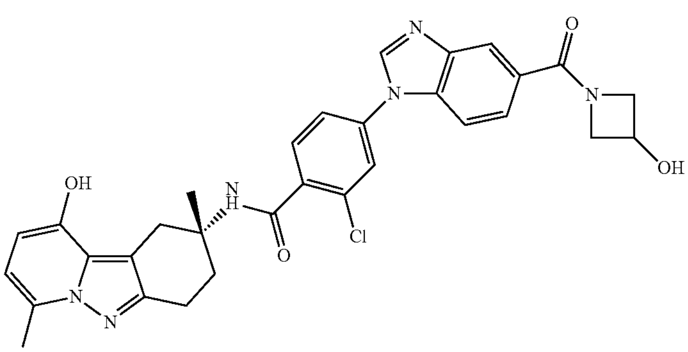 [SMILES: Cc1ccc(O)c2c3c(nn12)CC[C@@](C)(NC(=O)c1ccc(-n2cnc4cc(C(=O)N5CC(O)C5)ccc42)cc1Cl)C3] | 16.12 | 585.2 | 585.26 |
| 53 | 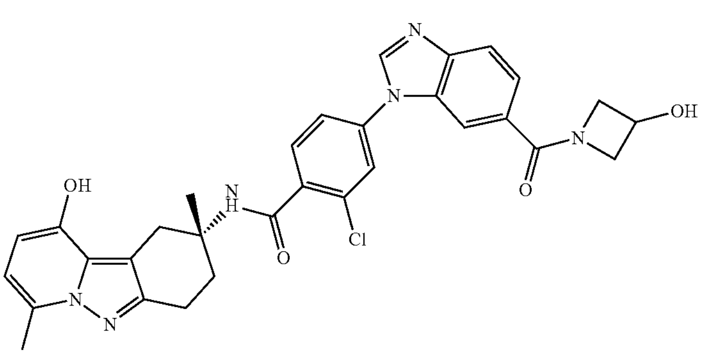 [SMILES: Cc1ccc(O)c2c3c(nn12)CC[C@@](C)(NC(=O)c1ccc(-n2cnc4ccc(C(=O)N5CC(O)C5)cc42)cc1Cl)C3] | 4.029 | 585.2 | 585.00 |

| Ex. | Structure | hFIXa IC50 (nM) | Exact Mass [M + H]+ | LCMS [M + H]+ |
|---|---|---|---|---|
| 54 | 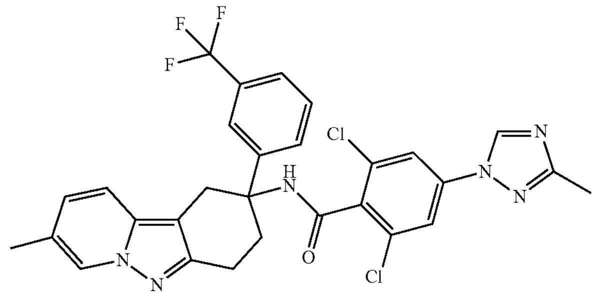 | 4.46 | 599.13 | 599.16 |

Example 65

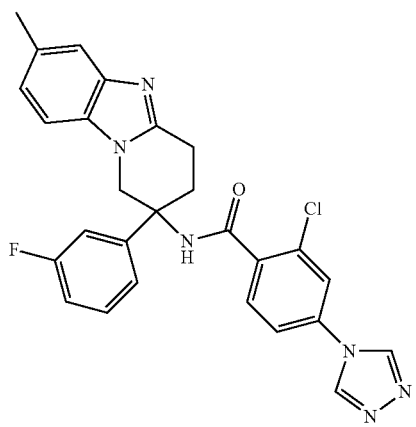 [SMILES: Cc1ccc2c(c1)nc1n2CC(NC(=O)c2ccc(-n3cnnc3)cc2Cl)(c2cccc(F)c2)CC1]

2-chloro-N-(2-(3-fluorophenyl)-7-methyl-1,2,3,4-tetrahydrobenzo[4,5]imidazo[1,2-a]pyridin-2-yl)-4-(4H-1,2,4-triazol-4-yl)benzamide

Step A. 3-(3-fluorophenyl)-6-oxopiperidine-3-carboxylic acid

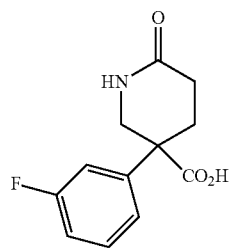 [SMILES: O=C1CCC(C(=O)O)(c2cccc(F)c2)CN1]

To a solution of ethyl 3-(3-fluorophenyl)-6-oxopiperidine-3-carboxylate (1 g, 3.77 mmol) in a 3:1 solution of tetrahydrofuran/methanol (25.13 mL) was added an aqueous solution of lithium hydroxide (0.271 g, 11.31 mmol) in 6.28 mL water and the resulting mixture was stirred at room temperature for 1 h. The solution was concentrated to remove volatiles and then diluted with 6N aqueous HCl to pH 3. The resultant mixture was extracted with 3:1 solution of chloroform/IPA (×3), dried over magnesium sulfate, filtered and concentrated under reduced pressure to afford 3-(3-fluorophenyl)-6-oxopiperidine-3-carboxylic acid without purification. MS: 238.0 (M+1).

Step B. enzyl (3-(3-fluorophenyl)-6-oxopiperidin-3-yl)carbamate

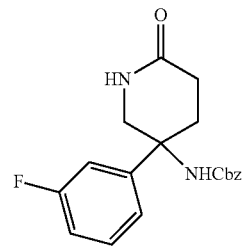 [SMILES: O=C1CCC(NC(=O)OCc2ccccc2)(c2cccc(F)c2)CN1]

To a stirred solution of 3-(3-fluorophenyl)-6-oxopiperidine-3-carboxylic acid (0.633 g, 2.67 mmol) in toluene (15 mL, 0.18M) was added triethylamine (0.0.744 mL, 5.34 mmol) followed by DPPA (0.652 mL, 2.94 mmol) and the resulting solution was allowed to continue stirring at room temperature. After 4 h, benzyl alcohol (1.387 mL, 13.34 mmol) was added and the resulting mixture was heated overnight at 90° C. The reaction was cooled to room temperature and concentrated under reduced pressure and the resulting residue was purified directly by normal phase HPLC (ISCO RediSep Rf, 24 g, gradient elution, 0-10% MeOH/DCM) to yield benzyl (3-(3-fluorophenyl)-6-oxopiperidin-3-yl)carbamate. MS: 343.1 (M+1).

Step C. benzyl (3-(3-fluorophenyl)-1-(4-methyl-2-nitrophenyl)-6-oxopiperidin-3-yl)carbamate

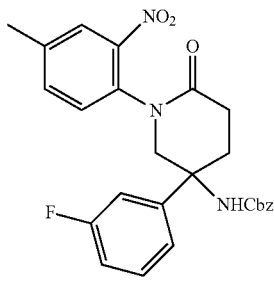 [SMILES: Cc1ccc(N2CC(NC(=O)OCc3ccccc3)(c3cccc(F)c3)CCC2=O)c([N+](=O)[O-])c1]

A mixture benzyl (3-(3-fluorophenyl)-6-oxopiperidin-3-yl)carbamate (0.100 g, 0.292 mmol), 1-bromo-4-methyl-2-nitrobenzene (0.069 g, 0.321 mmol), XantPhos (0.0169 g, 0.029 mmol), tris(dibenzylideneacetone)dipalladium(0) (0.0134 g, 0.015 mmol) and cesium carbonate (0.190 g, 0.584 mmol) was degassed, purged with nitrogen and diluted with 1 mL toluene. The resulting mixture was allowed to stir for 3 h at 90° C. The reaction was allowed to cool to room temperature and then filtered over a pad of celite washing with 3:1 solution of chloroform/IPA. The filtrate was concentrated under reduced pressure and the resulting residue was purified directly by normal phase HPLC (ISCO RediSep Rf, 12 g, gradient elution, 0-60% EtOAc/Hexane) to yield benzyl (3-(3-fluorophenyl)-1-(4-methyl-2-nitrophenyl)-6-oxopiperidin-3-yl)carbamate. MS: 478.0 (M+1).

Step D. benzyl (2-(3-fluorophenyl)-7-methyl-1,2,3,4-tetrahydrobenzo[4,5]imidazo[1,2-a]pyridin-2-yl)carbamate

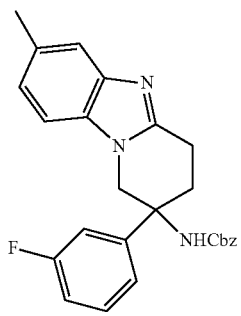 [SMILES: Cc1ccc2c(c1)nc1n2CC(NC(=O)OCc2ccccc2)(c2cccc(F)c2)CC1]

To a stirred solution of benzyl (3-(3-fluorophenyl)-1-(4-methyl-2-nitrophenyl)-6-oxopiperidin-3-yl)carbamate (0.116 g, 0.243 mmol) in acetic acid (0.695 mL, 12.15 mmol) was added iron (0.136 mg, 2.429 mmol) and the resulting mixture was allowed to stir for 1 h at 120° C. The reaction was allowed to cool to room temperature and then filtered over a pad of celite washing with EtOAc. The filtrate was concentrated under reduced pressure and the resulting residue was diluted with 3:1 chloroform/IPA. The resulting solution was free-based with aqueous NaHCO$_3$. The organic layer was separated, dried over MgSO$_4$, filtered and concentrated under reduced pressure to afford benzyl (2-(3-fluorophenyl)-7-methyl-1,2,3,4-tetrahydrobenzo[4,5]imidazo[1,2-a]pyridin-2-yl)carbamate without purification. MS: 430.0 (M+1).

Step E. 2-(3-fluorophenyl)-7-methyl-1,2,3,4-tetrahydrobenzo[4,5]imidazo[1,2-a]pyridin-2-amine

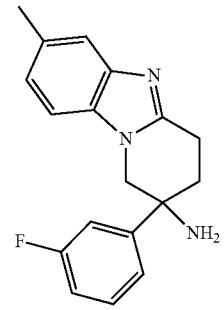 [SMILES: Cc1ccc2c(c1)nc1n2CC(N)(c2cccc(F)c2)CC1]

To a stirred solution of benzyl (2-(3-fluorophenyl)-7-methyl-1,2,3,4-tetrahydrobenzo[4,5]imidazo[1,2-a]pyridin-2-yl)carbamate (0.079 g, 0.184 mmol) in MeOH (1 mL) was added a catalytic amount of PdOH/C (0.0129 g, 0.018 mmol) and the resultant solution was degassed with N$_2$ and evacuated. A balloon atmosphere of H$_2$ was applied and the resultant mixture was stirred for 3 h. The solution was filtered over a pad of celite washing with DCM and MeOH. The filtrate was concentrated under reduced pressure to afford 2-(3-fluorophenyl)-7-methyl-1,2,3,4-tetrahydrobenzo[4,5]imidazo[1,2-a]pyridin-2-amine without purification. MS: 296.0 (M+1).

Step F. 2-chloro-N-(2-(3-fluorophenyl)-7-methyl-1,2,3,4-tetrahydrobenzo[4,5]imidazo[1,2-a]pyridin-2-yl)-4-(4H-1,2,4-triazol-4-yl)benzamide

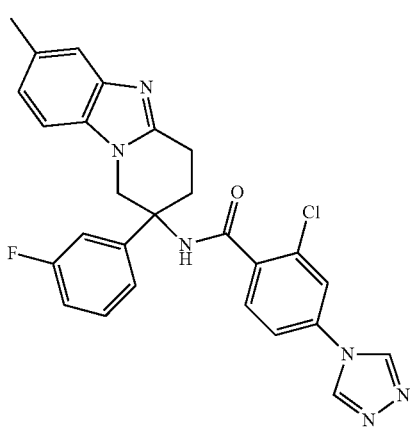 [SMILES: Cc1ccc2c(c1)nc1n2CC(NC(=O)c2ccc(-n3cnnc3)cc2Cl)(c2cccc(F)c2)CC1]

To a stirred solution of 2-(3-fluorophenyl)-7-methyl-1,2,3,4-tetrahydrobenzo[4,5]imidazo[1,2-a]pyridin-2-amine (0.0594 g, 0.201 mmol) and 2-chloro-4-(4H-1,2,4-triazol-4-yl)benzoic acid (0.045 g, 0.201 mmol) in 2 mL DMF was added sequentially HOAt (0.0356 mg, 0.262 mmol), EDC (0.0502 mg, 0.262 mmol), pyridine (0.0326 mL, 0.402 mmol), and DMAP (0.0012 g, 0.0101 mmol) and the resulting mixture was allowed to continue stirring for 3 h. The resulting solution was purified directly by reverse phase HPLC (Xterra, C18, 19×100 mm, gradient elution, 10-70% acetonitrile/water with 0.1% TFA) to yield a mixture of two enantiomers. This mixture was separated by chiral preparative SFC to afford 2-chloro-N-(2-(3-fluorophenyl)-7-methyl-1,2,3,4-tetrahydrobenzo[4,5]imidazo[1,2-a]pyridin-2-yl)-4-(4H-1,2,4-triazol-4-yl)benzamide. MS: 501.04 (M+1). $^1$H NMR (500 MHz, CD$_3$OD) δ 9.04 (s, 2H), 7.82 (s, 1H), 7.66-7.63 (m, 1H), 7.50-7.33 (m, 6H), 7.14-7.09 (m, 2H), 4.50-4.47 (m, 2H), 3.23-3.09 (m, 2H), 2.70-2.67 (m, 1H), 2.05-2.02 (m, 1H).

Example 67

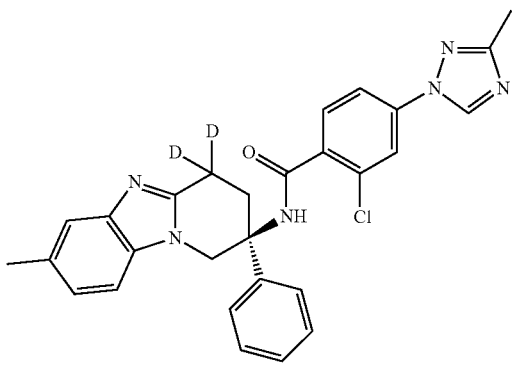

2-chloro-N-[(2S)-7-methyl-2-phenyl(4,4-d$_2$)-1,2,3,4-tetrahydropyrido[1,2-a]benzimidazol-2-yl]-4-(3-methyl-1H-1,2,4-triazol-1-yl)benzamide Step 1. (S)-benzyl (4,4-d$_2$-7-methyl-2-phenyl-1,2,3,4-tetrahydrobenzo[4,5]imidazo[1,2-a]pyridin-2-yl)carbamate To (S)-benzyl (1-(4-methyl-2-nitrophenyl)-6-oxo-3-phenylpiperidin-3-yl)carbamate (85 mg, 0.185 mmol) in D-Acetic Acid (3 ml) was stirred at 100° C. for 3 hours, LCMS showed bis-deuteration. Iron (20.66 mg, 0.370 mmol) was added into the reaction mixture. After stirring at 65° C. for 2 h, the mixture was cooled, diluted with dichloromethane, filtered through a pad of celite, washed with ice aqueous sodium hydrogen carbonate, dried over Na$_2$SO$_4$, filtered and the solvent was evaporated under reduced pressure to give (S)-benzyl (4,4-d$_2$-7-methyl-2-phenyl-1,2,3,4-tetrahydrobenzo[4,5]imidazo[1,2-a]pyridin-2-yl)carbamate. LCMS 414.22 (M+H)

Step 2. (S)-4,4-d$_2$-7-methyl-2-phenyl-1,2,3,4-tetrahydrobenzo[4,5]imidazo[1,2-a]pyridin-2-amine To the mixture of (S)-benzyl (4,4-d$_2$-7-methyl-2-phenyl-1,2,3,4-tetrahydrobenzo[4,5]imidazo[1,2-a]pyridin-2-yl)carbamate (70 mg, 0.169 mmol) in MeOH (2 ml) was added dihydroxypalladium (23.77 mg, 0.169 mmol) under H$_2$ balloon at r.t. in MeOH overnight. It was filtered and purified by Prep. TLC with 8% MeOH in CH$_2$Cl$_2$ to give (S)-4,4-d$_2$-7-methyl-2-phenyl-1,2,3,4-tetrahydrobenzo[4,5]imidazo[1,2-a]pyridin-2-amine. LCMS 280.30 (M+H)$^+$, $^1$H NMR (500 MHz, CD$_3$OD): $^1$H NMR (500 MHz, CD$_3$OD): 7.50 (m, 2H); 7.38 (m, 4H); 7.30 (m, 1H); 7.10 (m, 1H); 4.52 (m, 1H); 4.17 (m, 1H); 2.52 (m, 1H); 2.42 (s, 3H); 2.24 (m, 1H).

Step 3. 2-chloro-N-[(2S)-7-methyl-2-phenyl(4,4-d$_2$)-1,2,3,4-tetrahydropyrido[1,2-a]benzimidazol-2-yl]-4-(3-methyl-1H-1,2,4-triazol-1-yl)benzamide To dissolved 2-chloro-4-(3-methyl-1H-1,2,4-triazol-1-yl) benzoic acid (6.38 mg, 0.027 mmol) in DMF (0.5 ml) was added N1-((ethylimino)methylene)-N3,N3-dimethylpropane-1,3-diamine hydrochloride, EDC (5.15 mg, 0.027 mmol), 3H-[1,2,3]triazolo[4,5-b]pyridin-3-ol, HOAt (3.65 mg, 0.027 mmol) and stirred at r.t. for 10 min. Then, added (S)-4,4-d$_2$-7-methyl-2-phenyl-1,2,3,4-tetrahydrobenzo[4,5] imidazo[1,2-a]pyridin-2-amine (5 mg, 0.018 mmol) in DMF (0.5 ml) into above mixture and stirred at r.t. for 1.5 hr. The residue was purified by preparative HPLC Reverse phase (C-18), eluting with Acetonitrile/Water+0.1% TFA. It was purified again by Prep. TLC (8% MeOH in CH$_2$Cl$_2$) to give pure 2-chloro-N-[(2S)-7-methyl-2-phenyl(4,4-d)-1,2,3,4-tetrahydropyrido[1,2-a]benzimidazol-2-yl]-4-(3-methyl-1H-1,2,4-triazol-1-yl)benzamide. LCMS 499.16 (M+H)$^+$, $^1$H NMR (500 MHz, CD$_3$OD): 9.00 (s, 1H); 7.88 (s, 1H); 7.78 (m, 1H); 7.63 (m, 2H); 7.35-7.50 (m, 6H); 7.10 (m, 1H); 4.96 (m, 1H); 4.50 (m, 1H); 3.10 (m, 1H); 2.68 (m, 1H); 2.42 (s, 3H); 2.40 (s, 3H).

Example 104

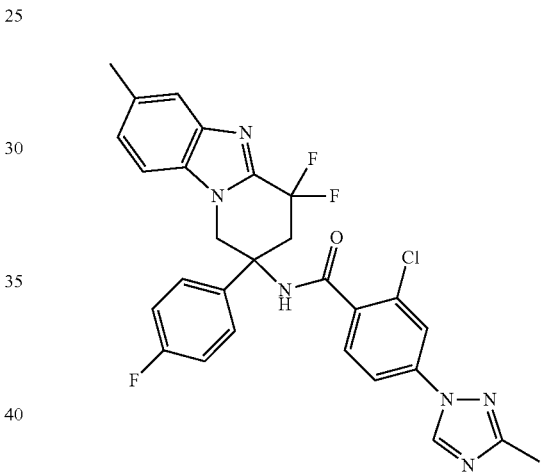

2-chloro-N-(4,4-difluoro-2-(4-fluorophenyl)-7-methyl-1,2,3,4-tetrahydrobenzo[4,5]imidazo[1,2-a]pyridin-2-yl)-4-(3-methyl-1H-1,2,4-triazol-1-yl)benzamide Step A. tert-butyl 3-(4-fluorophenyl)-1-(4-methyl-2-nitrophenyl)-6-oxopiperidine-3-carboxylate

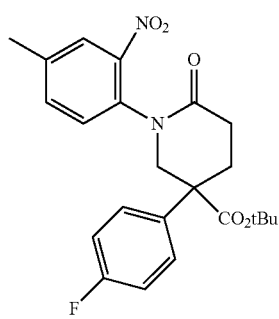 [SMILES: Cc1ccc(N2CC(C(=O)OC(C)(C)C)(c3ccc(F)cc3)CCC2=O)c([N+](=O)[O-])c1]

A mixture of tert-butyl 3-(4-fluorophenyl)-6-oxopiperidine-3-carboxylate (0.500 g, 1.71 mmol), 1-bromo-4-methyl-2-nitrobenzene (0.387 g, 1.79 mmol), XantPhos (0.099 g, 0.170 mmol), tris(dibenzylideneacetone)dipalladium(0) (0.078 g, 0.085 mmol) and cesium carbonate (1.111 g, 3.41 mmol) was degassed, purged with nitrogen and diluted with 5 mL toluene. The resulting mixture was allowed to stir for 3 h at 80° C. The reaction was allowed to cool to room temperature and then filtered over a pad of celite washing with 3:1 solution of chloroform/IPA. The filtrate was concentrated under reduced pressure and the resulting residue was purified directly by normal phase HPLC (ISCO RediSep Rf, 12 g, gradient elution, 0-60% EtOAc/Hexane) to yield tert-butyl 3-(4-fluorophenyl)-1-(4-methyl-2-nitrophenyl)-6-oxopiperidine-3-carboxylate. MS: 429.09 (M+1).

Step B. tert-butyl 5,5-difluoro-3-(4-fluorophenyl)-1-(4-methyl-2-nitrophenyl)-6-oxopiperidine-3-carboxylate

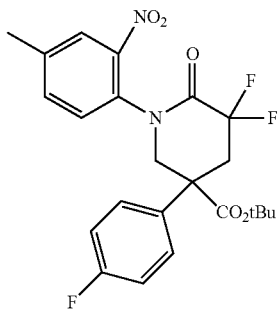 [SMILES: Cc1ccc(N2CC(C(=O)OC(C)(C)C)(c3ccc(F)cc3)CC(F)(F)C2=O)c([N+](=O)[O-])c1]

A solution of tert-butyl 3-(4-fluorophenyl)-1-(4-methyl-2-nitrophenyl)-6-oxopiperidine-3-carboxylate (0.508 g, 1.19 mmol) in tetrahydrofuran (6 mL, 0.2 M) was cooled to −78° C. with stirring and under an atmosphere of nitrogen. To this cooled solution was added 1M LiHMDS (3.32 mL, 3.32 mmol) in THF. After continued stirring for 45 min, a solution of n-fluorobenzenesulfonimide (0.935 g, 2.96 mmol) in THF (2 mL, 1.5 M) was added dropwise and the mixture was stirred for additional 2 hr. The solution was warmed to −20° C. After 30 min, the reaction was diluted with water (5 mL) and the resultant mixture was extracted with EtOAc (5 mL×3). The combined organic phases were dried over magnesium sulfate, filtered and concentrated under reduced pressure. The resulting residue was purified directly by normal phase HPLC (ISCO RediSep Rf, 24 g, gradient elution, 0-100% EtOAc/Hexane) to yield tert-butyl 5,5-difluoro-3-(4-fluorophenyl)-1-(4-methyl-2-nitrophenyl)-6-oxopiperidine-3-carboxylate. MS: 465.13 (M+1).

Step C. tert-butyl 4,4-difluoro-2-(4-fluorophenyl)-7-methyl-1,2,3,4-tetrahydrobenzo[4,5]imidazo[1,2-a]pyridine-2-carboxylate

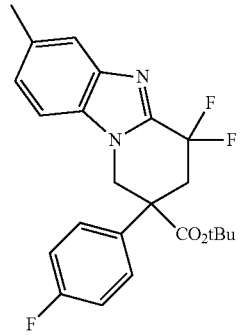

To a stirred solution of tert-butyl 5,5-difluoro-3-(4-fluorophenyl)-1-(4-methyl-2-nitrophenyl)-6-oxopiperidine-3-carboxylate (0.379 g, 0.816 mmol) in acetic acid (0.2.336 mL, 40.8 mmol) was added iron (0.456 g, 8.16 mmol) and the resulting mixture was allowed to stir for 1 h at 65° C. The reaction was allowed to cool to room temperature and then filtered over a pad of celite washing with EtOAc. The filtrate was concentrated under reduced pressure and the resulting residue was diluted with 3:1 chloroform/IPA. The resulting solution was free-based with aqueous NaHCO₃. The organic layer was separated, dried over MgSO₄, filtered and concentrated under reduced pressure to afford tert-butyl 4,4-difluoro-2-(4-fluorophenyl)-7-methyl-1,2,3,4-tetrahydrobenzo[4,5]imidazo[1,2-a]pyridine-2-carboxylate without purification. MS: 417.17 (M+1).

Step D. 2-carboxy-4,4-difluoro-2-(4-fluorophenyl)-7-methyl-1,2,3,4-tetrahydrobenzo[4,5]imidazo[1,2-a]pyridin-5-ium chloride

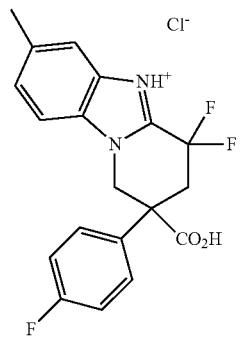 [SMILES: Cc1ccc2c(c1)[nH+]c1n2CC(C(=O)O)(c2ccc(F)cc2)CC1(F)F ; [Cl-]]

To a stirred solution of tert-butyl 4,4-difluoro-2-(4-fluorophenyl)-7-methyl-1,2,3,4-tetrahydrobenzo[4,5]imidazo[1,2-a]pyridine-2-carboxylate (0.322 g, 0.773 mmol) in DCM (2 mL, 0.4 M) was added an equal volume of TFA (2 mL) and the resultant solution was allowed to continue stirring for 1 h at which point the volatiles were removed under reduced pressure. The resulting residue was washed thoroughly with a 4N HCl in dioxane solution and then concentrated under reduced pressure to afford 2-carboxy-4,4-difluoro-2-(4-fluorophenyl)-7-methyl-1,2,3,4- tetrahydrobenzo[4,5]imidazo[1,2-a]pyridin-5-ium chloride without purification. MS: 361.04 (M+1).

Step E. benzyl (4,4-difluoro-2-(4-fluorophenyl)-7-methyl-1,2,3,4-tetrahydrobenzo[4,5]imidazo[1,2-a]pyridin-2-yl)carbamate

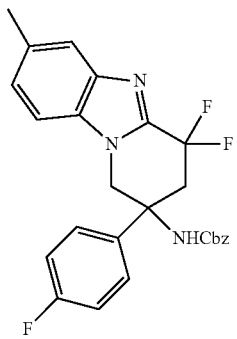 [SMILES: Cc1ccc2c(c1)nc1n2CC(NC(=O)OCc2ccccc2)(c2ccc(F)cc2)CC1(F)F]

To a stirred solution of 2-carboxy-4,4-difluoro-2-(4-fluorophenyl)-7-methyl-1,2,3,4-tetrahydrobenzo[4,5]imidazo[1,2-a]pyridin-5-ium chloride (0.307 g, 0.774 mmol) in dioxane (4.3 mL, 0.18M) was added triethylamine (0.485 mL, 3.48 mmol) followed by DPPA (0.0.189 mL, 0.851 mmol) and the resulting solution was allowed to continue stirring at room temperature. After 4 h, benzyl alcohol (0.402 mL, 3.87 mmol) was added and the resulting mixture was heated o/n at 90° C. The reaction was cooled to room temperature and concentrated under reduced pressure and the resulting residue was purified directly by normal phase HPLC (ISCO RediSep Rf, 24 g, gradient elution, 0-10% MeOH/DCM) to yield benzyl (4,4-difluoro-2-(4-fluorophenyl)-7-methyl-1,2,3,4-tetrahydrobenzo[4,5]imidazo[1,2-a]pyridin-2-yl)carbamate. MS: 466.13 (M+1).

Step F. 4,4-difluoro-2-(4-fluorophenyl)-7-methyl-1,2,3,4-tetrahydrobenzo[4,5]imidazo[1,2-a]pyridin-2-amine

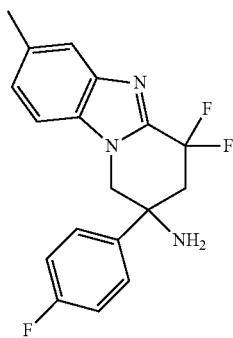 [SMILES: Cc1ccc2c(c1)nc1n2CC(N)(c2ccc(F)cc2)CC1(F)F]

To a cooled (0° C.) stirred solution of benzyl (4,4-difluoro-2-(4-fluorophenyl)-7-methyl-1,2,3,4-tetrahydrobenzo[4,5]imidazo[1,2-a]pyridin-2-yl)carbamate (0.140 g, 0.301 mmol) in DCM (2 mL, 015M) was added trimethylsilysl iodide (0.123 mL, 0.902 mmol) and the resultant solution was allowed to warm to room temperature. After 1 h, the reaction was diluted with water (2 mL) and subsequently extracted (2 mL×3) with DCM. The product remains in the aqueous layer which was evaporated and dried under reduced pressure yielding 4,4-difluoro-2-(4-fluorophenyl)-7-methyl-1,2,3,4-tetrahydrobenzo[4,5]imidazo[1,2-a]pyridin-2-amine without purification. MS: 332.16 (M+1).

Step G. 2-chloro-N-(4,4-difluoro-2-(4-fluorophenyl)-7-methyl-1,2,3,4-tetrahydrobenzo[4,5]imidazo[r, 2-a]pyridin-2-yl)-4-(3-methyl-1H-1,2,4-triazol-1-yl)benzamide

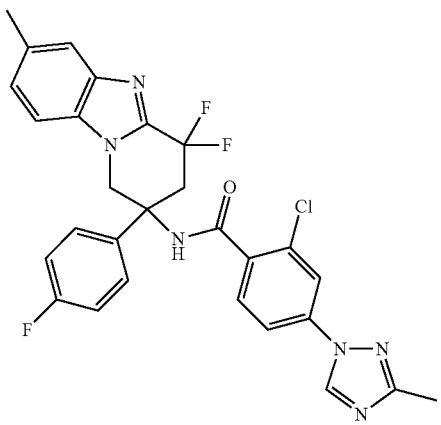

To a stirred solution of 4,4-difluoro-2-(4-fluorophenyl)-7-methyl-1,2,3,4-tetrahydrobenzo[4,5]imidazo[1,2-a]pyridin-2-amine (0.061 g, 0.185 mmol) and 2-chloro-4-(3-methyl-1H-1,2,4-triazol-1-yl)benzoic acid (0.044 g, 0.185 mmol) in 2 mL DMF was added sequentially HOAt (0.0328 mg, 0.241 mmol), EDC (0.0461 mg, 0.241 mmol), pyridine (0.0299 mL, 0.370 mmol), and DMAP (0.0011 g, 0.0093 mmol) and the resulting mixture was allowed to continue stirring for 3 h. The resulting solution was purified directly by reverse phase HPLC (Xterra, C18, 19×100 mm, gradient elution, 10-70% acetonitrile/water with 0.1% TFA) to yield a mixture of two enantiomers. This mixture was separated by chiral preparative SFC to afford the faster eluted 2-chloro-N-(4,4-difluoro-2-(4-fluorophenyl)-7-methyl-1,2,3,4-tetrahydrobenzo[4,5]imidazo[1,2-a]pyridin-2-yl)-4-(3-methyl-1H-1,2,4-triazol-1-yl)benzamide. MS: 551.13 (M+1). $^1$H NMR (500 MHz, CD$_3$OD) δ 8.99 (s, 1H), 7.87 (s, 1H), 7.70-7.69 (m, 3H), 7.56 (s, 1H), 7.47 (d, J=8.4 Hz, 1H), 7.35 (d, J=8.3 Hz, 1H), 7.27-7.21 (m, 3H), 4.95 (d, 13.2 Hz, 1H), 4.41 (d, 13.2 Hz, 1H), 4.05-4.02 (m, 1H), 3.47-3.39 (m, 1H), 2.48 (s, 3H), 2.40 (s, 3H).

The following compounds were synthesized using methods analogous to those described able from commercially available materials or intermediates whose syntheses are described above.

| Ex. | Structure | hFIXa IC50 (nM) | Exact Mass [M + H]+ | LCMS read |
|---|---|---|---|---|
| 55 | 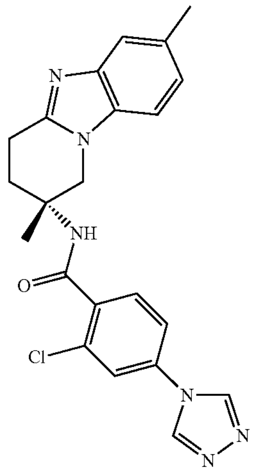 [SMILES: Cc1ccc2c(c1)nc1n2C[C@](C)(NC(=O)c2ccc(-n3cnnc3)cc2Cl)CC1] | 36.64 | 421.15 | 421.00 |
| 56 | 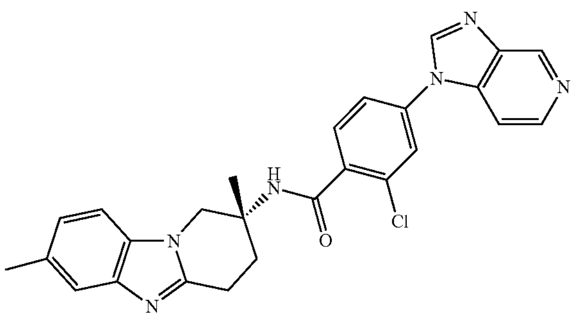 [SMILES: Cc1ccc2c(c1)nc1n2C[C@](C)(NC(=O)c2ccc(-n3cnc4cnccc43)cc2Cl)CC1] | 13.79 | 471.17 | 471.19 |
| 57 | 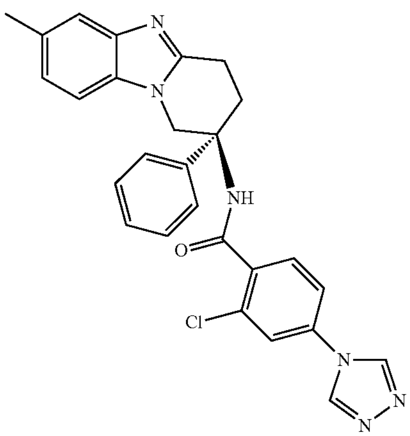 [SMILES: Cc1ccc2c(c1)nc1n2C[C@@](NC(=O)c2ccc(-n3cnnc3)cc2Cl)(c2ccccc2)CC1] | 1.422 | 483.17 | 471.19 |
| 58 | 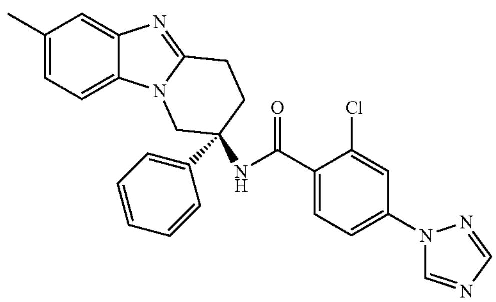 [SMILES: Cc1ccc2c(c1)nc1n2C[C@@](NC(=O)c2ccc(-n3cncn3)cc2Cl)(c2ccccc2)CC1] | 12.86 | 483.17 | 483.08 |

-continued
| Ex. | Structure | hFIXa IC50 (nM) | Exact Mass [M + H]+ | LCMS read |
|---|---|---|---|---|
| 59 | 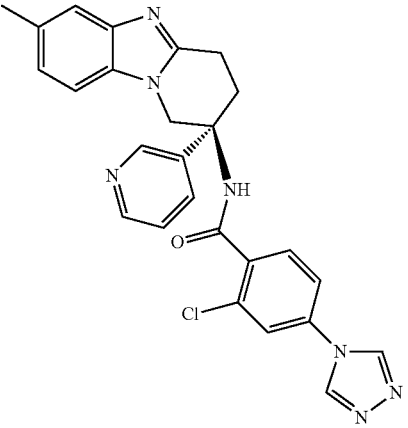 [SMILES: Cc1ccc2c(c1)nc1n2C[C@@](NC(=O)c2ccc(-n3cnnc3)cc2Cl)(c2cccnc2)CC1] | 12.54 | 484.17 | 484.22 |
| 60 | 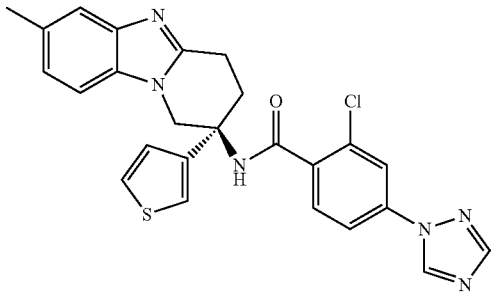 [SMILES: Cc1ccc2c(c1)nc1n2C[C@@](NC(=O)c2ccc(-n3cncn3)cc2Cl)(c2ccsc2)CC1] | 5.651 | 489.13 | 489.02 |
| 61 | 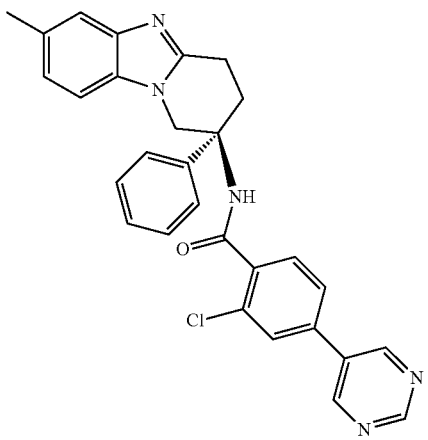 [SMILES: Cc1ccc2c(c1)nc1n2C[C@@](NC(=O)c2ccc(-c3cncnc3)cc2Cl)(c2ccccc2)CC1] | 5.551 | 494.17 | 494.08 |
| 62 | 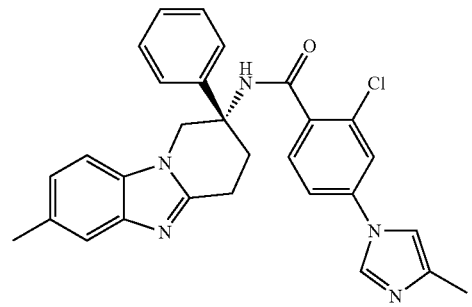 | 19.33 | 496.19 | 496.32 |

-continued

| Ex. | Structure | hFIXa IC50 (nM) | Exact Mass [M + H]+ | LCMS read |
|---|---|---|---|---|
| 63 | 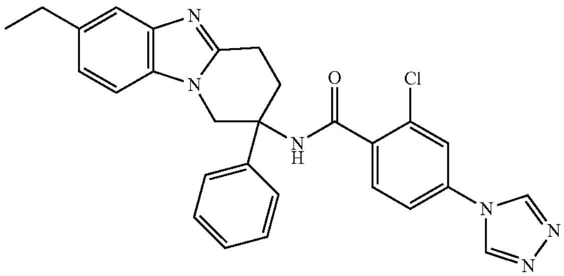 [SMILES: CCc1ccc2c(c1)nc1n2CC(NC(=O)c2ccc(-n3cnnc3)cc2Cl)(c2ccccc2)CC1] | 18.93 | 497.19 | 496.97 |
| 64 | 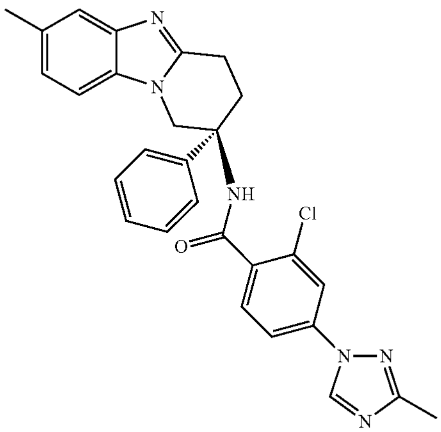 | 5.901 | 497.19 | 496.99 |
| 65 | 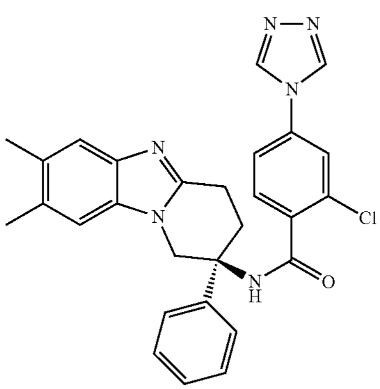 [SMILES: Cc1cc2nc3n(c2cc1C)C[C@@](NC(=O)c1ccc(-n2cnnc2)cc1Cl)(c1ccccc1)CC3] | 2.723 | 497.19 | 497.12 |
| 66 | 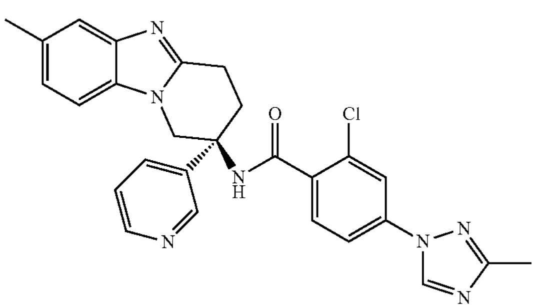 | 17.66 | 498.18 | 498.17 |

-continued

| Ex. | Structure | hFIXa IC50 (nM) | Exact Mass [M + H]+ | LCMS read |
|---|---|---|---|---|
| 67 | 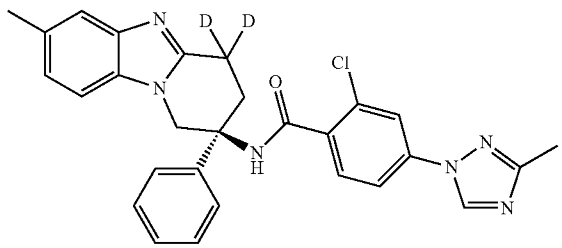 | 2.611 | 499.2 | 499.22 |
| 68 | 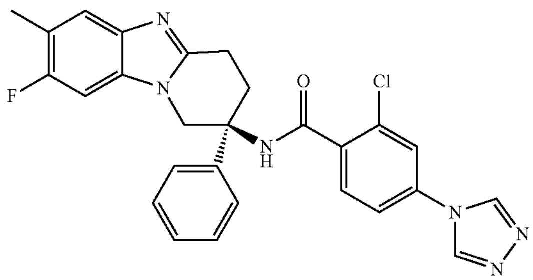 [SMILES: Cc1cc2nc3n(c2cc1F)C[C@@](NC(=O)c1ccc(-n2cnnc2)cc1Cl)(c1ccccc1)CC3] | 12.65 | 501.16 | 500.97 |
| 69 | 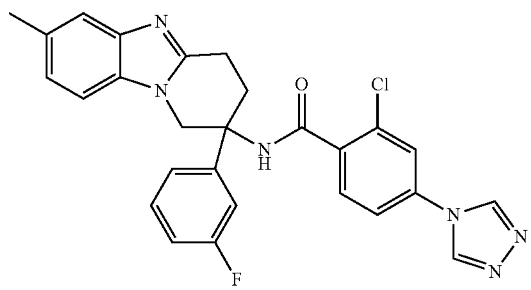 [SMILES: Cc1ccc2c(c1)nc1n2CC(NC(=O)c2ccc(-n3cnnc3)cc2Cl)(c2cccc(F)c2)CC1] | 4.207 | 501.16 | 501.04 |
| 70 | 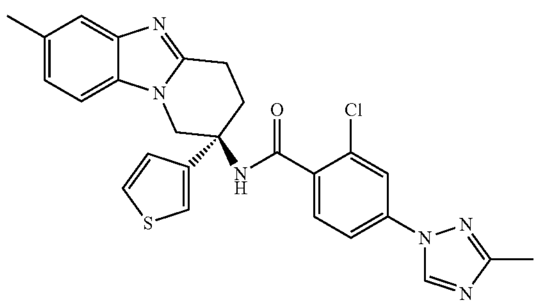 | 9.968 | 503.14 | 503.09 |
| 71 | 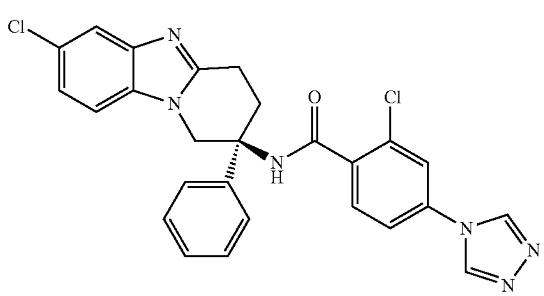 [SMILES: O=C(N[C@]1(c2ccccc2)CCc2nc3cc(Cl)ccc3n2C1)c1ccc(-n2cnnc2)cc1Cl] | 15.19 | 503.12 | 502.96 |

-continued

| Ex. | Structure | hFIXa IC50 (nM) | Exact Mass [M + H]+ | LCMS read |
|---|---|---|---|---|
| 72 | 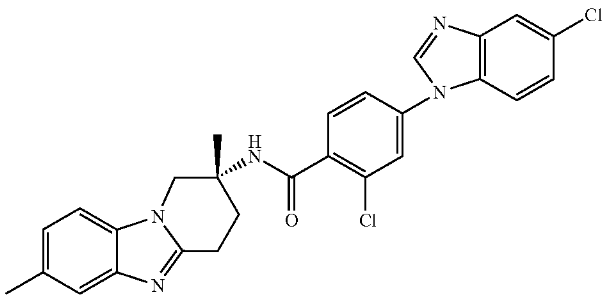 [SMILES: Cc1ccc2c(c1)nc1n2C[C@](C)(NC(=O)c2ccc(-n3cnc4cc(Cl)ccc43)cc2Cl)CC1] | 16.14 | 504.14 | 504.30 |
| 73 | 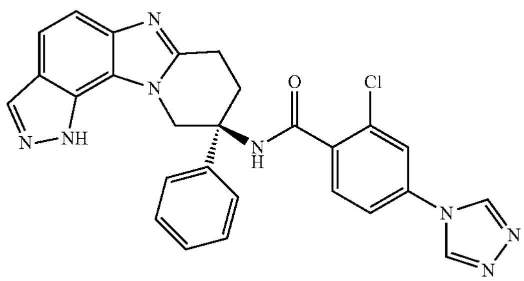 [SMILES: O=C(N[C@]1(c2ccccc2)CCc2nc3ccc4cn[nH]c4c3n2C1)c1ccc(-n2cnnc2)cc1Cl] | 6.351 | 509.16 | 508.80 |
| 74 | 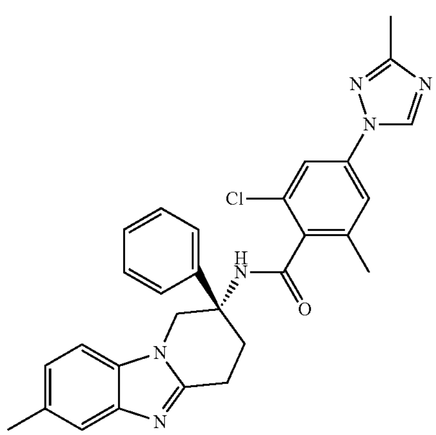 [SMILES: Cc1ccc2c(c1)nc1n2C[C@@](NC(=O)c2c(C)cc(-n3cnc(C)n3)cc2Cl)(c2ccccc2)CC1] | 10.44 | 511.2 | 511.35 |
| 75 | 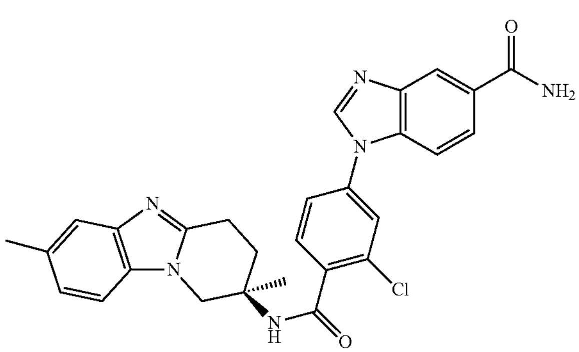 [SMILES: Cc1ccc2c(c1)nc1n2C[C@](C)(NC(=O)c2ccc(-n3cnc4cc(C(N)=O)ccc43)cc2Cl)CC1] | 8.916 | 513.18 | 512.82 |

-continued
| Ex. | Structure | hFIXa IC50 (nM) | Exact Mass [M + H]+ | LCMS read |
|---|---|---|---|---|
| 76 | 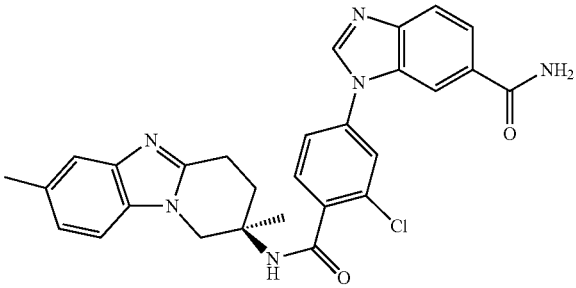 [SMILES: Cc1ccc2c(c1)nc1n2C[C@](C)(NC(=O)c2ccc(-n3cnc4ccc(C(N)=O)cc43)cc2Cl)CC1] | 9.388 | 513.18 | 512.82 |
| 77 | 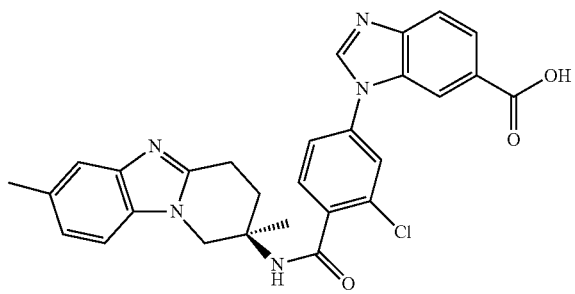 [SMILES: Cc1ccc2c(c1)nc1n2C[C@](C)(NC(=O)c2ccc(-n3cnc4ccc(C(=O)O)cc43)cc2Cl)CC1] | 15.91 | 514.16 | 513.83 |
| 78 | 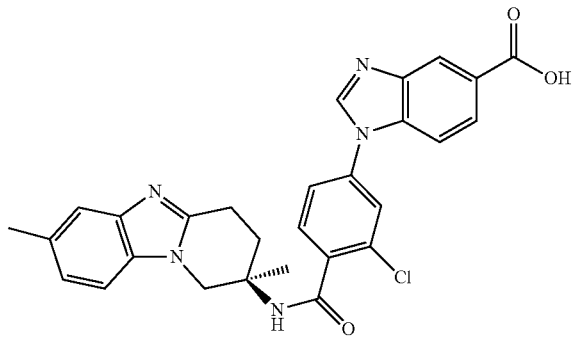 [SMILES: Cc1ccc2c(c1)nc1n2C[C@](C)(NC(=O)c2ccc(-n3cnc4cc(C(=O)O)ccc43)cc2Cl)CC1] | 10.24 | 514.16 | 513.83 |
| 79 | 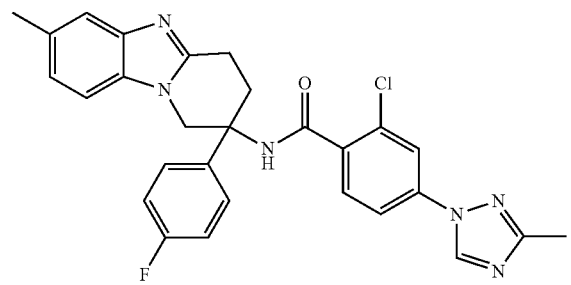 | 14.11 | 515.18 | 515.15 |
| 80 | 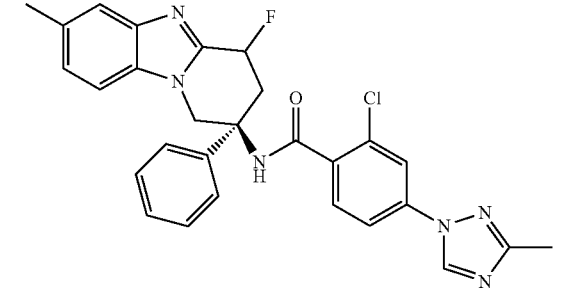 | 9.145 | 515.18 | 515.09 |

-continued

| Ex. | Structure | hFIXa IC50 (nM) | Exact Mass [M + H]+ | LCMS read |
|---|---|---|---|---|
| 81 | 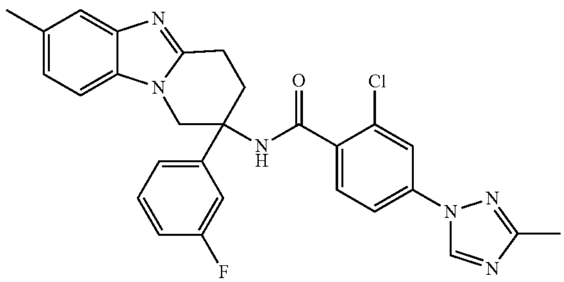 | 8.196 | 515.18 | 515.26 |
| 82 | 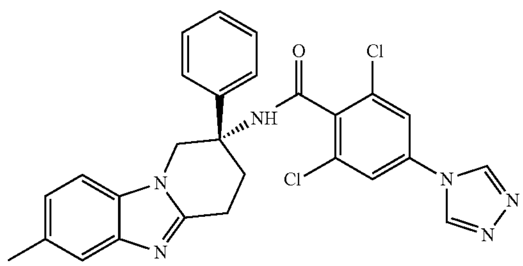 [SMILES: Cc1ccc2c(c1)nc1n2C[C@@](NC(=O)c2c(Cl)cc(-n3cnnc3)cc2Cl)(c2ccccc2)CC1] | 4.034 | 517.13 | 517.16 |
| 83 | 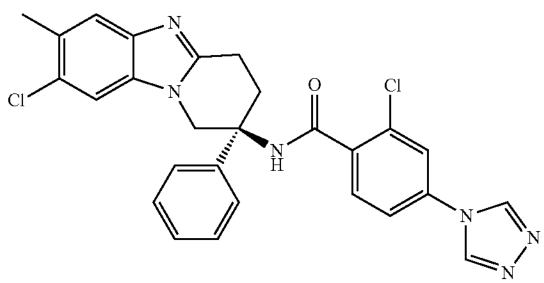 [SMILES: Cc1cc2nc3n(c2cc1Cl)C[C@@](NC(=O)c1ccc(-n2cnnc2)cc1Cl)(c1ccccc1)CC3] | 4.795 | 517.13 | 516.87 |
| 84 | 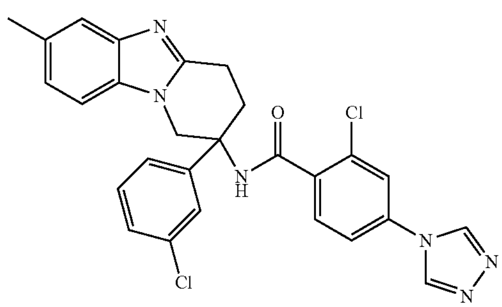 [SMILES: Cc1ccc2c(c1)nc1n2CC(NC(=O)c2ccc(-n3cnnc3)cc2Cl)(c2cccc(Cl)c2)CC1] | 5.659 | 517.13 | 517.00 |
| 85 | 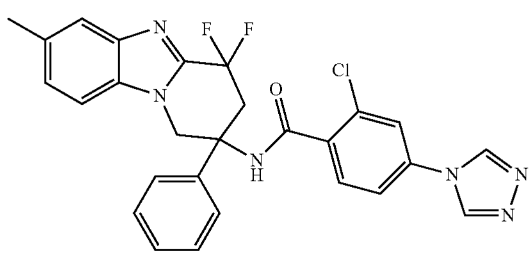 [SMILES: Cc1ccc2c(c1)nc1n2CC(NC(=O)c2ccc(-n3cnnc3)cc2Cl)(c2ccccc2)CC1(F)F] | 2.558 | 519.15 | 519.13 |

-continued

| Ex. | Structure | hFIXa IC50 (nM) | Exact Mass [M + H]+ | LCMS read |
|---|---|---|---|---|
| 86 | 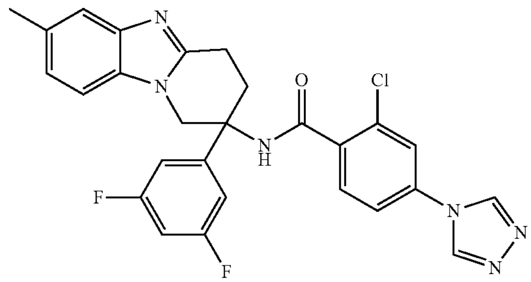 [SMILES: Cc1ccc2c(c1)nc1n2CC(NC(=O)c2ccc(-n3cnnc3)cc2Cl)(c2cc(F)cc(F)c2)CC1] | 7.215 | 519.15 | 519.13 |
| 87 | 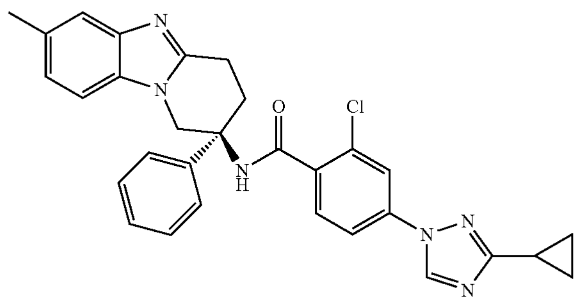 [SMILES: Cc1ccc2c(c1)nc1n2C[C@@](NC(=O)c2ccc(-n3cnc(C4CC4)n3)cc2Cl)(c2ccccc2)CC1] | 12.56 | 523.2 | 523.14 |
| 88 | 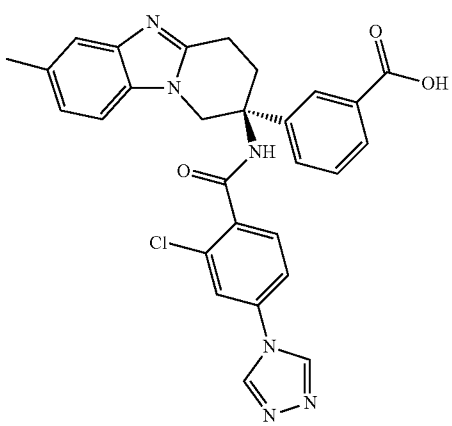 [SMILES: Cc1ccc2c(c1)nc1n2C[C@@](NC(=O)c2ccc(-n3cnnc3)cc2Cl)(c2cccc(C(=O)O)c2)CC1] | 2.856 | 527.16 | 527.10 |
| 89 | 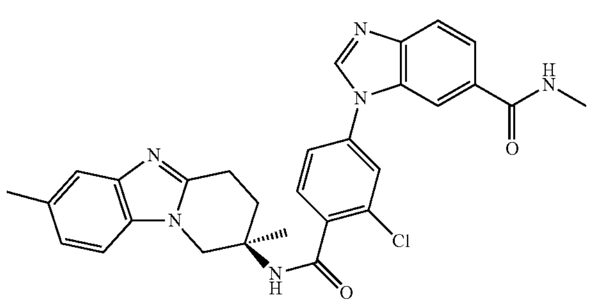 | 10.19 | 527.2 | 526.91 |

-continued

| Ex. | Structure | hFIXa IC50 (nM) | Exact Mass [M + H]+ | LCMS read |
|---|---|---|---|---|
| 90 | 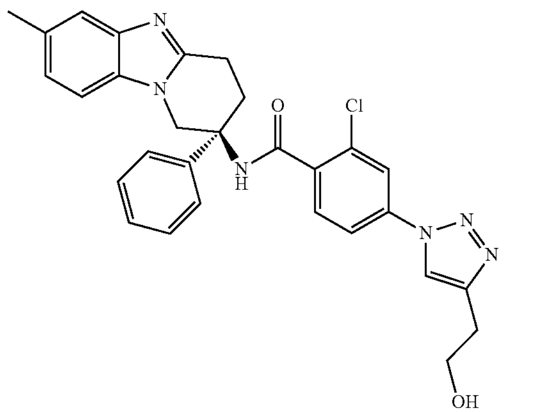 [SMILES: Cc1ccc2c(c1)nc1n2C[C@@](NC(=O)c2ccc(-n3cc(CCO)nn3)cc2Cl)(c2ccccc2)CC1] | 8.828 | 527.2 | 527.14 |
| 91 | 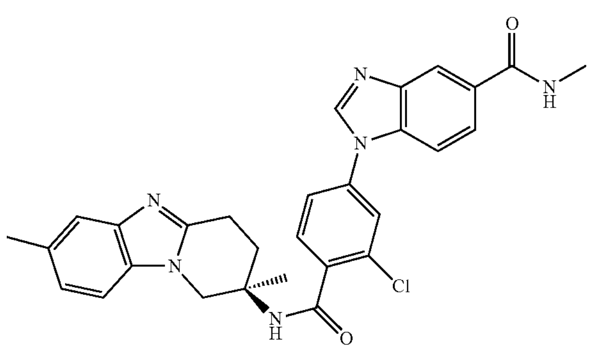 | 11.49 | 527.2 | 526.91 |
| 92 | 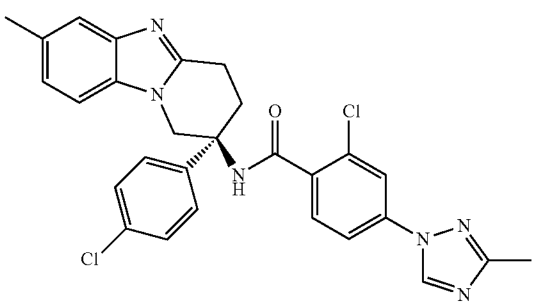 | 17.4 | 531.15 | 531.15 |
| 93 | 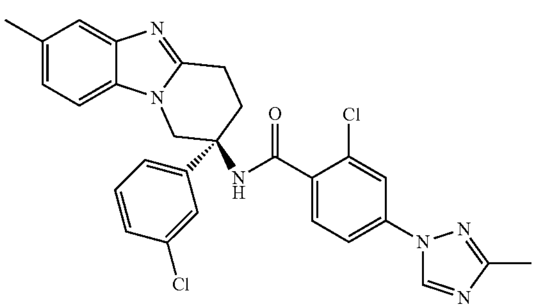 | 11.38 | 531.15 | 531.08 |

-continued

| Ex. | Structure | hFIXa IC50 (nM) | Exact Mass [M + H]+ | LCMS read |
|---|---|---|---|---|
| 94 | 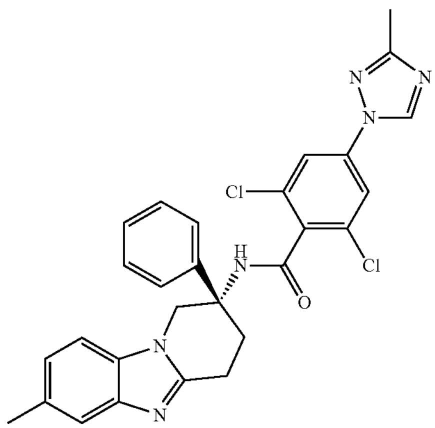 [SMILES: Cc1ccc2c(c1)nc1n2C[C@@](NC(=O)c2c(Cl)cc(-n3cnc(C)n3)cc2Cl)(c2ccccc2)CC1] | 3.835 | 531.15 | 531.31 |
| 95 | 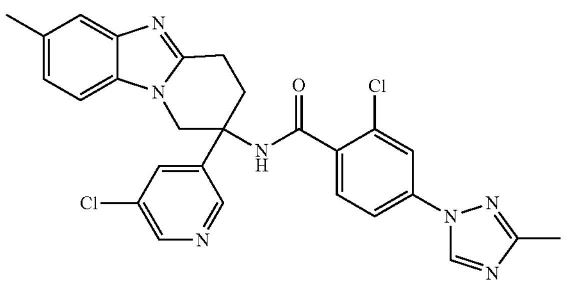 | 14.97 | 532.14 | 532.12 |
| 96 | 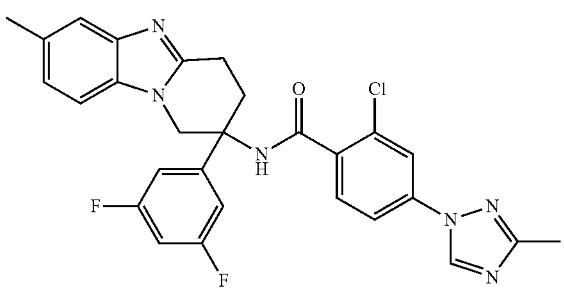 | 11.59 | 533.17 | 533.13 |
| 97 | 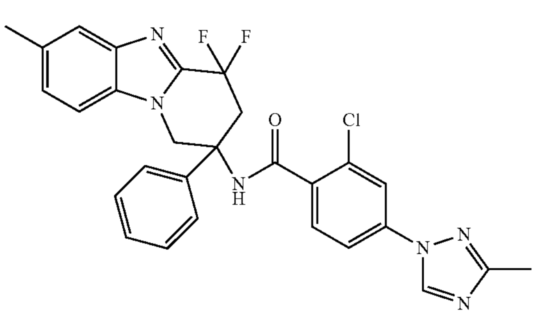 | 2.822 | 533.17 | 533.17 |

| Ex. | Structure | hFIXa IC50 (nM) | Exact Mass [M + H]+ | LCMS read |
|---|---|---|---|---|
| 98 | 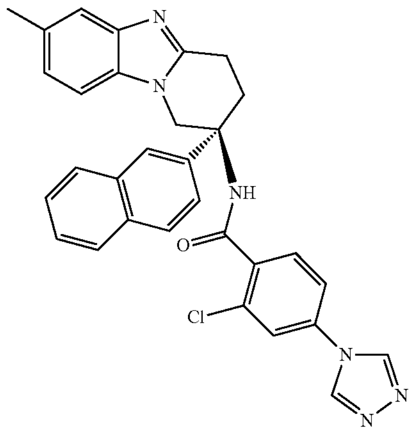 [SMILES: Cc1ccc2c(c1)nc1n2C[C@@](NC(=O)c2ccc(-n3cnnc3)cc2Cl)(c2ccc3ccccc3c2)CC1] | 2.918 | 533.19 | 533.10 |
| 99 | 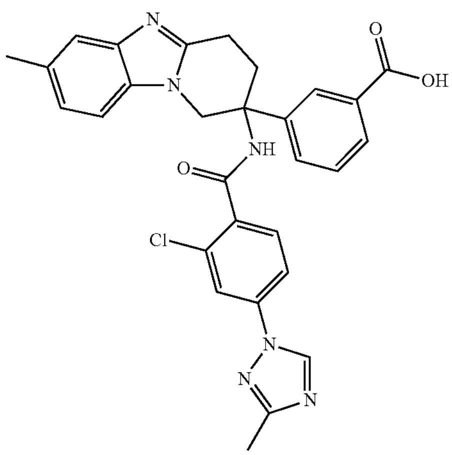 [SMILES: Cc1ccc2c(c1)nc1n2CC(NC(=O)c2ccc(-n3cnc(C)n3)cc2Cl)(c2cccc(C(=O)O)c2)CC1] | 4.272 | 541.18 | 541.20 |
| 100 | 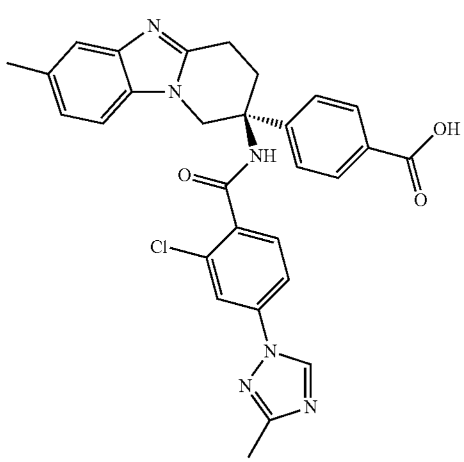 [SMILES: Cc1ccc2c(c1)nc1n2C[C@@](NC(=O)c2ccc(-n3cnc(C)n3)cc2Cl)(c2ccc(C(=O)O)cc2)CC1] | 6.596 | 541.18 | 541.22 |

-continued

| Ex. | Structure | hFIXa IC50 (nM) | Exact Mass [M + H]+ | LCMS read |
|---|---|---|---|---|
| 101 | 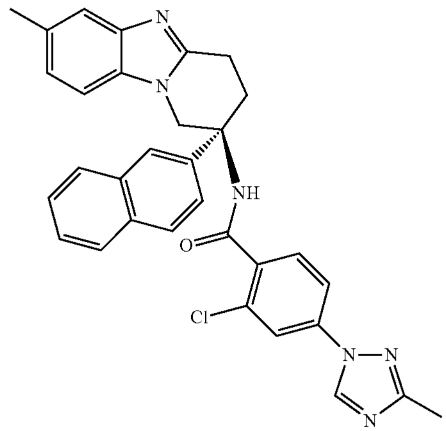 | 16.23 | 547.2 | 547.08 |
| 102 | 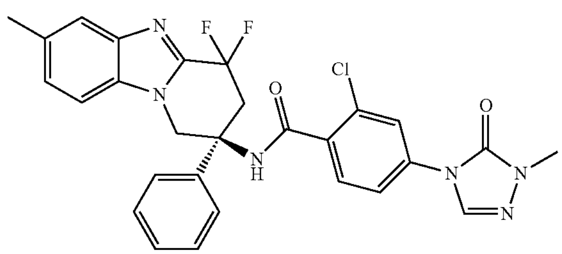 | 3.612 | 549.16 | 549.04 |
| 103 | 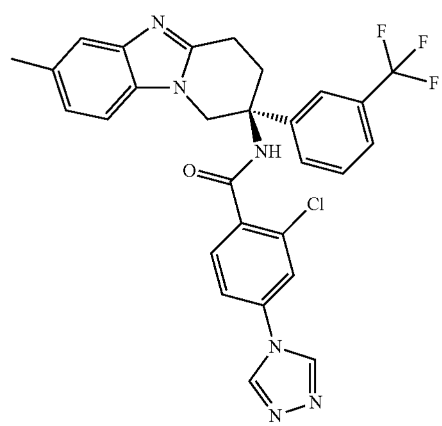 [SMILES: Cc1ccc2c(c1)nc1n2C[C@@](NC(=O)c2ccc(-n3cnnc3)cc2Cl)(c2cccc(C(F)(F)F)c2)CC1] | 7.261 | 551.16 | 551.06 |
| 104 | 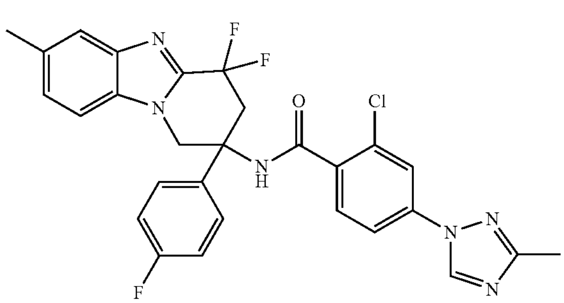 | 39.33 | 551.16 | 551.13 |

| Ex. | Structure | hFIXa IC50 (nM) | Exact Mass [M + H]+ | LCMS read |
|---|---|---|---|---|
| 105 | 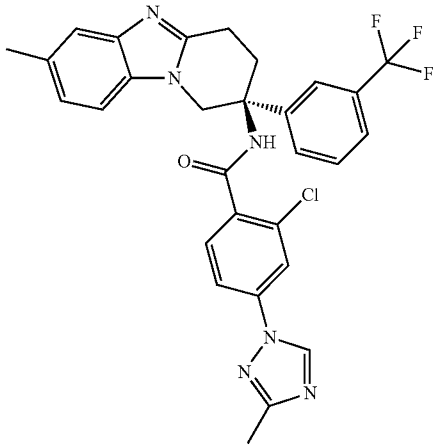 [SMILES: Cc1ccc2c(c1)nc1n2C[C@@](NC(=O)c2ccc(-n3cnc(C)n3)cc2Cl)(c2cccc(C(F)(F)F)c2)CC1] | 11.54 | 565.17 | 565.02 |
| 106 | 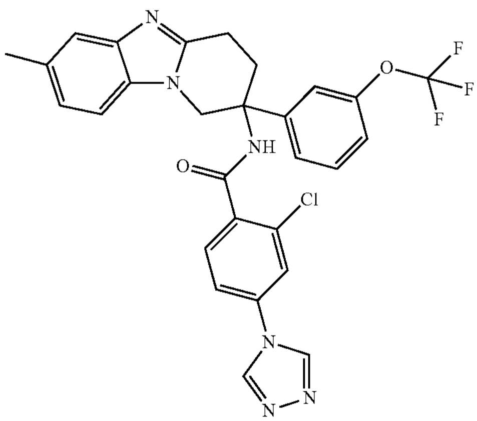 [SMILES: Cc1ccc2c(c1)nc1n2CC(NC(=O)c2ccc(-n3cnnc3)cc2Cl)(c2cccc(OC(F)(F)F)c2)CC1] | 13.82 | 567.15 | 567.15 |

Example 107

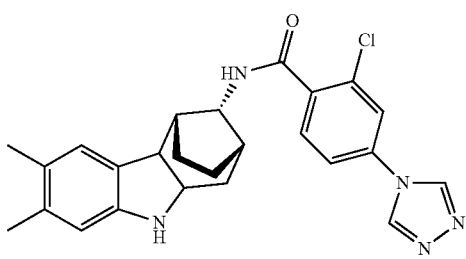

2-chloro-N-((7S,10R,11R)-3-meth yl-5,6,8,9,10-hexahydro-7,10-methanocyclohepta[b]indol-11-yl)-4-(4H-1,2,4-triazol-4-yl)benzamide Step A: (7S,10S,11R)-ethyl 2,3-dimethyl-5,6,7,8,9,10-hexahydro-7,10-methanocyclohepta[b]indole-11-carboxylate 3,4-Dimethylphenylhydrazine Hydrochloride (4.6 g, 26.6 mmol) and (1R,4S,8r)-ethyl 3-oxobibyclo[3.2.1]octane-8-carboxylate (5.23 g, 26.6 mmol) in a microwave vial was charge with acetic acid (53.3 mL). Reaction was stirred in a microwave reactor at 150° C. for 10 min. Volatiles were removed in vacuo. The residue was purified by column chromatography on silica gel, ISCO CombiFlash Rf 120 g column. Eluting with 0 to 50% ethyl acetate in hexane to give (7S,10S,11R)-ethyl 2,3-dimethyl-5,6,7,8,9,10-hexahydro-7,10-methanocyclohepta[b]indole-11-carboxylate. LCMS m/z=298.05 (M+H).

Step B: (7S,10S,11R)-2,3-dimethyl-5,6,7,8,9,10-hexahydro-7,10-methanocyclohepta[b]indole-11-carboxylic acid To a stirring solution of (7S,10S,11R)-ethyl 2,3-dimethyl-5,6,7,8,9,10-hexahydro-7,10-methanocyclohepta[b]indole-11-carboxylate (3.8 g, 12.78 mmol) in MeOH (128 mL) was added 5.0M NaOH (51.0 mL, 256 mmol). Reaction mixture was stirred at 60° C. under $N_2$ for 2 h. Volatiles were removed in vacuo. The resulting aqueous solution was washed with ethyl acetate. The aqueous layer was acidified by 1N HCl, and then extracted with ethyl acetate three times. The combined organic layer was washed with water and brine. Dried over $Na_2SO_4$ then filtered and concentrated in vacuo. The crude compound was further dried on high vacuum pump and carried on to next step without purification. LCMS m/z=270.06 (M+H).

Step C: benzyl ((7S,10R,11R)-2,3-dimethyl-5,6,7,8,
9,10-hexahydro-7,10-methanocyclohepta[b]indol-
11-yl)carbamate To a stirring suspension of (7S,10S,11R)-2,3-dimethyl-5,6,7,8,9,10-hexahydro-7,10-methanocyclohepta[b]indole-11-carboxylic acid (640 mg, 2.38 mmol) in Toluene (12 mL) was added triethylamine (0.994 mL, 7.13 mmol) following by addition of diphenylphosphoryl azide (0.614 mL, 2.85 mmol). The resulting mixture was stirred at room temperature for 3 h. Benzyl alcohol (0.247 mL, 2.38 mmol) was added. The reaction mixture was stirred at 100° C. overnight then cooled down to room temperature. Volatiles were removed in vacuo. The residue was purified by column chromatography on silica gel, ISCO CombiFlash Rf 40 g column, eluting with 0 to 50% ethyl acetate in hexane to give benzyl ((7S,10R,11R)-2,3-dimethyl-5,6,7,8,9,10-hexahydro-7,10-methanocyclohepta[b]indol-11-yl)carbamate. LCMS m/z=374.97 (M+H).

Step D: (7S,10R,11R)-2,3-dimethyl-5,6,7,8,9,10-hexahydro-7,10-methanocyclohepta[b]indol-11-amine To a stirring solution of benzyl ((7S,10R,11R)-2,3-dimethyl-5,6,7,8,9,10-hexahydro-7,10-methanocyclohepta[b]indol-11-yl)carbamate (150 mg, 0.401 mmol) in MeOH (4.0 mL) was added Pd/C (42.6, 0.401 mmol) under $N_2$ atmosphere. The resulting mixture was stirred at room temperature for 1.5 h under $N_2$. The reaction mixture was filtered thru pad of celite and flashed with MeOH three times. Then concentrated under reduce vacuum. Crude compound (7S,10R,11R)-2,3-dimethyl-5,6,7,8,9,10-hexahydro-7,10-methanocyclohepta[b]indol-11-amine was further dried on high vacuum pump and carried on to next step without purification. LCMS m/z=241.07 (M+H).

Step E: 2-chloro-N-((7S,10R,11R)-3-methyl-5,6,7,8,9,10-hexahydro-7,10-methanocyclohepta[b]indol-11-yl)-4-(4H-1,2,4-triazol-4-yl)benzamide To a stirring solution of (7S,10R,11R)-2,3-dimethyl-5,6,7,8,9,10-hexahydro-7,10-methanocyclohepta[b]indol-11-amine (76 mg, 0.316 mmol) and 2-Chloro-4-(4H-1,2,4-Triazol-4-yl)Benzoic Acid (78 mg, 0.348 mmol) in DMF (3.2 mL) was added 1-ethyl-3-(3-dimethylaminopropyl)carbodiimide (85 mg, 0.443 mmol) and 1-hydroxy-7-azabenzotriazole (60.3 mg, 0.443 mmol), followed by addition of Pyridine (77 uL, 0.949 mmol). Reaction mixture was stirred at room temperature overnight under $N_2$. The crude reaction mixture was diluted with DMF and purified by reverse phase HPLC (Gilson system, Sunfire PreP 5 uM C18 19×100 mm column, eluting with Acetonitrile/Water+0.1% TFA) to give 2-chloro-N-((7S,10R,11R)-3-methyl-5,6,7,8,9,10-hexahydro-7,10-methanocyclohepta[b]indol-11-yl)-4-(4H-1,2,4-triazol-4-yl)benzamide.
$^1$H NMR (499 MHz, CD$_3$OD): 9.05-9.06 (m, 2H); 7.94 (m, 1H); 7.75 (d, J=2.2 Hz, 1H); 7.52-7.58 (m, 2H); 7.15 (s, 1H); 7.02 (s, 1H); 4.37 (d, J=5.4 Hz, 2H); 3.38 (s, 1H); 3.19 (d, J=17.2 Hz, 1H); 2.86 (s, 1H); 2.56 (d, J=16.8 Hz, 1H); 2.29 (s, 6H); 2.2 (m, 1H); 2.1 (m, 1H); 1.83 (d, J=8.7 Hz, 1H); 1.6 (m, 1H).
LCMS m/z=446.15 (M+H).

Example 120

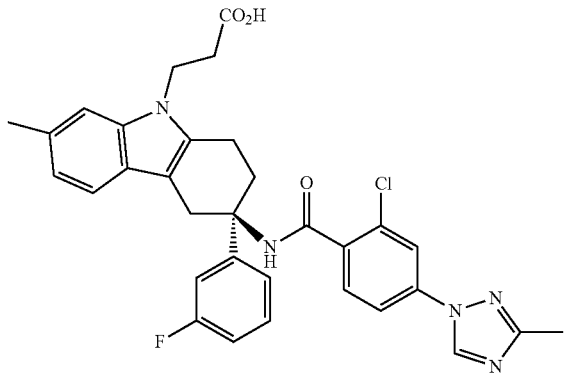

(R)-3-(3-(2-chloro-4-(3-methyl-1H-1,2,4-triazol-1-yl)benzamido)-3-(3-fluorophenyl)-7-methyl-3,4-dihydro-1H-carbazol-9(2H)-yl)propanoic acid Tert-butyl acrylate (22.44 mg, 0.175 mmol) was added to a stirred solution of (R)-2-chloro-N-(3-(3-fluorophenyl)-7-methyl-2,3,4,9-tetrahydro-1H-carbazol-3-yl)-4-(3-methyl-1H-1,2,4-triazol-1-yl)benzamide (30 mg, 0.058 mmol) and Cs$_2$CO$_3$ (38.0 mg, 0.117 mmol) in dry DMF (973 µl) and the reaction was stirred at room temperature overnight. The reaction mixture was neutralized with HOAc, then diluted with water and DMSO. The residue was purified by reversed-phase HPLC (C-18) eluting with acetonitrile/water (40% to 100% ACN in water) to afford (R)-tert-butyl 3-(3-(2-chloro-4-(3-methyl-1H-1,2,4-triazol-1-yl)benzamido)-3-(3-fluorophenyl)-7-methyl-3,4-dihydro-1H-carbazol-9(2H)-yl)propanoate.

TFA (630 µl, 8.18 mmol) was added to a stirred solution of (R)-tert-butyl 3-(3-(2-chloro-4-(3-methyl-1H-1,2,4-triazol-1-yl)benzamido)-3-(3-fluorophenyl)-7-methyl-3,4-dihydro-1H-carbazol-9(2H)-yl)propanoate (21 mg, 0.033 mmol) in dry DCM (1090 µl) and the reaction was stirred at room temperature for 3 h. LC/MS showed the reaction went to completion. The volatile was removed in vacuo. The residue was purified by reversed-phase HPLC (C-18) eluting with acetonitrile/water (10% to 90% ACN in water) to afford (R)-3-(3-(2-chloro-4-(3-methyl-1H-1,2,4-triazol-1-yl)benzamido)-3-(3-fluorophenyl)-7-methyl-3,4-dihydro-1H-carbazol-9(2H)-yl)propanoic acid. LCMS calc.=586.19; found=586.28 (M+H)$^+$. 1H NMR (500 MHz, CD3OD): δ 9.03 (s, 1H); 8.79 (s, 1H); 7.89 (d, J=2.1 Hz, 1H); 7.74 (dd, J=8.4, 2.0 Hz, 1H); 7.48 (d, J=8.4 Hz, 1H); 7.36-7.42 (m, 2H); 7.30-7.35 (m, 1H); 7.18 (s, 1H); 6.97-7.03 (m, 1H); 6.86 (d, J=8.0 Hz, 1H); 4.38 (q, J=6.7 Hz, 2H); 3.19-3.29 (m, 2H); 3.10-3.19 (m, 1H); 2.96-3.08 (m, 1H); 2.80-2.91 (m, 1H); 2.72 (t, J=6.9 Hz, 2H); 2.45-2.56 (m, 1H); 2.45 (s, 3H); 2.42 (s, 3H).

The following compounds were synthesized using methods analogous to those described above from commercially available materials or intermediates whose syntheses are described above.

| Ex. | Structure | hFIXa IC50 (nM) | Exact Mass [M + H]+ | LCMS |
|---|---|---|---|---|
| 107 | 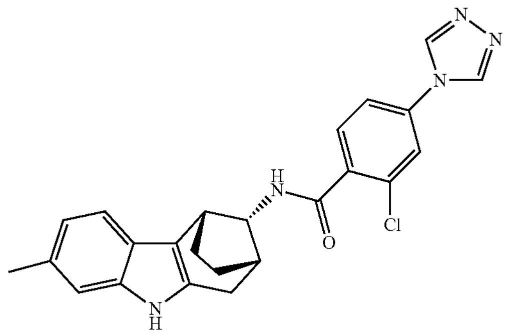 [SMILES: Cc1ccc2c3c([nH]c2c1)C[C@@H]1CC[C@H]3[C@@H]1NC(=O)c1ccc(-n2cnnc2)cc1Cl] | 54.26 | 432.16 | 432.15 |
| 108 | 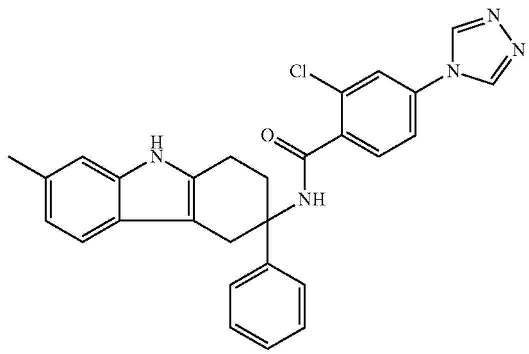 [SMILES: Cc1ccc2c3c([nH]c2c1)CCC(NC(=O)c1ccc(-n2cnnc2)cc1Cl)(c1ccccc1)C3] | 17.89 | 482.17 | 482.14 |
| 109 | 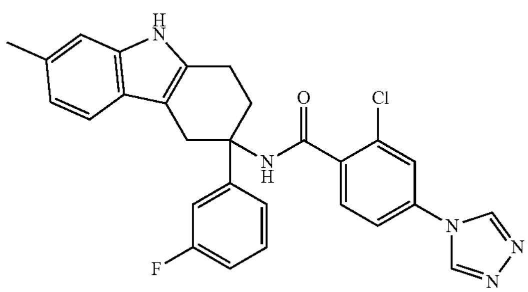 [SMILES: Cc1ccc2c3c([nH]c2c1)CCC(NC(=O)c1ccc(-n2cnnc2)cc1Cl)(c1cccc(F)c1)C3] | 8.396 | 500.17 | 500.09 |
| 110 | 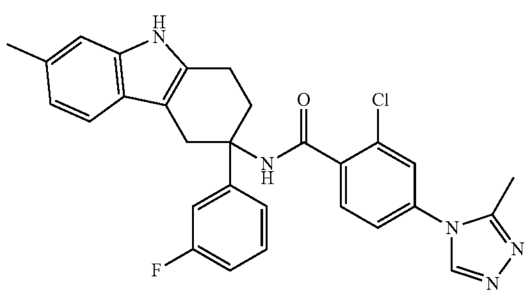 [SMILES: Cc1ccc2c3c([nH]c2c1)CCC(NC(=O)c1ccc(-n2cnnc2C)cc1Cl)(c1cccc(F)c1)C3] | 11.17 | 514.18 | 514.11 |
| 111 | 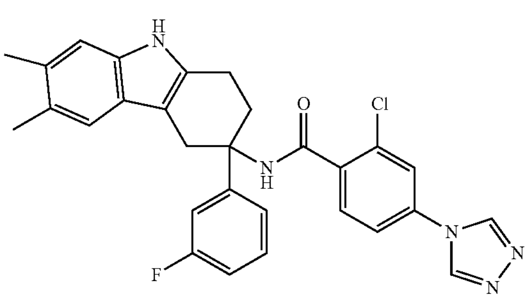 [SMILES: Cc1cc2[nH]c3c(c2cc1C)CC(NC(=O)c1ccc(-n2cnnc2)cc1Cl)(c1cccc(F)c1)CC3] | 16.62 | 514.18 | 513.91 |

| Ex. | Structure | hFIXa IC50 (nM) | Exact Mass [M + H]+ | LCMS |
|---|---|---|---|---|
| 112 | 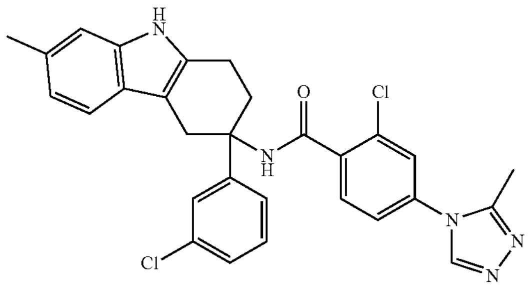 | 6.431 | 530.15 | 530.14 |
| 113 | 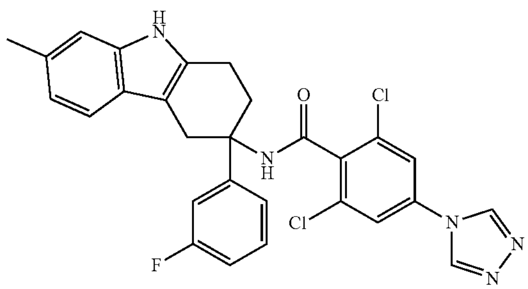 [SMILES: Cc1ccc2c3c([nH]c2c1)CCC(NC(=O)c1c(Cl)cc(-n2cnnc2)cc1Cl)(c1cccc(F)c1)C3] | 4.695 | 534.13 | 534.15 |
| 114 | 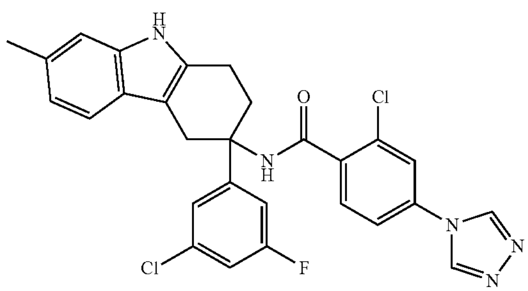 [SMILES: Cc1ccc2c3c([nH]c2c1)CCC(NC(=O)c1ccc(-n2cnnc2)cc1Cl)(c1cc(F)cc(Cl)c1)C3] | 15.19 | 534.13 | 534.06 |
| 15 | 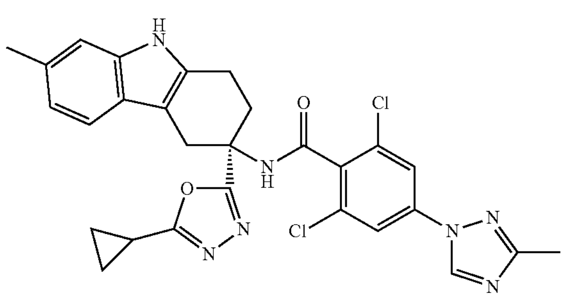 | 13.9 | 562.15 | 562.10 |
| 116 | 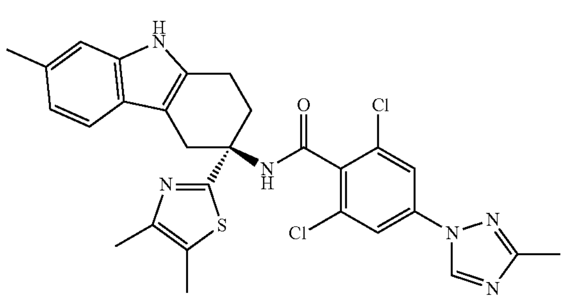 | 13.56 | 565.13 | 565.09 |

-continued

| Ex. | Structure | hFIXa IC50 (nM) | Exact Mass [M + H]+ | LCMS |
|---|---|---|---|---|
| 117 | 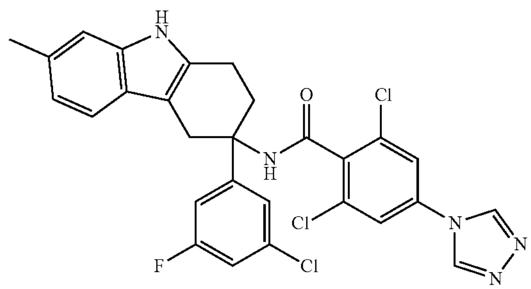 [SMILES: Cc1ccc2c3c([nH]c2c1)CCC(NC(=O)c1c(Cl)cc(-n2cnnc2)cc1Cl)(c1cc(F)cc(Cl)c1)C3] | 6.853 | 568.09 | 567.98 |
| 118 | 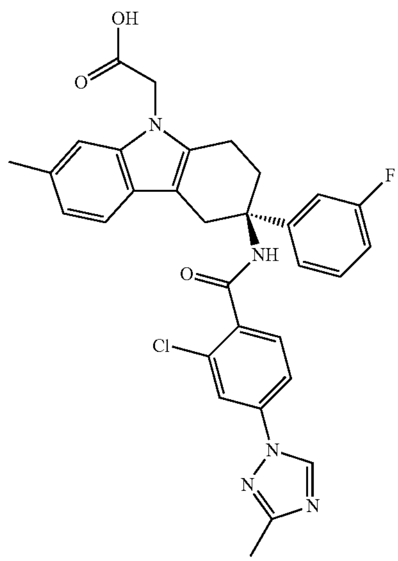 [SMILES: Cc1ccc2c3c(n(CC(=O)O)c2c1)CC[C@](NC(=O)c1ccc(-n2cnc(C)n2)cc1Cl)(c1cccc(F)c1)C3] | 8.593 | 572.19 | 572.13 |
| 119 | 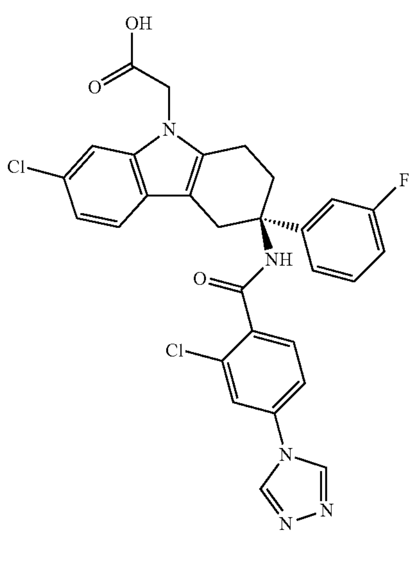 [SMILES: O=C(O)Cn1c2c(c3ccc(Cl)cc31)C[C@@](NC(=O)c1ccc(-n3cnnc3)cc1Cl)(c1cccc(F)c1)CC2] | 1.167 | 578.12 | 578.06 |

-continued

| Ex. | Structure | hFIXa IC50 (nM) | Exact Mass [M + H]+ | LCMS |
|---|---|---|---|---|
| 120 | 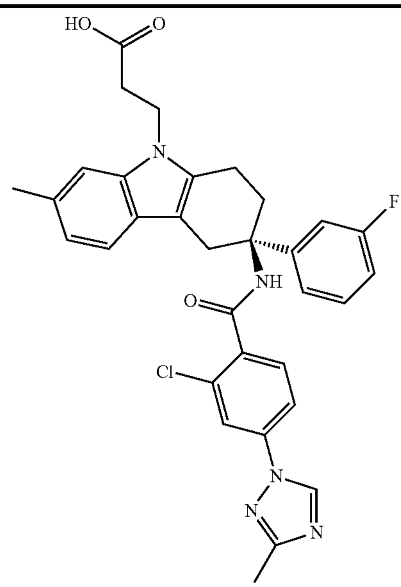 | 6.621 | 586.2 | 586.20 |
| 121 | 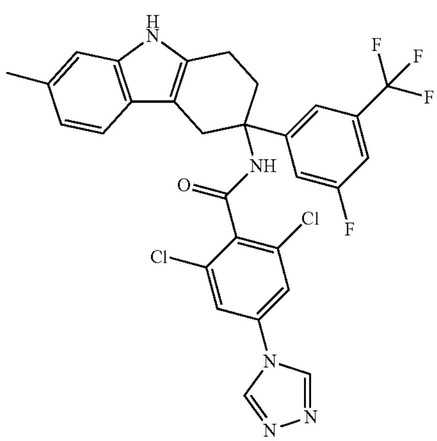 [SMILES: Cc1ccc2c3c([nH]c2c1)CCC(NC(=O)c1c(Cl)cc(-n2cnnc2)cc1Cl)(c1cc(F)cc(C(F)(F)F)c1)C3] | 19.24 | 602.11 | 602.01 |
| 122 | 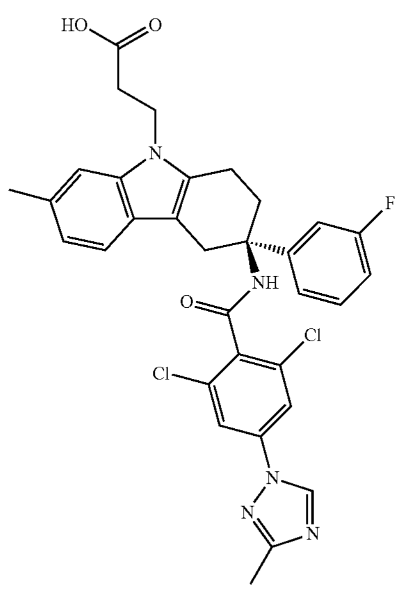 [SMILES: Cc1ccc2c3c(n(CCC(=O)O)c2c1)CC[C@](NC(=O)c1c(Cl)cc(-n2cnc(C)n2)cc1Cl)(c1cccc(F)c1)C3] | 11.67 | 620.16 | 620.12 |

-continued

| Ex. | Structure | hFIXa IC50 (nM) | Exact Mass [M + H]+ | LCMS |
|---|---|---|---|---|
| 123 | 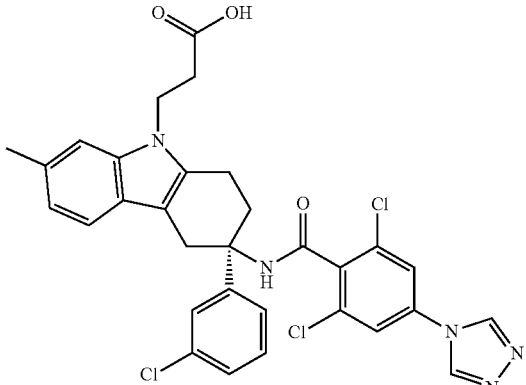 | 3.596 | 622.12 | 622.06 |

Example 131

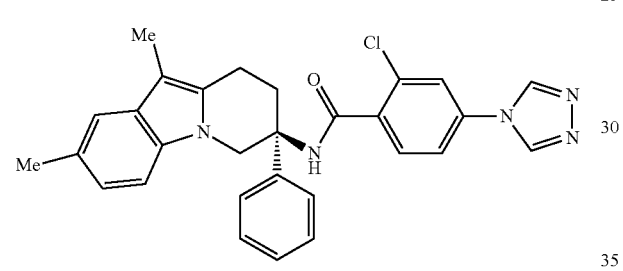

(S)-2-chloro-N-(2,10-dimethyl-7-phenyl-6,7,8,9-tetrahydropyrido[1,2-a]indol-7-yl)-4-(4H-1,2,4-triazol-4-yl)benzamide Placed (S)-2-chloro-N-(10-iodo-2-methyl-7-phenyl-6,7,8,9-tetrahydropyrido[1,2-a]indol-7-yl)-4-(4H-1,2,4-triazol-4-yl)benzamide (20 mg, 0.03 mmol) in a reaction vial. Moved the vial to a glovebox then added chloro[(tri-tert-butylphosphine)-2-(2-aminobiphenyl)] palladium(II) (1.7 mg, 3.3 μmol), followed by a solution of methylzinc(II) bromide (0.2 mL, 0.5 M, 0.1 mmol) then capped and stirred at room temperature for 1 hour. Removed the reaction from the glovebox, then diluted with ethyl acetate (1 mL) and THF (1 mL). Added Siliabond Triaminetetraacetate, sodium salt (300 mg, 0.59 mmol/g, 0.18 mmol), and stirred at room temperature for 30 minutes. Filtered, washing with ethanol (8 mL) and concentrated the combined filtrates in vacuo. Purified by mass-directed reverse phase HPLC to give (S)-2-chloro-N-(2,10-dimethyl-7-phenyl-6,7,8,9-tetrahydropyrido[1,2-a]indol-7-yl)-4-(4H-1,2,4-triazol-4-yl)benzamide. LCMS: 495.99 (M+1) $^1$H NMR (499 MHz, DMSO): δ 9.19 (s, 2H); 9.07 (s, 1H); 7.95 (s, 1H); 7.74 (s, 1H); 7.62 (d, J=8.0 Hz, 2H); 7.42-7.47 (m, 4H); 7.14-7.16 (m, 2H); 6.85 (d, J=8.3 Hz, 1H); 4.59 (d, J=12.2 Hz, 1H); 4.09 (d, J=12.2 Hz, 1H); 2.9-3.1 (m, 4H); 2.38 (s, 3H); 2.17 (s, 3H).

Example 138

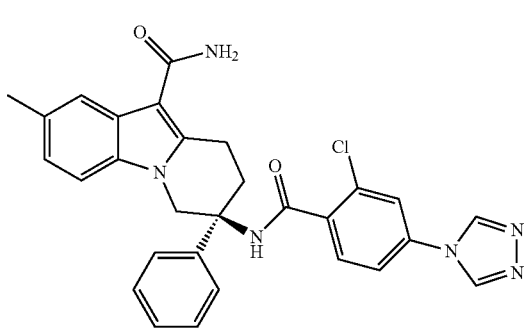 [SMILES: Cc1ccc2c(c1)c(C(N)=O)c1n2C[C@@](NC(=O)c2ccc(-n3cnnc3)cc2Cl)(c2ccccc2)CC1]

(S)-7-(2-chloro-4-(4H-1,2,4-triazol-4-yl)benzamido)-2-methyl-7-phenyl-6,7,8,9-tetrahydropyrido[1,2-a]indole-10-carboxamide Step A: (S)-2-methyl-7-nitro-7-phenyl-6,7,8,9-tetrahydropyrido[1,2-a]indole-10-carboxamide To the solution of (S)-2-methyl-7-nitro-7-phenyl-6,7,8,9-tetrahydropyrido[1,2-a]indole (0.9 g, 2.94 mmol) in CH$_2$Cl$_2$ (20 ml) at 0° C., chlorosulfonyl isocyanate (0.624 g, 4.41 mmol) was added dropwise. The reaction mixture was stirred at r.t. for 2 hr. H$_2$O was added and stirred for 1 hr. Added 200 ml of H$_2$O and extracted by CH$_2$Cl$_2$ 4×, washed the combined organic layers by brine and dried over MgSO$_4$, concentrated till dryness. The residue was purified by column chromatography on silica gel Biotage 40S, eluting with EtOAc/isohexane to give (S)-2-methyl-7-nitro-7-phenyl-6,7,8,9-tetrahydropyrido[1,2-a]indole-10-carboxamide. LCMS 350.13 (M+H)$^+$. $^1$H NMR (499 MHz, CD$_3$OD): 7.65-7.68 (m, 3H); 7.46-7.51 (m, 4H); 7.13 (d, J=8.4 Hz, 1H); 5.45 (d, J=13.9 Hz, 1H); 4.53 (d, J=13.8 Hz, 1H); 3.61 (s, 1H); 3.20 (m, 2H); 2.85 (m, 1H); 2.49 (s, 3H).

Step B. (S)-7-amino-2-methyl-7-phenyl-6,7,8,9-tetrahydropyrido[1,2-a]indole-10-carboxamide To the solution of (S)-2-methyl-7-nitro-7-phenyl-6,7,8,9-tetrahydropyrido[1,2-a]indole-10-carboxamide (89 mg, 0.255 mmol) in Ethanol (1) and Acetic Acid (1) was added Zinc (23.33 µl, 2.55 mmol) at r.t. Stirred the reaction mixture overnight. Filtered and washed by EtOAc, concentrated till dryness. The residue was purified by column chromatography on silica gel Biotage 12S, eluting with $CH_2Cl_2$/MeOH to give (S)-7-amino-2-methyl-7-phenyl-6,7,8,9-tetrahydropyrido[1,2-a]indole-10-carboxamide. LCMS 320.11 $(M+H)^+$. $^1H$ NMR (500 MHz, $CD_3OD$): 7.68 (s, 1H); 7.50 (d, J=7.8 Hz, 2H); 7.30-7.39 (m, 4H); 7.10 (d, J=8.5 Hz, 1H); 4.65 (t, J=12.6 Hz, 1H); 4.26 (d, J=12.7 Hz, 1H); 3.41 (dt, J=18.6, 6.4 Hz, 1H); 3.06 (dt, J=18.7, 6.9 Hz, 1H); 2.56 (dt, J=13.6, 6.5 Hz, 1H); 2.48 (s, 3H); 2.33 (dt, J=13.7, 6.8 Hz, 1H).

Step C. (S)-7-(2-chloro-4-(4H-1,2,4-triazol-4-yl) benzamido)-2-methyl-7-phenyl-6,7,8,9-tetrahydropyrido[1,2-a]indole-10-carboxamide Dissolved (S)-7-amino-2-methyl-7-phenyl-6,7,8,9-tetrahydropyrido[1,2-a]indole-10-carboxamide (81 mg, 0.255 mmol) and 2-chloro-4-(4H-1,2,4-triazol-4-yl)benzoic acid (86 mg, 0.383 mmol) in DMF (5 ml) and added Hunig's Base (0.089 ml, 0.510 mmol), HATU (194 mg, 0.510 mmol). The mixture was stirred at r.t. for 4 h. Added EtOAc and washed with $H_2O$ to remove DMF. The organic layer was washed by brine and dried over $MgSO_4$, concentrated till dryness. Purified by column chromatography on 180 g C18 column, eluting with Acetonitrile/Water+0.1% TFA. This product was repurified by prep. TLC (5% MeOH in CH2Cl2 to give (S)-7-(2-chloro-4-(4H-1,2,4-triazol-4-yl)benzamido)-2-methyl-7-phenyl-6,7,8,9-tetrahydropyrido[1,2-a]indole-10-carboxamide. LCMS 525.14 $(M+H)^+$, $^1H$ $^1H$ NMR (500 MHz, $CD_3OD$): 9.04 (s, 2H); 7.81 (s, 1H); 7.70 (s, 1H); 7.62 (t, J=7.5 Hz, 3H); 7.45 (dd, J=12.5, 7.8 Hz, 3H); 7.33 (d, J=8.5 Hz, 2H); 7.08 (m, 1H); 4.90 (m, 1H); 4.50 (m, 1H); 3.45 (m, 2H); 3.00 (m, 1H); 2.58 (m, 1H); 2.47 (s, 3H).

Example 135 & 146

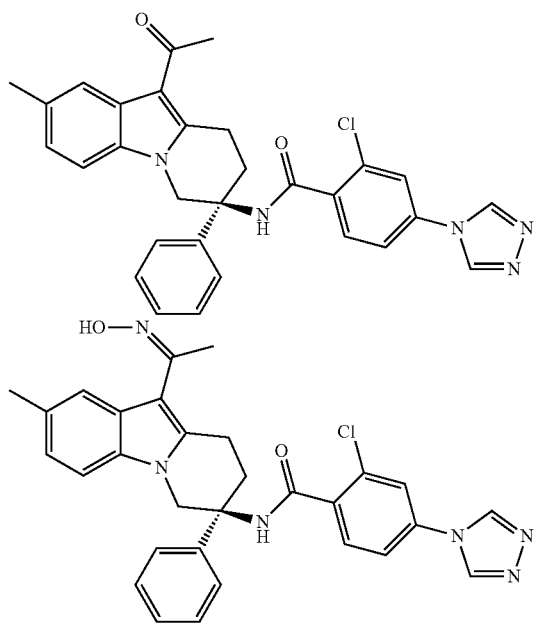

N-(10-acetyl-2-methyl-7-phenyl-6,7,8,9-tetrahydropyrido[1,2-a]indol-7-yl)-2-chloro-4-(4H-1,2,4-triazol-4-yl)benzamide and (E)-2-chloro-N-(10-(1-(hydroxyimino)ethyl)-2-methyl-7-phenyl-6,7,8,9-tetrahydropyrido[1,2-a]indol-7-yl)-4-(4H-1,2,4-triazol-4-yl)benzamide, TFA Step A: N-(10-acetyl-2-methyl-7-phenyl-6,7,8,9-tetrahydropyrido[1,2-a]indol-7-yl)-2-chloro-4-(4H-1,2,4-triazol-4-yl)benzamide To DMA was added phosphorus oxychloride (47.1 µl, 0.505 mmol). After stirring at r.t. for 10 min., this mixture was added to 2-chloro-N-(2-methyl-7-phenyl-6,7,8,9-tetrahydropyrido[1,2-a]indol-7-yl)-4-(4H-1,2,4-triazol-4-yl)benzamide, HCl (131 mg, 0.253 mmol) (9:20 a.m.). The mixture was heated at 85° C. for 3 h, LCMS showed that starting material was gone. Water (6.3 ml) and 1N NaOH (6.3 ml) was added to adjust the pH to 13-14, the mixture was stirred at r.t. for 1 h. Extracted with 10% of MeOH in DCM (100 ml×2). The combined solvents were dried by $Na_2SO_4$, filtered and the solvent was evaporated under reduced pressure. The crude residue was purified by TLC on silica gel plates, eluting with 8% of MeOH in DCM to give N-(10-acetyl-2-methyl-7-phenyl-6,7,8,9-tetrahydropyrido[1,2-a]indol-7-yl)-2-chloro-4-(4H-1,2,4-triazol-4-yl)benzamide (the third spot from top), and the second big spot from top is the starting material. LCMS 524.03 $(M+H)^+$.

Step B: (E)-2-chloro-N-(10-(1-(hydroxyimino)ethyl)-2-methyl-7-phenyl-6,7,8,9-tetrahydropyrido[1,2-a]indol-7-yl)-4-(4H-1,2,4-triazol-4-yl)benzamide, TFA A mixture of N-(10-acetyl-2-methyl-7-phenyl-6,7,8,9-tetrahydropyrido[1,2-a]indol-7-yl)-2-chloro-4-(4H-1,2,4-triazol-4-yl)benzamide (5.9 mg, 0.011 mmol) and hydroxylamine (1 µl, 0.016 mmol) in pyridine (0.2 ml) was heated at 80° C. for 2 h. No product was found after checked by LCMS, and more hydroxylamine (1 µl, 0.016 mmol) was added. The reaction was heated at 100° C. overnight. The pyridine was removed in vasuo, and the residue was then purified by Gilson with C-18 column reversed column and 0.1% of TFA in both water and MeCN, the desired product was obtained as a TFA salt. LCMS 539.01 $(M+H)^+$.

Example 149

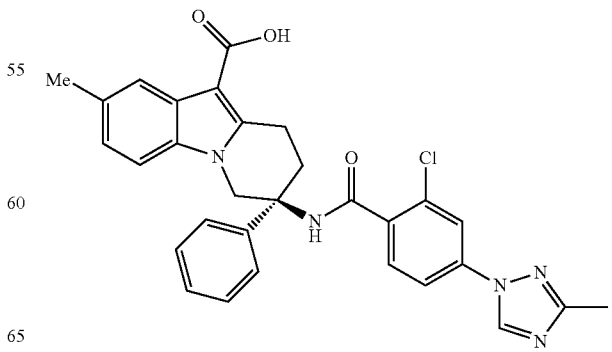

(S)-7-(2-methoxy-4-(3-methyl-1H-1,2,4-triazol-1-yl) benzamido)-2-methyl-7-phenyl-6,7,8,9-tetrahydro-pyrido[1,2-a]indole-10-carboxylic acid Step A. (S)-methyl 2-methyl-7-nitro-7-phenyl-6,7,8, 9-tetrahydropyrido[1,2-a]indole-10-carboxylate To a solution of (S)-2-methyl-7-nitro-7-phenyl-6,7,8,9-tetrahydropyrido[1,2-a]indole (500 mg, 1.632 mmol) in dry CH$_2$Cl$_2$ (10 ml)) at 0° C. was added phosgene (1.514 mL, 2.122 mmol). After stirred at 0° C. for 1 h, methanol (523 mg, 16.32 mmol) and triethylamine (495 mg, 4.90 mmol) were added to the solution. Then it was stirred at 0° C. for another 60 min. The reaction mixture was concentrated and the residue was purified by column chromatography on silica gel Biotage 40S, eluting with EtOAc/isohexane to give: (S)-methyl 2-methyl-7-nitro-7-phenyl-6,7,8,9-tetrahydropyrido[1,2-a]indole-10-carboxylate. LCMS 365 (M+H)$^+$. $^1$H NMR (500 MHz, CD$_3$OD): 7.85 (s, 1H); 7.64-7.66 (m, 2H); 7.51 (d, J=6.9 Hz, 2H); 7.47 (d, J=8.4 Hz, 2H); 7.10 (m, 1H); 5.42 (m, 1H); 4.48 (m, 1H); 3.89 (s, 3H); 3.60 (m, 1H); 3.22 (m, 1H); 3.18 (m, 1H); 2.85 (m, 1H); 2.46 (s, 3H).

Step B. (S)-methyl 2-methyl-7-amino-7-phenyl-6,7, 8,9-tetrahydropyrido[1,2-a]indole-10-carboxylate To a solution of (S)-methyl 2-methyl-7-nitro-7-phenyl-6, 7,8,9-tetrahydropyrido[1,2-a]indole-10-carboxylate (400 mg, 1.098 mmol) in ethanol (100 ml) and acetic acid (100 ml) was added zinc (10 ml, 1.098 mmol). The mixture was stirred at r.t. overnight, then filtered through celite and concentrated. The product was purified on silica gel flash chromatography (eluent: 5-methanol in DCM) to give (S)-methyl 2-methyl-7-amino-7-phenyl-6,7,8,9-tetrahydro-pyrido[1,2-a]indole-10-carboxylate. LCMS 335 (M+H)$^+$. $^1$H NMR (500 MHz, CD$_3$OD): 7.84 (s, 1H); 7.46 (d, J=7.8 Hz, 2H); 7.37 (d, J=8.3 Hz, 1H); 7.34-7.27 (m, 3H); 7.27 (d, J=7.3 Hz, 1H); 7.09 (d, J=8.2 Hz, 1H); 4.60 (m, 1H); 4.15 (m, 1H); 3.42 (m, 1H); 2.98 (m, 1H); 2.46 (s, 1H); 2.10 (m, 1H); 2.41 (s, 3H)

Step C: (S)-methyl 7-(2-chloro-4-(3-methyl-1H-1,2, 4-triazol-1-yl)benzamido)-2-methyl-7-phenyl-6,7,8, 9-tetrahydropyrido[1,2-a]indole-10-carboxylate To a solution of (S)-methyl 7-amino-2-methyl-7-phenyl-6,7,8,9-tetrahydropyrido[1,2-a]indole-10-carboxylate, intermediate 12 (200 mg, 0.598 mmol)) and 2-chloro-4-(3-methyl-1H-1,2,4-triazol-1-yl)benzoic acid (213 mg, 0.897 mmol)) in DMF (20 ml) were added N-ethyl-N-isopropyl-propan-2-amine (0.208 ml, 1.196 mmol), 2-(3H-[1,2,3]tri-azolo[4,5-b]pyridin-3-yl)-1,1,3,3-tetramethylisouronium hexafluorophosphate (V), HATU (455 mg, 1.196 mmol). The mixture was stirred at r.t. overnight. EtOAc was added and washed with H$_2$O to remove DMF. The organic layer was washed with brine, and dried over MgSO$_4$, and concentrated till dryness. Purified by column chromatography on 180 g C18 column, eluting with Acetonitrile/Water+0.1% TFA. Later, it was converted to free base: (S)-methyl 7-(2-chloro-4-(3-methyl-1H-1,2,4-triazol-1-yl)benz amido)-2-methyl-7-phenyl-6,7,8,9-tetrahydropyrido[1,2-a]indole-10-carboxylate. LCMS 522 (M+H $^1$H NMR (500 MHz, CD$_3$OD): 9.18 (s, 1H); 9.03 (s, 1H); 7.85-7.86 (m, 2H); 7.73-7.75 (m, 1H); 7.61 (d, J=7.8 Hz, 2H); 7.45-2.15 (m, 4H); 7.05 (d, J=8.2 Hz, 1H); 4.85 (m, 1H); 4.45 (m, 1H); 3.91 (s, 3H); 3.45 (m, 2H); 3.00 (m, 1H); 2.48 (m, 1H); 2.41 (s, 3H); 2.40 (s, 3H).

Step D: 2a, (S)-7-(2-chloro-4-(3-methyl-H-1,2,4-triazol-1-yl)benzamido)-2-methyl-7-phenyl-6,7,8,9-tetrahydropyrido[1,2-a]indole-10-carboxylic acid and 2b, (S)-7-(2-methoxy-4-(3-methyl-1H-1,2,4-triazol-1-yl)benzamido)-2-methyl-7-phenyl-6,7,8,9-tetrahydropyrido[1,2-a]indole-10-carboxylic acid To the mixture of (S)-methyl 7-(2-chloro-4-(3-methyl-1H-1,2,4-triazol-1-yl)benzamido)-2-methyl-7-phenyl-6,7,8, 9-tetrahydropyrido[1,2-a]indole-10-carboxylate (300 mg, 0.541 mmol) in MeOH (10 ml) and THF (10 ml), LiOH (12.97 mg, 0.541 mmol) in water (5 ml) was added. The mixture was stirred at r.t. overnight. LC-MS showed some starting material left. LiOH was added and the reaction mixture was heated to 80° C. for 2 days. The organic solvent was removed and dissolved in DMSO/H$_2$O/ACN. The solution was neutralized by addition of TFA and purified by preparative HPLC (sunfire column), eluting with Acetonitrile/Water+0.1% TFA, 0% to 60% then prep. TLC (6% MeOH/CH2Cl2) to give 2a, (S)-7-(2-chloro-4-(3-methyl-1H-1,2,4-triazol-1-yl)benzamido)-2-methyl-7-phenyl-6,7,8, 9-tetrahydropyrido[1,2-a]indole-10-carboxylic acid compound. LCMS 540.14 (M+H)$^+$. $^1$H NMR (500 MHz, CD$_3$OD): 8.97 (s, 1H); 7.93 (s, 1H); 7.83 (d, J=2.0 Hz, 1H); 7.68 (dd, J=8.4, 2.1 Hz, 1H); 7.60 (d, J=7.8 Hz, 2H); 7.44 (t, J=7.6 Hz, 2H); 7.34 (t, J=8.9 Hz, 2H); 7.23 (d, J=8.3 Hz, 1H); 7.01 (d, J=8.4 Hz, 1H); 4.82 (m, 1H); 4.38 (m, 1H); 3.45-3.48 (m, 2H); 2.88 (m, 1H); 2.50 (m, 1H); 2.41 (s, 3H); 2.40 (s, 3H) and 2b, (S)-7-(2-methoxy-4-(3-methyl-1H-1,2, 4-triazol-1-yl)benzamido)-2-methyl-7-phenyl-6,7,8,9-tetra-hydropyrido[1,2-a]indole-10-carboxylic acid. LCMS 536.14 (M+H)$^+$. $^1$H NMR (500 MHz, CD$_3$OD): 9.03 (s, 1H); 7.93 (s, 1H); 7.74 (d, J=8.3 Hz, 1H); 7.59 (d, J=7.8 Hz, 2H); 7.41-7.44 (m, 4H); 7.32 (t, J=7.8 Hz, 2H); 5.50 (s, 1H); 4.36 (s, 1H); 3.59 (s, 3H); 2.44 (d, J=15.8 Hz, 6H); 1.30 (s, 1H).

Example 155

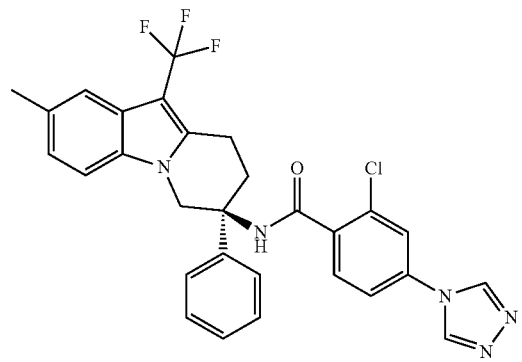 [SMILES: Cc1ccc2c(c1)c(C(F)(F)F)c1n2C[C@@](NC(=O)c2ccc(-n3cnnc3)cc2Cl)(c2ccccc2)CC1]

(S)-2-chloro-N-(2-methyl-7-phenyl-10-(trifluorom-ethyl)-6,7,8,9-tetrahydropyrido[12]indol-7-yl)-4-(4H-1,2,4-triazol-4-yl)benzamide To (32 mg, 0.066 mmol) of (S)-2-chloro-N-(2-methyl-7-phenyl-6,7,8,9-tetrahydropyrido[1,2]indol-7-yl)-4-(4H-1,2, 4-triazol-4-yl)benzamide in anhydrous DMSO was added trifluoromethyl iodide (116 uL, 1.7 M DMSO solution), Tris[2-(4,6-difluorophenyl) pyridinato-C²,N]iridium(III) (1.01 mg, 0.00132 mmol) and potassium carbonate (18.2 mg, 0.132 mmol) was placed in an N₂ atmosphere. The stirred suspension was irradiated with a blue LED light at room temperature for 18 h. The mixture was filtered through a syringe filter and purified by HPLC (C18, 20-80% MeCN in water with 0.1% TFA). The product fractions were collected and lyophilized to give (S)-2-chloro-N-(2-methyl-7-phenyl-10-(trifluoromethyl)-6,7,8,9-tetrahydropyrido[1,2]indol-7-yl)-4-(4H-1,2,4-triazol-4-yl)benzamide. LCMS calc.=549.97; found=549.95 (M+1)⁺. ¹H NMR (500 MHz, MeCN-d₃): δ 8.67 (s, 2H); 7.66 (d, J=1.9 Hz, 1H); 7.64 (d, J=5.4 Hz, 1H); 7.57-7.44 (m, 5H); 7.42 (d, J=7.3 Hz, 1H); 7.40 (d, J=7.3 Hz, 1H); 7.33 (d, J=8.5 Hz, 1H); 7.08 (m, 1H); 4.77 (d, J=12.9 Hz, 1H); 4.26 (d, J=13.7 Hz, 1H), 3.33 (m, 2H); 3.06 (m, 1H), 2.59 (dd, J=7.4 Hz, J=3.4 Hz, 1H); 2.45 (S, 3H).

Example 156

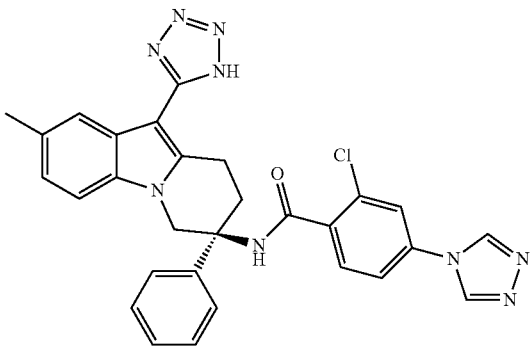 [SMILES: Cc1ccc2c(c1)c(-c1nnn[nH]1)c1n2C[C@@](NC(=O)c2ccc(-n3cnnc3)cc2Cl)(c2ccccc2)CC1]

(S)-2-chloro-N-(2-methyl-7-phenyl-10-(1H-tetrazol-5-yl)-6,7,8,9-tetrahydropyrido[1,2-a]indol-7-yl)-4-(4H-1,2,4-triazol-4-yl)benzamide, TFA To a solution of (S)-2-chloro-N-(10-cyano-2-methyl-7-phenyl-6,7,8,9-tetrahydropyrido[1,2-a]indol-7-yl)-4-(4H-1,2,4-triazol-4-yl)benzamide (98 mg, 0.193 mmol) in Toluene (1.6 ml) was added Sibutytin (IV) oxide (14.44 mg, 0.058 mmol) and azidotrimethylsilane (0.520 ml, 3.87 mmol). The mixture was heated at 110° C. overnight. The reaction temperature was maintained at 100° C. for 7 days. After the toluene was evaporated, it was purified by a reversed C-18 column which was eluted with 0.1% of TFA in both water and MeCN to give the desired product. LCMS 550.14 (M+H)⁺.

Example 160

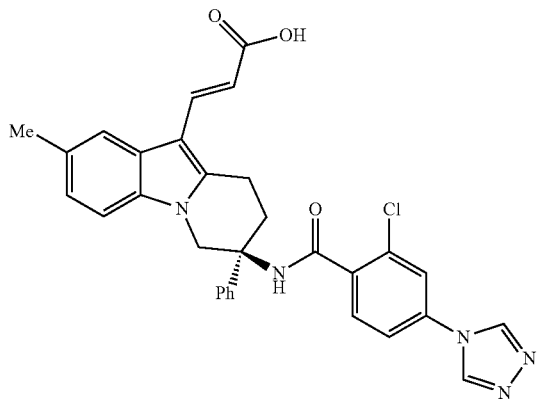 [SMILES: Cc1ccc2c(c1)c(/C=C/C(=O)O)c1n2C[C@@](NC(=O)c2ccc(-n3cnnc3)cc2Cl)(c2ccccc2)CC1]

(S,E)-3-(7-(2-chloro-4-(4H-1,2,4-triazol-4-yl)benzamido)-2-methyl-7-phenyl-6,7,8,9-tetrahydropyrido[1,2-a]indol-10-yl)acrylic acid Step A. (S)-2-methyl-7-amino-7-phenyl-6,7,8,9-tetrahydropyrido[1,2-a]indole To a solution of (S)-2-methyl-7-nitro-7-phenyl-6,7,8,9-tetrahydropyrido[1,2-a]indolein Ethanol (25 ml) and Acetic Acid (25 ml) was added zinc (0.299 ml, 32.6 mmol). The reaction mixture was stirred at r.t. overnight, then filtered and washed with EtOAc, concentrated till dryness. The residue was dissolved in CH₂Cl₂ and washed with Na₂CO₃ until PH=8. The organic layer was washed with brine and dried over MgSO₄, concentrated till dryness to give (S)-2-methyl-7-amino-7-phenyl-6,7,8,9-tetrahydropyrido[1,2-a]indole. LCMS 277 (M+H)⁺. ¹H NMR (500 MHz, CD₃OD): 7.38 (d, J=7.8 Hz, 2H); 7.18-7.28 (m, 5H); 6.92 (d, J=8.3 Hz, 1H); 6.02 (s, 1H); 4.29 (d, J=12.1 Hz, 1H); 3.87 (d, J=12.1 Hz, 1H); 2.99 (dt, J=17.0, 6.4 Hz, 1H); 2.58-2.64 (m, 1H); 2.39 (s, 3H); 2.25 (dt, J=13.1, 6.4 Hz, 1H); 1.97-2.02 (m, 1H)

Step B. (S)-2-chloro-N-(2-methyl-7-phenyl-6,7,8,9-tetrahydropyrido[1,2-a]indol-7-yl)-4-(4H-1,2,4-triazol-4-yl)benzamide To a solution of (S)-2-methyl-7-phenyl-6,7,8,9-tetrahydropyrido[1,2-a]indol-7-amine, (1.804 g, 6.53 mmol) and 2-chloro-4-(4H-1,2,4-triazol-4-yl)benzoic acid (2.189 g, 9.79 mmol) in DMF (150 ml) were added Hunig's Base (2.280 ml, 13.05 mmol), and HATU (4.96 g, 13.05 mmol). The mixture was stirred at r.t. for 4 h. EtOAc was added and washed with H₂O to remove DMF. The organic layer was washed with brine and dried over MgSO₄, concentrated till dryness. Purified by column chromatography on 180 g C18 column, eluting with Acetonitrile/Water. (S)-2-chloro-N-(2-methyl-7-phenyl-6,7,8,9-tetrahydropyrido[1,2-a]indol-7-yl)-4-(4H-1,2,4-triazol-4-yl)benzamide. LCMS 482 (M+H)⁺. ¹H NMR (500 MHz, CD₃OD): 9.03 (s, 2H); 7.88 (s, 1H); 7.68 (m, 3H); 7.42 (m, 3H); 7.52 (m, 1H); 7.21 (s, 1H); 7.20 (m, 1H); 6.93 (m, 1H); 6.12 (s, 1H); 4.63 (d, J=12.4 Hz, 1H); 4.38 (d, J=12.4 Hz, 1H); 3.22 (m, 1H); 3.00 (m, 2H); 2.50 (m, 1H); 2.39 (s, 3H)

Step C. (S)-2-chloro-N-(10-iodo-2-methyl-7-phenyl-6,7,8,9-tetrahydropyrido[1,2-a]indol-7-yl)-4-(4H-1,2,4-triazol-4-yl)benzamide To the solution of (S)-2-chloro-N-(2-methyl-7-phenyl-6,7,8,9-tetrahydropyrido[1,2-a]indol-7-yl)-4-(4H-1,2,4-triazol-4-yl)benzamide (1 g, 2.075 mmol) in CH$_2$Cl$_2$ (40 ml) at −10° C. was added NIS (0.467 g, 2.075 mmol) and stirred at this temp. for 1 hr. The reaction mixture was purified by column chromatography on silica gel 80, eluting with CH$_2$Cl$_2$/MeOH (0% to 10%) to give (S)-2-chloro-N-(10-iodo-2-methyl-7-phenyl-6,7,8,9-tetra hydropyrido[1,2-a]indol-7-yl)-4-(4H-1,2,4-triazol-4-yl)benzamide. LCMS 607 (M+H)$^+$, $^1$H NMR (500 MHz, CD$_3$OD): 9.02 (s, 2H); 7.79 (s, 1H); 7.58-7.62 (m, 3H); 7.40-7.50 (m, 3H); 7.36 (t, J=7.4 Hz, 1H); 7.21 (d, J=8.3 Hz, 1H); 7.08 (s, 1H); 7.00 (d, J=8.4 Hz, 1H); 4.80 (s, 1H); 4.52 (s, 1H); 2.95-3.20 (m, 3H); 2.53 (m, 1H); 2.42 (m, 3H)

Step D. (S,E)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)acrylate Added chloro[(tri-tert-butylphosphine)-2-(2-aminobiphenyl)]palladium(II) (8.43 mg, 0.016 mmol) to a vial containing (S)-2-chloro-N-(10-iodo-2-methyl-7-phenyl-6,7,8,9-tetrahydropyrido[1,2-a]indol-7-yl)-4-(4H-1,2,4-triazol-4-yl)benzamide (100 mg, 0.165 mmol), then added methyl acrylate (0.014 ml, 0.165 mmol) and DMA (1 ml). N-cyclohexyl-N-methylcyclohexanamine (0.070 ml, 0.329 mmol) was added, the vial was sealed and heated to 80° C. for 1 hr. The reaction mixture was filtered and washed with 1 mL DMSO. The residue was purified by preparative HPLC Reverse phase (C-18), eluting with Acetonitrile/Water to give (S,E)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)acrylate 2,2,2-trifluoroacetate. LCMS 566 (M+H)$^+$. $^1$H NMR (500 MHz, CD$_3$OD): 9.02 (s, 2H); 8.00 (s, 1H); 7.97 (s, 1H); 7.63 (m, 4H); 7.40-7.50 (m, 3H); 7.38 (m, 1H); 7.30 (m, 1H); 7.06 (m, 1H); 6.26 (m, 1H); 4.90 (m, 1H); 4.40 (m, 1H); 3.80 (s, 3H); 3.25 (m, 2H); 3.05 (m, 1H); 2.58 (m, 1H); 2.46 (s, 3H).

Step E. (S,E)-3-(7-(2-chloro-4-(4H-1,2,4-triazol-4-yl)benzamido)-2-methyl-7-phenyl-6,7,8,9-tetrahydropyrido[1,2-a]indol-10-yl)acrylic acid To the solution of (S,E)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)acrylate, (70 mg, 0.124 mmol) in MeOH (1 ml) was added lithium hydroxide (2.96 mg, 0.124 mmol). The mixture was stirred at r.t. overnight. After all of the organic solvent was removed, ACN/H$_2$O (1/9) was added. The residue was purified by column chromatography on silica gel 4 g column eluting with CH$_2$Cl$_2$/MeOH to give (S,E)-3-(7-(2-chloro-4-(4H-1,2,4-triazol-4-yl)benzamido)-2-methyl-7-phenyl-6,7,8,9-tetrahydropyrido[1,2-a]indol-10-yl)acrylic acid. LCMS 552 (M+H)$^+$. $^1$H NMR (500 MHz, CD$_3$OD): 9.02 (s, 2H); 7.75-7.78 (m, 2H); 7.66 (s, 1H); 7.60 (dd, J=21.3, 7.9 Hz, 3H); 7.33-7.45 (m, 4H); 7.23 (d, J=8.3 Hz, 1H); 7.00 (d, J=8.3 Hz, 1H); 4.80 (d, J=12.6 Hz, 1H); 4.33 (d, J=12.6 Hz, 1H); 3.23 (m, 2H); 3.0 (m, 1H); 2.50 (m, 1H); 2.42 (s, 3H).

Example 161

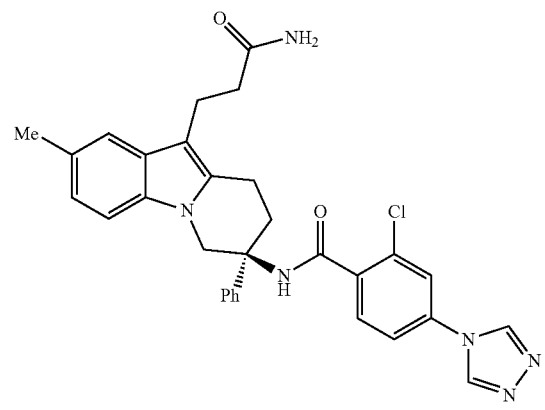 [SMILES: Cc1ccc2c(c1)c(CCC(N)=O)c1n2C[C@@](NC(=O)c2ccc(-n3cnnc3)cc2Cl)(c2ccccc2)CC1]

(S)—N-(10-(3-amino-3-oxopropyl)-2-methyl-7-phenyl-6,7,8,9-tetrahydropyrido[1,2-a]indol-7-yl)-2-chloro-4-(4H-1,2,4-triazol-4-yl)benzamide 2,2,2-trifluoroacetate To a solution of (S)-3-(7-(2-chloro-4-(4H-1,2,4-triazol-4-yl)benzamido)-2-methyl-7-phenyl-6,7,8,9-tetrahydropyrido[1,2-a]indol-10-yl)propanoic acid, (18 mg, 0.032 mmol) in DMF (0.5 ml) were added N1-((ethylimino)methylene)-N3,N3-dimethylpropane-1,3-diamine hydrochloride, EDC (9.34 mg, 0.049 mmol), 3H-[1,2,3]triazolo[4,5-b]pyridin-3-ol, HOAt (6.63 mg, 0.049 mmol). The mixture was stirred at r.t. for 10 min, then ammonia hydrochloride was added (8.69 mg, 0.162 mmol), and N-isopropyl-N-methylpropan-2-amine (0.030 ml, 0.195 mmol) in DMF (0.5 ml) were added into above mixture and stirred at r.t. over the weekend. The residue was purified by preparative HPLC Reverse phase (C-18), eluting with Acetonitrile/Water+0.1% TFA, to give (S)—N-(10-(3-amino-3-oxopropyl)-2-methyl-7-phenyl-6,7,8,9-tetrahydropyrido[1,2-a]indol-7-yl)-2-chloro-4-(4H-1,2,4-triazol-4-yl)benzamide 2,2,2-trifluoroacetate. LCMS 553.12 (M+H)$^+$, $^1$H NMR (500 MHz, CD$_3$OD): 9.15 (s, 1H); 9.05 (s, 2H); 7.81 (d, J=2.1 Hz, 1H); 7.61 (d, J=8.0 Hz, 3H); 7.40-7.45 (m, 3H); 7.31-7.34 (m, 1H); 7.17 (d, J=8.3 Hz, 1H); 6.92 (d, J=8.3 Hz, 1H); 4.67 (m, 1H); 4.37 (m, 1H); 3.19 (m, 1H); 2.99-3.04 (m, 4H); 2.51 (m, 3H); 2.42 (s, 3H);

Example 167

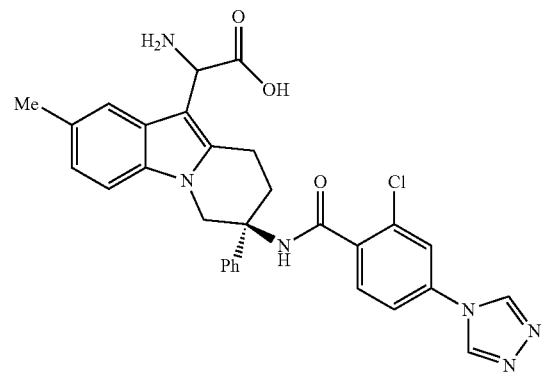 [SMILES: Cc1ccc2c(c1)c(C(N)C(=O)O)c1n2C[C@@](NC(=O)c2ccc(-n3cnnc3)cc2Cl)(c2ccccc2)CC1]

2-amino-2-((S)-7-(2-chloro-4-(4H-1,2,4-triazol-4-yl)
benzamido)-2-methyl-7-phenyl-6,7,8,9-tetrahydro-
pyrido[1,2-a]indol-10-yl)acetic acid Step A. (R,E)-
ethyl 2-((tert-butylsulfinyl)imino)acetate To a solution of ethyl glyoxalate (421 mg, 4.13 mmol) in CH$_2$Cl$_2$ (18 ml) was added (R)-(+)-2-methyl-2-propanesulfinamide (500 mg, 4.13 mmol) and molecular sieves (4 A, 1 g). After stirring at rt for 58 h, the mixture was filtered through a pad of Na sulphate/celite, concentrated and used as crude for next step. $^1$H NMR (500 MHz, CD2Cl2): 7.10-7.50 (m, 1H); 4.20 (m, 2H); 1.00-1.60 (m, 12H).

Step B. ethyl 2-((R)-1,1-dimethylethylsulfinamido)-
2-((S)-2-methyl-7-nitro-7-phenyl-6,7,8,9-tetrahydro-
pyrido[1,2-a]indol-10-yl)acetate To (S)-2-methyl-7-nitro-7-phenyl-6,7,8,9-tetrahydropyrido[1,2-a]indole (800 mg, 2.61 mmol) in CH$_2$Cl$_2$ (20 ml) was added (R,E)-ethyl 2-((tert-butylsulfinyl)imino)acetate (697 mg, 3.39 mmol) and copper(II) trifluoromethanesulfonate (283 mg, 0.783 mmol). After stirring for 1 h, the mixture was loaded on the on prep TLC on silica gel column, eluting with 60% EtOAc/isohexane to give ethyl 2-((R)-1,1-dimethylethylsulfinamido)-2-((S)-2-methyl-7-nitro-7-phenyl-6,7,8,9-tetrahydropyrido[1,2-a]indol-10-yl)acetate. LCMS 512.10 (M+H)$^+$, $^1$H NMR (500 MHz, CD$_3$OD): 7.50-7.60 (m, 4H); 7.40 (m, 1H); 7.30 (m, 2H); 7.10 (m, 1H); 5.35 (m, 1H); 5.30 (s, 1H); 4.45 (m, 1H); 4.10-4.25 (m, 2H); 3.30 (m, 2H); 3.10 (m, 1H); 2.80 (m, 1H); 1.20 (s, 9H); 1.18 (m, 3H).

Step C. ethyl 2-((S)-7-amino-2-methyl-7-phenyl-6,
7,8,9-tetrahydropyrido[1,2-a]indol-10-yl)-2-(1,1-
dimethylethylsulfinamido)acetate Stirred the mixture of ethyl 2-(1,1-dimethylethyl sulfinamido)-2-((S)-2-methyl-7-nitro-7-phenyl-6,7,8,9-tetrahydropyrido[1,2-a]indol-10-yl)acetate (500 mg, 0.977 mmol) and zinc (128 mg, 1.955 mmol) in EtOH (5 ml)) and Acetic Acid (5 ml) at r.t. for 3 hr. The reaction mixture was filtered and washed with EtOAc, then concentrated till dryness. The residue was purified by column chromatography on silica gel Biotage 12M column, eluting with CH$_2$Cl$_2$/MeOH to give ethyl 2-((S)-7-amino-2-methyl-7-phenyl-6,7,8,9-tetrahydropyrido[1,2-a]indol-10-yl)-2-(1,1-dimethylethylsulfinamido)acetate. LCMS 482.22 (M+H)$^+$. $^1$H NMR (500 MHz, CD$_3$OD): $^1$H NMR (500 MHz, CD$_3$OD): 7.46 (d, J=7.8 Hz, 2H); 7.26-7.34 (m, 5H); 6.99 (d, J=8.3 Hz, 1H); 5.22 (s, 1H); 4.59 (m, 1H); 4.05-4.17 (m, 3H); 3.15 (dt, J=17.3, 6.3 Hz, 1H); 2.77 (dd, J=8.1, 6.0 Hz, 1H); 2.47 (dt, J=13.3, 6.3 Hz, 1H); 2.39 (s, 3H); 2.21 (dd, J=13.4, 6.8 Hz, 1H); 1.10-1.12 (m, 12H).

Step D. ethyl 2-((S)-7-(2-chloro-4-(4H-1,2,4-triazol-
4-yl)benzamido)-2-methyl-7-phenyl-6,7,8,9-tetrahy-
dropyrido[1,2-a]indol-10-yl)-2-((R)-1,1-dimethyl-
ethyl sulfinamido)acetate To a solution of 2-chloro-4-(4H-1,2,4-triazol-4-yl)benzoic acid (13.93 mg, 0.062 mmol) in DMF (2 ml) were added N1-((ethylimino)methylene)-N3,N3-dimethylpropane-1,3-diamine hydrochloride, EDC (17.91 mg, 0.093 mmol), 3H-[1,2,3]triazolo[4,5-b]pyridin-3-ol, HOAt (12.72 mg, 0.093 mmol). The reaction mixture was stirred at r.t. for 10 min, followed by the addition of ethyl 2-((S)-7-amino-2-methyl-7-phenyl-6,7,8,9-tetrahydropyrido[1,2-a]indol-10-yl)-2-((R)-1,1-dimethylethylsulfinamido)acetate (30 mg, 0.062 mmol) in DMF (2 ml) into above mixture and stirring at r.t. for 1.5 hr. The residue was purified by preparative HPLC Reverse phase (C-18), eluting with Acetonitrile/Water to give ethyl 2-((S)-7-(2-chloro-4-(4H-1,2,4-triazol-4-yl)benzamido)-2-methyl-7-phenyl-6,7,8,9-tetra hydropyrido[1,2-a]indol-10-yl)-2-((R)-1,1-dimethylethylsulfinamido)acetate. LCMS 687.26 (M+H)$^+$, 1H NMR (500 MHz, CD$_3$OD): 9.25 (s, 1H); 9.09 (s, 2H); 7.83 (d, J=2.1 Hz, 1H); 7.63 (d, J=7.9 Hz, 3H); 7.52 (d, J=8.3 Hz, 1H); 7.44 (t, J=7.7 Hz, 2H); 7.35-7.37 (m, 2H); 7.23 (d, J=8.3 Hz, 1H); 5.28 (s, 1H); 4.80 (m, 1H); 4.30 (m, 1H); 4.10-4.25 (m, 2H); 3.10-3.25 (m, 2H); 2.60 (m, 1H); 2.38 (m, 4H); 1.19-1.20 (m, 12H).

Step E. 2-((S)-7-(2-chloro-4-(4H-1,2,4-triazol-4-yl)
benzamido)-2-methyl-7-phenyl-6,7,8,9-tetrahydro-
pyrido[1,2-a]indol-10-yl)-2-((R)-1,1-dimethylethyl-
sulfinamido)acetic acid To the mixture of ethyl 2-((S)-7-(2-chloro-4-(4H-1,2,4-triazol-4-yl)benzamido)-2-methyl-7-phenyl-6,7,8,9-tetrahydropyrido[1,2-a]indol-10-yl)-2-((R)-1,1-dimethylethyl sulfinamido)acetate, EXAMPLE 10 (50 mg, 0.062 mmol) in MeOH (3 ml) and THF (3 ml)), LiOH in Water (2 ml) was added. The mixture was stirred at r.t. overnight. LiOH was added and the reaction mixture was heated to 80° C. for 2 days. The organic solvent was removed and the residue was dissolved in DMSO/H$_2$O/CAN, which was neutralized by the addition of TFA and purified by preparative HPLC (sunfire column), eluting with Acetonitrile/Water, 0% to 60% to give 2-((S)-7-(2-chloro-4-(4H-1,2,4-triazol-4-yl)benzamido)-2-methyl-7-phenyl-6,7,8,9-tetrahydropyrido[1,2-a]indol-10-yl)-2-((R)-1,1-dimethylethyl sulfinamido)acetic acid. LCMS 659.20 (M+H)$^+$, $^1$H NMR (500 MHz, CD$_3$OD): 9.06 (s, 2H); 7.80 (d, J=2.1 Hz, 1H); 7.65 (d, J=7.8 Hz, 2H); 7.56 (d, J=8.3 Hz, 1H); 7.36-7.46 (m, 5H); 7.21 (d, J=8.3 Hz, 1H); 6.94 (d, J=8.3 Hz, 1H); 5.28 (s, 1H); 4.80 (m, 1H); 4.31 (s, 1H); 3.29 (m, 1H); 3.10 (m, 1H); 2.62 (m, 1H); 2.40 (m, 4H); 1.19 (s, 9H).

Step F. 2-amino-2-((S)-7-(2-chloro-4-(4H-1,2,4-
triazol-4-yl)benzamido)-2-methyl-7-phenyl-6,7,8,9-
tetrahydropyrido[1,2-a]indol-10-yl)acetic acid To a solution of 2-((S)-7-(2-chloro-4-(4H-1,2,4-triazol-4-yl)benzamido)-2-methyl-7-phenyl-6,7,8,9-tetrahydropyrido[1,2-a]indol-10-yl)-2-((R)-1,1-dimethylethylsulfinamido) acetic acid (30 mg, 0.039 mmol) in MeOH (1 ml) was added HCl in dioxene (1 ml, 4.00 mmol). The reaction mixture was stirred at r.t. overnight. The residue was purified by preparative HPLC Reverse phase (C-18), eluting with acetonitrile/water. It was redissolved in THF/CH$_3$OH (1 ml/1 ml) and sat. LiOH in H$_2$O was added 0.5 ml. It was stirred at r.t. overnight. The residue was purified by preparative HPLC Reverse phase (C-18), eluting with Acetonitrile/Water to give 2-amino-2-((S)-7-(2-chloro-4-(4H-1,2,4-triazol-4-yl)benzamido)-2-methyl-7-phenyl-6,7,8,9-tetrahydropyrido[1,2-a]indol-10-yl)acetic acid. LCMS 555.09 (M+H)$^+$, $^1$H NMR (500 MHz, CD$_3$OD): 9.06 (s, 2H); 7.80 (d, J=2.1 Hz, 1H); 7.65 (d, J=7.8 Hz, 2H); 7.56 (d, J=8.3 Hz, 1H); 7.36-7.46 (m, 5H); 7.21 (d, J=8.3 Hz, 1H); 6.94 (d, J=8.3 Hz, 1H); 5.26 (s, 1H); 4.80 (m, 1H); 4.38 (s, 1H); 3.10-3.25 (m, 2H); 2.60 (m, 1H); 2.40 (m, 4H).

Step G. ethyl 2-amino-2-((S)-7-(2-chloro-4-(4H-1,2,
4-triazol-4-yl)benzamido)-2-methyl-7-phenyl-6,7,8,
9-tetrahydropyrido[1,2-a]indol-10-yl)acetate To a solution of ethyl 2-((S)-7-(2-chloro-4-(4H-1,2,4-triazol-4-yl)benzamido)-2-methyl-7-phenyl-6,7,8,9-tetrahydropyrido[1,2-a]indol-10-yl)-2-((R)-1,1-dimethylethylsulfinamido) acetate 2,2,2-trifluoroacetate (25 mg, 0.031 mmol) in MeOH (1 ml) was added HCl in dioxene (1 ml, 4.00 mmol), followed by stirring at r.t. overnight. The residue was purified by preparative HPLC Reverse phase (C-18), eluting with Acetonitrile/Water to give ethyl 2-amino-2-((S)-7-(2-chloro-4-(4H-1,2,4-triazol-4-yl)benzamido)-2-methyl-7-phenyl-6,7,8,9-tetrahydropyrido[1,2-a]indol-10-yl)acetate 2,2,2-trifluoro acetate. LCMS 555.09 (M+H)+, 1H NMR (500 MHz, CD3OD): 9.06 (s, 2H); 7.80 (d, J=2.1 Hz, 1H); 7.65 (d, J=7.8 Hz, 2H); 7.56 (d, J=8.3 Hz, 1H); 7.36-7.46 (m, 5H); 7.21 (d, J=8.3 Hz, 1H); 6.94 (d, J=8.3 Hz, 1H); 5.26 (s, 1H); 4.80 (m, 1H); 4.38 (s, 1H); 3.10-3.25 (m, 2H); 2.60 (m, 1H); 2.40 (m, 4H).

Example 169

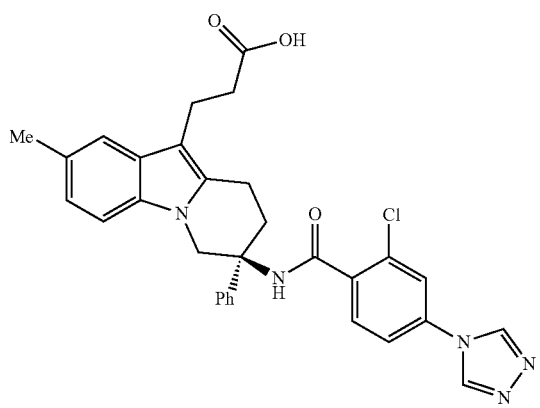 [SMILES: Cc1ccc2c(c1)c(CCC(=O)O)c1n2C[C@@](NC(=O)c2ccc(-n3cnnc3)cc2Cl)(c2ccccc2)CC1]

(S)-3-(7-(2-chloro-4-(4H-1,2,4-triazol-4-yl)benzamido)-2-methyl-7-phenyl-6,7,8,9-tetrahydropyrido[1,2-a]indol-10-yl)propanoic acid Step A. (S)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)propanoate To a solution of (S,E)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)acrylate, (30 mg, 0.053 mmol) in Ethyl acetate (2 ml) was added platinum(IV) oxide (12.04 mg, 0.053 mmol). The mixture was stirred under H2 balloon at r.t. overnight, then filtered and concentrated. The residue was purified by preparative HPLC Reverse phase (C-18), eluting with Acetonitrile/Water+0.1% TFA, to give (S)-methyl 3-(7-(2-chloro-4-(4H-1,2,4-triazol-4-yl)benzamido)-2-methyl-7-phenyl-6,7,8,9-tetrahydropyrido[1,2-a]indol-10-yl)propanoate). LCMS 568 (M+H)+.

Step B. (S)-3-(7-(2-chloro-4-(4H-1,2,4-triazol-4-yl)benzamido)-2-methyl-7-phenyl-6,7,8,9-tetrahydropyrido[1,2-a]indol-10-yl)propanoic acid To the solution of (S)-methyl 3-(7-(2-chloro-4-(3-methyl-1H-1,2,4-triazol-1-yl)benzamido)-2-methyl-7-phenyl-6,7,8,9-tetrahydropyrido[1,2-a]indol-10-yl)propanoate 2,2,2-trifluoroacetate (8 mg, 0.011 mmol) in MeOH (1 ml) and THF (1 ml) was added LiOH (0.550 mg, 0.023 mmol) in water (0.5 ml). The mixture was stirred at r.t. overnight, then filtered and concentrated till dryness. Purified by prep. tlc (8% MeOH/CH2Cl2) to give (S)-3-(7-(2-chloro-4-(3-methyl-1H-1,2,4-triazol-1-yl)benzamido)-2-methyl-7-phenyl-6,7,8,9-tetrahydropyrido[1,2-a]indol-10-yl)propanoic acid. LCMS 554 (M+H)+, 1H NMR (500 MHz, CD3OD): 9.04 (s, 2H); 7.81 (d, J=2.1 Hz, 1H); 7.59-7.63 (m, 3H); 7.40-7.44 (m, 3H); 7.32-7.35 (m, 2H); 7.16 (d, J=8.3 Hz, 1H); 6.91 (d, J=8.2 Hz, 1H); 4.70 (d, J=12 Hz, 1H); 4.30 (d, J=12 Hz, 1H); 3.58 (m, 1H); 3.20 (m, 1H); 3.02 (m, 3H); 2.57 (m, 3H); 2.42 (s, 3H).

Example 172

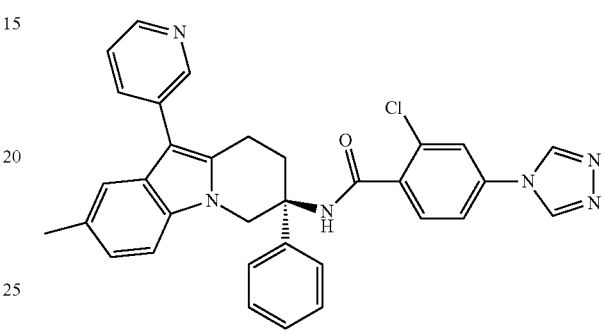

2-chloro-N-[(7S)-2-methyl-7-phenyl-10-pyridin-3-yl-6,7,8,9-tetrahydropyrido[1,2-a]indol-7-yl]-4-(4H-1,2,4-triazol-4-yl)benzamide (S)-2-chloro-N-(10-iodo-2-methyl-7-phenyl-6,7,8,9-tetrahydropyrido[1,2-a]indol-7-yl)-4-(4H-1,2,4-triazol-4-yl)benzamide (23 mg, 0.04 mmol) was placed in a reaction vial. In a separate vial, 3-(4,4,5,5-tetramethyl-1,3,2-dioxaborolan-2-yl)pyridine (13 mg, 0.06 mmol) was placed. Both vials were moved into a glovebox. To the vial containing (S)-2-chloro-N-(10-iodo-2-methyl-7-phenyl-6,7,8,9-tetrahydropyrido[1,2-a]indol-7-yl)-4-(4H-1,2,4-triazol-4-yl)benzamide was added chloro[(tri-tert-butylphosphine)-2-(2-aminobiphenyl)]palladium(II) (1.9 mg, 3.8 μmol), followed by THF (0.25 mL) and stirring at room temperature for three minutes. This solution was added to the vial containing 3-(4,4,5,5-tetramethyl-1,3,2-dioxaborolan-2-yl)pyridine (13 mg, 0.06 mmol). To the resulting mixture was added a solution for tripotassium phosphate (0.11 mL, 1 M, 0.11 mmol) which had been thoroughly sparged with nitrogen and stored inside the glovebox. The resulting mixture was capped and moved back outside of the glovebox, then heated at 50° C. for 14 hours. After cooling the mixture to room temperature Siliabond DMT (5 mg, 0.49 mmol/g, 2.5 mol) and DMSO (1 mL) were added to the mixture which was then stirred for 20 minutes. Filtered the mixture through a filter plate (0.45 μm) then purified by mass-directed reverse phase HPLC to give 2-chloro-N-[(7S)-2-methyl-7-phenyl-10-pyridin-3-yl-6,7,8,9-tetrahydropyrido[1,2-a]indol-7-yl]-4-(4H-1,2,4-triazol-4-yl)benzamide.

LCMS: 559.17 (M+1)

1H NMR (499 MHz, DMSO): δ 9.19 (s, 2H); 8.77 (s, 1H); 8.49 (s, 1H); 7.92-7.96 (m, 2H); 7.75 (d, J=8.3 Hz, 1H); 7.67 (d, J=7.7 Hz, 2H); 7.54 (m, 2H); 7.4-7.5 (m, 4H); 7.32-7.38 (m, 2H); 6.98 (d, J=8.3 Hz, 1H); 4.78 (d, J=12.4 Hz, 1H); 4.16 (d, J=12.4 Hz, 1H); 3.23-3.45 (m, 2H); 3.10-3.20 (m, 1H); 3.01-3.10 (m, 1H); 2.40 (s, 3H).

Example 192, 193 & 194

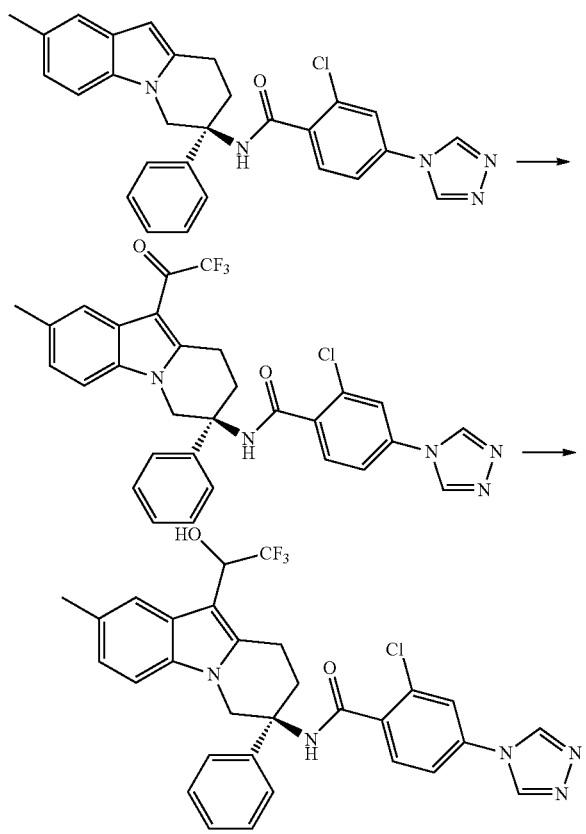

2-chloro-N-(2-methyl-7-phenyl-10-(2,2,2-trifluoro-acetyl)-6,7,8,9-tetrahydropyrido[1,2-a]indol-7-yl)-4-(4H-1,2,4-triazol-4-yl)benzamide, TFA To dissolved 2-chloro-N-(2-methyl-7-phenyl-6,7,8,9-tetrahydropyrido[1,2-a]indol-7-yl)-4-(4H-1,2,4-triazol-4-yl)benzamide, TFA (55 mg, 0.087 mmol) and trifluoroacetic acid (0.020 ml, 0.262 mmol) in a flask with dry DMF (15 ml) was added phosphorus oxychloride (0.033 ml, 0.349 mmol). The mixture was stirred at same r.t. overnight. After evaporating the DMF, the residue was purified by a reversed Gilson C-18 reversed column and eluted with 0.1% of TFA in both water and MeCN. The CF$_3$ ketone compound was obtained as a TFA salt. LCMS 577.88 (M+H)$^+$.

2-chloro-N-(2-methyl-7-phenyl-10-((R)-2,2,2-trifluoro-1-hydroxyethyl)-6,7,8,9-tetrahydropyrido[1,2-a]indol-7-yl)-4-(4H-1,2,4-triazol-4-yl)benzamide And 2-chloro-N-(2-methyl-7-phenyl-10-((S)-2,2,2-trifluoro-1-hydroxyethyl)-6,7,8,9-tetrahydropyrido[1,2-a]indol-7-yl)-4-(4H-1,2,4-triazol-4-yl)benzamide To 2-chloro-N-(2-methyl-7-phenyl-10-(2,2,2-trifluoro-acetyl)-6,7,8,9-tetrahydropyrido[1,2-a]indol-7-yl)-4-(4H-1,2,4-triazol-4-yl)benzamide, TFA (28.7 mg, 0.040 mmol) in dry THF (1068 μl) was added abd tge reaction mixture was cooled at 0° C. for 15 min followed by addition of sodium borohydride (2.3 mg, 0.061 mmol). The reaction was stirred at 0° C. for 1 h, then purified by TLC plate (DCM:MeOH/15:1), The first spot from TLC plate gave the desired product (blue spot) and another isomer was obtained, both of them gave same MW. LCMS 580.07 (M+H)$^+$.

Example 205

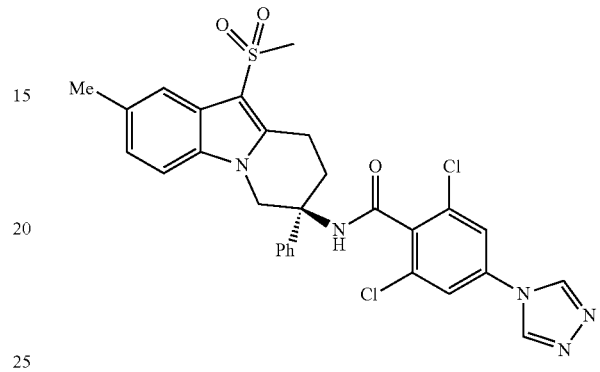

(S)-2,6-dichloro-N-(2-methyl-10-(methylsulfonyl)-7-phenyl-6,7,8,9-tetrahydropyrido[1,2-a]indol-7-yl)-4-(4H-1,2,4-triazol-4-yl)benzamide Step A. (S)-10-iodo-2-methyl-7-nitro-7-phenyl-6,7,8,9-tetrahydropyrido[1,2-a]indole To the solution of (S)-2-methyl-7-nitro-7-phenyl-6,7,8,9-tetrahydropyrido[1,2-a]indole (500 mg, 1.632 mmol) in CH$_2$Cl$_2$ (60 ml) at −10° C. was added 1-iodopyrrolidine-2,5-dione (367 mg, 1.632 mmol). The reaction mixture was stirred at this temp. for 1 hr. Purified the reaction mixture by column chromatography on silica gel 80, eluting with CH$_2$Cl$_2$/MeOH (0% to 10%) to give (S)-10-iodo-2-methyl-7-nitro-7-phenyl-6,7,8,9-tetrahydropyrido[1,2-a]indole. LCMS 433 (M+H)$^+$, $^1$H NMR (500 MHz, CD$_3$OD): 7.64 (d, J=7.3 Hz, 2H); 7.49 (m, 3H); 7.38 (d, J=8.7 Hz, 1H); 7.07 (d, J=5.1 Hz, 2H); 5.39 (m, 1H); 4.50 (m, 1H); 3.25 (m, 1H); 3.08 (m, 1H); 2.84 (m, 2H); 2.45 (s, 3H).

Step B. (S)-2-methyl-10-(methylsulfonyl)-7-nitro-7-phenyl-6,7,8,9-tetrahydropyrido[1,2-a]indole To a solution of (S)-10-iodo-2-methyl-7-nitro-7-phenyl-6,7,8,9-tetrahydropyrido[1,2-a]indole, intermediate 12 (200 mg, 0.463 mmol) in DMSO (2 ml) were added sodium methane sulfinate (1086 mg, 10.64 mmol), copper(I) trifluoromethanesulfonate benzene complex (23.29 mg, 0.046 mmol) and N,N'-dimethylethylenediamine (8.16 mg, 0.093 mmol). The reaction mixture was stirred at 100° C. (oil bath) overnight. The reaction mixture was purified by preparative HPLC (sunfire column), eluting with Acetonitrile/Water+0.1% TFA, 30% to 100%) to give (S)-2-methyl-10-(methylsulfonyl)-7-nitro-7-phenyl-6,7,8,9-tetrahydropyrido[1,2-a]indole. LCMS 355 (M+H)$^+$, $^1$H NMR (500 MHz, CD$_3$OD): 7.68 (s, 1H); 7.49-7.51 (m, 2H); 7.34-7.41 (m, 3H); 7.28 (t, J=7.3 Hz, 1H); 7.13 (d, J=8.4 Hz, 1H); 4.50 (d, J=12.6 Hz, 1H); 4.18 (d, J=12.6 Hz, 1H); 3.30 (m, 1H); 3.10 (m, 1H); 3.06 (s, 3H); 2.46 (m, 4H); 2.19 (dt, J=13.5, 6.4 Hz, 1H)

Step C. (S)-2-methyl-10-(methylsulfonyl)-7-phenyl-6,7,8,9-tetrahydropyrido[1,2-a]indol-7-amine To a solution of (S)-2-methyl-10-(methyl sulfonyl)-7-nitro-7-phenyl-6,7,8,9-tetrahydro pyrido[1,2-a]indole (178 mg, 0.463 mmol) in Ethanol (3.00 ml) and Acetic Acid (3 ml) was added zinc (303 mg, 4.63 mmol). The reaction mixture was stirred at r.t. for 2 hr, then Filtered, washed with EtOAc, and concentrated till dryness. The residue was dissolved in $CHCl_3$/IPA (3/1) and washed with $NaHCO_3$ to neutralize acid. The combined organic layer was washed with brine, dried over $MgSO_4$, concentrated till dryness and used as is for next step. LCMS 355 (M+H)$^+$, $^1$H NMR (500 MHz, $CD_3OD$): 7.68 (s, 1H); 7.49-7.51 (m, 2H); 7.34-7.41 (m, 3H); 7.28 (t, J=7.3 Hz, 1H); 7.13 (d, J=8.4 Hz, 1H); 4.50 (d, J=12.6 Hz, 1H); 4.18 (d, J=12.6 Hz, 1H); 3.30 (m, 1H); 3.10 (m, 1H); 3.06 (s, 3H); 2.46 (m, 4H); 2.19 (dt, J=13.5, 6.4 Hz, 1H)

Step D. (S)-2,6-dichloro-N-(2-methyl-10-(methylsulfonyl)-7-phenyl-6,7,8,9-tetrahydropyrido[1,2-a]indol-7-yl)-4-(4H-1,2,4-triazol-4-yl)benzamide To a solution of (S)-2-methyl-10-(methylsulfonyl)-7-phenyl-6,7,8,9-tetrahydro pyrido[1,2-a]indol-7-amine, intermediate 13 (30 mg, 0.085 mmol) in DMF (5 ml) were added 2-(3H-[1,2,3]triazolo[4,5-b]pyridin-3-yl)-1,1,3,3-tetramethylisouronium hexafluorophosphate(V) (64.4 mg, 0.169 mmol), N-ethyl-N-isopropylpropan-2-amine (21.88 mg, 0.169 mmol) and 2,6-dichloro-4-(4H-1,2,4-triazol-4-yl)benzoic acid (32.8 mg, 0.127 mmol). The reaction mixture was stirred at 65° C. overnight. The reaction mixture was purified by preparative HPLC (sunfire column), eluting with Acetonitrile/Water+0.1% TFA, 0% to 60%), then further purified by prep. TLC (5% MeOH in CH2Cl2 to give (S)-2,6-dichloro-N-(2-methyl-10-(methylsulfonyl)-7-phenyl-6,7,8,9-tetrahydropyrido[1,2-a]indol-7-yl)-4-(4H-1,2,4-triazol-4-yl)benzamide. LCMS 594 (M+H)$^+$, $^1$H NMR (500 MHz, $CD_3OD$): 9.40 (s, 1H); 9.06 (s, 2H); 7.80 (s, 1H); 7.75 (m, 2H); 7.68 (s, 1H); 7.50-7.30 (m, 4H); 7.15 (m, 1H); 5.30 (m, 1H); 4.45 (m, 1H); 3.60-3.40 (m, 2H); 3.13 (s, 3H); 2.90 (m, 1H); 2.55 (m, 1H); 2.47 (s, 3H).

The following compounds were synthesized using methods analogous to those described above from commercially available materials or intermediates whose syntheses are described above.

| Ex. | Structure | hFIXa IC50 (nM) | Exact Mass [M + H]+ | LCMS read |
|---|---|---|---|---|
| 124 | 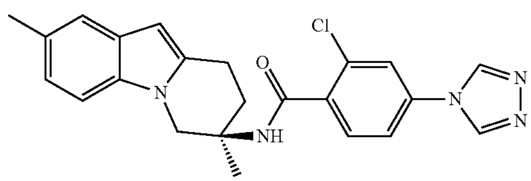 [SMILES: Cc1ccc2c(c1)cc1n2C[C@](C)(NC(=O)c2ccc(-n3cnnc3)cc2Cl)CC1] | 135.9 | 420.16 | 420.03 |
| 125 | 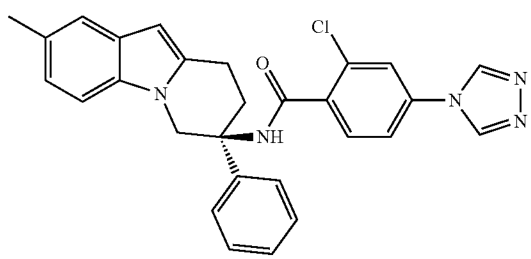 [SMILES: Cc1ccc2c(c1)cc1n2C[C@@](NC(=O)c2ccc(-n3cnnc3)cc2Cl)(c2ccccc2)CC1] | 34.82 | 482.17 | 482.06 |
| 126 | 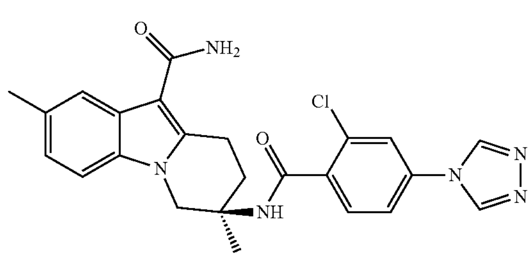 [SMILES: Cc1ccc2c(c1)c(C(N)=O)c1n2C[C@](C)(NC(=O)c2ccc(-n3cnnc3)cc2Cl)CC1] | 17.81 | 463.16 | 462.97 |

-continued

| Ex. | Structure | hFIXa IC50 (nM) | Exact Mass [M + H]+ | LCMS read |
|---|---|---|---|---|
| 127 | 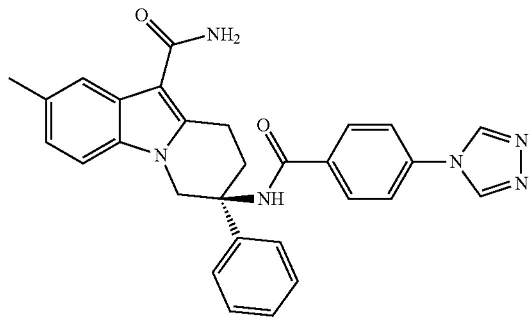 [SMILES: Cc1ccc2c(c1)c(C(N)=O)c1n2C[C@@](NC(=O)c2ccc(-n3cnnc3)cc2)(c2ccccc2)CC1] | 2.64 | 491.22 | 491.06 |
| 128 | 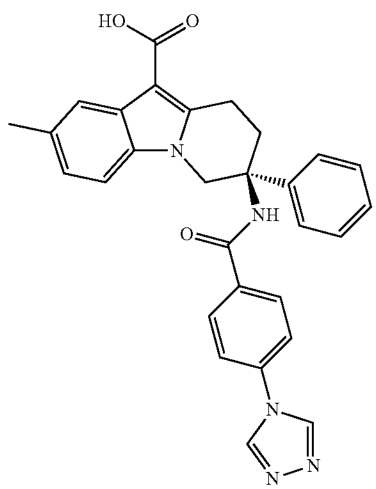 [SMILES: Cc1ccc2c(c1)c(C(=O)O)c1n2C[C@@](NC(=O)c2ccc(-n3cnnc3)cc2)(c2ccccc2)CC1] | 0.5956 | 492.2 | 492.14 |
| 129 | 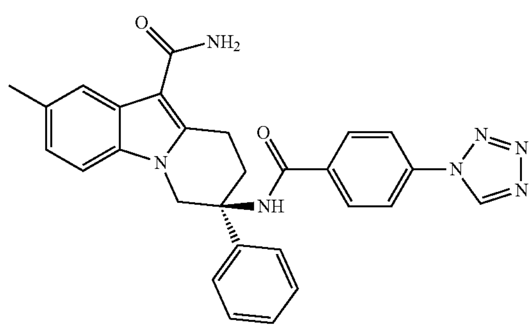 [SMILES: Cc1ccc2c(c1)c(C(N)=O)c1n2C[C@@](NC(=O)c2ccc(-n3cnnn3)cc2)(c2ccccc2)CC1] | 10.79 | 492.21 | 491.92 |
| 130 | 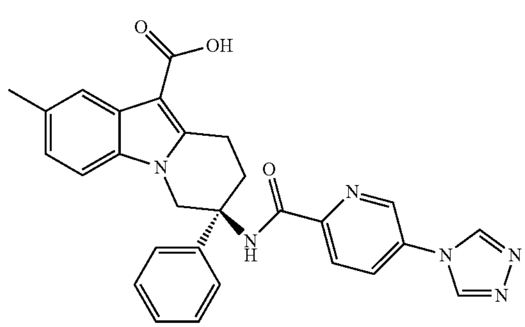 [SMILES: Cc1ccc2c(c1)c(C(=O)O)c1n2C[C@@](NC(=O)c2ccc(-n3cnnc3)cn2)(c2ccccc2)CC1] | 2.534 | 493.2 | 493.07 |

-continued

| Ex. | Structure | hFIXa IC50 (nM) | Exact Mass [M + H]+ | LCMS read |
|---|---|---|---|---|
| 131 | 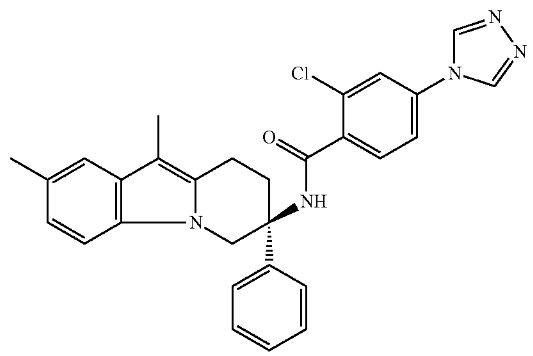 [SMILES: Cc1ccc2c(c1)c(C)c1n2C[C@@](NC(=O)c2ccc(-n3cnnc3)cc2Cl)(c2ccccc2)CC1] | 6.323 | 496.19 | 495.99 |
| 132 | 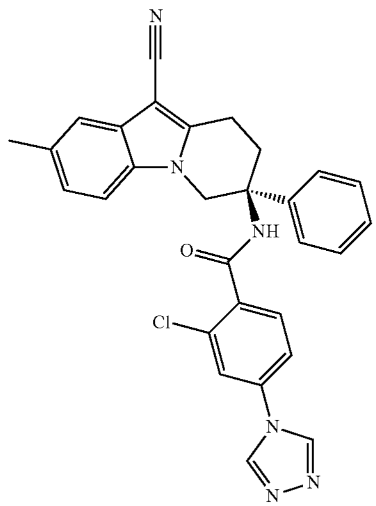 [SMILES: Cc1ccc2c(c1)c(C#N)c1n2C[C@@](NC(=O)c2ccc(-n3cnnc3)cc2Cl)(c2ccccc2)CC1] | 5.108 | 507.17 | 507.03 |
| 133 | 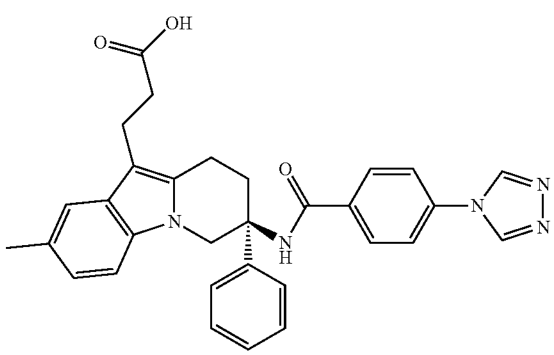 [SMILES: Cc1ccc2c(c1)c(CCC(=O)O)c1n2C[C@@](NC(=O)c2ccc(-n3cnnc3)cc2)(c2ccccc2)CC1] | 3.586 | 520.23 | 520.25 |
| 134 | 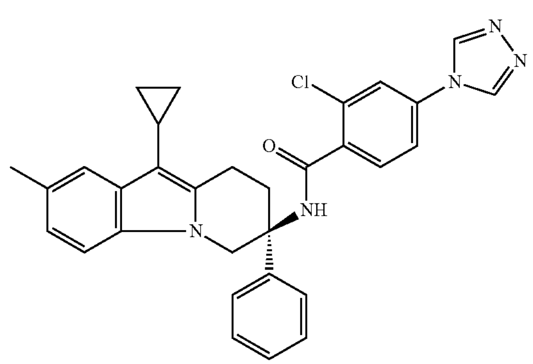 [SMILES: Cc1ccc2c(c1)c(C1CC1)c1n2C[C@@](NC(=O)c2ccc(-n3cnnc3)cc2Cl)(c2ccccc2)CC1] | 7.994 | 522.21 | 522.15 |

-continued

| Ex. | Structure | hFIXa IC50 (nM) | Exact Mass [M + H]+ | LCMS read |
|---|---|---|---|---|
| 135 | 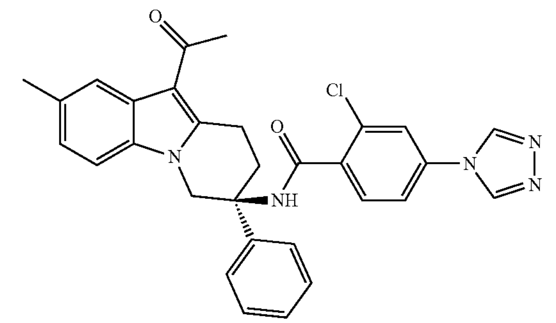 [SMILES: CC(=O)c1c2n(c3ccc(C)cc13)C[C@@](NC(=O)c1ccc(-n3cnnc3)cc1Cl)(c1ccccc1)CC2] | 2.008 | 524.19 | 524.03 |
| 136 | 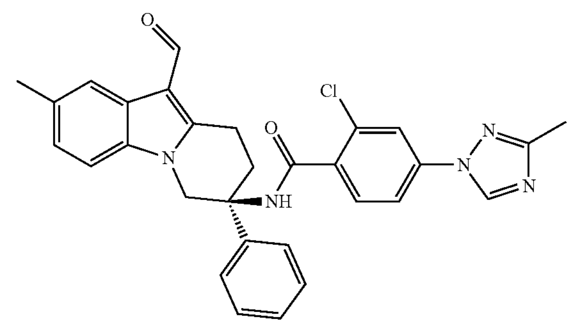 | 5.892 | 524.19 | 524.12 |
| 137 | 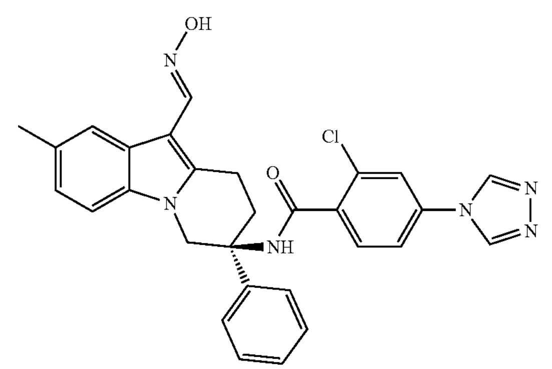 [SMILES: Cc1ccc2c(c1)c(/C=N/O)c1n2C[C@@](NC(=O)c2ccc(-n3cnnc3)cc2Cl)(c2ccccc2)CC1] | 2.385 | 525.18 | 524.99 |
| 138 | 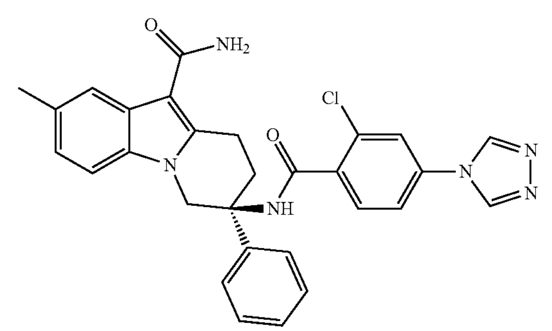 [SMILES: Cc1ccc2c(c1)c(C(N)=O)c1n2C[C@@](NC(=O)c2ccc(-n3cnnc3)cc2Cl)(c2ccccc2)CC1] | 1.248 | 525.18 | 525.06 |

-continued

| Ex. | Structure | hFIXa IC50 (nM) | Exact Mass [M + H]+ | LCMS read |
|---|---|---|---|---|
| 139 | 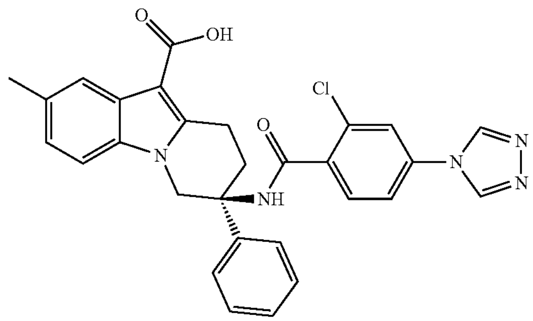 [SMILES: Cc1ccc2c(c1)c(C(=O)O)c1n2C[C@@](NC(=O)c2ccc(-n3cnnc3)cc2Cl)(c2ccccc2)CC1] | 7.983 | 526.16 | 537.98 |
| 140 | 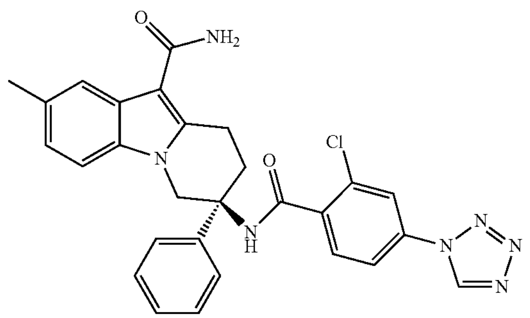 [SMILES: Cc1ccc2c(c1)c(C(N)=O)c1n2C[C@@](NC(=O)c2ccc(-n3cnnn3)cc2Cl)(c2ccccc2)CC1] | 8.626 | 526.18 | 526.09 |
| 141 | 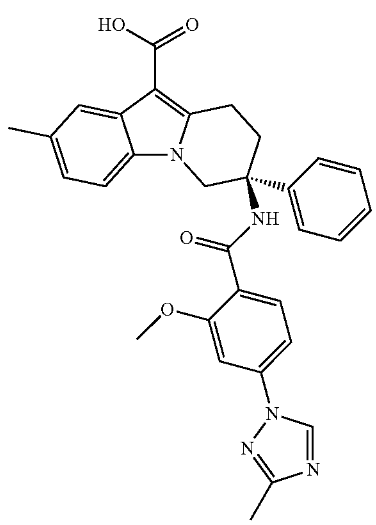 [SMILES: COc1cc(-n2cnc(C)n2)ccc1C(=O)N[C@]1(c2ccccc2)CCc2c(C(=O)O)c3cc(C)ccc3n2C1] | 4.146 | 536.23 | |

-continued
| Ex. | Structure | hFIXa IC50 (nM) | Exact Mass [M + H]+ | LCMS read |
|---|---|---|---|---|
| 142 | 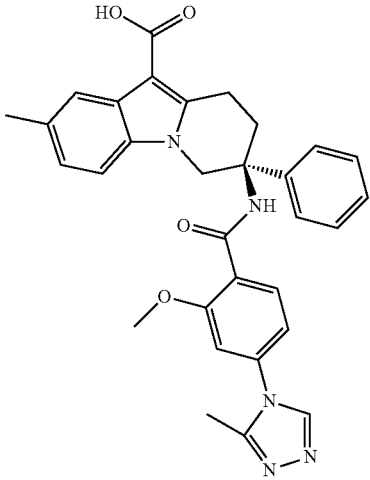 [SMILES: COc1cc(-n2cnnc2C)ccc1C(=O)N[C@]1(c2ccccc2)CCc2c(C(=O)O)c3cc(C)ccc3n2C1] | 5.048 | 536.23 | 536.17 |
| 143 | 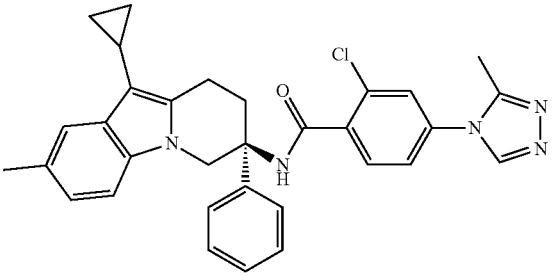 [SMILES: Cc1ccc2c(c1)c(C1CC1)c1n2C[C@@](NC(=O)c2ccc(-n3cnnc3C)cc2Cl)(c2ccccc2)CC1] | 9.812 | 536.22 | 536.24 |
| 144 | 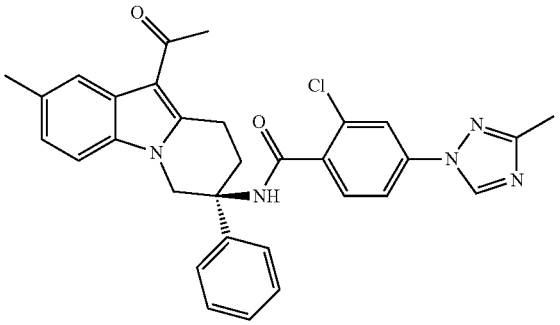 | 1.852 | 538.2 | 538.08 |
| 145 | 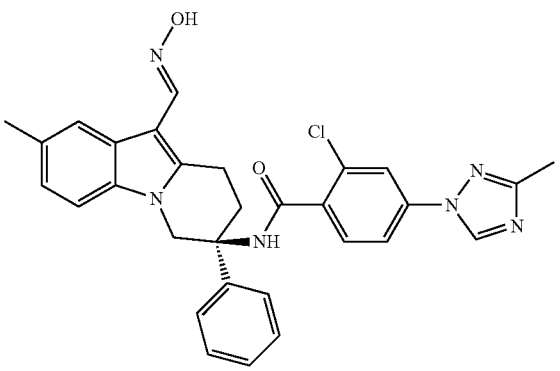 | 4.285 | 539.2 | 539.15 |

-continued

| Ex. | Structure | hFIXa IC50 (nM) | Exact Mass [M + H]+ | LCMS read |
|---|---|---|---|---|
| 146 | 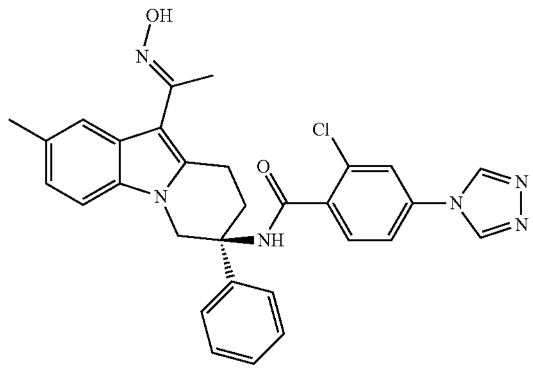 [SMILES: C/C(=N\O)c1c2n(c3ccc(C)cc13)C[C@@](NC(=O)c1ccc(-n3cnnc3)cc1Cl)(c1ccccc1)CC2] | 3.328 | 539.2 | 539.01 |
| 147 | 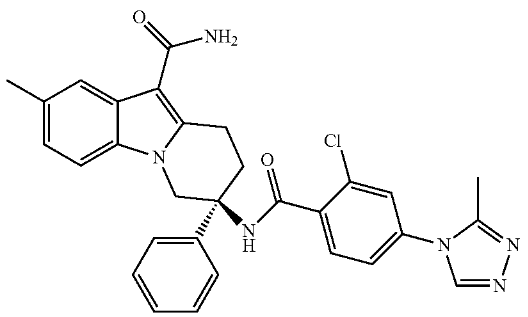 [SMILES: Cc1ccc2c(c1)c(C(N)=O)c1n2C[C@@](NC(=O)c2ccc(-n3cnnc3C)cc2Cl)(c2ccccc2)CC1] | 2.053 | 539.2 | 539.13 |
| 148 | 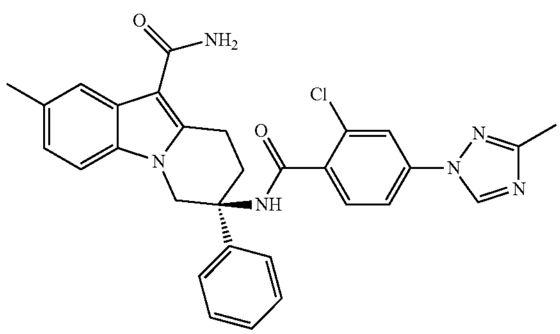 | 2.986 | 539.2 | 538.91 |
| 149 | 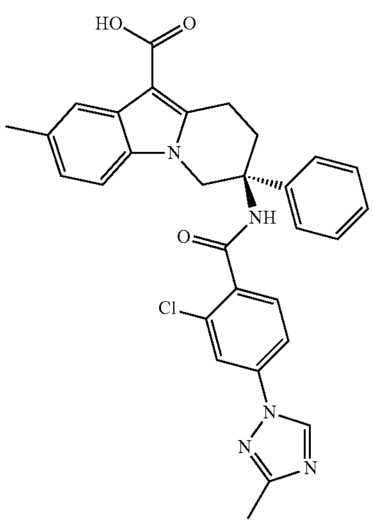 [SMILES: Cc1ccc2c(c1)c(C(=O)O)c1n2C[C@@](NC(=O)c2ccc(-n3cnc(C)n3)cc2Cl)(c2ccccc2)CC1] | 1.03 | 540.18 | 540.12 |

-continued

| Ex. | Structure | hFIXa IC50 (nM) | Exact Mass [M + H]+ | LCMS read |
|---|---|---|---|---|
| 150 | 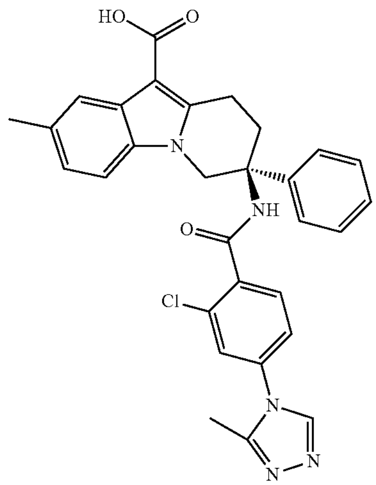 [SMILES: Cc1ccc2c(c1)c(C(=O)O)c1n2C[C@@](NC(=O)c2ccc(-n3cnnc3C)cc2Cl)(c2ccccc2)CC1] | 1.603 | 540.18 | 540.09 |
| 151 | 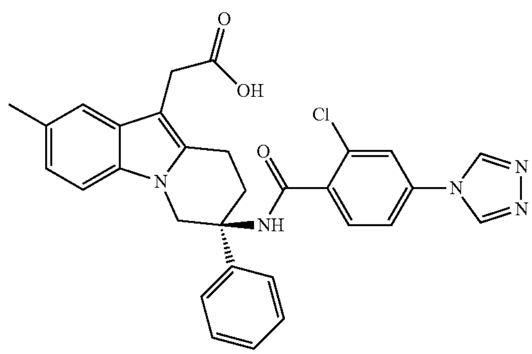 [SMILES: Cc1ccc2c(c1)c(CC(=O)O)c1n2C[C@@](NC(=O)c2ccc(-n3cnnc3)cc2Cl)(c2ccccc2)CC1] | 2.867 | 540.18 | 538.01 |
| 152 | 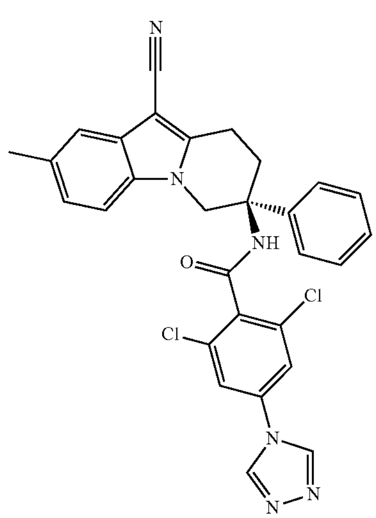 [SMILES: Cc1ccc2c(c1)c(C#N)c1n2C[C@@](NC(=O)c2c(Cl)cc(-n3cnnc3)cc2Cl)(c2ccccc2)CC1] | 2.802 | 541.13 | 541.03 |

-continued
| Ex. | Structure | hFIXa IC50 (nM) | Exact Mass [M + H]+ | LCMS read |
|---|---|---|---|---|
| 153 | 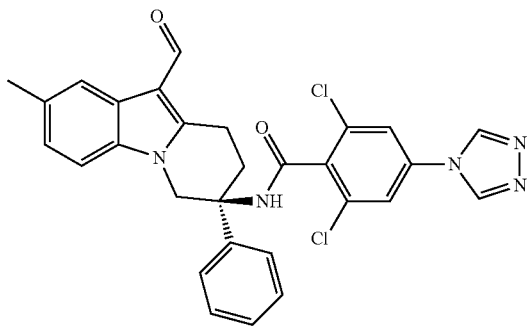 [SMILES: Cc1ccc2c(c1)c(C=O)c1n2C[C@@](NC(=O)c2c(Cl)cc(-n3cnnc3)cc2Cl)(c2ccccc2)CC1] | 1.608 | 544.13 | 544.03 |
| 154 | 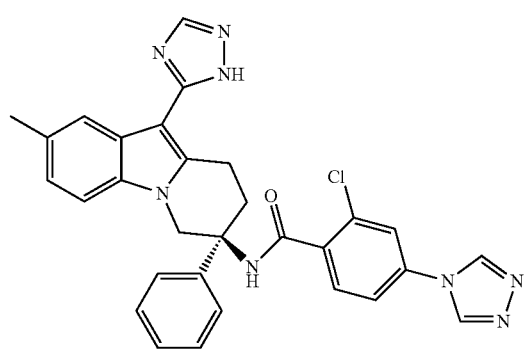 [SMILES: Cc1ccc2c(c1)c(-c1ncn[nH]1)c1n2C[C@@](NC(=O)c2ccc(-n3cnnc3)cc2Cl)(c2ccccc2)CC1] | 14.73 | 549.19 | 549.05 |
| 155 | 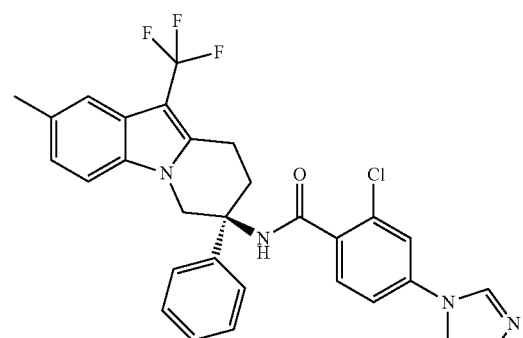 | 8.416 | 550.16 | 549.95 |
| 156 | 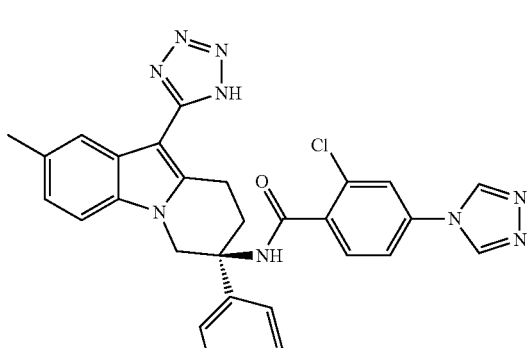 | 2.375 | 550.19 | 550.14 |

-continued

| Ex. | Structure | hFIXa IC50 (nM) | Exact Mass [M + H]+ | LCMS read |
|---|---|---|---|---|
| 157 | 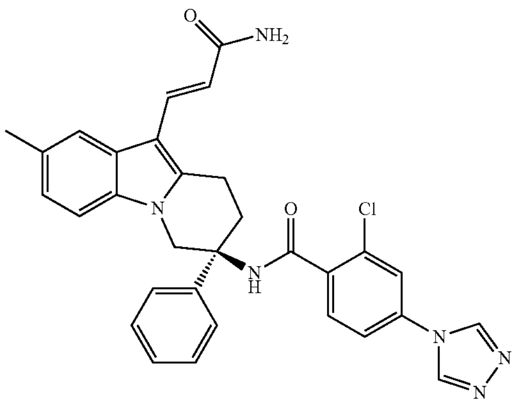 [SMILES: Cc1ccc2c(c1)c(/C=C/C(N)=O)c1n2C[C@@](NC(=O)c2ccc(-n3cnnc3)cc2Cl)(c2ccccc2)CC1] | 2.026 | 551.2 | 571.09 |
| 158 | 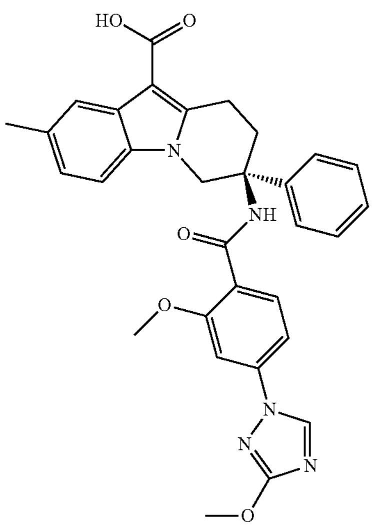 [SMILES: COc1ncn(-c2ccc(C(=O)N[C@]3(c4ccccc4)CCc4c(C(=O)O)c5cc(C)ccc5n4C3)c(OC)c2)n1] | 8.548 | 552.22 | 552.11 |
| 159 | 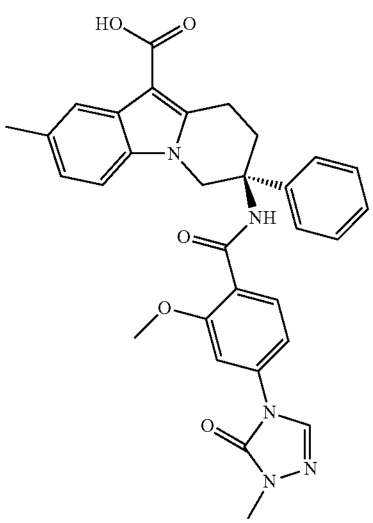 [SMILES: COc1cc(-n2cnn(C)c2=O)ccc1C(=O)N[C@]1(c2ccccc2)CCc2c(C(=O)O)c3cc(C)ccc3n2C1] | 5.972 | 552.22 | 552.15 |

-continued

| Ex. | Structure | hFIXa IC50 (nM) | Exact Mass [M + H]+ | LCMS read |
|---|---|---|---|---|
| 160 | 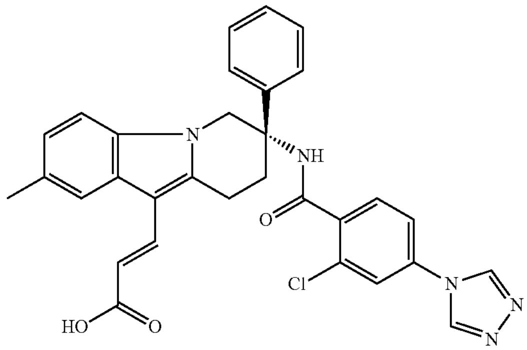 [SMILES: Cc1ccc2c(c1)c(/C=C/C(=O)O)c1n2C[C@@](NC(=O)c2ccc(-n3cnnc3)cc2Cl)(c2ccccc2)CC1] | 0.8198 | 552.18 | 552.20 |
| 161 | 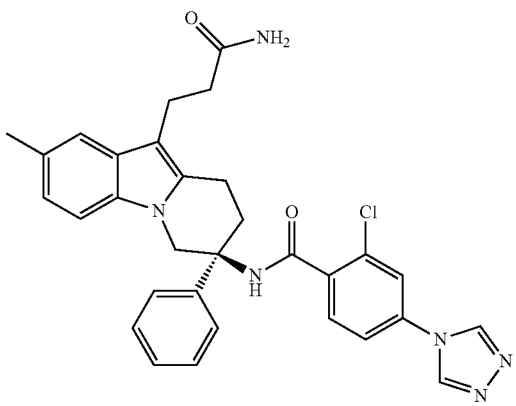 | 19.13 | 553.21 | 553.12 |
| 162 | 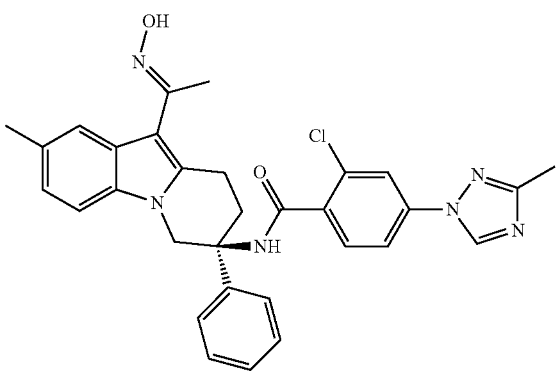 | 4.12 | 553.21 | 553.05 |
| 163 | 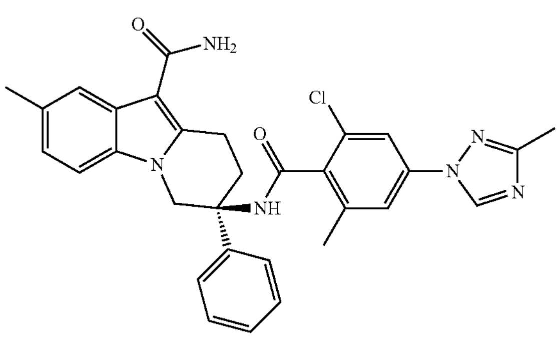 | 2.589 | 553.21 | 553.07 |

-continued

| Ex. | Structure | hFIXa IC50 (nM) | Exact Mass [M + H]+ | LCMS read |
|---|---|---|---|---|
| 164 | 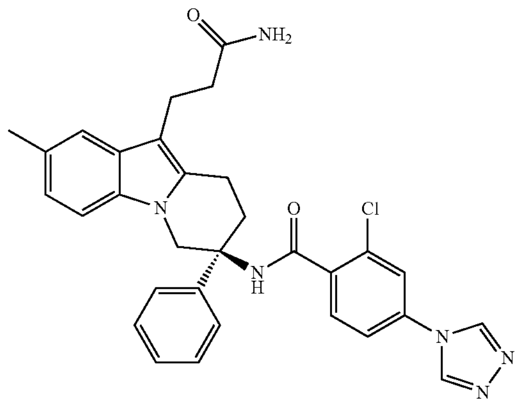 [SMILES: Cc1ccc2c(c1)c(CCC(N)=O)c1n2C[C@@](NC(=O)c2ccc(-n3cnnc3)cc2Cl)(c2ccccc2)CC1] | 2.549 | 554.2 | 554.08 |
| 165 | 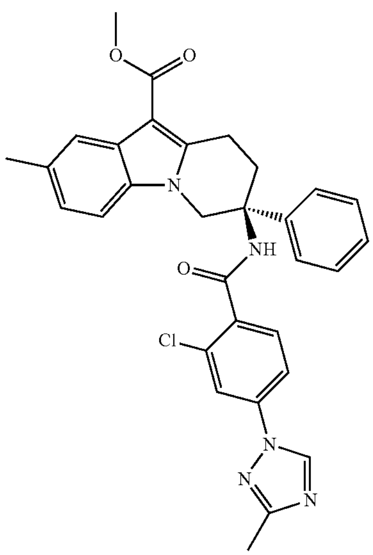 [SMILES: COC(=O)c1c2n(c3ccc(C)cc13)C[C@@](NC(=O)c1ccc(-n3cnc(C)n3)cc1Cl)(c1ccccc1)CC2] | 6.961 | 554.2 | 554.20 |
| 166 | 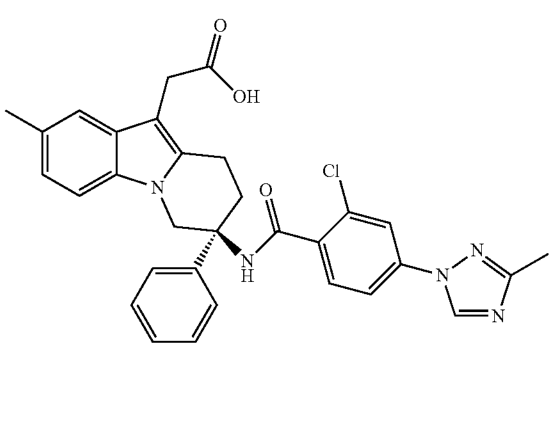 | 4.707 | 554.2 | 554.12 |

| Ex. | Structure | hFIXa IC50 (nM) | Exact Mass [M + H]+ | LCMS read |
|---|---|---|---|---|
| 167 | 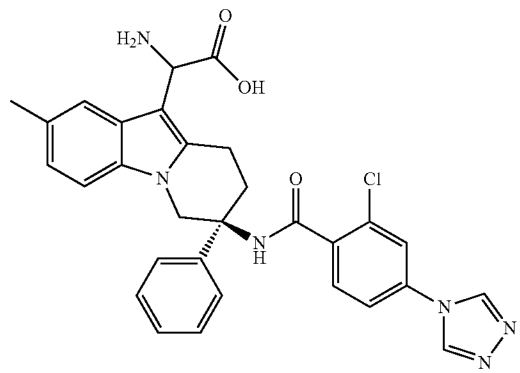 [SMILES: Cc1ccc2c(c1)c(C(N)C(=O)O)c1n2C[C@@](NC(=O)c2ccc(-n3cnnc3)cc2Cl)(c2ccccc2)CC1] | 15.81 | 555.19 | 555.09 |
| 168 | 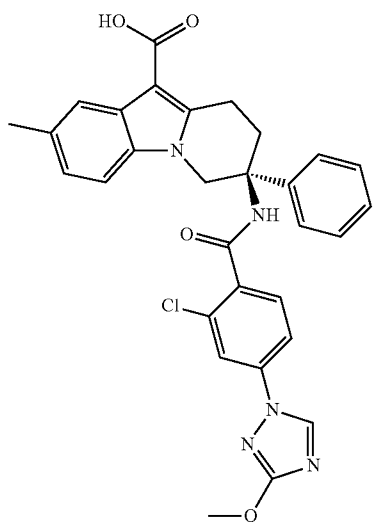 [SMILES: COc1ncn(-c2ccc(C(=O)N[C@]3(c4ccccc4)CCc4c(C(=O)O)c5cc(C)ccc5n4C3)c(Cl)c2)n1] | 0.6363 | 556.17 | 556.02 |
| 169 | 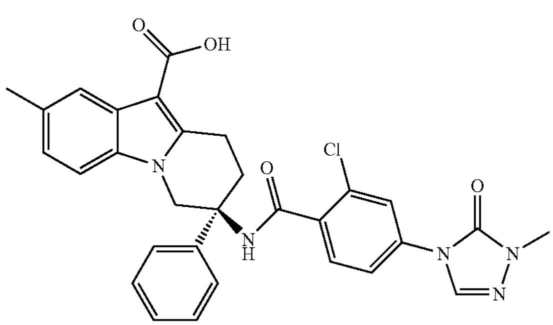 | 1.683 | 556.17 | 556.09 |

| Ex. | Structure | hFIXa IC50 (nM) | Exact Mass [M + H]+ | LCMS read |
|---|---|---|---|---|
| 170 | 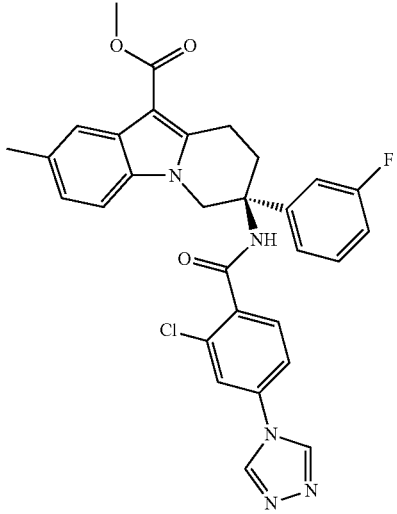 [SMILES: COC(=O)c1c2n(c3ccc(C)cc13)C[C@@](NC(=O)c1ccc(-n3cnnc3)cc1Cl)(c1cccc(F)c1)CC2] | 4.583 | 558.17 | 558.08 |
| 171 | 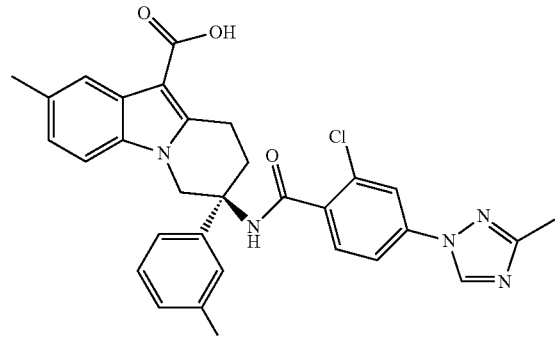 | 0.7913 | 558.17 | 558.10 |
| 172 | 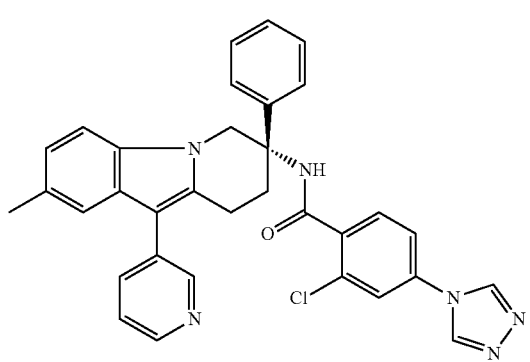 [SMILES: Cc1ccc2c(c1)c(-c1cccnc1)c1n2C[C@@](NC(=O)c2ccc(-n3cnnc3)cc2Cl)(c2ccccc2)CC1] | 4.269 | 559.2 | 559.17 |

-continued

| Ex. | Structure | hFIXa IC50 (nM) | Exact Mass [M + H]+ | LCMS read |
|---|---|---|---|---|
| 173 | 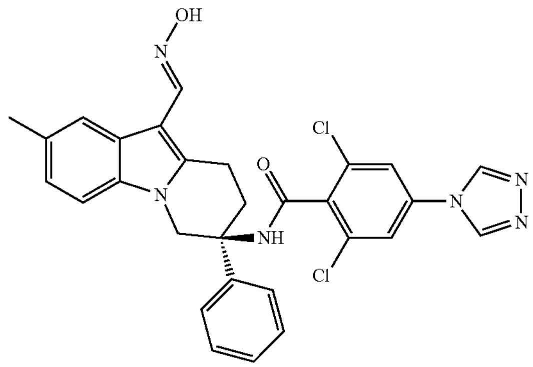 [SMILES: Cc1ccc2c(c1)c(/C=N/O)c1n2C[C@@](NC(=O)c2c(Cl)cc(-n3cnnc3)cc2Cl)(c2ccccc2)CC1] | 1.746 | 559.14 | 559.07 |
| 174 | 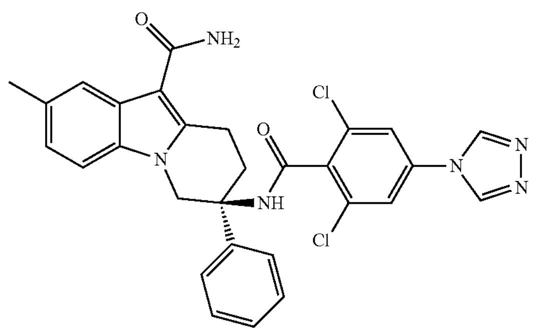 [SMILES: Cc1ccc2c(c1)c(C(N)=O)c1n2C[C@@](NC(=O)c2c(Cl)cc(-n3cnnc3)cc2Cl)(c2ccccc2)CC1] | 1.445 | 559.14 | NA |
| 175 | 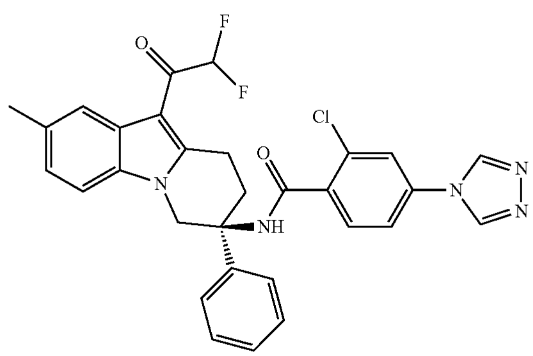 [SMILES: Cc1ccc2c(c1)c(C(=O)C(F)F)c1n2C[C@@](NC(=O)c2ccc(-n3cnnc3)cc2Cl)(c2ccccc2)CC1] | 1.988 | 560.17 | NA |
| 176 | 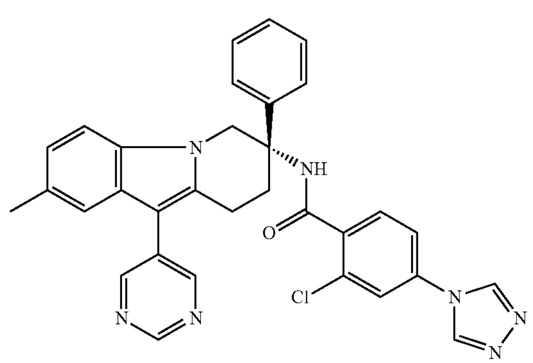 [SMILES: Cc1ccc2c(c1)c(-c1cncnc1)c1n2C[C@@](NC(=O)c2ccc(-n3cnnc3)cc2Cl)(c2ccccc2)CC1] | 6.258 | 560.2 | 560.13 |

-continued

| Ex. | Structure | hFIXa IC50 (nM) | Exact Mass [M + H]+ | LCMS read |
|---|---|---|---|---|
| 177 | 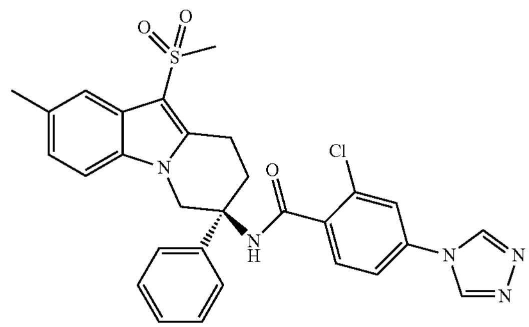 [SMILES: Cc1ccc2c(c1)c(S(C)(=O)=O)c1n2C[C@@](NC(=O)c2ccc(-n3cnnc3)cc2Cl)(c2ccccc2)CC1] | 18.34 | 560.15 | 560.20 |
| 178 | 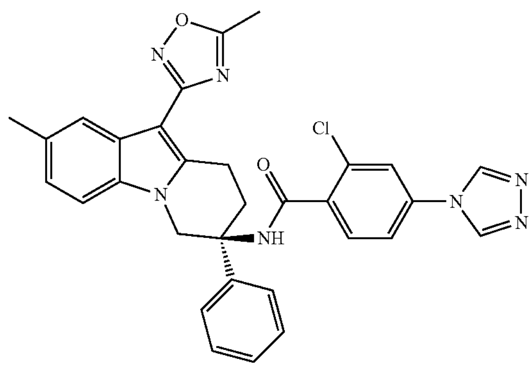 [SMILES: Cc1ccc2c(c1)c(-c1noc(C)n1)c1n2C[C@@](NC(=O)c2ccc(-n3cnnc3)cc2Cl)(c2ccccc2)CC1] | 3.737 | 564.19 | 563.91 |
| 179 | 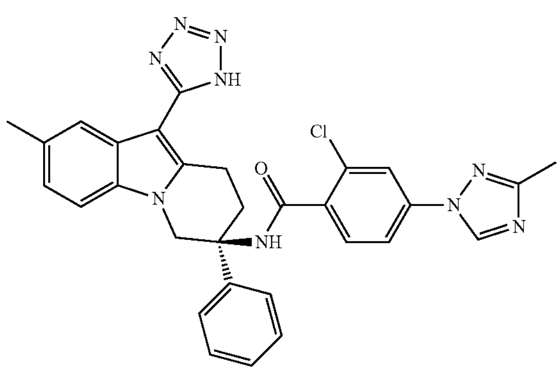 | 4.224 | 564.2 | 564.18 |
| 180 | 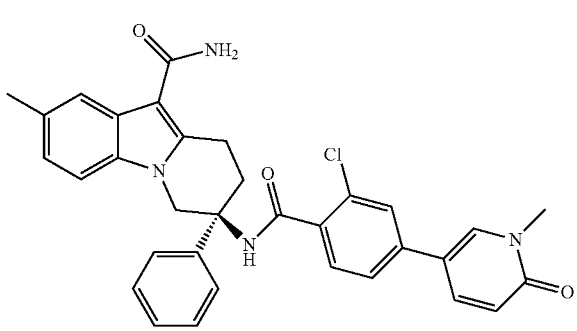 [SMILES: Cc1ccc2c(c1)c(C(N)=O)c1n2C[C@@](NC(=O)c2ccc(-c3ccc(=O)n(C)c3)cc2Cl)(c2ccccc2)CC1] | 3.158 | 565.2 | 565.19 |

| Ex. | Structure | hFIXa IC50 (nM) | Exact Mass [M + H]+ | LCMS read |
|---|---|---|---|---|
| 181 | 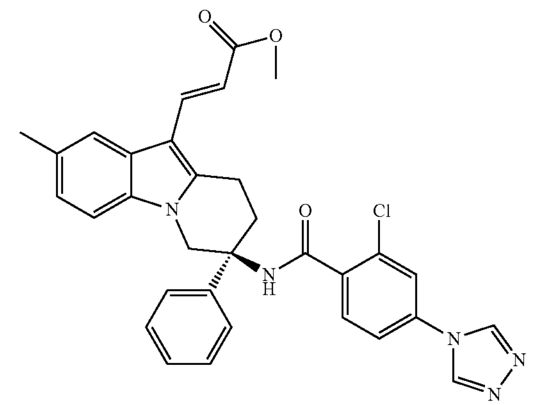 [SMILES: COC(=O)/C=C/c1c2n(c3ccc(C)cc13)C[C@@](NC(=O)c1ccc(-n3cnnc3)cc1Cl)(c1ccccc1)CC2] | 3.601 | 566.2 | 566.11 |
| 182 | 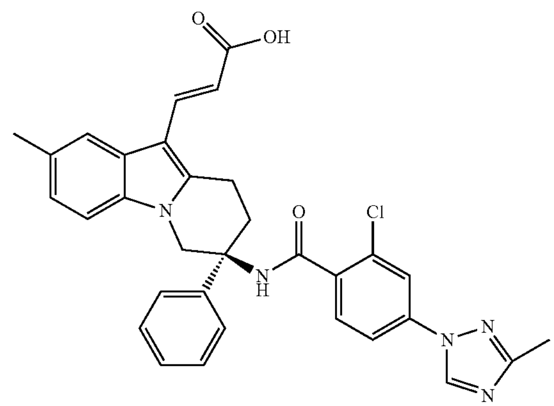 | 1.18 | 566.2 | 566.10 |
| 183 | 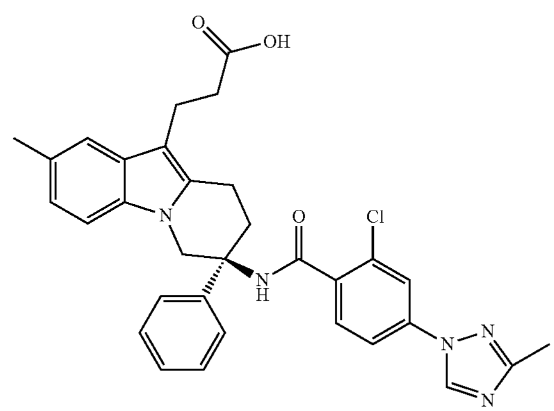 | 2.686 | 568.21 | 568.15 |
| 184 | 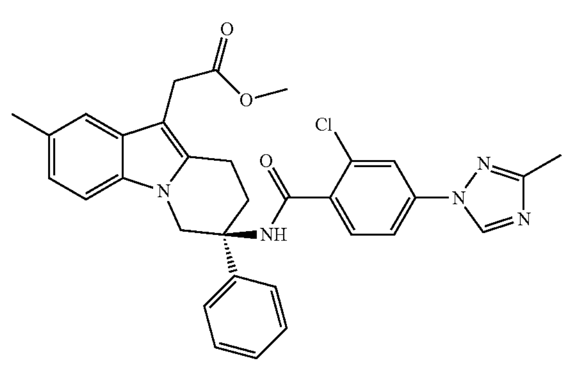 | 4.679 | 568.21 | 659.11 |

-continued

| Ex. | Structure | hFIXa IC50 (nM) | Exact Mass [M + H]+ | LCMS read |
|---|---|---|---|---|
| 185 | 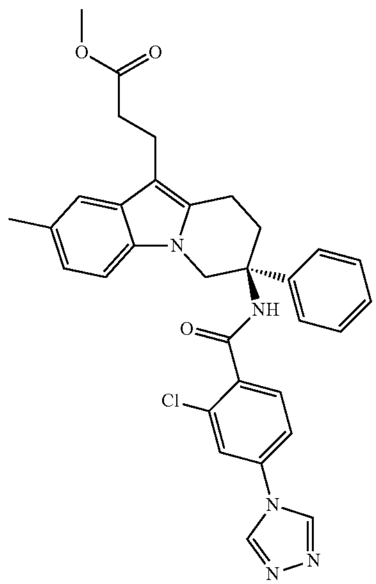 [SMILES: COC(=O)CCc1c2n(c3ccc(C)cc13)C[C@@](NC(=O)c1ccc(-n3cnnc3)cc1Cl)(c1ccccc1)CC2] | 19.15 | 568.21 | 568.13 |
| 186 | 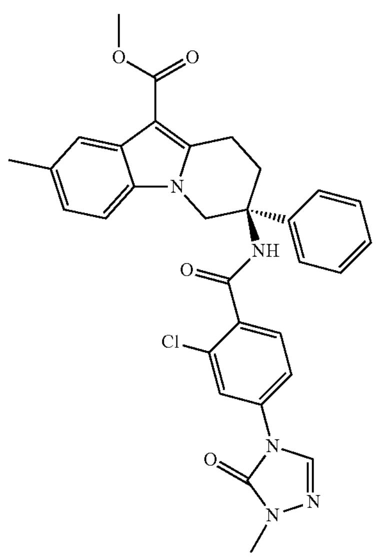 [SMILES: COC(=O)c1c2n(c3ccc(C)cc13)C[C@@](NC(=O)c1ccc(-n3cnn(C)c3=O)cc1Cl)(c1ccccc1)CC2] | 7.122 | 570.19 | 570.04 |
| 187 | 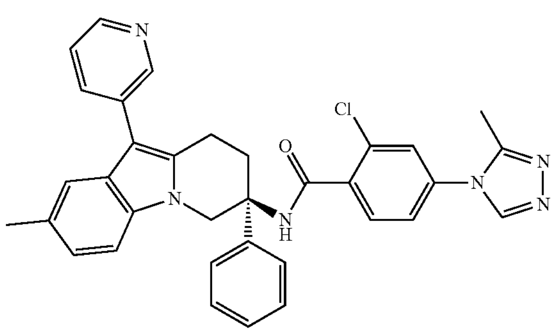 [SMILES: Cc1ccc2c(c1)c(-c1cccnc1)c1n2C[C@@](NC(=O)c2ccc(-n3cnnc3C)cc2Cl)(c2ccccc2)CC1] | 3.51 | 573.22 | 573.25 |

-continued

| Ex. | Structure | hFIXa IC50 (nM) | Exact Mass [M + H]+ | LCMS read |
|---|---|---|---|---|
| 188 | 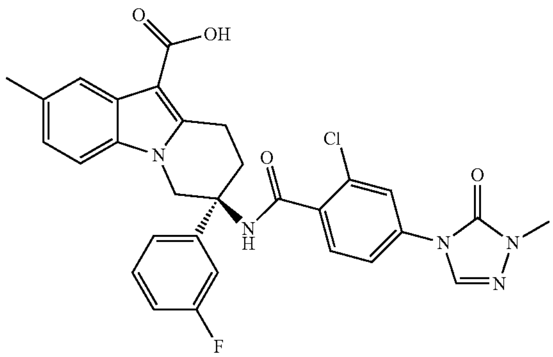 | 0.5093 | 574.17 | 574.08 |
| 189 | 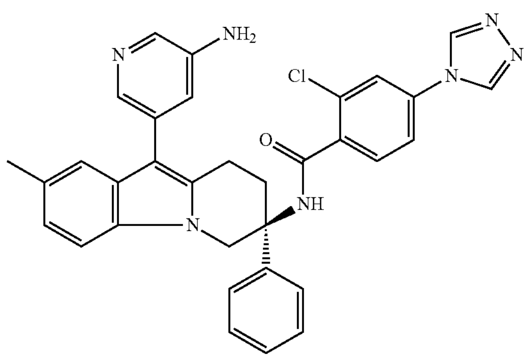 [SMILES: Cc1ccc2c(c1)c(-c1cncc(N)c1)c1n2C[C@@](NC(=O)c2ccc(-n3cnnc3)cc2Cl)(c2ccccc2)CC1] | 1.583 | 574.21 | 574.07 |
| 190 | 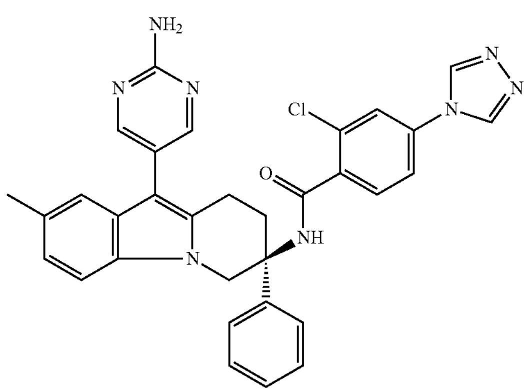 [SMILES: Cc1ccc2c(c1)c(-c1cnc(N)nc1)c1n2C[C@@](NC(=O)c2ccc(-n3cnnc3)cc2Cl)(c2ccccc2)CC1] | 7.105 | 575.21 | 575.13 |
| 191 | 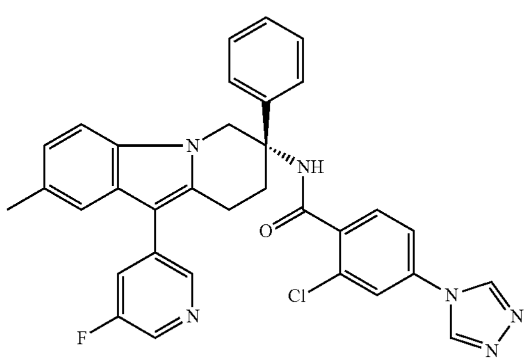 [SMILES: Cc1ccc2c(c1)c(-c1cncc(F)c1)c1n2C[C@@](NC(=O)c2ccc(-n3cnnc3)cc2Cl)(c2ccccc2)CC1] | 5.17 | 577.19 | 577.18 |

| Ex. | Structure | hFIXa IC50 (nM) | Exact Mass [M + H]+ | LCMS read |
|---|---|---|---|---|
| 192 | 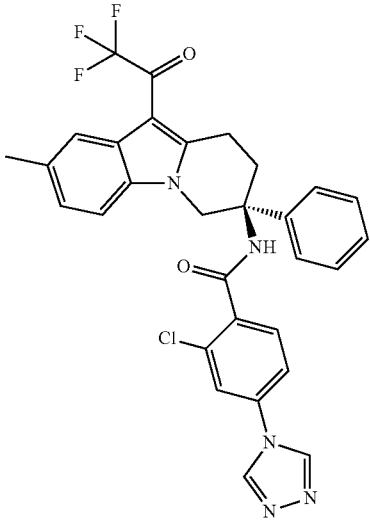 [SMILES: Cc1ccc2c(c1)c(C(=O)C(F)(F)F)c1n2C[C@@](NC(=O)c2ccc(-n3cnnc3)cc2Cl)(c2ccccc2)CC1] | 5.186 | 578.16 | 577.88 |
| 193 | 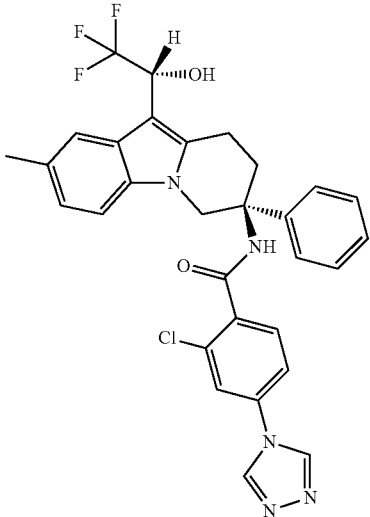 [SMILES: Cc1ccc2c(c1)c([C@@H](O)C(F)(F)F)c1n2C[C@@](NC(=O)c2ccc(-n3cnnc3)cc2Cl)(c2ccccc2)CC1] | 5.717 | 580.17 | 580.07 |
| 194 | 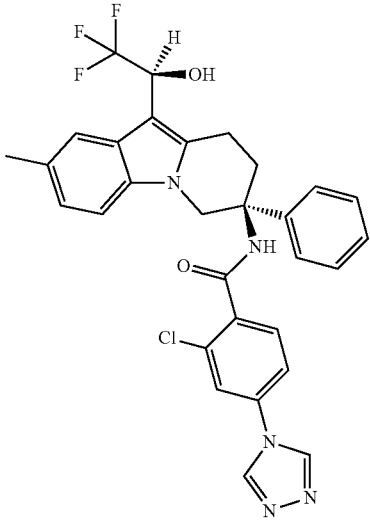 [SMILES: Cc1ccc2c(c1)c([C@H](O)C(F)(F)F)c1n2C[C@@](NC(=O)c2ccc(-n3cnnc3)cc2Cl)(c2ccccc2)CC1] | 5.549 | 580.17 | 580.07 |

-continued

| Ex. | Structure | hFIXa IC50 (nM) | Exact Mass [M + H]+ | LCMS read |
|---|---|---|---|---|
| 195 | 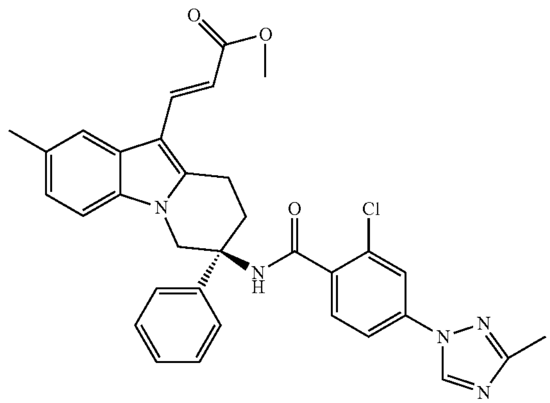 | 9.969 | 580.21 | 580.19 |
| 196 | 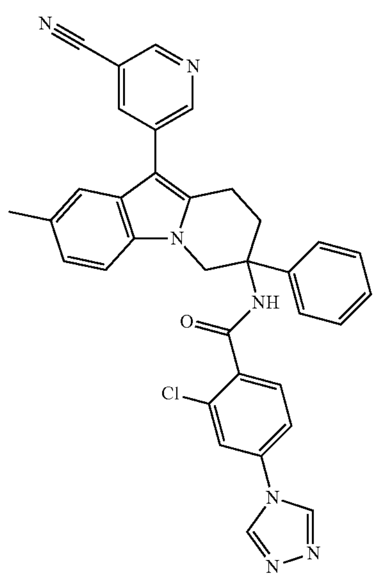 [SMILES: Cc1ccc2c(c1)c(-c1cncc(C#N)c1)c1n2CC(NC(=O)c2ccc(-n3cnnc3)cc2Cl)(c2ccccc2)CC1] | 11.89 | 584.2 | 584.16 |
| 197 | 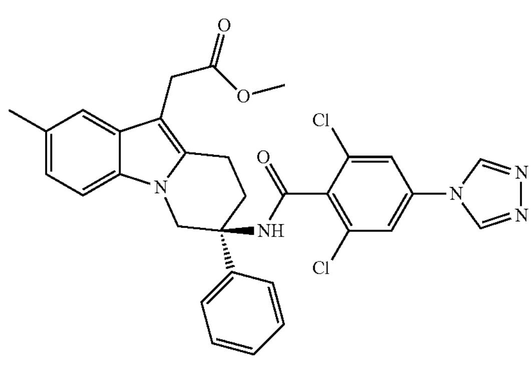 [SMILES: COC(=O)Cc1c2n(c3ccc(C)cc13)C[C@@](NC(=O)c1c(Cl)cc(-n3cnnc3)cc1Cl)(c1ccccc1)CC2] | 1.87 | 588.16 | 573.93 |

-continued

| Ex. | Structure | hFIXa IC50 (nM) | Exact Mass [M + H]+ | LCMS read |
|---|---|---|---|---|
| 198 | 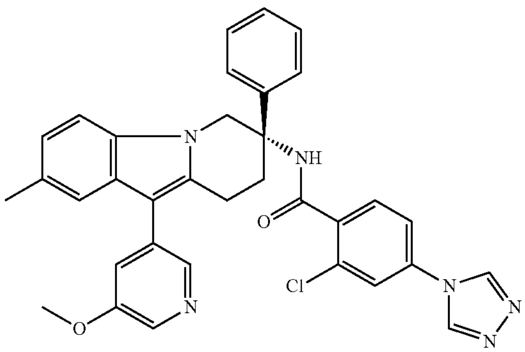 [SMILES: COc1cncc(-c2c3n(c4ccc(C)cc24)C[C@@](NC(=O)c2ccc(-n4cnnc4)cc2Cl)(c2ccccc2)CC3)c1] | 3.265 | 589.21 | 589.26 |
| 199 | 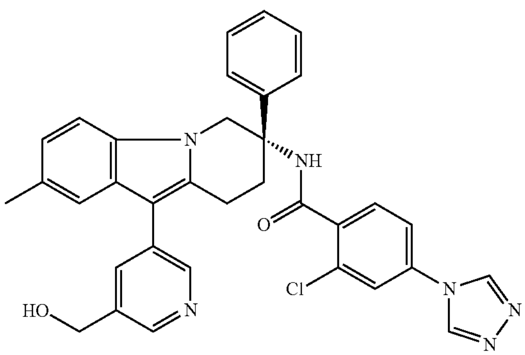 [SMILES: Cc1ccc2c(c1)c(-c1cncc(CO)c1)c1n2C[C@@](NC(=O)c2ccc(-n3cnnc3)cc2Cl)(c2ccccc2)CC1] | 2.746 | 589.21 | 589.20 |
| 200 | 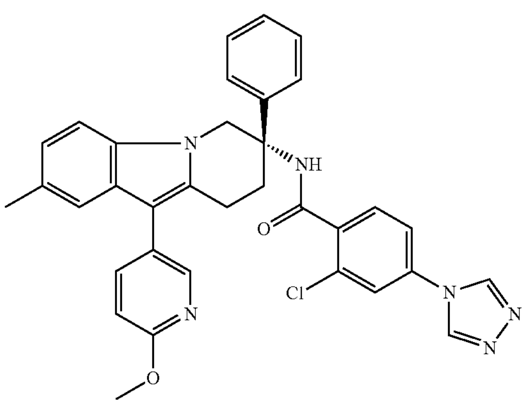 [SMILES: COc1ccc(-c2c3n(c4ccc(C)cc24)C[C@@](NC(=O)c2ccc(-n4cnnc4)cc2Cl)(c2ccccc2)CC3)cn1] | 2.63 | 589.21 | 588.98 |
| 201 | 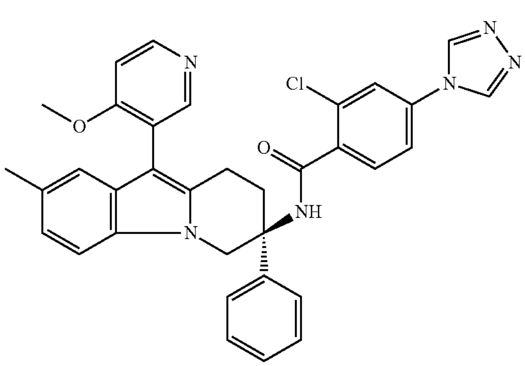 [SMILES: COc1ccncc1-c1c2n(c3ccc(C)cc13)C[C@@](NC(=O)c1ccc(-n3cnnc3)cc1Cl)(c1ccccc1)CC2] | 14.88 | 589.21 | 589.24 |

-continued

| Ex. | Structure | hFIXa IC50 (nM) | Exact Mass [M + H]+ | LCMS read |
|---|---|---|---|---|
| 202 | 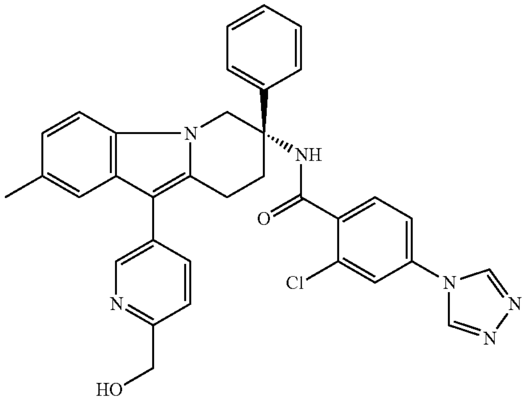 [SMILES: Cc1ccc2c(c1)c(-c1ccc(CO)nc1)c1n2C[C@@](NC(=O)c2ccc(-n3cnnc3)cc2Cl)(c2ccccc2)CC1] | 5.777 | 589.21 | 589.16 |
| 203 | 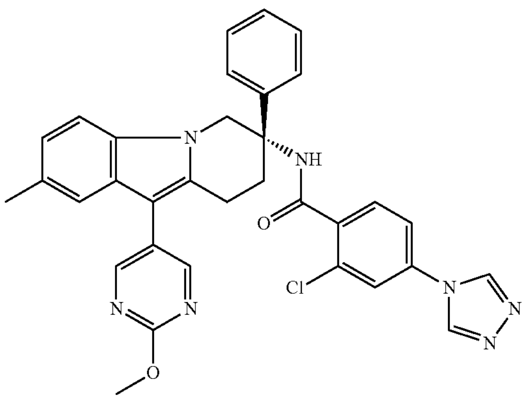 [SMILES: COc1ncc(-c2c3n(c4ccc(C)cc24)C[C@@](NC(=O)c2ccc(-n4cnnc4)cc2Cl)(c2ccccc2)CC3)cn1] | 1.714 | 590.21 | 590.07 |
| 204 | 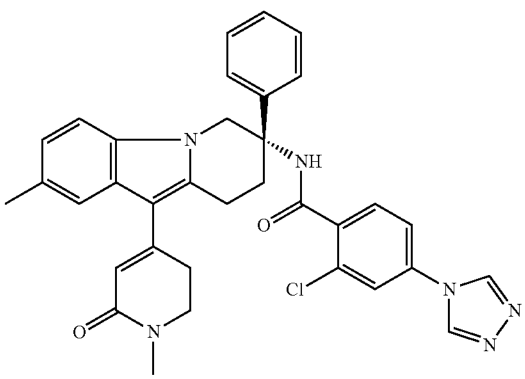 [SMILES: Cc1ccc2c(c1)c(C1=CC(=O)N(C)CC1)c1n2C[C@@](NC(=O)c2ccc(-n3cnnc3)cc2Cl)(c2ccccc2)CC1] | 4.043 | 591.23 | 591.08 |
| 205 | 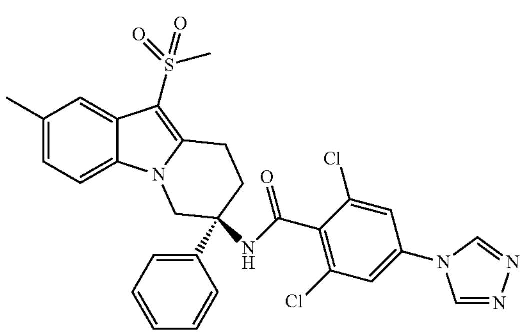 [SMILES: Cc1ccc2c(c1)c(S(C)(=O)=O)c1n2C[C@@](NC(=O)c2c(Cl)cc(-n3cnnc3)cc2Cl)(c2ccccc2)CC1] | 5.303 | 594.11 | 594.12 |

-continued
| Ex. | Structure | hFIXa IC50 (nM) | Exact Mass [M + H]+ | LCMS read |
|---|---|---|---|---|
| 206 | 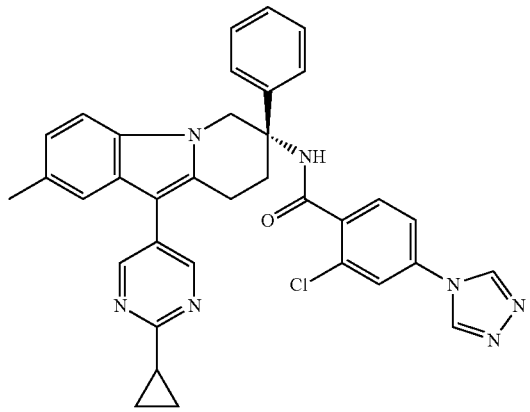 [SMILES: Cc1ccc2c(c1)c(-c1cnc(C3CC3)nc1)c1n2C[C@@](NC(=O)c2ccc(-n3cnnc3)cc2Cl)(c2ccccc2)CC1] | 1.583 | 600.23 | 600.17 |
| 207 | 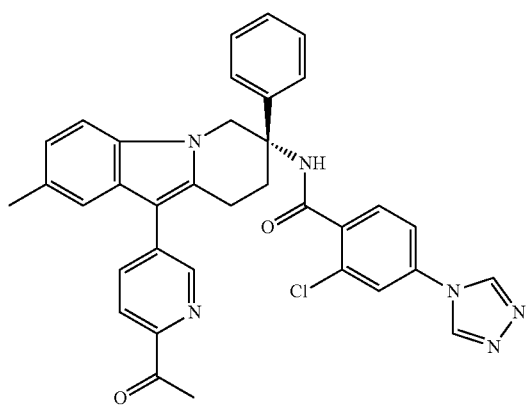 [SMILES: CC(=O)c1ccc(-c2c3n(c4ccc(C)cc24)C[C@@](NC(=O)c2ccc(-n4cnnc4)cc2Cl)(c2ccccc2)CC3)cn1] | 6.939 | 601.21 | 601.06 |
| 208 | 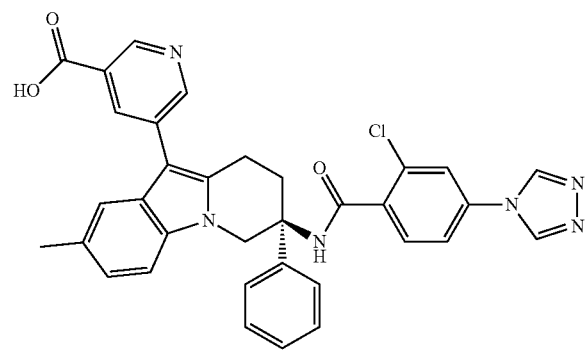 [SMILES: Cc1ccc2c(c1)c(-c1cncc(C(=O)O)c1)c1n2C[C@@](NC(=O)c2ccc(-n3cnnc3)cc2Cl)(c2ccccc2)CC1] | 8.27 | 603.19 | 603.17 |
| 209 | 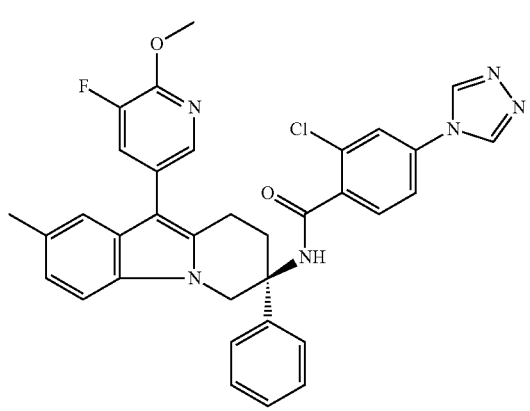 [SMILES: COc1ncc(-c2c3n(c4ccc(C)cc24)C[C@@](NC(=O)c2ccc(-n4cnnc4)cc2Cl)(c2ccccc2)CC3)cc1F] | 6.178 | 607.2 | 607.12 |

-continued

| Ex. | Structure | hFIXa IC50 (nM) | Exact Mass [M + H]+ | LCMS read |
|---|---|---|---|---|
| 210 | 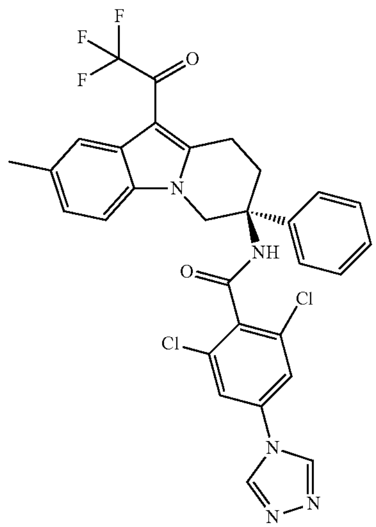 [SMILES: Cc1ccc2c(c1)c(C(=O)C(F)(F)F)c1n2C[C@@](NC(=O)c2c(Cl)cc(-n3cnnc3)cc2Cl)(c2ccccc2)CC1] | 13.62 | 612.12 | 612.02 |
| 211 | 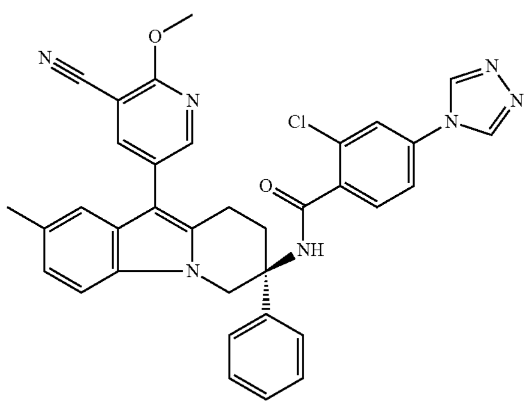 [SMILES: COc1ncc(-c2c3n(c4ccc(C)cc24)C[C@@](NC(=O)c2ccc(-n4cnnc4)cc2Cl)(c2ccccc2)CC3)cc1C#N] | 6.768 | 614.21 | 614.26 |
| 212 | 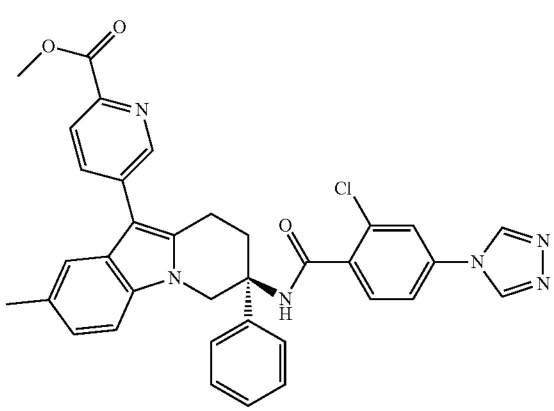 [SMILES: COC(=O)c1ccc(-c2c3n(c4ccc(C)cc24)C[C@@](NC(=O)c2ccc(-n4cnnc4)cc2Cl)(c2ccccc2)CC3)cn1] | 7.187 | 617.21 | 617.27 |

| Ex. | Structure | hFIXa IC50 (nM) | Exact Mass [M + H]+ | LCMS read |
|---|---|---|---|---|
| 213 | 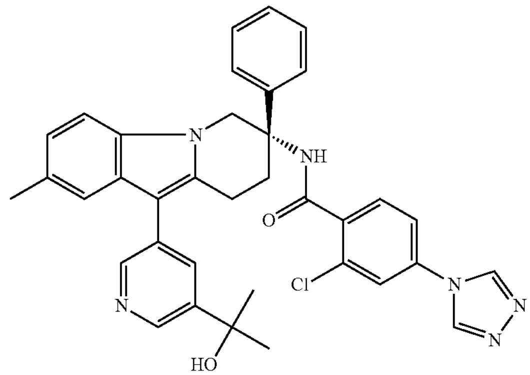 [SMILES: Cc1ccc2c(c1)c(-c1cncc(C(C)(C)O)c1)c1n2C[C@@](NC(=O)c2ccc(-n3cnnc3)cc2Cl)(c2ccccc2)CC1] | 4.371 | 617.24 | 617.24 |

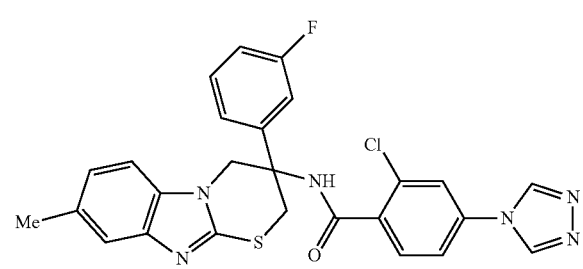

Example 214

2-chloro-N-(3-(3-fluorophenyl)-8-methyl-3,4-dihydro-2H-benzo[4,5]imidazo[2,1-b][1,3]thiazin-3-yl)-4-(4H-1,2,4-triazol-4-yl)benzamide Step A. ethyl 2-cyano-2-(3-fluorophenyl)acetate A 500 m round bottomed flask was charged with KOtBu (34.8 g, 310 mmol) and $Pd_2dba_3$ (3.12 g, 3.40 mmol) in dry and degassed toluene (250 ml) at RT under nitrogen with stirring. Then, 2,8,9-triisobutyl-2,5,8,9-tetraaza-1-phosphabicyclo[3.3.3]undecane (4.86 ml, 13.6 mmol) was added followed by 1-bromo-3-fluorobenzene (19 ml, 170 mmol). The resulting mixture was stirred for 20 min at RT, and then ethyl cyanoacetate (20 ml, 188 mmol) was added. The resulting mixture was heated at 110° C. for 72 h. Then, the mixture was cooled to RT and quenched with 1N aq HCl. The mixture was extracted twice with DCM, the combined organic phase was dried with $MgSO_4$ and the solvent removed in vacuo to give product that was purified by column chromatography ($SiO_2$, Biotage 40M×3) using AcOEt:hexanes 1% to 10% to give ethyl 2-cyano-2-(3-fluorophenyl)acetate. $^1$H-NMR (400 MHz, $CDCl_3$) δ (ppm): 7.43 (1H, m), 7.30 (1H, m), 7.22 (1H, m), 7.18 (1H, m), 4.75 (1H, s), 4.30 (2H, q), 1.30 (3H, t).

Step B. ethyl 2-amino-2-cyano-2-(3-fluorophenyl)acetate

A solution of ethyl 2-cyano-2-(3-fluorophenyl)acetate (17.959 g, 87 mmol) in dry THF (100 ml) was added to a solution of 2M LDA (47.7 ml, 95 mmol) in dry THF (300 ml) at −15° C. with stirring under a nitrogen atmosphere. After 25 min, (aminooxy)diphenylphosphine oxide (28.5 g, 121 mmol) (Organic Preparations and Procedures International, 43:475-476, 2011) was portionwise added over a period of 5 min at −15° C. The resulting mixture was allowed to slowly warm up to RT over a period of 16 h. The mixture was quenched with 1N aq HCl until pH 2-3, then basified with aq sat $NaHCO_3$ and extracted twice with DCM. The combined organic phase was dried and the solvent evaporated in vacuo to give product that was purified by column chromatography ($SiO_2$, Biotage, 40M×2) using AcOEt:Hexanes 1% to 50% to give i-c ethyl 2-amino-2-cyano-2-(3-fluorophenyl)acetate. $^1$H-NMR (400 MHz, $CDCl_3$) δ (ppm): 7.55 (1H, m), 7.42 (2H, m), 7.18 (1H, m), 4.40-4.22 (2H, m), 2.50 (1H, br s), 1.28 (3H, t).

Step C. ethyl 2-((tert-butoxycarbonyl)amino)-2-cyano-2-(3-fluorophenyl)acetate

A 500 ml round bottomed flask was charged with $Boc_2O$ (43.5 g, 199 mmol) and ethyl 2-amino-2-cyano-2-(3-fluorophenyl)acetate (14.76 g, 66.4 mmol). The resulting mixture was heated at 100° C. for 16 h. Then, $Boc_2O$ (22 g, 101 mmol) was added and the mixture heated to 100° C. for another 16 h. The mixture was cooled to RT and the volatiles removed in vacuo. The resulting oil was diluted with a small amount of DCM and purified by column chromatography ($SiO_2$, Biotage 40M×3) using AcOEt:hexanes 1% to 10% to give ethyl 2-((tert-butoxycarbonyl)amino)-2-cyano-2-(3-fluorophenyl)acetate. $^1$H-NMR (400 MHz, $CDCl_3$) δ (ppm): 7.58-7.39 (3H, m), 7.19 (1H, m), 5.80 (1H, br s), 4.40-4.22 (2H, m), 1.60-1.38 (9H, br s), 1.30 (3H, t).

Step D. ethyl 3-amino-2-((tert-butoxycarbonyl)amino)-2-(3-fluorophenyl)propanoate Cobalt (II) chloride (22.5 g, 170 mmol) was added to a solution of ethyl 2-((tert-butoxycarbonyl)amino)-2-cyano-2-(3-fluorophenyl)acetate (11.19 g, 34.7 mmol) in dry MeOH (500 ml) at RT with stirring. The resulting solution was stirred at RT for 10 min, then cooled to −20° C. and $NaBH_4$ (4.13 g, 109 mmol) was added portionwise. The mixture was stirred at RT for 30 min. Then, $NaBH_4$ (4.0 g, 106 mmol) was added portionwise. The resulting mixture was stirred for 30 min. Then $CoCl_2$ (8.4 g, 65 mmol) was added followed by additional $NaBH_4$ (4.0 g, 106 mmol). After 30 min the reaction was finished by LCMS. The mixture was quenched with water and extracted three times with DCM/MeOH 15% acidifying the aqueous phase to pH 4-5. The combined organic phase was dried and the solvent evaporated in vacuo to give a residue that was purified by column chromatography (SiO$_2$, Biotage, 40S×3) using AcOEt:hexanes 1 to 100% to give ethyl 3-amino-2-((tert-butoxycarbonyl)amino)-2-(3-fluorophenyl)propanoate. $^1$H-NMR (400 MHz, CDCl$_3$) δ (ppm): 7.38 (1H, m), 7.21 (1H, m), 7.18 (1H, m), 7.01 (1H, m), 6.16 (1H, br s), 4.30-4.18 (2H, m), 3.76 (1H, m), 3.62 (1H, d), 1.40 (9H, br s), 1.25 (3H, t). LCMS m/z 327.2 (M+H).

Step E. tert-butyl (1-amino-2-(3-fluorophenyl)-3-hydroxypropan-2-yl)carbamate

A solution of 1M LiAlH$_4$ in THF (38 ml, 38.1 mmol) was slowly added over a period of 10 min to a solution of ethyl 3-amino-2-((tert-butoxycarbonyl)amino)-2-(3-fluorophenyl)propanoate (4.538 g, 13.9 mmol) in dry THF (100 ml) at −78° C. with stirring under a nitrogen atmosphere. The resulting mixture was stirred for 4.5 h allowing it to slowly warm up to RT. Then, the mixture was cooled to 0° C. and quenched with water and then 1N NaOH. The mixture was stirred for 5 min and extracted twice with DCM. The combined organic phase was washed with aq Na/K tartrate, the layers were separated and the aq phase was extracted once with DCM. The combined organic phase was dried and the solvent evaporated to give tert-butyl (1-amino-2-(3-fluorophenyl)-3-hydroxypropan-2-yl)carbamate. $^1$H-NMR (400 MHz, CDCl$_3$) δ (ppm): 7.38 (1H, m), 7.11 (1H, m), 7.03 (1H, m), 6.98 (1H, m), 6.19 (1H, br s), 3.99 (1H, m), 3.90 (1H, m), 3.41 (1H, m), 3.05 (1H, m), 1.42 (9H, br s). LCMS m/z 285.1 (M+H).

Step F. tert-butyl (2-(3-fluorophenyl)-1-hydroxy-3-((4-methyl-2-nitrophenyl)amino)propan-2-yl)carbamate A 250 ml round bottomed flask was charged with tert-butyl (1-amino-2-(3-fluorophenyl)-3-hydroxypropan-2-yl)carbamate (2.373 g, 8.35 mmol), potassium carbonate (1.50 g, 10.9 mmol), 3-fluoro-4-nitrotoluene (1.424 g, 9.2 mmol) and dry DMF (15 ml). The resulting mixture was stirred for 60 h at RT. Water was added and the mixture was extracted three times with DCM. The combined organic phase was dried and the solvents evaporated in vacuo to give product that was purified by column chromatography (SiO$_2$, Biotage 40S) using AcOEt:hexanes 1 to 25% to give tert-butyl (2-(3-fluorophenyl)-1-hydroxy-3-((4-methyl-2-nitrophenyl)amino)propan-2-yl)carbamate. $^1$H-NMR (400 MHz, CDCl$_3$) δ (ppm): 8.03 (1H, br s), 7.99 (1H, s), 7.42 (1H, m), 7.27 (1H, m), 7.22 (1H, m), 7.17 (1H, m), 7.09 (1H, m), 6.84 (1H, d), 5.42 (1H, br s), 4.18 (1H, m), 4.02-3.84 (3H, m), 3.22 (1H, br s), 2.31 (3H, s), 1.42 (9H, br s). LCMS m/z 364.2 (M+H).

Step G. tert-butyl (1-((2-amino-4-methylphenyl)amino)-2-(3-fluorophenyl)-3-hydroxypropan-2-yl)carbamate A suspension of Raney® Nickel in water (1.2 ml) was added to a solution of tert-butyl (2-(3-fluorophenyl)-1-hydroxy-3-((4-methyl-2-nitrophenyl)amino)propan-2-yl)carbamate (1.45 g, 3.46 mmol) MeOH (150 ml) at RT with stirring. Then, the mixture was put under 2 atm (balloon) of hydrogen and stirred at RT for 16 h. After that time TLC and LCMS showed reaction finished. The mixture was diluted with MeOH and filtered through a pad of celite. Volatiles were removed in vacuo to give tert-butyl (1-((2-amino-4-methylphenyl)amino)-2-(3-fluorophenyl)-3-hydroxypropan-2-yl)carbamate. $^1$H-NMR (400 MHz, CDCl$_3$) δ (ppm): 7.40 (1H, m), 7.20 (1H, m), 7.14 (1H, m), 7.05 (1H, m), 6.62 (2H, m), 6.58 (2H, m), 5.90 (1H, br s), 4.32 (1H, m), 4.18 (1H, m), 4.06 (1H, m), 3.56 (2H, s), 3.50 (1H, m), 3.38 (1H, s), 3.10 (1H, br s), 2.22 (3H, s), 1.46 (9H, br s). LCMS m/z 390.3 (M+H).

Step H. tert-butyl (3-(3-fluorophenyl)-8-methyl-3,4-dihydro-2H-benzo[4,5]imidazo[2,1-b][1,3]thiazin-3-yl)carbamate A 250 ml round bottomed flask was charged with tert-butyl (1-((2-amino-4-methylphenyl)amino)-2-(3-fluorophenyl)-3-hydroxypropan-2-yl)carbamate (218 mg, 0.56 mmol) and thiocarbonyl diimidazole (299 mg, 1.68 mmol) in dry THF (20 ml). The resulting mixture was stirred at RT for 2.5 h until LCMS showed the reaction was finished. DCM was added and volatiles were removed in vacuo to give a residue that was purified by column chromatography (SiO$_2$, Biotage 25S) using AcOEt:hexanes 1 to 100% to give tert-butyl (3-(3-fluorophenyl)-8-methyl-3,4-dihydro-2H-benzo[4,5]imidazo[2,1-b][1,3]thiazin-3-yl)carbamate. $^1$H-NMR (400 MHz, CDCl$_3$) δ (ppm): 8.42 (1H, m), 8.01 (1H, m), 7.72 (1H, m), 7.40-6.98 (3H, m), 6.72 (1H, m), 6.03 (1H, br s), 5.60 (1H, m), 5.38 (1H, m), 4.37 (1H, m), 4.16 (1H, m), 2.37 (3H, s), 1.40 (9H, br s). LCMS m/z 414.2 (M+H).

Step I. 3-(3-fluorophenyl)-8-methyl-3,4-dihydro-2H-benzo[4,5]imidazo[2,1-b][1,3]thiazin-3-amine TFA (2 ml, 26 mmol) was slowly added to a solution of tert-butyl (3-(3-fluorophenyl)-8-methyl-3,4-dihydro-2H-benzo[4,5]imidazo[2,1-b][1,3]thiazin-3-yl)carbamate (128 mg, 0.31 mmol) in dry DCM (10 ml) at RT with stirring. The resulting mixture was stirred for 5 h, then aq NH$_3$ was added and the mixture was extracted twice with DCM. The combined organic phase was dried, and the solvent evaporated in vacuo to give 3-(3-fluorophenyl)-8-methyl-3,4-dihydro-2H-benzo[4,5]imidazo[2,1-b][1,3]thiazin-3-amine. $^1$H-NMR (400 MHz, CDCl$_3$) δ (ppm): 7.50-7.40 (3H, m), 7.18-7.00 (4H, m), 4.25 (1H, m), 4.15 (1H, m), 3.80 (1H, m), 3.03 (1H, m), 2.49 (3H, s).

Step J. 2-chloro-N-(3-(3-fluorophenyl)-8-methyl-3,4-dihydro-2H-benzo[4,5]imidazo[2,1-b][1,3]thiazin-3-yl)-4-(4H-1,2,4-triazol-4-yl)benzamide A sealed tube was charged with AtOH (71 mg, 0.49 mmol), EDC (100 mg, 0.50 mmol) and acid 2-chloro-4-(4H-1,2,4-triazol-4-yl)benzoic acid (117 mg, 0.49 mmol) in dry DMF (1 ml) at RT under a nitrogen atmosphere with stirring. Then, a solution of amine 3-(3-fluorophenyl)-8-methyl-3,4-dihydro-2H-benzo[4,5]imidazo[2,1-b][1,3]thiazin-3-amine (103 mg, 0.33 mmol) and dry pyridine (0.113 ml, 1.33 mmol) in dry DMF (3 ml) was added. The resulting solution was stirred at RT for 16 h under a nitrogen atmosphere. Then, aq sat NaHCO$_3$ was added and the mixture was extracted twice with DCM. The combined organic phase was dried with MgSO$_4$ and the volatiles removed in vacuo (bath temperature 55° C.) to give a product that was purified by column chromatography (SiO$_2$, Biotage 25S) using DCM: 10% MeOH (aq NH$_3$) 1% to 30% to give racemic 2-chloro-N-(3-(3-fluorophenyl)-8-methyl-3,4-dihydro-2H- benzo[4,5]imidazo[2,1-b][1,3]thiazin-3-yl)-4-(4H-1,2,4-triazol-4-yl)benzamide. $^1$H-NMR (400 MHz, CDCl$_3$) δ (ppm): 8.55 (2H, s), 7.50 (1H, m), 7.43-7.27 (7H, m), 7.22 (1H, m), 7.17 (1H, m), 5.58 (1H, d), 4.43 (1H, d), 4.18 (1H, d), 3.94 (1H, d), 3.38 (1H, s), 2.42 (3H, s). LCMS m/z 519.3 (M+H). The single enantiomers were separated by chiral SFC.

Example 215

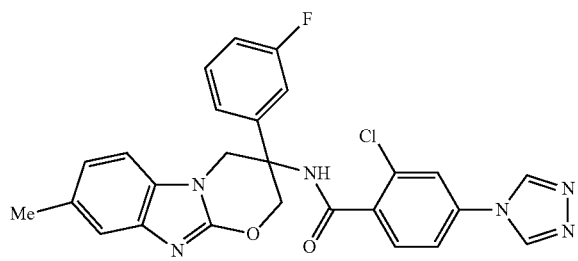 [SMILES: Cc1ccc2c(c1)nc1n2CC(NC(=O)c2ccc(-n3cnnc3)cc2Cl)(c2cccc(F)c2)CO1]

2-chloro-N-[3-(3-fluorophenyl)-8-methyl-3,4-dihydro-2H-[1,3]oxazino[3,2-a]benzimidazol-3-yl]-4-(4H-1,2,4-triazol-4-yl)benzamide Step A. tert-butyl (2-(3-fluorophenyl)-1-hydroxy-3-(5-methyl-2-thioxo-2,3-dihydro-1H-benzo[d]imidazol-1-yl)propan-2-yl)carbamate To a stirring solution of tert-butyl (1-((2-amino-4-methylphenyl)amino)-2-(3-fluorophenyl)-3-hydroxypropan-2-yl)carbamate (100 mg, 0.257 mmol) in THF (12 mL) was added 1,1'-thiocarbonyldimidazole (59.5 mg, 0.334 mmol). The reaction mixture was stirred at room temperature under N$_2$ for 2 h then passed thru a pad of silica gel, and flushed with ethyl acetate. Volatiles were removed in vacuo to give tert-butyl (2-(3-fluorophenyl)-1-hydroxy-3-(5-methyl-2-thioxo-2,3-dihydro-1H-benzo[d]imidazol-1-yl)propan-2-yl)carbamate. Carried to next step without purification.

Step B. tert-butyl (3-(3-fluorophenyl)-8-methyl-3,4-dihydro-2H-benzo[4,5]imidazo[2,1-b][1,3]oxazin-3-yl)carbamate To a stirring solution of tert-butyl (2-(3-fluorophenyl)-1-hydroxy-3-(5-methyl-2-thioxo-2,3-dihydro-1H-benzo[d]imidazol-1-yl)propan-2-yl)carbamate (110 mg, 0.255 mmol) in 1,2-dichloroethane (7.5 mL) was added Mercuric acetate (122 mg, 0.382 mmol). The reaction was stirred at room temperature for 1 h, then 35° C. overnight. The reaction mixture was cooled down to room temperature and diluted with CH$_2$Cl$_2$. The resulting reaction mixture was passed thru a short self-pad silica gel column and flashed with ethyl acetate. Volatiles were removed in vacuo. The residue was purified by column chromatography on silica gel, ISCO CombiFlash Rf 12 g column, eluting with 0 to 40% ethyl acetate in hexane to give tert-butyl (3-(3-fluorophenyl)-8-methyl-3,4-dihydro-2H-benzo[4,5]imidazo[2,1-b][1,3]oxazin-3-yl)carbamate.

$^1$H NMR (499 MHz, CDCl$_3$): 7.42-7.47 (m, 2H); 7.22 (m, 2H); 7.11 (dd, J=12.7, 8.0 Hz, 2H); 7.03 (d, J=8.1 Hz, 1H); 5.36 (s, 1H); 4.85 (broad 1H); 4.67 (d, J=11.6 Hz, 1H); 4.44-4.47 (m, 2H); 2.48 (s, 3H); 1.34 (s, 9H).

LCMS m/z=398.1 (M+H)

Step C. 3-(3-fluorophenyl)-8-methyl-3,4-dihydro-2H-benzo[4,5]imidazo[2,1-b][1,3]oxazin-3-amine To a stirring solution of tert-butyl (3-(3-fluorophenyl)-8-methyl-3,4-dihydro-2H-benzo[4,5]imidazo[2,1-b][1,3]oxazin-3-yl)carbamate (25 mg, 0.063 mmol) in CH$_2$Cl$_2$ (1.0 mL) was added Trifluoroacetic acid (0.5 mL). The reaction mixture was stirred under N$_2$ at room temperature for 45 min. Volatiles were removed in vacuo. The resulting mixture was diluted with ethyl acetate and basified with 1N NaOH. The aqueous layer was extracted with ethyl acetate three times. Then the combined organic layer was washed with water and brine, and then dried over Na$_2$SO$_4$ and filtered. The solvent was removed in vacuo then further dried in high vacuum pump for 3 h. The crude 3-(3-fluorophenyl)-8-methyl-3,4-dihydro-2H-benzo[4,5]imidazo[2,1-b][1,3]oxazin-3-amine obtained was carried on to next step without purification. LCMS m/z=298.3 (M+H)

Step D. 2-chloro-N-[3-(3-fluorophenyl)-8-methyl-3,4-dihydro-2H-[1,3]oxazino[3,2-a]benzimidazol-3-yl]-4-(4H-1,2,4-triazol-4-yl)benzamide To a stirring solution of 3-(3-fluorophenyl)-8-methyl-3,4-dihydro-2H-benzo[4,5]imidazo[2,1-b][1,3]oxazin-3-amine (20 mg, 0.067 mmol) in DMF (0.841 mL) was added 1-ethyl-3-(3-dimethylaminopropyl)carbodiimide (19.34 mg, 0.101 mmol) and hydroxybenzotriazole (15.45 mg, 0.101 mmol), following by addition of pyridine (21.8 uL, 0.269 mmol). Reaction was stirred at room temperature overnight. The crude reaction was diluted with DMF and purified by reverse phase HPLC (Gilson system, Sunfire PreP 5 uM C18 19×100 mm column, eluting with Acetonitrile/Water+0.1% TFA) to give 2-chloro-N-[3-(3-fluorophenyl)-8-methyl-3,4-dihydro-2H-[1,3]oxazino[3,2-a]benzimidazol-3-yl]-4-(4H-1,2,4-triazol-4-yl)benzamide. $^1$H NMR (499 MHz, CD$_3$OD): 9.07 (s, 2H); 7.87 (d, J=2.2 Hz, 1H); 7.55 (dd, J=8.4, 2.3 Hz, 1H); 7.39-7.45 (m, 4H); 7.09 (t, J=8.2 Hz, 1H); 7.01 (d, J=8.1 Hz, 1H); 6.83 (s, 1H); 6.73 (d, J=8.1 Hz, 1H); 5.31 (d, J=9.0 Hz, 1H); 4.42 (m, 2H); 4.11 (d, 2H); 1.26 (s, 3H). LCMS m/z 503.26 (M+H).

| Ex. | Structure | hFIXa IC50 (nM) | Exact Mass [M + H]+ | LCMS Read |
|---|---|---|---|---|
| 214 | 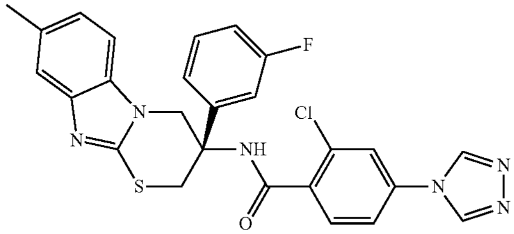 [SMILES: Cc1ccc2c(c1)nc1n2C[C@@](NC(=O)c2ccc(-n3cnnc3)cc2Cl)(c2cccc(F)c2)CS1] | 5.4 | 519.12 | 519.3 |
| 215 | 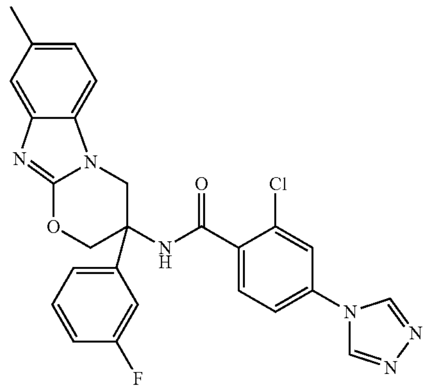 [SMILES: Cc1ccc2c(c1)nc1n2CC(NC(=O)c2ccc(-n3cnnc3)cc2Cl)(c2cccc(F)c2)CO1] | 6835 | 503.14 | 503.26 |

Determination of Inhibitory Activity Against Factor IXa

Formation of a clot to stem bleeding at a site of blood vessel injury involves the coordinated activity of a group of plasma proteins that initiate and propagate fibrin formation and subsequently protect fibrin from premature degradation. Factor IX is a key component of the plasma system that forms a fibrin clot at a site of vascular injury. The activity of Factor IXa is measured by monitoring the cleavage of the fluorescent peptide, $CH_3SO_2$-D-CHG-Gly-Arg-AFC.AcOH ("CHG" is cyclohexyl-glycine and "AFC" is trifluoro aminomethyl coumarin). Factor IXa cleaves the amide bond between Arg and AFC, thereby releasing the AFC fluorophore. The free AFC can be detected with a fluorescence detector at an excitation wavelength of 405 nM and emission wavelength of 510 nM.

What is claimed is:

1. A compound of the formula:

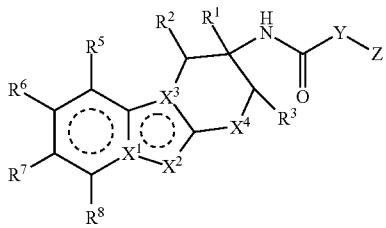

wherein the dotted lines represent aromatic rings;
$X^1$ is C;
$X^2$ is $CR^{12}$;
$X^3$ is N;
$X^4$ is $CR^{4a}R^{4b}$;
Y is heteroaryl or aryl, which is optionally substituted with one or two substituents independently selected from the group consisting of halo, $R^9$, $OR^9$, (C=O)$NH_2$ and (C=O)OH;

Z is heteroaryl, which is optionally substituted with one or two substituents independently selected from the group consisting of halo, oxo, $R^9$, $OR^9$, (C=O)$NR^9R^{10}$, (C=O)$R^9$, (C=O)$OR^9$, (C=O)heterocyclyl-OH and $C_{3-6}$ cycloalkyl; or heterocyclyl, which is optionally substituted with one or two substituents independently selected from the halo, cyano, oxo or $C_{1-6}$ alkyl;

$R^1$ is
  b) $C_{1-6}$ alkyl, wherein said alkyl is optionally substituted with one to three substituents independently selected from the group consisting of halo and hydroxy,
  c) aryl, wherein said aryl is optionally substituted with one or two substituents independently selected from the group consisting of halo, $R^9$, $OR^9$ and (C=O)$OR^9$, or
  d) heteroaryl, wherein said heteroaryl group is optionally substituted with one or two substituents independently selected from the group consisting of halo, $R^9$, $OR^9$, (C=O)$NR^9$, (C=O)$OR^9$ and $C_{3-6}$ cycloalkyl (which is optionally substituted with $R^9$);

$R^2$ is H, halo, hydroxy, cyano or $C_{1-6}$ alkyl;
$R^3$ is H, halo, hydroxy, cyano or $C_{1-6}$ alkyl;
or $R^2$ and $R^3$ can be taken together with the carbon atoms to which they are attached to form a 5 or 6 membered cycloalkyl ring;
$R^{4a}$ is H, halo, hydroxy, cyano or $C_{1-6}$ alkyl;
$R^{4b}$ is H, halo, hydroxy, cyano or $C_{1-6}$ alkyl;
$R^5$ is H, halo, hydroxy, cyano or $C_{1-6}$ alkyl;
$R^6$ is H, halo, hydroxy, cyano or $C_{1-6}$ alkyl;
$R^7$ is H, halo, hydroxy, cyano or $C_{1-6}$ alkyl;
$R^8$ is H, halo, hydroxy, cyano or $C_{1-6}$ alkyl;
$R^9$ is H or $C_{1-6}$ alkyl, which is optionally substituted with one to three substituents independently selected from the group consisting of halo and hydroxy;
$R^{10}$ is H or $C_{1-6}$ alkyl, which is optionally substituted with one to three substituents independently selected from the group consisting of halo and hydroxy;
$R^{11}$ is hydrogen, $C_{1-6}$ alkyl or $C_{1-6}$ alkyl-(C=O)$OR^9$;

R¹² is
a) hydrogen,
b) halo,
c) cyano,
d) (C=O)R⁹,
e) (C=O)OR⁹,
e) (C=O)NR⁹R¹⁰,
f) SO₂R⁹,
g) C$_{1-6}$ alkyl, which is optionally substituted with one to four substituents independently selected from the group consisting of halo, cyano, C$_{3-6}$ cycloalkyl, OR⁹, NR⁹R¹⁰, (C=O)OR⁹, (C=O)NR⁹R¹⁰, CH=CH(C=O)OR⁹, CH=CH(C=O)NR⁹R¹⁰ and CF₃,
h) C$_{2-6}$ alkenyl, which is optionally substituted with one to four substituents independently selected from the group consisting of halo, OR⁹, NR⁹R¹⁰, (C=O)OR⁹ and (C=O)NR⁹R¹⁰,
i) heteroaryl, which is optionally substituted with one or two substitutents independently selected from the group consisting of halo, cyano, oxo, C$_{3-6}$ cycloalkyl, R⁹, OR⁹, NR⁹R¹⁰, (C=O)R⁹ and (C=O)OR⁹,
j) heterocyclyl, which is optionally substituted with one or two substituents independently selected from the halo, cyano, oxo or C$_{1-6}$ alkyl,
k) C$_{3-6}$ cycloalkyl, or
l) C(R⁹)=NOH;
or a pharmaceutically acceptable salt thereof.

2. The compound of claim 1 wherein Y is aryl, which is optionally substituted with one or two substituents independently selected from the group consisting of halo, R⁹ and OR⁹, or a pharmaceutically acceptable salt thereof.

3. The compound of claim 1 wherein Z is triazolyl, benzimidazolyl, pyrimidinyl, imidazopyridinyl, imidazolyl or pyridinyl, wherein said groups are optionally substituted with one or two substituents independently selected from the group consisting of halo, oxo, R⁹, OR⁹, (C=O)NR⁹R¹⁰, (C=O)R⁹, (C=O)OR⁹, (C=O)heterocyclyl-OH and C$_{3-6}$ cycloalkyl, or a pharmaceutically acceptable salt thereof.

4. The compound of claim 1 wherein Z is triazolyl, which is optionally substituted with one or two substituents independently selected from the group consisting of halo, oxo, R⁹, OR⁹ and C$_{3-6}$ cycloalkyl, or a pharmaceutically acceptable salt thereof.

5. The compound of claim 1 wherein R¹ is phenyl, which is optionally substituted with one or two substituents independently selected from the group consisting of halo, R⁹, OR⁹ and (C=O)OR⁹, or a pharmaceutically acceptable salt thereof.

6. The compound of claim 1 wherein R² is H, R³ is H, R$^{4a}$ is H, R$^{4b}$ is H, or a pharmaceutically acceptable salt thereof.

7. The compound of claim 1 selected from:
2-chloro-N-[(7R)-2,7-dimethyl-6,7,8,9-tetrahydropyrido[1,2-a]indol-7-yl]-4-(4H-1,2,4-triazol-4-yl)benzamide;
2-chloro-N-[(7S)-2-methyl-7-phenyl-6,7,8,9-tetrahydropyrido[1,2-a]indol-7-yl]-4-(4H-1,2,4-triazol-4-yl)benzamide;
(7R)-7-({[2-chloro-4-(4H-1,2,4-triazol-4-yl)phenyl]carbonyl}amino)-2,7-dimethyl-6,7,8,9-tetrahydropyrido[1,2-a]indole-10-carboxamide;
(7S)-2-methyl-7-phenyl-7-({[4-(4H-1,2,4-triazol-4-yl)phenyl]carbonyl}amino)-6,7,8,9-tetrahydropyrido[1,2-a]indole-10-carboxamide;
(7S)-2-methyl-7-phenyl-7-({[4-(4H-1,2,4-triazol-4-yl)phenyl]carbonyl}amino)-6,7,8,9-tetrahydropyrido[1,2-a]indole-10-carboxylic acid;
(7S)-2-methyl-7-phenyl-7-({[4-(1H-tetrazol-1-yl)phenyl]carbonyl}amino)-6,7,8,9-tetrahydropyrido[1,2-a]indole-10-carboxamide;
(7S)-2-methyl-7-phenyl-7-({[5-(4H-1,2,4-triazol-4-yl)pyridin-2-yl]carbonyl}amino)-6,7,8,9-tetrahydropyrido[1,2-a]indole-10-carboxylic acid;
2-chloro-N-[(7S)-2,10-dimethyl-7-phenyl-6,7,8,9-tetrahydropyrido[1,2-a]indol-7-yl]-4-(4H-1,2,4-triazol-4-yl)benzamide;
2-chloro-N-[(7S)-10-cyano-2-methyl-7-phenyl-6,7,8,9-tetrahydropyrido[1,2-a]indol-7-yl]-4-(4H-1,2,4-triazol-4-yl)benzamide;
3-[(7S)-2-methyl-7-phenyl-7-({[4-(4H-1,2,4-triazol-4-yl)phenyl]carbonyl}amino)-6,7,8,9-tetrahydropyrido[1,2-a]indol-10-yl]propanoic acid;
2-chloro-N-[(7S)-10-cyclopropyl-2-methyl-7-phenyl-6,7,8,9-tetrahydropyrido[1,2-a]indol-7-yl]-4-(4H-1,2,4-triazol-4-yl)benzamide;
N-[(7S)-10-acetyl-2-methyl-7-phenyl-6,7,8,9-tetrahydropyrido[1,2-a]indol-7-yl]-2-chloro-4-(4H-1,2,4-triazol-4-yl)benzamide;
2-chloro-N-[(7S)-10-formyl-2-methyl-7-phenyl-6,7,8,9-tetrahydropyrido[1,2-a]indol-7-yl]-4-(3-methyl-1H-1,2,4-triazol-1-yl)benzamide;
2-chloro-N-{(7S)-10-[(E)-(hydroxyimino)methyl]-2-methyl-7-phenyl-6,7,8,9-tetrahydropyrido[1,2-a]indol-7-yl}-4-(4H-1,2,4-triazol-4-yl)benzamide;
(7S)-7-({[2-chloro-4-(4H-1,2,4-triazol-4-yl)phenyl]carbonyl}amino)-2-methyl-7-phenyl-6,7,8,9-tetrahydropyrido[1,2-a]indole-10-carboxamide;
(7S)-7-({[2-chloro-4-(4H-1,2,4-triazol-4-yl)phenyl]carbonyl}amino)-2-methyl-7-phenyl-6,7,8,9-tetrahydropyrido[1,2-a]indole-10-carboxylic acid;
(7S)-7-({[2-chloro-4-(1H-tetrazol-1-yl)phenyl]carbonyl}amino)-2-methyl-7-phenyl-6,7,8,9-tetrahydropyrido[1,2-a]indole-10-carboxamide;
(7S)-7-({[2-methoxy-4-(3-methyl-1H-1,2,4-triazol-1-yl)phenyl]carbonyl}amino)-2-methyl-7-phenyl-6,7,8,9-tetrahydropyrido[1,2-a]indole-10-carboxylic acid;
(7S)-7-({[2-methoxy-4-(3-methyl-4H-1,2,4-triazol-4-yl)phenyl]carbonyl}amino)-2-methyl-7-phenyl-6,7,8,9-tetrahydropyrido[1,2-a]indole-10-carboxylic acid;
2-chloro-N-[(7S)-10-cyclopropyl-2-methyl-7-phenyl-6,7,8,9-tetrahydropyrido[1,2-a]indol-7-yl]-4-(3-methyl-4H-1,2,4-triazol-4-yl)benzamide;
N-[(7S)-10-acetyl-2-methyl-7-phenyl-6,7,8,9-tetrahydropyrido[1,2-a]indol-7-yl]-2-chloro-4-(3-methyl-1H-1,2,4-triazol-1-yl)benzamide;
2-chloro-N-{(7S)-10-[(E)-(hydroxyimino)methyl]-2-methyl-7-phenyl-6,7,8,9-tetrahydropyrido[1,2-a]indol-7-yl}-4-(3-methyl-1H-1,2,4-triazol-1-yl)benzamide;
2-chloro-N-{(7S)-10-[(1E)-N-hydroxyethanimidoyl]-2-methyl-7-phenyl-6,7,8,9-tetrahydropyrido[1,2-a]indol-7-yl}-4-(4H-1,2,4-triazol-4-yl)benzamide;
(7S)-7-({[2-chloro-4-(3-methyl-4H-1,2,4-triazol-4-yl)phenyl]carbonyl}amino)-2-methyl-7-phenyl-6,7,8,9-tetrahydropyrido[1,2-a]indole-10-carboxamide;
(7S)-7-({[2-chloro-4-(3-methyl-H-1,2,4-triazol-1-yl)phenyl]carbonyl}amino)-2-methyl-7-phenyl-6,7,8,9-tetrahydropyrido[1,2-a]indole-10-carboxamide;
(7S)-7-({[2-chloro-4-(3-methyl-H-1,2,4-triazol-1-yl)phenyl]carbonyl}amino)-2-methyl-7-phenyl-6,7,8,9-tetrahydropyrido[1,2-a]indole-10-carboxylic acid;
(7S)-7-({[2-chloro-4-(3-methyl-4H-1,2,4-triazol-4-yl)phenyl]carbonyl}amino)-2-methyl-7-phenyl-6,7,8,9-tetrahydropyrido[1,2-a]indole-10-carboxylic acid;

[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]acetic acid;

2,6-dichloro-N-[(7S)-10-cyano-2-methyl-7-phenyl-6,7,8,9-tetrahydropyrido[1,2-a]indol-7-yl]-4-(4H-1,2,4-triazol-4-yl)benzamide;

2,6-dichloro-N-[(7S)-10-formyl-2-methyl-7-phenyl-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-(1H-1,2,4-triazol-5-yl)-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-(trifluoromethyl)-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-(1H-tetrazol-5-yl)-6,7,8,9-tetrahydropyrido[1,2-a]indol-7-yl]-4-(4H-1,2,4-triazol-4-yl)benzamide;

N-{(7S)-10-[(1E)-3-amino-3-oxoprop-1-en-1-yl]-2-methyl-7-phenyl-6,7,8,9-tetrahydropyrido[1,2-a]indol-7-yl}-2-chloro-4-(4H-1,2,4-triazol-4-yl)benzamide;

(7S)-7-({[2-methoxy-4-(3-methoxy-1H-1,2,4-triazol-1-yl)phenyl]carbonyl}amino)-2-methyl-7-phenyl-6,7,8,9-tetrahydropyrido[1,2-a]indole-10-carboxylic acid;

(7S)-7-({[2-methoxy-4-(1-methyl-5-oxo-1,5-dihydro-4H-1,2,4-triazol-4-yl)phenyl]carbonyl}amino)-2-methyl-7-phenyl-6,7,8,9-tetrahydropyrido[1,2-a]indole-10-carboxylic acid;

(2E)-3-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]prop-2-enoic acid;

N-[(7S)-10-(3-amino-3-oxopropyl)-2-methyl-7-phenyl-6,7,8,9-tetrahydropyrido[1,2-a]indol-7-yl]-2-chloro-4-(4H-1,2,4-triazol-4-yl)benzamide;

2-chloro-N-{(7S)-10-[(1E)-N-hydroxyethanimidoyl]-2-methyl-7-phenyl-6,7,8,9-tetrahydropyrido[1,2-a]indol-7-yl}-4-(3-methyl-1H-1,2,4-triazol-1-yl)benzamide;

(7S)-7-({[2-chloro-6-methyl-4-(3-methyl-1H-1,2,4-triazol-1-yl)phenyl]carbonyl}amino)-2-methyl-7-phenyl-6,7,8,9-tetrahydropyrido[1,2-a]indole-10-carboxamide;

3-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]propanoic acid;

methyl (7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indole-10-carboxylate;

[(7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indol-10-yl]acetic acid;

amino[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]acetic acid;

(7S)-7-({[2-chloro-4-(3-methoxy-1H-1,2,4-triazol-1-yl)phenyl]carbonyl}amino)-2-methyl-7-phenyl-6,7,8,9-tetrahydropyrido[1,2-a]indole-10-carboxylic acid;

(7S)-7-({[2-chloro-4-(1-methyl-5-oxo-1,5-dihydro-4H-1,2,4-triazol-4-yl)phenyl]carbonyl}amino)-2-methyl-7-phenyl-6,7,8,9-tetrahydropyrido[1,2-a]indole-10-carboxylic acid;

methyl (7S)-7-({[2-chloro-4-(4H-1,2,4-triazol-4-yl)phenyl]carbonyl}amino)-7-(3-fluorophenyl)-2-methyl-6,7,8,9-tetrahydropyrido[1,2-a]indole-10-carboxylate;

(7S)-7-({[2-chloro-4-(3-methyl-1H-1,2,4-triazol-1-yl)phenyl]carbonyl}amino)-7-(3-fluorophenyl)-2-methyl-6,7,8,9-tetrahydropyrido[1,2-a]indole-10-carboxylic acid;

2-chloro-N-[(7S)-2-methyl-7-phenyl-10-pyridin-3-yl-6,7,8,9-tetrahydropyrido[1,2-a]indol-7-yl]-4-(4H-1,2,4-triazol-4-yl)benzamide;

2,6-dichloro-N-{(7S)-10-[(E)-(hydroxyimino)methyl]-2-methyl-7-phenyl-6,7,8,9-tetrahydropyrido[1,2-a]indol-7-yl}-4-(4H-1,2,4-triazol-4-yl)benzamide;

(7S)-7-({[2,6-dichloro-4-(4H-1,2,4-triazol-4-yl)phenyl]carbonyl}amino)-2-methyl-7-phenyl-6,7,8,9-tetrahydropyrido[1,2-a]indole-10-carboxamide;

2-chloro-N-[(7S)-10-(difluoroacetyl)-2-methyl-7-phenyl-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-pyrimidin-5-yl-6,7,8,9-tetrahydropyrido[1,2-a]indol-7-yl]-4-(4H-1,2,4-triazol-4-yl)benzamide;

2-chloro-N-[(7S)-2-methyl-10-(methyl sulfonyl)-7-phenyl-6,7,8,9-tetrahydropyrido[1,2-a]indol-7-yl]-4-(4H-1,2,4-triazol-4-yl)benzamide;

2-chloro-N-[(7S)-2-methyl-10-(5-methyl-1,2,4-oxadiazol-3-yl)-7-phenyl-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-(1H-tetrazol-5-yl)-6,7,8,9-tetrahydropyrido[1,2-a]indol-7-yl]-4-(3-methyl-1H-1,2,4-triazol-1-yl)benzamide;

(7S)-7-({[2-chloro-4-(1-methyl-6-oxo-1,6-dihydropyridin-3-yl)phenyl]carbonyl}amino)-2-methyl-7-phenyl-6,7,8,9-tetrahydropyrido[1,2-a]indole-10-carboxamide;

methyl (2E)-3-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]prop-2-enoate;

(2E)-3-[(7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indol-10-yl]prop-2-enoic acid;

3-[(7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indol-10-yl]propanoic acid;

methyl [(7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indol-10-yl]acetate;

methyl 3-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]propanoate;

methyl (7S)-7-({[2-chloro-4-(1-methyl-5-oxo-1,5-dihydro-4H-1,2,4-triazol-4-yl)phenyl]carbonyl}amino)-2-methyl-7-phenyl-6,7,8,9-tetrahydropyrido[1,2-a]indole-10-carboxylate;

2-chloro-N-[(7S)-2-methyl-7-phenyl-10-pyridin-3-yl-6,7,8,9-tetrahydropyrido[1,2-a]indol-7-yl]-4-(3-methyl-4H-1,2,4-triazol-4-yl)benzamide;

(7S)-7-({[2-chloro-4-(1-methyl-5-oxo-1,5-dihydro-4H-1,2,4-triazol-4-yl)phenyl]carbonyl}amino)-7-(3-fluorophenyl)-2-methyl-6,7,8,9-tetrahydropyrido[1,2-a]indole-10-carboxylic acid;

N-[(7S)-10-(5-aminopyridin-3-yl)-2-methyl-7-phenyl-6,7,8,9-tetrahydropyrido[1,2-a]indol-7-yl]-2-chloro-4-(4H-1,2,4-triazol-4-yl)benzamide;

6,7,8,9-tetrahydropyrido[1,2-a]indol-7-yl]-2-chloro-4-(4H-1,2,4-triazol-4-yl)benzamide 2-chloro-N-[(7S)-10-(5-fluoropyridin-3-yl)-2-methyl-7-phenyl-6,7,8,9-tetrahydropyrido[1,2-a]indol-7-yl]-4-(4H-1,2,4-triazol-4-yl)benzamide;

2-chloro-N-[(7S)-2-methyl-7-phenyl-10-(trifluoroacetyl)-6,7,8,9-tetrahydropyrido[1,2-a]indol-7-yl]-4-(4H-1,2,4-triazol-4-yl)benzamide;

2-chloro-N-{(7S)-2-methyl-7-phenyl-10-[(1R)-2,2,2-trifluoro-1-hydroxyethyl]-6,7,8,9-tetrahydropyrido[1,2-a]indol-7-yl}-4-(4H-1,2,4-triazol-4-yl)benzamide;

2-chloro-N-{(7S)-2-methyl-7-phenyl-10-[(1S)-2,2,2-trifluoro-1-hydroxyethyl]-6,7,8,9-tetrahydropyrido[1,2-a]indol-7-yl}-4-(4H-1,2,4-triazol-4-yl)benzamide;

methyl (2E)-3-[(7S)-7-({[2-chloro-4-(3-methyl-1H-1,2,4-triazol-1-yl)phenyl]carbonyl}amino)-2-methyl-7-phenyl-6,7,8,9-tetrahydropyrido[1,2-a]indol-10-yl]prop-2-enoate;

2-chloro-N-[10-(5-cyanopyridin-3-yl)-2-methyl-7-phenyl-6,7,8,9-tetrahydropyrido[1,2-a]indol-7-yl]-4-(4H-1,2,4-triazol-4-yl)benzamide;

methyl [(7S)-7-({[2,6-dichloro-4-(4H-1,2,4-triazol-4-yl)phenyl]carbonyl}amino)-2-methyl-7-phenyl-6,7,8,9-tetrahydropyrido[1,2-a]indol-10-yl]acetate;

2-chloro-N-[(7S)-10-(5-methoxypyridin-3-yl)-2-methyl-7-phenyl-6,7,8,9-tetrahydropyrido[1,2-a]indol-7-yl]-4-(4H-1,2,4-triazol-4-yl)benzamide;

2-chloro-N-{(7S)-10-[5-(hydroxymethyl)pyridin-3-yl]-2-methyl-7-phenyl-6,7,8,9-tetrahydropyrido[1,2-a]indol-7-yl}-4-(4H-1,2,4-triazol-4-yl)benzamide;

2-chloro-N-[(7S)-10-(6-methoxypyridin-3-yl)-2-methyl-7-phenyl-6,7,8,9-tetrahydropyrido[1,2-a]indol-7-yl]-4-(4H-1,2,4-triazol-4-yl)benzamide;

2-chloro-N-[(7S)-10-(4-methoxypyridin-3-yl)-2-methyl-7-phenyl-6,7,8,9-tetrahydropyrido[1,2-a]indol-7-yl]-4-(4H-1,2,4-triazol-4-yl)benzamide;

2-chloro-N-{(7S)-10-[6-(hydroxymethyl)pyridin-3-yl]-2-methyl-7-phenyl-6,7,8,9-tetrahydropyrido[1,2-a]indol-7-yl}-4-(4H-1,2,4-triazol-4-yl)benzamide;

2-chloro-N-[(7S)-10-(2-methoxypyrimidin-5-yl)-2-methyl-7-phenyl-6,7,8,9-tetrahydropyrido[1,2-a]indol-7-yl]-4-(4H-1,2,4-triazol-4-yl)benzamide;

2-chloro-N-[(7S)-2-methyl-10-(1-methyl-6-oxo-1,2,3,6-tetrahydropyridin-4-yl)-7-phenyl-6,7,8,9-tetrahydropyrido[1,2-a]indol-7-yl]-4-(4H-1,2,4-triazol-4-yl)benzamide;

2,6-dichloro-N-[(7S)-2-methyl-10-(methylsulfonyl)-7-phenyl-6,7,8,9-tetrahydropyrido[1,2-a]indol-7-yl]-4-(4H-1,2,4-triazol-4-yl)benzamide;

2-chloro-N-[(7S)-10-(2-cyclopropylpyrimidin-5-yl)-2-methyl-7-phenyl-6,7,8,9-tetrahydropyrido[1,2-a]indol-7-yl]-4-(4H-1,2,4-triazol-4-yl)benzamide;

N-[(7S)-10-(6-acetylpyridin-3-yl)-2-methyl-7-phenyl-6,7,8,9-tetrahydropyrido[1,2-a]indol-7-yl]-2-chloro-4-(4H-1,2,4-triazol-4-yl)benzamide;

5-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]pyridine-3-carboxylic acid;

2-chloro-N-[(7S)-10-(5-fluoro-6-methoxypyridin-3-yl)-2-methyl-7-phenyl-6,7,8,9-tetrahydropyrido[1,2-a]indol-7-yl]-4-(4H-1,2,4-triazol-4-yl)benzamide;

2,6-dichloro-N-[(7S)-2-methyl-7-phenyl-10-(trifluoroacetyl)-6,7,8,9-tetrahydropyrido[1,2-a]indol-7-yl]-4-(4H-1,2,4-triazol-4-yl)benzamide;

2-chloro-N-[(7S)-10-(5-cyano-6-methoxypyridin-3-yl)-2-methyl-7-phenyl-6,7,8,9-tetrahydropyrido[1,2-a]indol-7-yl]-4-(4H-1,2,4-triazol-4-yl)benzamide;

methyl 5-[(7S)-7-({[2-chloro-4-(4H-1,2,4-triazol-4-yl)phenyl]carbonyl}amino)-2-methyl-7-phenyl-6,7,8,9-tetrahydropyrido[1,2-a]indol-10-yl]pyridine-2-carboxylate;

2-chloro-N-{(7S)-10-[5-(1-hydroxy-1-methylethyl)pyridin-3-yl]-2-methyl-7-phenyl-6,7,8,9-tetrahydropyrido[1,2-a]indol-7-yl}-4-(4H-1,2,4-triazol-4-yl)benzamide;

or a pharmaceutically acceptable salt thereof.

8. A pharmaceutical composition comprising a compound of claim 1 or a pharmaceutically acceptable salt thereof and a pharmaceutically acceptable carrier.

9. A method for inhibiting thrombus formation in blood or treating thrombus formation in blood comprising administering a composition of claim 8 to a mammal in need of thereof.

10. A method of treating deep vein thrombosis in a mammal comprising administering a composition of claim 8 to a mammal in need thereof.

11. A method of inhibiting Factor IXa comprising administering a composition of Compound 8 to a mammal in need thereof.

* * * * *